United States Patent [19]

Manning et al.

[11] Patent Number: 5,426,105

[45] Date of Patent: Jun. 20, 1995

[54] CONFORMATIONALLY RESTRICTED ANGIOTENSIN II ANTAGONISTS

[75] Inventors: Robert E. Manning, St. Louis; Horng-Chih Huang, Chesterfield, both of Mo.

[73] Assignee: G.D. Searle & Co., Skokie, Ill.

[21] Appl. No.: 127,147

[22] Filed: Sep. 24, 1993

[51] Int. Cl.[6] .................. A61K 31/435; C07D 487/04
[52] U.S. Cl. .................... 514/214; 514/299; 514/300; 514/303; 514/322; 514/323; 514/381; 540/578; 540/579; 540/593; 546/112; 546/119; 546/120; 546/121; 546/199; 546/201; 548/252; 548/253; 548/254
[58] Field of Search ............ 546/112, 119, 120, 121, 546/199, 201; 540/578, 579, 593; 548/252, 253, 254; 514/214, 299, 300, 303, 322, 323, 381

[56] References Cited

U.S. PATENT DOCUMENTS 5,270,322 12/1993 Ries et al. .................... 546/121

*Primary Examiner*—Bernard Dentz
*Attorney, Agent, or Firm*—Bulock: Joseph W.

[57] ABSTRACT

Conformationally restricted compounds are described which are therapeutically effective as angiotensin II antagonists for the treatment of circulatory disorders. Compounds of particular interest are of Formula I

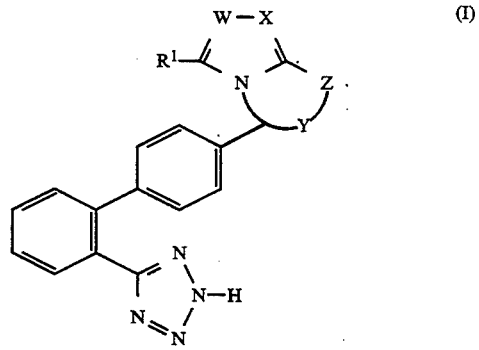

wherein W is N or $CH_2$; wherein X is N or $CR^2$; wherein Y is $(CH_2)_n$ and n is 1 to 3; wherein Z is $C=R^3$ or $CR^4R^5$, or wherein Y and Z together forms $-CR^6=CR^7-$, $-CR^6=CR^7-CH_2$ or $-CR^6=CR^7-CH_2-CH^2-$; wherein the remainder of the variables are as defined in the specification; or a pharmaceutically suitable salt or tautomer thereof.

25 Claims, No Drawings

CONFORMATIONALLY RESTRICTED ANGIOTENSIN II ANTAGONISTS

FIELD OF THE INVENTION

Conformationally restricted non-peptide angiotensin II (AII) antagonists are described for use in treatment of circulatory disorders such as hypertension and congestive heart failure. Of particular interest are heteroatom-containing fused bicyclic compounds having a substituted biphenyl moiety attached thereto.

BACKGROUND OF THE INVENTION

Angiotensin II is the primary hormone active in the renin-angiotensin system and elicits effects on the regulation of arterial pressure, volume homeostasis and hypertension. Activation of the renin-angiotensin cascade begins with renin secretion from the juxtaglomerular apparatus of the kidney and culminates in the formation of angiotensin II, the primary active species of this system. Angiotensin II is an octapeptide which is a potent vasoconstrictor and also promotes aldosterone secretion, promotes sodium and fluid retention, inhibits renin secretion and increases vasopressin secretion.

Previous studies have shown that antagonizing angiotensin II at the receptor level is a viable approach to controlling the renin-angiotensin system. There are several known angiotensin II antagonists, many of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limits their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Ext. Ther.*, 247(1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 13–21 (1988)]. A family of 1-benzylimidazole-5-acetate derivatives has been shown to have competitive angiotensin II antagonist properties [A. T. Chiu et al, *J. Pharmacol. Exp. Ther.*, 250(3), 867–874 (1989)]. U.S. Pat. No. 4,816,463 to Blankey et al describes a family of 4,5,6,7-tetrahydro-1H-imidazo(a,5-c)-tetrahydro-pyridine derivatives useful as antihypertensives, some of which are reported to antagonize the binding of labeled angiotensin II to a rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841 published 12 Jul. 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of 1,2,4-triazole compounds having substituents attached to the nitrogen atom at the one-position of the 1H-triazole. For example, U.S. Pat. No. 4,118,487 to Regel et al describes a family of azol-1-yl-methane compounds for use as antimycotic and antibacterial agents including, specifically, the compound (1-biphenyl-4-yl-1-phenyl)methyl-1H-1,2,4-triazole. U.S. Pat. No. 4,381,306 to Regel et al describes a family of hydroxypropyl-triazole compounds for use as antimycotic agents including, specifically, the compound (1,2,4-triazol-1-yl)methyl-4-chlorobenzyl-biphenyl-4-yl-carbinol. U.S. Pat. No. 4,480,114 to Regel describes a family of 2-(4-biphenyl)-2-(halophenyl)-oxirane compounds having antimycotic activity including, specifically, the compound (1,2,4-triazol-1-yl)methyl-4-chlorophenyl-4-chlorobiphenyl-4-yl-carbinol.

However, not much is known about the conformations and interactions of these non-peptide antagonists with the vascular angiotensin II receptors. It has been established in the literature that there are distinct angiotensin II receptor subtypes with differing functions [A. T. Chiu et al, *Biochem. Biophys. Res. Comm.*, 165, 196–203 (1989)]. The receptor subtypes affecting vascular constriction is believed to be an important target for the treatment of hypertension [P. C. Wong et al, *J. Pharmacol. Exp. Ther.*, 255, 584–592 (1990)]. Compounds which conformationally restrict the possible orientations of the pharmacophores incorporated therein may maximize the interaction between those pharmacophores and the binding site of the receptor subtype or subtypes of interest. Therefore, conformationally restricted angiotensin II antagonists may increase the selectivity to the specific receptor subtype of interest, thereby reducing possible side effects associated with binding to the other receptor subtypes not involved in the hypertension pathway.

There are several families of conformationally restricted angiotensin II antagonists reported in the literature. For example, tricyclic benzoxazepines [A. P. Thomas et al, *J. Med. Chem.*, 35, 877–885 (1992)] were used to potentially lock in a phenyl group in an energetically favorable conformation. Conformationally restricted imidazoles having a biphenyl radical substituted with bulky side groups to sterically limit the rotation of the phenyl groups and form a more rigid spatial relationship were described in P. R. Bovy et al, *J. Med. Chem.*, 34, 2410–2414 (1991). These previous attempts to lock the conformation of angiotensin II antagonists do not stabilize conformations axial to a heterocyclic ring by means of orthogonally attaching a substituted biphenyl radical to a non-aromatic bridging ring.

DESCRIPTION OF THE INVENTION

A series of bicyclic-substituted biphenylmethylene-type compounds which exhibit angiotensin II antagonism are disclosed herein, where the compounds lock the conformation around the methylene group to better mimic high affinity angiotensin II binding site conformations. Specifically, this invention relates to compounds comprising a substituted biphenylmethylene radical attached in a conformationally restricted manner through incorporation in a heterocyclic fused ring system. More specifically, angiotensin II antagonists are described wherein the biphenyl radical may contain an acidic radical such as a tetrazole radical.

Even more specifically, the invention relates to compounds of Formula I

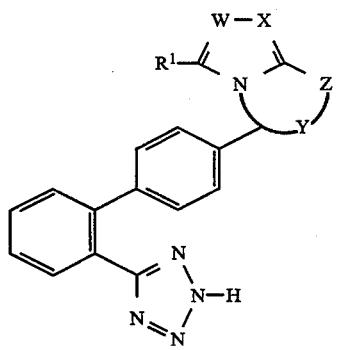

wherein W is N or $CH_2$;
wherein X is N or $CR^2$;
wherein Y is $(CH_2)_n$ and n is 1 to 3;
wherein Z is $C=R^3$ or $CR^4R^5$, or
wherein Y and Z together forms $—CR^6=CR^7—$, $—CR^6\alpha CR^7—CH_2$ or $—CR^6\alpha CR^7—CH_2—CH_2—$;
wherein $R^1$ is alkyl;
wherein $R^2$ is selected from hydrido, halo, alkyl and aryl;
wherein $R^3$ is selected from oxygen, sulfur, hydroxyamino, alkylidene, alkylcarboxyalkylidene and carboxyalkylidene;
wherein $R^4$ is selected from hydrido, alkyl, amino, hydroxyalkyl, carboxyl, carboxyalkyl, aryl, aralkyl, aralkoxy, alkylcarboxyalkyl, hydroxyl, carboxyaralkyl, phthalimidyl,

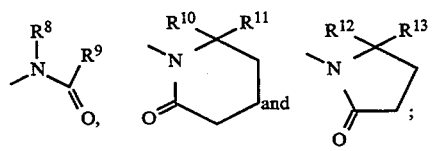

wherein $R^5$ is hydrido or hydroxyl;
wherein $R^6$ is selected from hydrido, alkyl, halo, hydroxyalkyl, carboxyalkyl, carboxyl, alkylcarboxyalkyl, aryl and aralkyl;
wherein $R^7$ is hydrido or halo;
wherein $R^8$ is selected from hydrido, alkyl and aralkyl;
wherein $R^9$ is selected from alkyl, aryl, aralkyl, carboxyl, hydrazidylcarboalkyl and carboxyalkyl;
wherein $R^{10}$ is hydrido or alkyl;
wherein $R^{11}$ is selected from hydrido, alkyl, hydroxyalkyl and carboxyl, or
wherein $R^{10}$ and $R^{11}$ taken together is =O;
wherein $R^{12}$ is hydrido or alkyl; and
wherein $R^{13}$ is selected from hydrido, alkyl, hydroxyalkyl and carboxyl, or
wherein $R^{12}$ and $R^{13}$ taken together is =O;
or a pharmaceutically suitable salt or tautemer thereof.

The compounds of Formula I are further substituted wherein $R^4$ is selected from aryl or aralkyl only when $R^2$ if present is hydrido or halo;
wherein $R^4$ is alkyl when $R^5$ is hydroxyl;

wherein $R^8$ is aralkyl when $R^2$, if present, is hydrido or halo;
wherein $R^9$ and $R^8$ are not both aralkyl; and
wherein $R^{11}$ and $R^{13}$ is alkyl when $R^2$ is aryl or halo;
or a pharmaceutically suitable salt thereof.

More specifically, the compounds of Formula I are further substituted wherein $R^1$ is n-propyl or n-butyl;
wherein $R^2$ is selected from hydrido, chloro, methyl, ethyl, n-propyl and n-butyl, 2-ethylphenyl and 2,6-dimethylphenyl;
wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;
wherein $R^4$ is selected from hydrido, ethyl, n-propyl, t-butoxycarbonylmethyl, t-butoxycarbonylpropyl, hydroxyl, hydroxymethyl, phenylmethoxy, $—(CH_2)_3CO_2H$, $—CH_2CO_2H$, amino, $—(CH_2)_2CO_2H$, $—CH(CH_2C_6H_5)CO_2H$, $—CH(C_2H_5)CH_2CO_2H$, phenethyl, $—CH(CH_2C_6H_5)CH_2CO_2H$, phenyl, 2-ethylphenyl, benzyl, 2,6-dimethylphenyl,

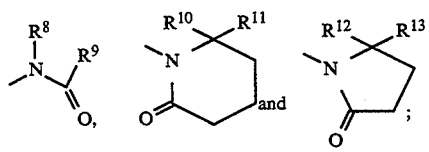

provided $R^4$ is selected from phenyl, benzyl and phenethyl only when $R^2$, if present, is hydrido or chloro;
wherein $R^5$ is hydrido or hydroxyl, provided that when $R^5$ is hydroxyl, $R^4$ is ethyl or n-propyl;
wherein $R^6$ is selected from hydrido, ethyl, n-propyl, hydroxymethyl, $—(CH_2)_3CO_2H$, $—CH_2CO_2H$, $—(CH_2)_2CO_2H$, t-butoxycarbonylmethyl, t-butoxycarbonylpropyl, $—CH(CH_2C_6H_5)CO_2H$, $—CH(C_2H_5)CH_2CO_2H$, $—CH(CH_2C_6H_5)CH_2CO_2H$, phenyl, 2-ethylphenyl, 2,6-dimethylphenyl, phenethyl and benzyl;
wherein $R^7$ is selected from hydrido, bromo, fluoro, chloro and iodo;
wherein $R^8$ is selected from hydrido, methyl, ethyl, propyl and benzyl, provided that $R^8$ is benzyl where $R^2$, if present, is hydrido or chloro;
wherein $R^9$ is selected from methyl, ethyl, phenyl, benzyl, $—(CH_2)_2CONHNH_2$, $—CH_2CO_2H$ and $—(CH_2)_2CO_2H$, provided that $R^9$ and $R^8$ are not both benzyl;
wherein $R^{10}$ is hydrido or methyl;
wherein $R^{11}$ is selected from hydrido, methyl, ethyl, hydroxymethyl and formyl, or
wherein $R^{10}$ and $R^{11}$ taken together is =O;
wherein $R^{12}$ is hydrido or methyl; and
wherein $R^{13}$ is selected from hydrido, methyl, ethyl, hydroxymethyl and formyl, or
wherein $R^{12}$ and $R^{13}$ taken together is =O; or a pharmaceutically suitable salt thereof.

Within Formula I there is a sub-class of compounds represented by compounds of Formula II

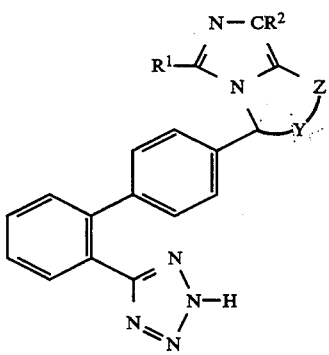

(II)

wherein Y is (CH₂)ₙ and n is 1 to 3;
wherein Z is C=R³ or CR⁴R⁵, or
wherein Y and Z together forms —CR⁶=CR⁷—, —CR⁶=CR⁷—CH₂— or —CR⁶=CR⁷—CH₂—CH₂—;
wherein R¹ is alkyl;
wherein R² is selected from hydrido, halo, alkyl and aryl;
wherein R³ is selected from oxygen, sulfur, hydroxyamino, alkylidene alkylcarboxyalkylidene and carboxyalkylidene;
wherein R⁴ is selected from hydrido, alkyl, amino, hydroxyalkyl, carboxyl, carboxyalkyl, alkylcarboxyalkyl, aryl, aralkyl, hydroxyl, aralkoxy, carboxyaralkyl, phthalimidyl,

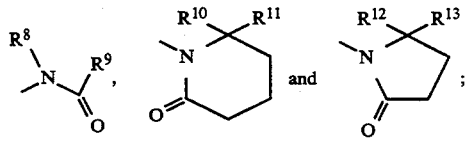

wherein R⁵ is hydrido or hydroxyl;
wherein R⁶ is selected from hydrido, alkyl, halo, hydroxyalkyl, carboxyl, carboxyalkyl, alkylcarboxyalkyl, aryl, aralkyl and hydroxyl;
wherein R⁷ is hydrido or halo;
wherein R⁸ is selected from hydrido, alkyl and aralkyl; wherein R⁹ is selected from alkyl, aryl, aralkyl, carboxyl, carboxyalkyl and hydrazidylcarboalkyl;
wherein R¹⁰ is hydrido or alkyl;
wherein R¹¹ is selected from hydrido, alkyl, hydroxyalkyl, carboxyl and carboxyalkyl, or
wherein R¹⁰ and R¹¹ taken together is =O;
wherein R¹² is hydrido or alkyl;
wherein R¹³ is selected from hydrido, alkyl, hydroxyalkyl, carboxyl and carboxyalkyl, or
wherein R¹² and R¹³ taken together is =O; or a pharmaceutically suitable salt thereof.

The compounds of Formula II are further substituted wherein R⁴ is aryl or aralkyl only when R² is hydrido or halo;
wherein R⁴ is alkyl when R⁵ is hydroxyl;
wherein R⁷ is aralkyl when R², if present, is hydrido or halo;
wherein R⁸ and R⁹ are not both aralkyl;
wherein R¹¹ is alkyl when R² is aryl or halo; and
wherein R¹³ is alkyl when R² is aryl or halo; or a pharmaceutically suitable salt thereof.

A more preferred class of compounds consists of those compounds of Formula II wherein R⁶ is selected from hydrido, ethyl, hydroxymethyl, —CH₂CO₂H, and —(CH₂)₃CO₂H, or R⁶ is aryl or aralkyl, provided R² is hydrido, and R³ is selected from oxygen, sulfur, hydroxyamino, CHCO₂H and CHCO₂C(CH₃)₃; or a pharmaceutically suitable salt thereof.

An even more preferred class of compounds consists of those compounds of Formula II wherein R¹ is n-propyl or n-butyl;
wherein R² is selected from hydrido, chloro, methyl, ethyl, n-propyl, n-butyl, 2-ethylphenyl and 2,6-dimethylphenyl;
wherein R³ is selected from oxygen, sulfur, hydroxyamino, CHCO₂H and CHCO₂C(CH₃)₃;
wherein R⁴ is selected from hydrido, ethyl, n-propyl, hydroxymethyl, t-butoxycarbonylmethyl, hydroxyl, amino, t-butoxycarbonylpropyl, —(CH₂)₃CO₂H, —CH₂CO₂H, —(CH₂)₂CO₂H, —CH(CH₂C₆H₅)CO₂H, —CH(C₂H₅)CH₂CO₂H, —CH(CH₂C₆H₅)CH₂CO₂H, phenyl, 2-ethylphenyl, 2,6-dimethylphenyl, phenethyl, benzyl, phenylmethoxy,

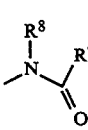

provided R⁴ is selected from phenyl, benzyl and phenethyl only when R² is hydrido or chloro;
wherein R⁵ is hydrido or hydroxyl, provided that when R⁵ is hydroxyl, R⁴ is ethyl or n-propyl;
wherein R⁶ is selected from hydrido, ethyl, n-propyl, hydroxymethyl, —(CH₂)₃CO₂H, —CH₂CO₂H, —(CH₂)₂CO₂H, t-butoxycarbonylmethyl, t-butoxycarbonylpropyl, —CH(CH₂C₆H₅)CO₂H, —CH(C₂H₅)CH₂CO₂H, —CH(CH₂C₆H₅)CH₂CO₂H, phenyl, 2-ethylphenyl, 2,6-dimethylphenyl, phenethyl and benzyl;
wherein R⁷ is selected from hydrido, fluoro, bromo, chloro and iodo;
wherein R⁸ is selected from hydrido, methyl, ethyl, propyl and benzyl, provided that R⁸ is benzyl where R² if present is hydrido or chloro;
wherein R⁹ is selected from methyl, ethyl, phenyl, benzyl, —(CH₂)₂CONHNH₂, —CH₂CO₂H and —(CH₂)₂CO₂H, provided that R⁹ and R⁸ are not both benzyl;
wherein R¹⁰ is hydrido or methyl;
wherein R¹¹ is selected from hydrido, methyl, ethyl, hydroxymethyl and carboxy, or
wherein R¹⁰ and R¹¹ taken together is =O;
wherein R¹² is hydrido or methyl; and
wherein R¹³ is selected from hydrido, methyl, ethyl, hydroxymethyl and formyl, or
wherein R¹² and R¹³ taken together is =O; or a pharmaceutically suitable salt thereof.

A family of specific compounds of particular interest within Formula II consists of compounds and pharmaceutically-acceptable salts thereof, as follows:

1,3-Dibutyl-5,6-dihydro-5-[2'-(1H-tetrazol-5-yl)[1,1'-biphenyl]-4-yl]imidazo[1,5-a]pyridine;

7-Bromo-1,3-dibutyl-5,6-dihydro-5-[2'-(1H-tetrazol-5-yl)[1,1'-biphenyl]-4-yl]imidazo[1,5-a]pyridine;

1,3-Dibutyl-5,6,7,8-tetrahydro-5-[2'-(1H-tetrazol-5-yl)[1,1'-biphenyl]-4-yl]imidazo[1,5-a]pyridine;

1,3-Dibutyl-5,6,7,8-tetrahydro-5-[2'-(1H-tetrazol-5-yl)[1,1'-biphenyl]-4-yl]imidazo[1,5-a]pyridin-8-ol;

1,3-Dibutyl-5,6-dihydro-5-[2'-(1H-tetrazol-5-yl) [1,1'-biphenyl]-4-yl]imidazo[1,5-a]pyridin(5H)-one;
1,3-Dibutyl-5,6-dihydro-8-phenyl-5-[2'-(1H-tetrazol-5-yl)[1,1'-biphenyl]-4-yl]imidazo[1,5-a]pyridine;
[1,3-Dibutyl-6,7-dihydro-5-[2'-(1H-tetrazol-5-yl) [1,1'-biphenyl]-4-yl]imidazo[1,5-a]pyridin-8(5H)-ylidene]acetic acid;
-[1,3-Dibutyl-5,6,7,8-tetrahydro-5-[2'-(1H-tetrazol-5-yl)[1,1'-biphenyl]-4-yl]imidazo[1,5-a]pyridin-8-yl]-2,5-pyrrolidinedione;
4-[1,3-Dibutyl-5,6,7,8-tetrahydro-5-[2'-(1H-tetrazol-5-yl)[1,1'-biphenyl]-4-yl]imidazo[1,5-a]pyridin-8-yl]amino]-4-oxobutanoic acid, hydrazide;
1,3-Dibutyl-6,7-dihydro-5-[2'-(1H-tetrazol-5-yl) [1,1'-biphenyl]-4-yl]-5H-imidazo[1,5-a]azepine;
3-Butyl-5,6-dihydro-5-[2'-(1H-tetrazol-5-yl)[1,1'-biphenyl]-4-yl]imidazo[1,5-a]pyridine;
3-Butyl-5,6-dihydro-5-[2'-(1H-tetrazol-5-yl)[1,1'-biphenyl]-4-yl]imidazo[1,5-a]pyridin-8(5H) -one;
3-Butyl-5,6,7,8-tetrahydro-5-[2'-(1H-tetrazol-5-yl) [1,1'-biphenyl]-4-yl]imidazo[1,5-a]pyridin-cis-8-ol;
3-Butyl-5,6,7,8-tetrahydro-5-[2'-(1H-tetrazol-5-yl) [1,1'-biphenyl]-4yl-]imidazo[1,5-a]pyridin-trans-8-ol;
1,1-Dimethylethyl [3-butyl-6,7-dihydro-5-[2'-(1H-tetrazol-5-yl)[1,1'-biphenyl]-4-yl]imidazo[1,5-a]pyridin-8(5H)-ylidene]acetate;
[3-Butyl-6,7-dihydro-5-[2'-(1H-tetrazol-5-yl)[1,1'-biphenyl]-4-yl]imidazo[1,5-a]pyridin-8(5H)-ylidene]acetic acid;
1,1-Dimethylethyl 3-butyl-5,6-dihydro-5-[2'-(1H-tetrazol-5-yl)[1,1'-biphenyl]-4-yl]imidazo[1,5-a]pyridin-8-acetate;
3-Butyl-5,6-dihydro-5-[2'-(1H-tetrazol-5-yl)[1,1'-biphenyl]-4-yl]imidazo[1,5-a]pyridin-8-acetic acid;
1,1-Dimethylethyl 3-butyl-5,6,7,8-tetrahydro-5-[2'-1H-tetrazol-5-yl)[1,1'-biphenyl]-4-yl]imidazo[1,5-a]pyridin-cis-8-acetate;
3-Butyl-5,6,7,8-tetrahydro-5-[2'-(1H-tetrazol-5-yl) [1,1'-biphenyl]-4-yl]imidazo[1,5-a]pyridin-cis-8-acetic acid;
1,3-Dibutyl-5,6-dihydro-N-hydroxy-5-[2'-(1H-tetrazol-5-yl)[1.1'-biphenyl]-4-yl]imidazol[1,5-a]pyridin-8(7H)-imine;
1-[3-Butyl-5,6,7,8-tetrahydro-5-[2'-(1H-tetrazol-5-yl) [1,1'-biphenyl]-4-yl]imidazo [1,5-a]pyridin-8-yl]phthalimide;
3-Butyl-5,6,7,8-tetrahydro-8-amino-5-[2'-(1H-tetrazol-5-yl)[1,1'-biphenyl]-4-yl]imidazo[1,5-a]pyridine;
1,3 -Dibutyl-8-phenyl-5,6-dihydro-5-{2'-(1H-tetrazol-5-yl){1,1'-biphenyl]-4-yl]imidazo[1,5-a]pyridine;
1-[3-Butyl-5,6,7,8-tetrahydro-5-[2'-(1H-tetrazol-5-yl) [1,1'-biphenyl]-4-yl]imidazo[1,5-a]pyridin-8-yl]-cis-2,5-pyrrolidinedione;
1-[3-Butyl-5,6,7,8-tetrahydro-5-[2'-(1H-tetrazol-5-yl) [1,1'-biphenyl]-4-yl]imidazo[1,5-a]pyridin-8-yl]-trans-2,5-pyrrolidinedione;
1-[3-Butyl-1-chloro-5,6,7,8-tetrahydro-5-[2'-(1H-tetrazol-5-yl)[1,1'-biphenyl]-4-yl]imidazo[1,5-a]pyridin-8-yl]-cis-2,5 -pyrrolidinedione;
1-[3-Butyl-1-chloro-5,6,7,8-tetrahydro-5-[2'-(1H-tetrazol-5-yl)[1,1'-biphenyl]-4-yl]imidazo[1,5a]pyridin-8-yl]-trans-2,5-pyrrolidinedione; and
3-Butyl-8-phenylmethoxy-5,6,7,8-tetrahydro-5-[2'-(1H-tetrazol-5-yl)[1,1'-biphenyl]-4-yl]imidazo[1,5-a]pyridine.

Within Formula I there is another sub-class of compounds as represented by compounds of Formula III

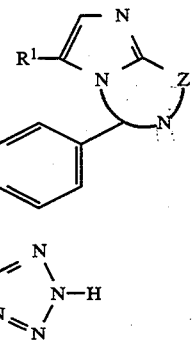

(III)

wherein Y is $(CH_2)_n$ and n is 1 to 3;
wherein Z is $C=R^3$ or $CR^4R^5$, or
wherein Y and Z together forms $-CR^6=CR^7-$, $-CR^6=CR^7-CH_2-$ or $-CR^6=CR^7-CH_2-CH_2-$;
wherein $R^1$ is alkyl;
wherein $R^3$ is selected from oxygen, sulfur, hydroxyamino, alkylidene and carboxyalkylidene;
wherein $R^4$ is selected from hydrido, alkyl, carboxyl, hydroxyalkyl, carboxyalkyl, carboxyaralkyl, aryl, aralkyl, alkylcarboxyalkyl, hydroxyl, amino, phthalimidyl, aralkoxy,

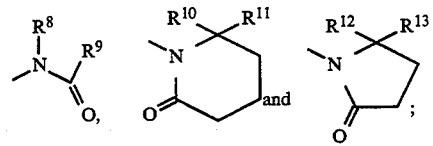

wherein $R^5$ is hydrido or hydroxyl;
wherein $R^6$ is selected from hydrido, alkyl, carboxyl, halo, hydroxyalkyl, carboxyalkyl, alkylcarboxyalkyl, hydrazidylcarboalkyl, aryl, aralkyl, hydroxyl and amino;
wherein $R^7$ is hydrido or halo;
wherein $R^8$ is selected from hydrido, alkyl and aralkyl;
wherein $R^9$ is selected from alkyl, aryl, aralkyl, carboxyl and carboxyalkyl;
wherein $R^{10}$ is hydrido or alkyl;
wherein $R^{11}$ is selected from hydrido, alkyl, hydroxyalkyl, carboxyl and carboxyalkyl, or
wherein $R^{11}$ and $R^{10}$ taken together is $=O$;
wherein $R^{12}$ is hydrido or alkyl; and
wherein $R^{13}$ is selected from hydrido, alkyl, hydroxyalkyl, carboxyl and carboxyalkyl, or
wherein $R^{12}$ and $R^{13}$ taken together is $=O$; or a pharmaceutically suitable salt thereof.

A more preferred class of compounds consists of those compounds of Formula III wherein $R^4$ is alkyl when $R^5$ is hydroxyl, and wherein $R^8$ and $R^9$ are not both aralkyl; and wherein $R^6$ is selected from hydrido, alkyl of $C_1$ to $C_6$, aryl, aralkyl, hydroxyalkyl and carboxyalkyl; or a pharmaceutically suitable salt thereof.

Preferably, the compounds of Formula III are substituted wherein $R^6$ is selected from ethyl, n-propyl, 2-ethylphenyl, 2,6-dimethylphenyl, benzyl, phenethyl, hydroxymethyl and $-CH_2CO_2H$; and wherein $R^3$ is selected from $C(CH_2C_6H_5)CO_2H$, $C(C_2H_5)CH_2CO_2H$, $C(CH_2C_6H_5)CH_2CO_2H$, $CHCO_2H$ and $CHC_2H_5$; or a pharmaceutically suitable salt thereof.

An even more preferred class of compounds consists of those compounds of Formula III wherein $R^1$ is n-propyl or n-butyl;

wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;

wherein $R^4$ is selected from hydrido, ethyl, n-propyl, hydroxymethyl, t-butoxycarbonylmethyl, hydroxyl, benzyl, t-butoxycarbonylpropyl, $-(CH_2)_3CO_2H$, $-CH_2CO_2H$, $-CH_2)_2CO_2H$, $-CH(CH_2C_6H_5)CO_2H$, $-CH(C_2H_5)CH_2CO_2H$, $-CH(CH_2C_6H_5)CH_2CO_2H$, phenylmethoxy, 2-ethylphenyl, 2,6-dimethylphenyl, amino, phenethyl, phenyl,

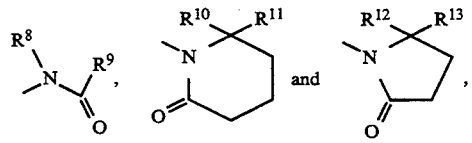

provided $R^4$ is selected from phenyl, benzyl and phenethyl only when $R^2$ if present is hydrido or chloro;

wherein $R^5$ is hydrido or hydroxyl, provided that when $R^5$ is hydroxyl, $R^4$ is ethyl or n-propyl;

wherein $R^6$ is selected from hydrido, ethyl, n-propyl, hydroxymethyl, $-(CH_2)_3CO_2H$, $-CH_2CO_2H$, $-(CH_2)_2CO_2H$, t-butoxycarbonylmethyl, t-butoxycarbonylpropyl, $-CH(CH_2C_6H_5)CO_2H$, $-CH(C_2H_5)CH_2CO_2H$, $-CH(CH_2C_6H_5)CH_2CO_2H$, phenyl, 2-ethylphenyl, 2,6-dimethylphenyl, phenethyl and benzyl;

wherein $R^7$ is selected from hydrido, bromo, chloro, fluoro and iodo;

wherein $R^8$ is selected from hydrido, methyl, ethyl, propyl and benzyl, provided that $R^8$ is benzyl where $R^2$, if present, is hydrido or chloro;

wherein $R^9$ is selected from methyl, ethyl, phenyl, benzyl, $-(CH_2)_2CONHNH_2$, $-CH_2CO_2H$ and $-(CH_2)_2CO_2H$, provided that $R^9$ and $R^8$ are not both benzyl;

wherein $R^{10}$ is hydrido or methyl;

wherein $R^{11}$ is selected from hydrido, methyl, ethyl, hydroxymethyl and carboxy, or wherein $R^{11}$ and $R^{10}$ taken together is $=O$;

wherein $R^{12}$ is hydrido or methyl; and wherein $R^{13}$ is selected from hydrido, methyl, ethyl, hydroxymethyl and carboxy, or wherein $R^{13}$ and $R^{12}$ taken together is $=O$; or a pharmaceutically suitable salt thereof.

Within Formula I, another preferred sub-class of compounds is represented by compounds of Formula IV

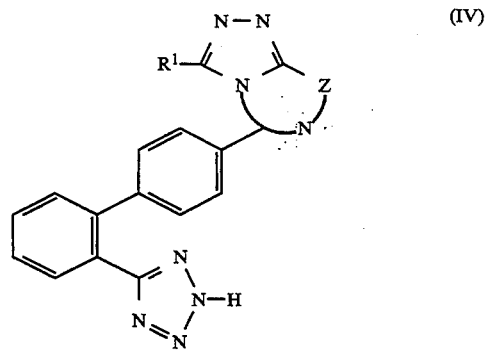

wherein Y is $(CH_2)_n$ and n is 1 to 3;
wherein Z is $C=R^3$ or $CR^4R^5$, or
wherein Y and Z together forms $-CR^6=CR^7-$, $-CR^6=CR^7-CH_2-$ or $-CR^6=CR^7-CH_2-CH_2-$;
wherein $R^1$ is alkyl;
wherein $R^3$ is selected from oxygen, sulfur, hydroxyamino, alkylidene and carboxyalkylidene;
wherein $R^4$ is selected from hydrido, alkyl, carboxyl, hydroxyalkyl, carboxyalkyl, carboxyaralkyl, phthalimidyl, alkylcarboxyalkyl, aryl, aralkyl, hydroxyl, amino, aralkoxy,

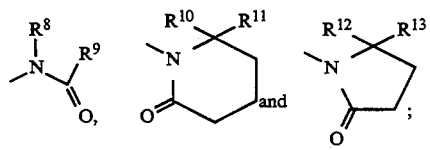

wherein $R^5$ is hydride or hydroxyl;
wherein $R^6$ is selected from hydride, alkyl, carboxyl, hydroxyalkyl, carboxyalkyl, alkylcarboxyalkyl, aryl, aralkyl, hydroxyl and amine;
wherein $R^7$ is hydride or halo;
wherein $R^8$ is selected from hydrido, alkyl and aralkyl;
wherein $R^9$ is selected from alkyl, aryl, aralkyl, hydrazidylcarboalkyl, carboxyl and carboxyalkyl;
wherein $R^{10}$ is hydrido or alkyl;
wherein $R^{11}$ is selected from hydrido, alkyl, hydroxyalkyl, carboxyl and carboxyalkyl, or
wherein $R^{11}$ and $R^{10}$ taken together is $=O$;
wherein $R^{12}$ is hydrido or alkyl; and
wherein $R^{13}$ is selected from hydrido, alkyl, hydroxyalkyl, carboxyl and carboxyalkyl, or
wherein $R^{12}$ and $R^{13}$ taken together is $=O$;
or a pharmaceutically suitable salt thereof.

A more preferred class of compounds consists of those compounds of Formula IV wherein $R^4$ is alkyl when $R^5$ is hydroxyl and wherein $R^8$ and $R^9$ are not both aralkyl; wherein $R^6$ is selected from hydrido, alkyl of $C_1$ to $C_6$, aryl, aralkyl, hydroxyalkyl and carboxyalkyl; and wherein $R^3$ is selected from $C(CH_2C_6H_5)CO_2H$, $C(C_2H_5)CH_2CO_2H$, $C(CH_2C_6H_5)CH_2CO_2H$, $CHCO_2H$ and $CHC_2H_5$; or a pharmaceutically suitable salt thereof.

A further preferred class of compounds consists of those compounds of Formula IV wherein $R^6$ is selected from ethyl, n-propyl, 2-ethylphenyl, 2,6-dimethylphenyl, benzyl, phenethyl, hydroxymethyl or $-CH_2CO_2H$; or a pharmaceutically suitable salt thereof.

An even more preferred class of compounds consists of those compounds of Formula IV wherein $R^1$ is n-propyl or n-butyl;

wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;

wherein $R^4$ is selected from hydrido, ethyl, n-propyl, hydroxymethyl, t-butoxycarbonylmethyl, hydroxyl, amino, t-butoxycarbonylpropyl, $-(CH_2)_3CO_2H$, $-CH_2CO_2H$, $-(CH_2)_2CO_2H$, $-CH(CH_2C_6H_5)CO_2H$, $-CH(C_2H_5)CH_2CO_2H$, $-CH(CH_2C_6H_5)CH_2CO_2H$, phenylmethoxy, 2-ethylphenyl, 2,6-dimethylphenyl, phenyl, phenethyl, benzyl,

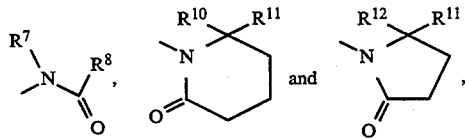

provided $R^4$ is selected from phenyl, benzyl and phenethyl only when $R^2$, is present, is hydrido or chloro;

wherein $R^5$ is hydrido or hydroxyl, provided that when $R^5$ is hydroxyl, $R^4$ is ethyl or n-propyl;

wherein $R^6$ is selected from hydrido, ethyl, n-propyl, hydroxymethyl, $-(CH_2)_3CO_2H$, $-CH_2CO_2H$, $-(CH_2)_2CO_2H$, t-butoxycarbonylmethyl, t-butoxycarbonylpropyl, $-CH(CH_2C_6H_5)CO_2H$, $-CH(C_2H_5)CH_2CO_2H$, $-CH(CH_2C_6H_5)CH_2CO_2H$, phenyl, 2-ethylphenyl, 2,6-dimethylphenyl, phenethyl and benzyl;

wherein $R^7$ is selected from hydrido, bromo, chloro, iodo and fluoro;

wherein $R^8$ is selected from hydrido, methyl, ethyl, propyl and benzyl, provided that $R^8$ is benzyl where $R^2$, if present, is hydrido or chloro;

wherein $R^9$ is selected from methyl, ethyl, phenyl, benzyl, $-(CH_2)_2CONHNH_2$, $-CH_2CO_2H$ and $-(CH_2)_2CO_2H$, provided that $R^9$ and $R^8$ are not both benzyl;

wherein $R^{10}$ is hydrido or methyl;

wherein $R^{11}$ is selected from hydrido, methyl, ethyl, hydroxymethyl and carboxy, or wherein $R^{11}$ and $R^{10}$ taken together is $=O$;

wherein $R^{12}$ is hydrido or methyl; and wherein $R^{13}$ is selected from hydrido, methyl, ethyl, hydroxymethyl and carboxy, or wherein $R^{13}$ and $R^{12}$ taken together is $=O$; or a pharmaceutically suitable salt thereof.

Within Formula I there is a fourth sub-class of compounds of interest which consists of compounds as represented by Formula V

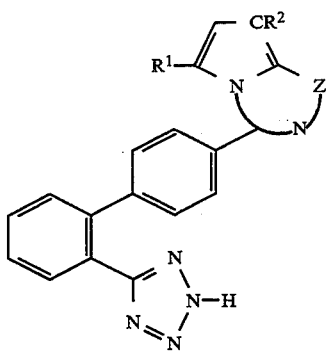

wherein Y is $(CH_2)_n$ and n is 1 to 3;

wherein Z is $C=R^3$ or $CR^4R^5$, or wherein Y and Z together forms $-CR^6=CR^7-$, $-CR^6=CR^7-CH_2-$ or $-CR^6=CR^7-CH_2-CH_2-$;

wherein $R^1$ is alkyl;

wherein $R^2$ is selected from hydrido, halo, alkyl and aryl;

wherein $R^3$ is selected from oxygen, sulfur, alkylidene, carboxyalkylidene and hydroxyamino;

wherein $R^4$ is selected from hydrido, alkyl, hydroxyalkyl, carboxyl, alkylcarboxyalkyl, carboxyalkyl, carboxyaralkyl, aryl, aralkyl, hydroxyl, amino, aralkoxy, phthalimidyl,

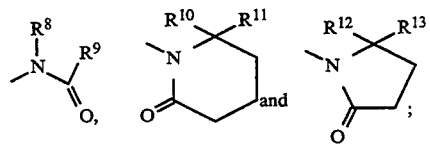

wherein $R^5$ is hydrido or hydroxyl;

wherein $R^6$ is selected from hydrido, alkyl, hydroxyalkyl, carboxyl, alkylcarboxyalkyl, carboxyalkyl, aryl, aralkyl and hydroxyl;

wherein $R^7$ is halo or hydrido;

wherein $R^8$ is selected from hydrido, alkyl and aralkyl;

wherein $R^9$ is selected from alkyl, aryl, aralkyl, hydrazidylcarboalkyl, carboxyl and carboxyalkyl;

wherein $R^{10}$ is hydrido or alkyl;

wherein $R^{11}$ is selected from hydrido, alkyl, hydroxyalkyl, carboxyl and carboxyalkyl, or wherein $R^{10}$ and $R^{11}$ taken together is $=O$;

wherein $R^{12}$ is hydrido or alkyl; and wherein $R^{13}$ is selected from hydrido, alkyl, hydroxyalkyl, carboxyl and carboxyalkyl, or wherein $R^{13}$ and $R^{12}$ taken together is $=O$;

or a pharmaceutically suitable salt thereof.

A more preferred class of compounds consists of those compounds of Formula V wherein $R^4$ is aryl or aralkyl only when $R^2$ is hydrido or halo;

wherein $R^3$ is selected from oxygen, sulfur, hydroxyamino, $CHCO_2C(CH_3)$ and $CHCO_2H$;

wherein $R^4$ is alkyl where $R^5$ is hydroxyl;

wherein $R^8$ is aralkyl where $R^2$, if present, is hydrido or halo;

wherein $R^8$ and $R^9$ are not both aralkyl;

wherein $R^{11}$ is alkyl when $R^2$ is aryl or halo; and wherein $R^{13}$ is alkyl when $R^2$ is aryl or halo; or a pharmaceutically suitable salt thereof.

A further preferred class of compounds consists of those compounds of Formula V wherein $R^6$ is selected from hydrido, ethyl, hydroxymethyl, —$CH_2CO_2H$ and —$(CH_2)_3CO_2H$; or is aryl or aralkyl provided $R^2$ is hydrido; or a pharmaceutically suitable salt thereof.

An even more preferred class of compounds consists of those compounds of Formula V wherein $R^1$ is n-propyl or n-butyl;

wherein $R^2$ is selected from hydrido, chloro, methyl, ethyl, n-propyl, n-butyl, 2-ethylphenyl and 2,6-dimethylphenyl;

wherein $R^3$ is selected from oxygen, sulfur, hydroxyamino, $CHCO_2H$ and $CHCO_2C(CH_3)_3$;

wherein $R^4$ is selected from hydrido, ethyl, n-propyl, hydroxymethyl, t-butoxycarbonylmethyl, hydroxyl, amino, t-butoxycarbonylpropyl, —$(CH_2)_3CO_2H$, —$CH_2CO_2H$, —$(CH_2)_2CO_2H$, —$CH(CH_2C_6H_5)CO_2H$, —$CH(C_2H_5)CH_2CO_2H$, —$CH(CH_2C_6H_5)CH_2CO_2H$, phenylmethoxy, 2-ethylphenyl, 2,6-dimethylphenyl, phenyl phenethyl, benzyl,

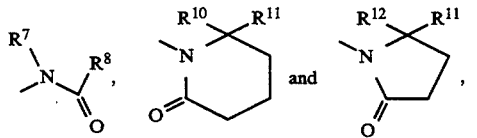

provided $R^4$ is selected from phenyl, benzyl and phenethyl only when $R^2$ is hydrido or chloro;

wherein $R^5$ is hydrido or hydroxyl, provided that when $R^5$ is hydroxyl, $R^4$ is ethyl or n-propyl;

wherein $R^6$ is selected from hydrido, ethyl, n-propyl, hydroxymethyl, —$(CH_2)_3CO_2H$, —$CH_2CO_2H$, —$(CH_2)_2CO_2H$, t-butoxycarbonylmethyl, t-butoxycarbonylpropyl, —$CH(CH_2C_6H_5)CO_2H$, —$CH(C_2H_5)CH_2CO_2H$, —$CH(CH_2C_6H_5)CH_2CO_2H$, phenyl, 2-ethylphenyl, 2,6-dimethylphenyl, phenethyl and benzyl;

wherein $R^7$ is selected from hydrido, chloro, bromo, fluoro and iodo;

wherein $R^8$ is selected from hydrido, methyl, ethyl, propyl and benzyl, provided that $R^8$ is benzyl where $R^2$, if present, is hydrido or chloro;

wherein $R^9$ is selected from methyl, ethyl, phenyl, benzyl, —$(CH_2)_2CONHNH_2$, —$CH_2CO_2H$ and —$(CH_2)_2CO_2H$, provided that $R^9$ and $R^8$ are not both benzyl;

wherein $R^{10}$ is hydrido or methyl;

wherein $R^{11}$ is selected from hydrido, methyl, ethyl, hydroxymethyl and carboxy or wherein $R^{11}$ and $R^{10}$ taken together is =O;

wherein $R^{12}$ is hydrido or methyl; and wherein $R^{13}$ is selected from hydrido, methyl, ethyl, hydroxymethyl and carboxy or wherein $R^{13}$ and $R^{12}$ taken together is =O; or a pharmaceutically suitable salt thereof.

The term "conformationally restricted" denotes a compound having a reduced number of possible geometries a radical can attain within the molecule. These limited conformations or orientations of the radical of interest in spatial relationship to other portions of the molecule can impact the potency of such compounds by better mimicking the binding conformation of the target, such as a receptor or enzyme. Certain radicals such as aralkyl and those including alkyl bridges, account for a substantial range of potential conformations, such as by rotation around a single methylene.

The phrase "acidic" such as used to define the substituents on the biphenyl radical is intended to embrace chemical groups which, when attached to the biphenyl radical of Formula I, confers acidic character to the compound of Formula I. "Acidic character" means proton-donor capability, that is, the capacity of the compound of Formula I to be a proton donor in the presence of a proton-receiving substance, such as water. Typically an acidic group should be selected to have proton-donor capability such that the product compound of Formula I has a $PK_a$ in a range from about one to about nine. More typically the compound of Formula I has a $PK_a$ in a range from about two to about seven. An example of an acidic group containing at least one acidic hydrogen is a carboxyl group (—COOH) or a tetrazolyl radical.

The term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms preferably from 2 to about 8 carbon atoms. The alkenyl radical may be attached through a double bond to a carbon atom in the fused ring. Examples of suitable alkenyl radicals include ethenyl, propenyl, allyl, 1,4-butadienyl and the like. The term "aryl", alone or in combination, means a carbocyclic aromatic system containing one, two or three rings wherein such rings may be attached together in a pendent manner or may be fused. Examples of "aryl" include phenyl or naphthyl radicals either of which optionally carries one or more substituents selected from alkyl, alkoxy, halogen, hydroxy, amino, nitro and the like, as well as p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "heterocyclic ring system" means a saturated or partially unsaturated monocyclic, bicyclic or tricyclic heterocycle which contains one or more hetero atoms as ring atoms, selected from nitrogen, oxygen, silicon and sulfur, which is optionally substituted by halogen, alkyl, alkoxy, oxo and the like. Examples of such heterocyclic groups are pyrrolidinyl, imidizolyl, triazolyl, piperidinyl, piperazinyl, morpholinyl, thiamorpholinyl, pyrrolyl, phthalimidyl, succinimidyl, maleimidyl and the like. The term "alkoxy" embraces linear or branched oxy-containing radicals each having alkyl portions of one to ten carbon atoms, such as a methoxy group. The term "aralkoxy" means a radical having an aryl group attached to an alkoxy radical as described above. Phenylmethoxy is an example of sauc a radical. The term "halo" means fluorine, chlorine, bromine or iodine. The term "aralkyl", alone or in combination, means an alkyl radical as defined above in which one hydrogen atom is replaced by an aryl radical as defined above, such as benzyl, 2-phenethyl and the like. The term "carboxyalkenyl" means a radical containing an acidic —$CO_2H$ group attached to one carbon atom of an alkenyl group as defined above, another carbon of the alkenyl group connected via a double bond to a carbon atom on the fused ring. Examples of such "carboxyalkenyl" groups include $CHCO_2H$, $C(CH_2C_6H_5)CO_2H$, $C(C_2H_5)CH_2CO_2H$, $C(C_2H_5)CO_2H$ and $C(CH_2C_6H_5)CH_2CO_2H$. The term "alkylcarboxyalkenyl" means an ester radical containing an alkyl group, as defined above, attached via a carbon atom to a "carboxyalkenyl" group as defined above. Examples of such "alkylcarboxyalkenyl" groups include CHCO$_2$C(CH$_3$)$_3$. "Hydroxyalkyl" means a hydroxy substituted alkyl group wherein the hydroxy group is attached to an alkyl group as defined above. Examples of such "hydroxyalkyl" groups include —CH$_2$OH, —(CH$_2$)$_2$OH and —(CH$_2$)$_4$OH. "Carboxyalkyl" means a radical containing an acidic —CO$_2$H carboxy group attached via the carbon atom to an alkyl group as defined above. Examples of such "carboxyalkyl" groups include —CH$_2$CO$_2$H, —CH(CH$_2$C$_6$H$_5$)CO$_2$H, —CH(C$_2$H$_5$)CH$_2$CO$_2$H, —CH(C$_2$H$_5$)CO$_2$H and CH(CH$_2$C$_6$H$_5$)CH$_2$CO$_2$H. (CH$_2$)$_3$CO$_2$H, —(CH$_2$)$_2$CO$_2$H and —CH(CH$_2$C$_6$H$_5$)CO$_2$H. The term "alkylcarboxyalkyl" means a radical containing an alkyl group, as defined above, attached via a carbon atom to a "carboxyalkyl" group as defined above. Examples of such "alkylcarboxyalkyl" groups include (CH$_3$)$_3$CO$_2$CCH$_2$—. "Carboxyaralkyl" means a radical containing an acidic —CO$_2$H carboxy group attached via the carbon atom to an aryl portion of an aralkyl group as defined above. Examples of such "carboxyaralkyl" groups include —CH$_2$C$_6$H$_4$CO$_2$H. The term "hydrido" denotes a single hydrogen atom (H). This hydrido group may be attached, for example, to an oxygen atom to form a hydroxyl group or two hydrido groups may be attached too a carbon atom to form a methylene (—CH$_2$) radical. The term "hydroxyamino" embraces singly or multiply hydroxy substituted amine groups, including NOH. Hydrazidocarboalkyl" denotes a radical having a carbonyl between a hydrazine portion and an alkyl portion, and includes —(CH$_2$)$_2$—CONHNH$_2$.

Also included in the family of compounds of Formula I are isomeric forms including diastereoisomers, regioisomers, tautomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, malic, propionic, succinic, glycolic, gluconic, lactic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylgluca-mine) and procaine. All of these salts may be prepared by conventional means from the corresponding compound of Formula I by reacting, for example, the appropriate acid or base with the compound of Formula I.

General Synthetic Procedure

General synthetic methods for preparing the compounds of the invention are illustrated in the following Schemes. It is understood by those familiar with the art of organic synthesis that some functionality present in certain compounds of the invention may be incompatible with a particular synthetic sequence. Depending on the reactions and techniques employed, an alternative route, an altered order of steps, or a strategy of protection and deprotection may be necessary to prepare those compounds. In all cases, to achieve optimal yields the reaction conditions (such as reagents, solvent, temperature, and time) may need some modification.

[1,5-a]Imidazole-based conformationally restricted angiotensin II antagonists may be prepared as shown in Scheme I to Scheme IV. Isomeric [1,2-a]imidazole-based conformationally restricted angiotensin II antagonists may be prepared as shown in Scheme V to Scheme VIII. Pyrrole-based conformationally restricted angiotensin II antagonists may be prepared as shown in Scheme IX to Scheme XII. Triazole-based conformationally restricted angiotensin II antagonists may be prepared as shown in Scheme XIII to Scheme XVI.

| Abbreviations Used in Schemes and Procedures | |
|---|---|
| Reagents: | |
| NBS | N-bromosuccinimide |
| AIBN | azo(bis)isobutyronitrile |
| HOAc | acetic acid |
| NaOAc | sodium acetate |
| TEA | triethylamine |
| PPh$_3$ | triphenylphosphine |
| TFA | trifluoroacetic acid |
| LDA | lithium diisopropylamide |
| KOt-Bu | potassium tert-butoxide |
| Solvent: | |
| DME | 1,2-dimethoxyethane |
| DMF | N,N-dimethylformamide |
| DMSO | dimethylsulfoxide |
| IPA | isopropanol |
| EtOAc | ethyl acetate |
| THF | tetrahydrofuran |
| Other: | |
| BOC | tertiary butoxycarbonyl |
| SEM | 2-trimethylsilyl-ethoxymethyl |
| MS(FAB) or FABMS | Fast atom bombardment mass spectroscopy |
| LG | leaving group, e.g. halide, tosylate, triflate, etc. |
| n- | normal- |
| Ph | phenyl |
| PLG | leaving group or a functional |
| group that | can be easily converted to a |
| leaving | group |
| rt | room temperature |
| sec- | secondary- |
| tert- | tertiary |
| Tf | SO$_2$CF$_3$ |
| TMS | trimethylsilyl |
| Tosylate (TsO) | OSO$_2$-(4-methyl)phenyl |
| Triflate (TfO) | OSO$_2$CF$_3$ |
| Trityl | triphenylmethyl |
| Ts | SO$_2$-(4-methyl)phenyl |

An appropriately substituted imidazole 1, the heterocyclic starting material, may be prepared as described in the literature [Klaus Hofmann, in "Imidazole and its Derivatives" of *The Chemistry of Heterocyclic Com-* pounds, Arnold Weissberger Ed., Wiley Interscience New York, 1953]. The imidazole 1 in N,N-dimethylformamide (DMF) is treated with base, such as potassium tert-butoxide, followed by addition of appropriate alkylating agent 2 to give the coupled product 3 (Scheme I). For compounds where X is a substituted phenyl group, several procedures have been published for the preparations of the alkylating agent 2 [a) D. J., Carini; J. V. Duncia, Eur. Pat. Appl. 253310, 1988; b) D. J. Carini; J. V. Duncia; P. E. Aldrich; A. T. Chiu; A. L. Johnson; M. E. Pierce; W. A. Price; J. B. Santella; G. J. Wells; R. R. Wexler; P. C. Wong; S. E. Yoo; P. B. M. W. Timmermans, *J. Med. Chem.*, 34, 2525–2547 (1991)].

The coupled imidazole 3 itself may be an angiotensin II receptor antagonist, but it may also be used as a key intermediate in the preparation of the compounds of the invention. Imidazole 3 in THF (or DME) is treated with base (such as n-BuLi or LDA) at −78° C. (or −65° C., if DME is used as solvent), followed by addition of an appropriate alkylating agent or other electrophiles 4 (the acetal shown in Scheme I may be other aldehyde masking group or equivalent, and LG is a leaving group such as halide, mesylate, triflate or tosylate). The resulting masked aldehyde 5 was stirred with NaOAc in aqueous acetic acid at reflux for a few days (1 to 5 days) to give one of the compounds of the invention, a cyclized imidazole 6.

The imidazole 6 may be used as an intermediate to prepare other substituted compounds with appropriate functional group transformations and preparation of some of those compounds are illustrated in Scheme II and III (all of the intermediates shown in the sequences are also angiotensin II receptor antagonists). For example, The unsaturated imidazole 6 and NBS in CCl4 is stirred at reflux to give a bromide 7. The bromide 7 may be treated with organolithium, such as n-BuLi or tert-BuLi, followed by addition of an appropriate electrophile, (such as alkyl halides, carbon dioxide, aldehyde, ketone and others) to give the addition product 8. The olefin 8 may be hydrogenated to give its saturated product 9.

SCHEME I

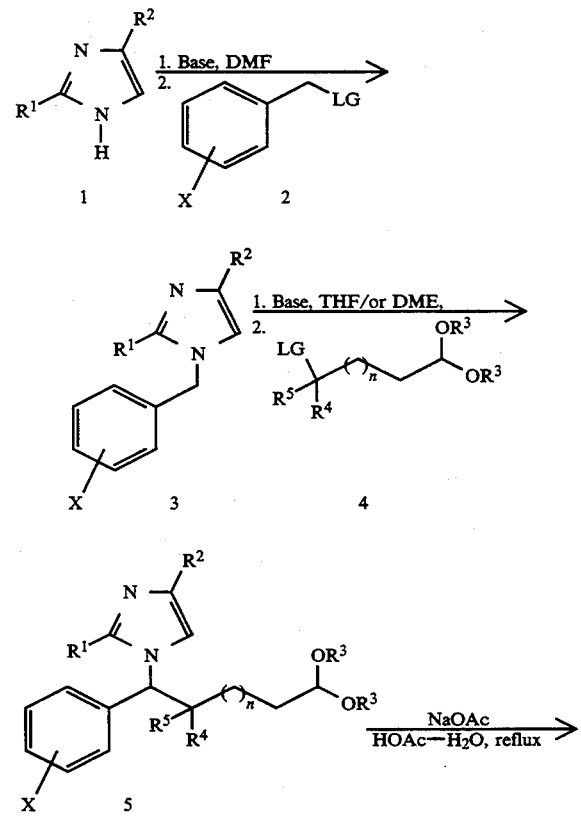

LG: a leaving group, e.g. halide, tosylate, triflate, mesylate.

-continued
SCHEME I

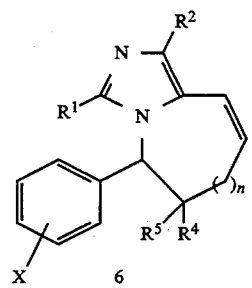

SCHEME II

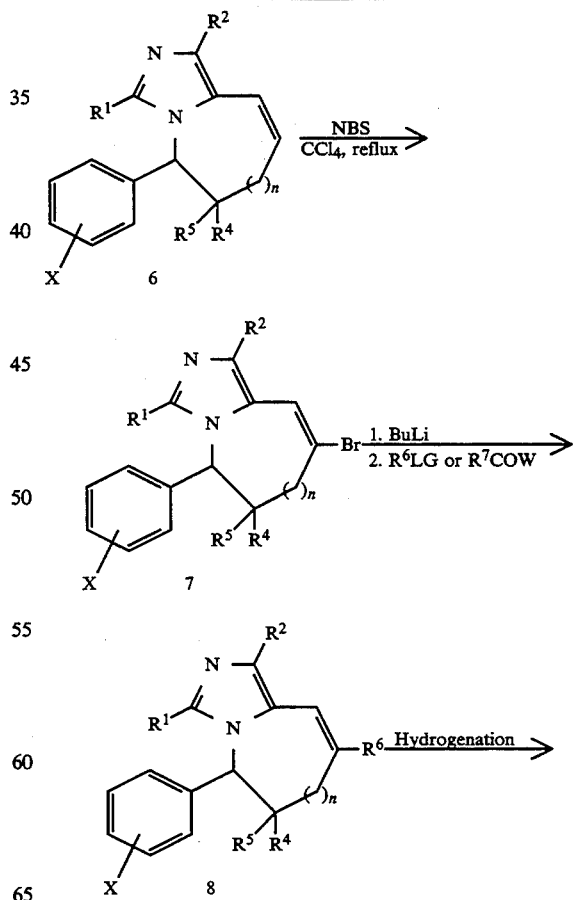

LG: as defined in Scheme I
W: H, alkyl, aryl, alkoxyl, N,O-dimethyl hydroxyamino -continued
SCHEME II

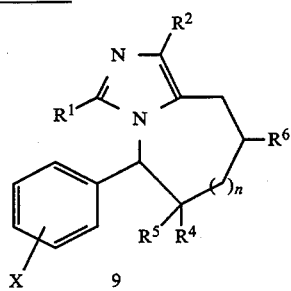

Alternatively, as illustrated in Scheme III, the unsaturated imidazole 6 may be treated with NBS in wet DMSO to give a bromohydrin which may be reduced with nBu₃SnH to an alcohol 10 and the oxidation of the alcohol with MnO₂ will afford a ketone 11. The ketone 11 may be condensed with appropriately substituted amine, then reduced to an amine 12 with an appropriate reducing agent (e.g. NaBH₄, or hydrogen over catalyst). The amine 12 may also be prepared directly from olefin 6 under bromination condition (NBS, CH₃CN) in the presence of large excess of succinimide. The amine 12 may be used to prepare other derivatives. Alternatively, the alcohol 10 may be treated with triphenylphosphine, diethoxyazo dicarboxylate and an imide (e.g. phthalimide) to give an imide analogue which may be converted to an amine 12 [Mitsunobu, O. *Synthesis*, 1981, 1–27].

The ketone 11 may be treated with appropriate organometallic reagents (such as Grignard, organolithium, organocerium, organozinc reagents or related reagents) to give the addition product, a tertiary alcohol [a) T. Imamoto; T. Kusumoto; Y. Tawarayama; Y. Sugiura; T. Mira; Y. Hatanaka; M. Yokoyama, *J. Org. Chem.*, 49, 3904–3912 (1984). b) D. Bonneville, *J. Org. Chem.*, 6, 462 (1941). c) T. Hirao; D. Misu; K. Yao; T. Agawa, *Tetrahedron Letter*, 27, 929–932 (1986)]. The alcohol may be dehydrated to give an olefin 13 or an isomeric mixture of olefins 13. The olefin 13 may be treated with base, such as LDA and kinetically quenched at low temperature with either organic acid or appropriate electrophile at low temperature to give the isomerized olefin 14. The olefins 13 or 14 may be hydrogenated to its saturated analogue 15.

SCHEME III

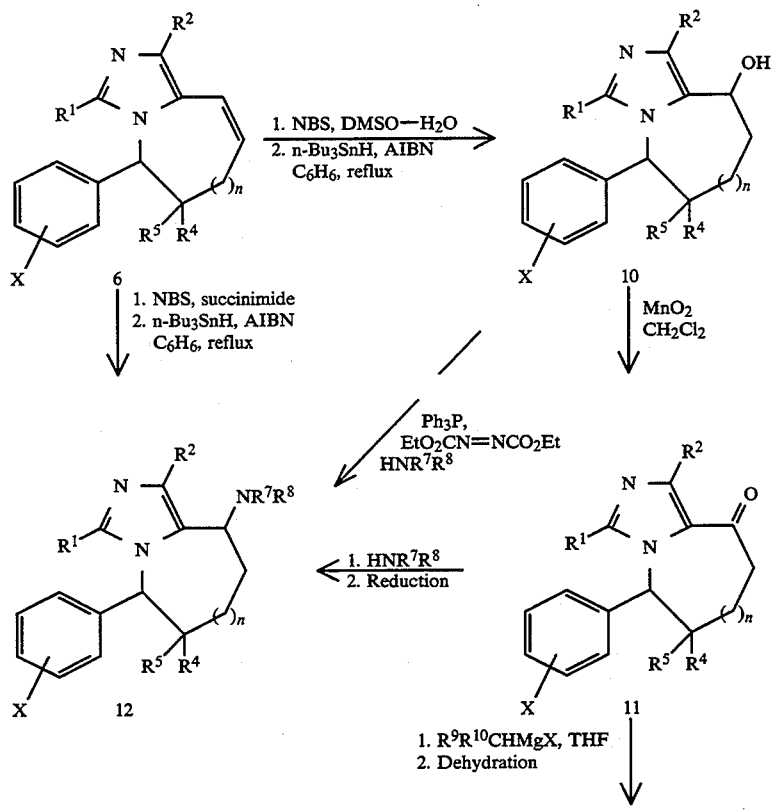

SCHEME III

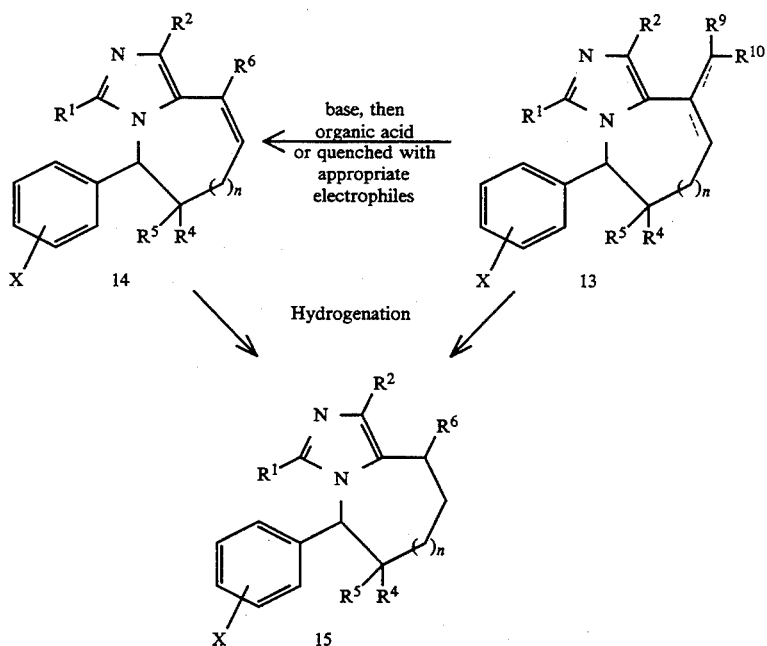

In Scheme IV, an alternative preparation for the compounds of the invention is described. An appropriately substituted imidazole 1 may be treated with one equivalent of base, then protected as SEM or BOC derivative. The protected imidazole then is treated with another equivalent of base [a) B. H. Lipshutz; B. Huff; W. Hagen, *Tetrahedron Letter*, 2-9, 3411-3414 (1988). b) C. C. Tang; D. Davalian; P. Huang; R. Breslow, *J. American Chemical Society*, 100, 3918 (1978)] followed by addition of electrophile 17 or 18. Electrophiles 17 and 18 can be prepared from $HC(=O)(CR^4R^5)(CH_2)_nC(=O)LG$ and an appropriate organometallic reagent such as $XC_6H_4MgBr$. If necessary, the resulting lithium anion obtained from the procedure described above may be converted to other organometallic reagents according to well-established procedures [a) T. Imamoto; T. Kusumoto; Y. Tawarayama; Y. Sugiura; T. Mira; Y. Hatanaka; M. Yokoyama, *J. Org. Chem.*, 49, 3904-3912 (1984) b) D. Bonneville, *J. Org. Chem.*, 6, 462 (1941) c) T. Hirao; D. Hisu; K. Yao; T. Agawa, *Tetrahedron Letter*, 27, 929-932 (1986)].

If PLG is a hydroxyl group and Z is a proton, the resulting addition product 19, may be cyclized with triphenylphosphine and diethyl azodicarboxylate [Mitsunobu, O. *Synthesis*, 1981, 1-27]. If PLG is or is converted to a leaving group, such as halides, tosylate, and Z is a proton, the cyclization may be achieved with a weak base in DMF (e.g. $K_2CO_3$, $Cs_2CO_3$) to give a ketone 11. The ketone 11 may be reduced to an alcohol 10 with $NaBH_4$ in methanol. The alcohol 10 may be dehydrated to olefin 6 with acid (e.g. HOAc and heat) or thionyl chloride and pyridine. Other compounds may be prepared from compounds 6, 10, or 11 as described in Scheme II and III.

SCHEME IV

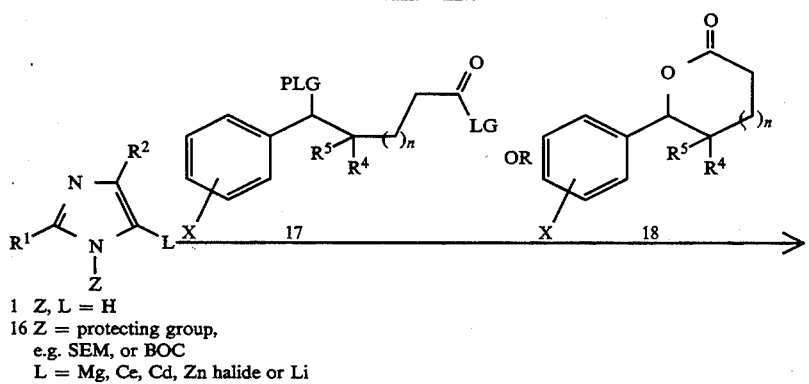

1 Z, L = H
16 Z = protecting group,
  e.g. SEM, or BOC
L = Mg, Ce, Cd, Zn halide or Li

SCHEME IV -continued

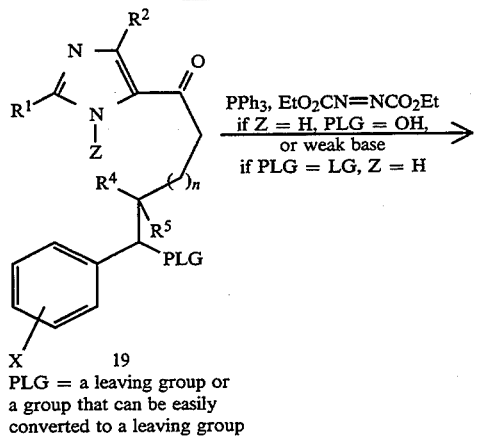

PLG = a leaving group or
a group that can be easily converted to a leaving group

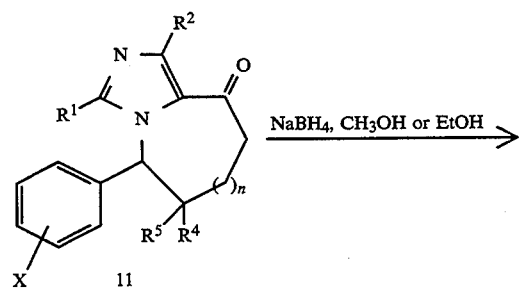

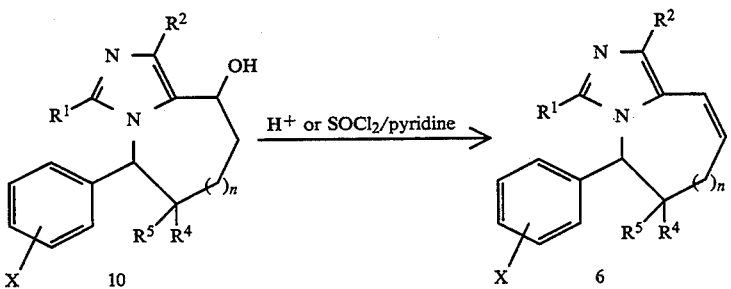

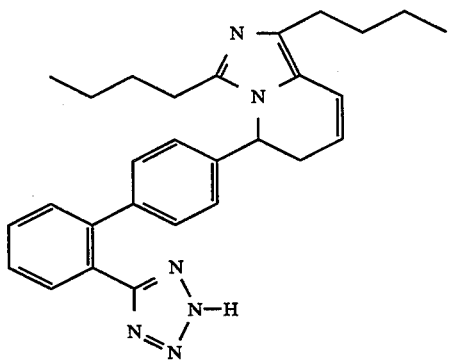

1,3-Dibutyl-5,6-dihydro-5-[2'-(1H-tetrazol-5-yl)[1,1'-biphenyl]-4-yl]imidazo[1,5-a]pyridine Step 1: Preparation of 2,4-dibutylimidazole A mixture of 12 g (0.09 mol) of ethyl valeryl imidate, 8.6 g (0.074 mol) of 1-hydroxy-2-hexanone, and 100 mL of liquid ammonia was heated in a bomb at 100° C. for 12 h. The bomb was cooled, vented, and the contents were concentrated. The residue was purified by chromatography, eluting with chlorformethyl acetate-TEA to give 7.2 g (44%) of the desired biphenyl dibutylimidazole intermediate as a brown oil: $^1$H NHR (CDCl$_3$) δ 0.91 (t, J=7.31 Hz, 6H), 1.36 (septet, J=7.38 Hz, 4H), 1.50–1.75 (m, 4H), 2.55 (t, J=8.01 Hz, 2H), 2.68 (t, J=8.01 Hz, 2H), 6.61 (s, 1H).

Step 2: Preparation of Biphenyl Imidazole

To a solution of 478 mg (2.65 mmol) of 2,4-dibutylimidazole (obtained from Step 1) in 5.3 mL of DMF was added 3.45 mL (3.45 mmol) of potassium tert-butoxide (1M in THF), and the resulting solution was stirred at room temperature for 30 min. To the dark brown mixture was added 2.75 g (3.45 mmol) of the bromomethyl biphenyl. The reaction mixture was stirred at room temperature for 12 h, and concentrated in vacuo. The residue was purified by chromatography to give 737 mg (42%) of the trityl-protected biphenyl imidazole as a yellow oil which solidified as a glass: $^1$H NMR (CDCl$_3$) δ 0.89 (q, J=7.5 Hz, 6H), 1.23–1.45 (m, 4H), 1.50–1.73 (m, 4H), 2.53 (quintet, J=8.2 Hz, 4H), 4.85 (s, 2H), 6.36 (s, 1H), 6.79 (d, J=8.1 Hz, 2H), 6.92 (d, J=7.8 Hz, 6H), 7.09 (d, J=8.1 Hz, 2H), 7.16–7.40 (m, 10H), 7,40–7.55 (m, 2H), 7.94 (dd, J=6.9, 2.1 Hz, 1H).

Step 3: Preparation of Dimethyl Acetal Imidazole

To a solution of 2.09 g (3.18 mmol) of the biphenyl imidazole (obtained from Step 2) in 16 mL of DME cooled at −45° C. (acetonitrile-dry ice) was added 2.8 mL of 1.45M (4.06 mmol) of n-butyllithium in hexane over a 4 min period. The resulting dark purple solution was stirred cold for another 15 min, followed by addition of 1.0 mL (6.59 mmol) of 3-bromopropionaldehyde dimethyl acetal in one portion. The mixture was stirred cold for 40 min, then was warmed to −10° C. over a 40 min period. The reaction was quenched with aqueous NH₄Cl, extracted with three 20 mL portions of diethyl ether. The combined extracts were washed with brine, dried (MgSO₄) and concentrated in vacuo. The crude acetal biphenyl imidazole was used directly in the subsequent Step 4 without purification. The ¹H NMR spectrum of the crude mixture indicated a >9:1 ratio of the desired alkylated product to the recovered starting material (based on the integration areas of singlet peaks at δ 6.48 and 6.28, respectively). HPLC analysis also agreed with the result from the ¹H NMR study (C18 column, 60% acetonitrile in water containing 0.05% of TFA, flow rate 1.5 mL/min, retention time 8.45 min and 7.21 min, respectively).

In some experiments, the acetal biphenyl imidazole was isolated by chromatography (SiO₂) as a pale yellow oil: ¹H NMR (CDCL₃) δ 0.75–1.0 (m, 6H), 1.2–1.45 (m, 4H), 1.45–1.72 (m, 6H), 1.85–2.10 (m, 2H), 2,54 (t, J=7.04 Hz, 4H), 3.26 (s, 3H), 3.27 (s, 3H), 4.31 (t, J=5.45 Hz, 1H), 4.98 (dd, J=9.82, 4.95 Hz, 1H), 6.55 (s, 1H), 6.80–7.00 [m (with d at 6.89, J=7.31 Hz), 8H], 7.09 (d, J=8.08 Hz, 2H), 7.15–7.40 (m, 10H), 7.40–7.55 (m, 2H), 7.94 (dd, J=6.89, 2.16 Hz, 1H); MS(FAB) m/e (relative intensity): 759 (100, M+H), 517 (20), 474 (30).

Step 4: Preparation of Bicyclic Imidazole

A solution of 2.1 g (3.18 mmol) of the crude biphenyl acetal imidazole (obtained from Step 3) and 5.3 g (88 mmol) of NaOAc in 13 mL of water and 40 mL of glacial acetic acid was stirred at reflux for 64 h, cooled and concentrated in vacuo. The residue was dissolved in methylene chloride and filtered. The filtrate was stirred with 2 g (7.2 mmol) of trityl chloride and 3 mL (21.5 mmol) of TEA at room temperature overnight (16 h) and concentrated in vacuo. The residue was purified by chromatography to give 1.2 g (54%) of trityl-protected biphenyl bicyclic imidazole: ¹H NMR (CDCl₃) δ 0.78 (t, J=7.25 Hz, 3H), 0.96 (t, J=7.25 Hz, 3H), 1.20 (septet, J=7.65 Hz, 2H), 1.35–1.60 [m (with quintet at 1.43, J=7.65 Hz), 4H], 1.60–1.80 {m, 2H}, 2.25 (dd, J=16.9, 6.54 Hz, 1H), 2.32–2.40 (m, 2H), 2.64 (t, J=7.66 Hz, 2H), 2.90 (ddt, J=16.92, 7.25, 2.82 Hz, 1H), 5.2–5.29 [m (with d at 5.21, J=6.85 Hz), 2H], 6.46 (dd, J=9.67, 2.82 Hz, 1H), 6.57 (d, J=8.46 Hz, 2H), 6.88 (d, J=7.65 Hz, 6H), 7.02 (d, J=8.06 Hz, 2H), 7.20–7.38 (m, 10 H), 7.38–7.52 (m, 2H), 7.90 (dd, J=6.85, 2.02 Hz, 1H).

Step 5: Detritylation of the Trityl Tetrazole

A solution of 100 mg (0.144 mmol) of the trityl-protected biphenyl bicyclic imidazole (obtained from Step 4) was stirred with 1 mL of water and 6 mL of acetic acid at room temperature for 18 h. The solution was concentrated in vacuo, stirred in 3 mL of aqueous NaHCO₃ and washed with three 3 mL portions of ether. The aqueous residue was acidified with 3N HCl to pH 4 and extracted with methylene chloride. The combined extracts were dried (MgSO₄) and concentrated to give 59 mg of the title compound of Example 1 as an oil which solidified as a glass: mp 140.2°–144.0° C. (decomposed); ¹H NMR (CD₃OD) δ 0.68 (t, J=7.27 Hz, 3H), 0.83 (t, J=7.3 Hz, 3H), 1.0–1.42 (m, 8H), 2.4–2.7 (m, 5H), 2.9–3.10 (m, 1H), 5.62 (d, J=7.5 Hz, 1H), 5.7–5.82 (m, 1H), 6.52 (dd, J=10, 3 Hz, 1H), 6.69 (d, J=8.01 Hz, 2H), 6.93 (d, J=8.16 Hz, 2H), 7.2–7.5 (m, 4H); HRMS. calcd for M+H: 453.2767. Found: 453.2791.

EXAMPLE 2

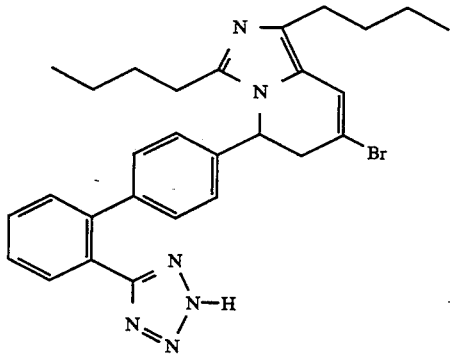

7-Bromo-1,3-dibutyl-5,6-dihydro-5-[2'-(1H-tetrazol-5-yl) [1,1'-biphenyl]-4-yl]imidazo[1,5-a]pyridine Step 1: Preparation of Bromo Olefin Imidazole A solution of 70 mg (0.101 mmol) of trityl-protected bicyclic imidazole {obtained from Step 4 of Example 1), 20 mg (0.112 mmol) of NBS and 7 mg (catalytic) of AIBN in 2.8 mL of CCl₄ was stirred at reflux for 2 h. The reaction mixture was diluted with CCl₄ and washed with water. The organic layer was dried (MgSO₄) and concentrated in vacuo. The residue was purified by chromatography to give 36 mg of brominated olefin as a yellow solid: ¹H NMR (CDCl₃) δ 0.76 (t, J=7.35 Hz, 3H), 0.95 (t, J=7.2 Hz, 3H), 1.16 (septet, J=7.38 Hz, 2H), 1.20–1.32 (m, 3H), 1.35–1.55 (m, 4H), 1.60–1.75 {m, 2H}, 2.20–2.35 (m, 2H), 2.58 (t, J=7.74 Hz, 2H), 2.69 (dd, J=17.3, 1.21 Hz, 1H), 3.40 (ddd, J=17.33, 7.25, 2.82 Hz, 1H), 5.20 (d, J=7.25 Hz, 1H), 6.60 {d, J=8.05 Hz, 2H), 6.80 (d, J=2.82 Hz, 1H), 6.91 (d, J=7.39 Hz, 6H), 7.05 (d, J=8.31 Hz, 2H), 7.18–7.38 {m, 10H), 7.46 (quintet of doublets, J=6.67, 1.7 Hz, 2H), 7.90 (dd, J=7.03, 2.01 Hz, 1H).

Step K: Detritylation of the Trityl Tetrazole

A solution of 33 mg (0.0427 mmol) of bromo olefin (obtained from Step 1) in 0.8 mL of water and 5 mL of acetic acid was stirred at room temperature for 5 h and concentrated in vacuo. The residue was worked up as described in Step 5 of Example 1 to give 20 mg of the title compound of Example 2 as an oil which solidified as a glass: mp 148°–160° C. (decomposed); ¹H NMR (CDCl₃) δ 0.68–0.85 (m,6H), 1.0–1.30 (m, 6H), 1.30–1.60 (m, 2H), 1.85–2.08 (m, 2H), 2.20 (septet, J=6.88 Hz, 2H), 2.96 (d, J=17.05 Hz, 1H), 3.39–3.53 (m, 1H), 5.34 (d, J=6.27 Hz, 1H , 6.54 (d, J=8.08 Hz, 2H), 6.63 (d, J=2.78 Hz, 1H , 7.02 (d, J=8.28 Hz, 2H), 7.42 (dd, J=7.57, 1.04 Hz, 1H), 7.45–7.60 (m, 2H), 7.76 (d, J=6.34 Hz, 1H; HRMS. calcd for M+H: 531.1872. Found: 531.1834.

EXAMPLE 3

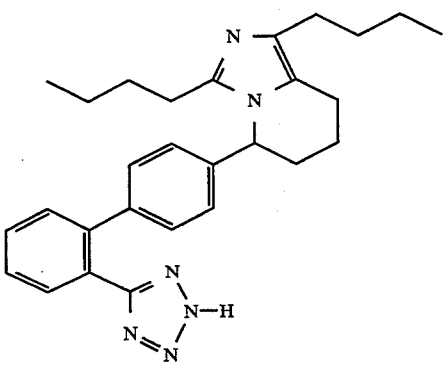

1,3-Dibutyl-5,6,7,8-tetrahydro-5-[2'-(1H-tetrazol-5-yl)[1,1'-biphenyl]-4-yl]imidazo[1,5-a]pyridine A suspension of 45 mg (0.1 mmol) of biphenyl bicyclic imidazole (the title compound of Example 1) and 20 mg (0.019 mmol) of 10% palladium on charcoal in 2 mL of absolute ethanol was agitated on a Parr apparatus under 50 psi of hydrogen gas at room temperature for 3.5 h. The mixture was filtered through a pad of celite and concentrated in vacuo to give 39 mg of the title compound of Example 3 as an oil which solidified as a glass: mp 108°-113° C. (decomposed); $^1$H NMR (CD$_3$OD) δ 0.83 (t, J=7.22 Hz, 3H), 0.98 (t, J=7.26 Hz, 3H), 1.15-1.90 (m, 10H), 2.08-2.23 (m, 1H), 2.35-2.60 (m, 3H), 2.35-2.85 (m, 3H), 2.90-3.05 (m, 1H), 5.72 (br s, 1H), 6.96 (d, J=8.46 Hz, 2H), 7.17 (d, J=8.46 Hz, 2H), 7.50-7.63 (m, 2H), 7.63-7.78 (m, 2H); HRMS. calcd for M+H: 455.2923. Found: 455.2965.

EXAMPLE 4

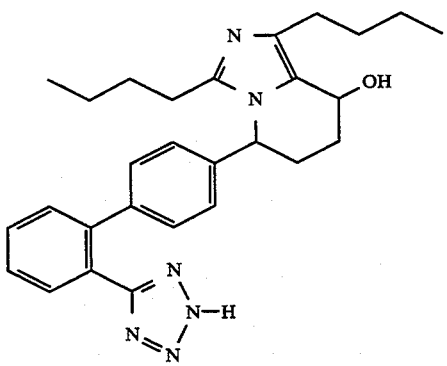

1,3-Dibutyl-5,6,7,8-tetrahydro-5-[2'-(1H-tetrazol-5-yl)[1,1'-biphenyl]-4-yl]imidazo[1,5-a]pyridin-8-ol Step 1: Preparation of the Bromohydrin Intermediate To a solution of 1.89 g (2.72 mmol) of biphenyl olefin imidazole (obtained from Step 4 of Example 1) in 1.37 mL (0.076 mmol) of water and 19.6 mL of DMSO at room temperature was added 509 mg (2.86 mmol) of NBS in one portion. The resulting orange solution was stirred at room temperature for 1 h, quenched with 100 mL of water and 12 mL of saturated Na$_2$SO$_3$, extracted with 150 mL of methylene chloride. The combined extracts were washed with two 60 mL portions of water, and the combined aqueous layers were extracted with 40 mL of methylene chloride. The combined extracts were washed with brine, dried (MgSO$_4$) and concentrated in vacuo to give 2.12 g of the crude bromohydrin which was used directly in the subsequent Step 2 without further purification.

Step 2: Preparation of Trityl Tetrazolyl Hydroxy imidazole

To 2.12 g (2.72 mmol) of the crude bromohydrin (obtained from Step 1) in 42 mL of degassed dry benzene was added 4.3 mL (14.7 mmol) of n-Bu$_3$SnH and 400 mg (2.4 mmol) of AIBN in one portion and the resulting solution was stirred at reflux for 2 h. The mixture was concentrated in vacuo and partitioned between 20 mL of hexane and 80 mL of acetonitrile. The acetonitrile layer was washed with two fresh 20 mL portions of hexane, and the combined hexane layer was extracted with another 50 mL of acetonitrile. The combined acetonitrile solution was concentrated in vacuo to give 2.5 g of the crude biphenyl hydroxy imidazole. The crude product was used directly in Example 5 without further purification. However, in some experiment, the crude mixture was purified by chromatography to give trityl-protected biphenyl hydroxy imidazole as a solid: $^1$H NMR (CDCl$_3$) δ 0.70 (t, J=7.25 Hz, 3H), 0.96 (t, J=7.31 Hz, 3H), 0.98-1.17 (m, 2H), 1.33-1.55 (m, 4H), 1.58-1.85 (m, 4H), 1.90-2.05 (m, 2H), 2.05-2.18 (m, 2H), 2.60-2.75 (m, 2H), 4.96 (br t, J=6.05 Hz, 2H), 6.81 (d, J=8.46 Hz, 2H), 6.92 (d, J=6.84 Hz, 6H), 7.12 (d, J=8.05 Hz, 2H), 7.18-7.40 (m, 10H), 7.5-7.55 (m, 2H), 7.92 (dd, J=7.25 Hz, 2.02 Hz, 1H); MS(FAB) m/e (relative intensity) 713 (75, M+H), 469 (35), 428 (100).

Step 3: Detritylation of Trityl-Protected Imidazole

A solution of 42 mg (0.059 mmol) of purified trityl tetrazolyl hydroxy imidazole (obtained from Step 2) in 0.8 mL of water and 4 mL of acetic acid was stirred at room temperature for 6 h, and concentrated in vacuo. The residue was dissolved in a minimum amount of methanol, diluted with methylene chloride, then triturated with ether to give 23 mg (82%) of the title compound of Example 4 as a solid: $^1$H NMR (CDCl$_3$) δ 0.81 (t, J=7.25 Hz, 3H), 0.99 (t, J=7.26 Hz, 3H), 1.18-1.35 (m, 2H), 1.69 (quintet, J=7.26 Hz, 2H), 1.78-1.93 (m, 1H), 1.96-2.10 (m, 1H), 2.17-2.58 (m, 4H), 2.70-2.95 (m, 2H), 4.98 (dd, J=7.25, 5.24 Hz, 1H), 5.59 (t, J=5.0 Hz, 1H), 7.11 (d, J=8.46 Hz, 2H), 7.20 (d, J=8.46 Hz, 2H), 7.50-7.65 (m, 2H), 7.65-7.77 (m, 2H); MS(FAB) m/e (relative intensity): 471(100, M+H), 443 (13), 428(30); HRMS. calcd for M+H: 471.2872. Found: 471. 2887.

EXAMPLE 5

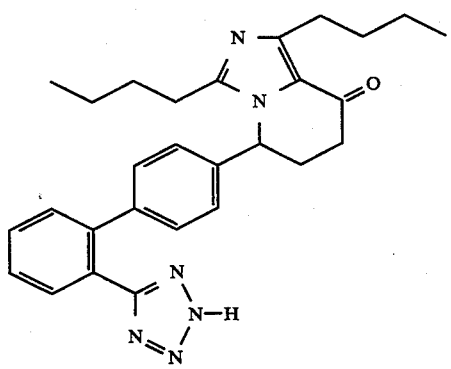

1,3-Dibutyl-5,6-dihydro-5-[2'-(1H-tetrazol-5-yl)[1,1'-biphenyl]-4-yl]imidazo[1,5-a]pyridin-8(5H)-one Step 1: Preparation of Trityl-Protected Keto Imidazole A suspension of 2.5 g (2.72 mmol) of the crude product (obtained from Step 2 of Example 4) and 13 g of active $MnO_2$ in 18 mL of methylene chloride was stirred at room temperature for 4 days. The mixture was filtered through a pad of celite, rinsed with IPA-methylene chloride, and concentrated in vacuo. The residue was purified by chromatography to give 0.28 g (15%) of olefinic starting material (the trityl protected title compound of Example 1), 0.73 g (38%) of biphenyl hydroxy imidazole (the trityl protected title compound of Example 4) and 0.32 g (17%) of trityl-protected biphenyl keto imidazole as an oil which solidified as a glass: $^1H$ NMR ($CDCl_3$) δ 0.77 (t, J=7.25 Hz, 3H), 0.97 (t, J=7.25 Hz, 3H), 1.17 (septet, J=7.25 Hz, 2H), 1.33 –1.66 [m (with quintet at 1.47, J=7.65 Hz), 4H], 1.65-1.82 (m, 2H), 2.0-2.25 (m, 3H), 2.36 (t, J=7.65 Hz, 2H), 2.45-2.63 (m, 1H), 3.04 (septet, J=3.8 Hz, 2H), 5.38 (br d, J=3.22 Hz, 1H), 6.62 (d, J=8.05 Hz, 2H), 6.90 (d, J=7.65 Hz, 6H), 7.13 (d, J=8.05 Hz, 2H), 7.18-7.38 (m, 10H), 7.40-7.55 (m, 2H), 7.97 (dd, J=6.44, 2.42 Hz, 1H).

The $^1H$ NMR spectrum of the biphenyl hydroxy imidazole obtained from the above purification indicated the presence of another compound which coeluted with the biphenyl hydroxy imidazole. This mixture was used in Example 8 to provide the title compound of Example 8.

Step 2: Detritylation of Trityl-Protected Imidazole

A solution of 39 mg (0.055 mmol) of trityl-protected keto imidazole (obtained from Step 1) in 0.8 mL of water and 4 mL of acetic acid was stirred at room temperature for 6 h, and concentrated in vacuo. The residue was worked up as described in Step 5 of Example 1 to give 22 mg (85%) of the title compound of Example 5 as an oil which solidified as a glass: mp 107°–116 ° C. (decomposed); $^1H$ NMR ($CD_3OD$) δ 0.82 (t, J=7.25 Hz, 3H), 0.95 (t, J=7.25 Hz, 3H), 1.17-1.32 (m, 2H), 1.32-1.58 [m (with septet at 1.39, J=7.66 Hz), 4H], 1.66 (quintet, J=7.25 Hz, 2H), 2.28-2.45 (m, 3H), 2.53 (t, J=7.7 Hz, 2H), 2.59-2.75 (m, 1H), 2.95 (td, J=7.66, 3.62 Hz, 2H), 5.77 (d, J=3.62 Hz, 1H), 6.85 (d, J=8.06 Hz, 2H), 7.14 (d, J=8.46 Hz, 2H), 7.53 (t, J=6.84 Hz, 2H), 7.62 (td, J=6.04, 1.6 Hz, 2H); HRMS. calcd for M+H: 469.2716. Found: 469.2748.

EXAMPLE 6

To 105 mg (0,148 mmol) of ketone biphenyl (from step 1 of Example 5) in 1.5 mL of THF at −78° C. was added dropwise 298 μL (0.149 mmol) of phenyllithium (o,5M in cyclohexane/diethyl ether), and the resulting dark brown solution was stirred cold for 2 hour, then was allowed to warm to room temperature and stirred for 10 min. The reaction was quenched with aqueous $NH_4Cl$ and extracted with methylene chloride. The combined extracts were dried and concentrated in vacuo. The crude product was used directly in the subsequent Step 2 without further purification.

Step 2: Preparation of Conjugated Phenyl Imidazole Biphenyl

To 177 mg (0.148 mmol) of phenyl hydroxy imidazole (from Step 1) and 50 μL of pyridine in 1.5 mL of methylene chloride at 0° C. was added 32 μL of thionyl chloride, and the resulting brown solution was stirred at room temperature for 2 hour. The reaction mixture was washed with water, dried and concentrated in vacuo. The residue was purified over silica gel to give 105 mg (92%) of conjugated phenyl imidazole biphenyl as an oil which solidified upon standing.

Step 2: Detritylation of Trityl Tetrazole

A solution of 105 mg (0.136 mmol) of trityl-protected phenyl imidazole (obtained from Step 2) in 0.5 mL of water and 5 mL of acetic acid was stirred at room temperature for 16 h, and concentrated in vacuo. The residue was worked up as described in Step 5 of Example 1. The product obtained was recrystallized to give 51 mg (71%) of the title compound of Example 6 as an solid: mp 158°-170° C. (decomposed); $^1H$ NMR ($CDCl_3$) δ 0.47 (t, J=7.25 Hz, 3H), 0.60–0.87 [m (with t at 0.80, J=7.25 Hz), 5H], 0.88-1.13 (m, 2H), 1.22 (quintet, J=8.06 Hz, 2H), 1.42-1.63 (m, 2H), 1.63-1.85 (m, 2H), 2.12-2.33 (m, 1H), 2.40-2.60 {m, 1H), 2.82 (dd, J=16.5, 7.25 Hz, 1H), 3.07 (dd, J=16.5, 5.24 Hz, 1H), 5.42 (d, J=6.05 Hz, 1H), 5.50 (d, J=6.45 Hz, 1H), 6.73 (d, J=8.06 Hz, 2H), 7.04 (d, J=8.06 Hz, 2H), 7.14-7.22 (m, 2H), 7.38-7.55 {m, 6H), 7.70 (d, J=7.26 Hz, 1H); $^{13}C$ NMR ($CDCl_3$) δ 13.12 ($CH_3$), 13.46 ($CH_3$), 21.83 ($CH_2$), 22.21 ($CH_2$), 24.97 ($CH_2$), 25.34 ($CH_2$), 29.56 ($CH_2$), 31.62 ($CH_2$), 31.98 ($CH_2$), 53.29 (CH), 118.87 (CH), 123.17 (C), 124.67 (CH), 126.05 (C), 127.50 (CH), 127.61 (CH), 128.00 (CH), 128.09 (CH), 126.20 (CH), 129.36 (CH), 129.77 (CH), 130.24 (CH), 130.97 (CH), 132.93 (C), 137.35 (C), 37.42 (C), 140.10 (C), 140.34 (C), 146.57 {C), 157.38 (C); MS(FAB) m/e (relative intensity): 529(100, M+H); HRMS. calcd for M+H: 529.3080. Found: 529.3045.

EXAMPLE 7

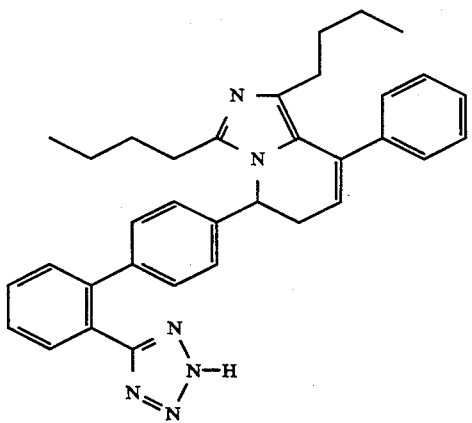

1,3-Dibutyl-5,6-dihydro-8-phenyl-5-[2'-(1H-tetrazol-5-yl) [1,1'-biphenyl]-4-yl]imidazo[1,5-a]pyridine
Step 1: Preparation of Protected Phenyl Hydroxy Imidazole Biphenyl

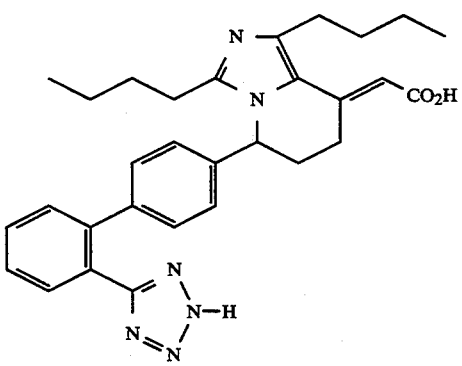

[1,3-Dibutyl-6,7-dihydro-5-[2'-(1H-tetrazol-5-yl)[1,1'-biphenyl]-4-yl]imidazo[1,5-a]pyridin-8(5H)-ylidene]acetic acid Step 1: Preparation of the Tert-Butyl Ester To a suspension of 50 mg (2.058 mmol) of magnesium in 2.5 mL of THF at 45° C. was added 16 μL of 1,2-dibromoethane in two portions, 5 min apart. The resulting mixture was stirred at 45° C. for 10 min, followed by dropwise addition of a solution of 170 mg (0.239 mmol) of biphenyl keto imidazole (obtained from Step 1 of Example 5) and 190 μL (1.18 mmol) of tert-butyl bromoacetate in 1.5 mL of THF at 45° C. over a 1 h period. The resulting solution was stirred for an additional 15 min, and was cooled and quenched with aqueous NH4Cl. The mixture was extracted with ether, dried (MgSO4) and concentrated in vacuo. The crude mixture could be used in the subsequent Step 2 without further purification. In this particular experiment, the crude product was purified by chromatography to give 179 mg (91%) of the hydroxy intermediate: $^1$H NMR (CDCl3) δ 0.72 (t, J=7.65 Hz, 3H), 0.98 (t, J=7.65 Hz, 3H), 1.11 (septet, J=7.66 Hz, 2H), 1.30-1.55 [m (with s at 1.47, 9H), 14HI, 1.65-1.90 (m, 5H), 2.10-2.35 (m, 3H), 2.67 (d, J=15.7 Hz, 1H), 2.72-2.9 [m (with d at 2.83, J=15.7 Hz), 2H], 4.10-4.25 (br s, 1H), 5.13 (d, J=3.22 Hz, 1H), 6.61 (d, J=8.06 Hz, 2H), 6.93 (d, J=7.25 Hz, 6H), 7.08 (8.06 Hz, 2H), 7.18-7.38 (m, 10H), 7.46 (quintet of doublets, J=6.85, 2.02 Hz, 2H), 7.90 (dd, J=6.85, 2.01 Hz, 1H).

Step 2: Preparation of Unsaturated Tert-Butyl Ester

To a solution of 115 mg (0.139 mmol) of the biphenyl imidazolyl ester intermediate (obtained from Step 1) and 30 μL (0.371 mmol) of pyridine in 1 mL of methylene chloride at 0° C. was added dropwise 20 μL (0.274 mmol) of thionyl chloride. The resulting dark brown solution was stirred at room temperature for 1 h, diluted with water and extracted with ether. The combined extracts were dried (MgSO4) and concentrated in vacuo. The residue was purified by chromatography to give 107 mg (95%) of the unsaturated ester intermediate as an oil which solidified as a glass: $^1$H NMR (CDCl3) δ 0.75 (t, J=7.25 Hz, 3H), 1.02 (t, J=7.25 Hz, 3H), 1.14 (septet, J=7.25 Hz, 2H), 1.35-1.65 [m (with s at 1.47), 13H], 1.77 (quintet, J=7.25 Hz, 2H), 1.90-2.10 (m, 1H), 2.10-2.25 (m, 2H), 2.29 (t, J=7.65 Hz, 2H), 2.86 (t, J=8.06 Hz, 2H), 3.40-3.60 (m, 1H), 5.26 (s, 1H), 6.00 (s, 1H), 6.60 (d, J=8.06 Hz, 2H), 6.91 (d, J=8.1 Hz, 6H), 7.09 (d, J=8.46 Hz, 2H), 7.18-7.49 (m, 10H), 7.47 (quintet of doublets, J=6.45, 2.01 Hz, 2H), 7.93 (dd, J=6.85, 2.02 Hz, 1H).

Step 3: Detritylation of Trityl-Protected Biphenyl and Deprotection of Tert-Butyl Ester Group A solution of 98 mg (0,121 mmol) of trityl tetrazolyl butyl ester (obtained from Step 2) in 0.8 mL of water and 3 mL of acetic acid was stirred at room temperature for 17 h and concentrated in vacuo. The residue was worked up as described in Step 5 of Example 1 to give the free tetrazole intermediate. The intermediate was dissolved in 3 mL of CDCl3 and 1 mL of TFA, and the progress of the reaction was monitored by $^1$H NMR. The resulting yellow solution was stirred at room temperature for 2 h and concentrated in vacuo. The crude product was purified over reverse phase chromatography to give 30 mg of the title compound of Example 7 as a solid: mp 155°-178° C. (decomposed); $^1$H NMR (CD3OD) δ 1.10 (t, j=7.31 Hz, 3H), 1.29 (t, J=7.29 Hz, 3H), 1.40-1.68 (m, 2H), 1.68-1.89 (m, 4H), 1.99 (quintet, J=7.31 Hz, 2H), 2.40-2.75 (m, 3H), 2.78 (t, J=7.93 Hz, 2H), 3.12 t, J=7.83 Hz, 2H), 3.84 (d, J=16.47 Hz, 1H), 5.91 (s, 1H), 6.44 (s, 1H), 7.07 (d, J=8.08 Hz, 2H), 7.40 d, J=8.28 Hz, 2H), 7.68-7.78 (m, 2H), 7.78-7.90 (m, 2H); HRMS. calcd for M+H: 511.2821. Found: 511.2769.

EXAMPLE 8

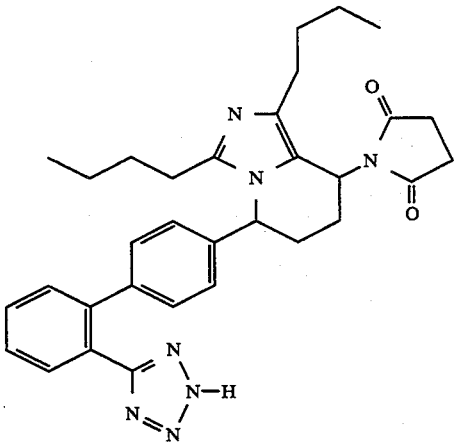

1-[1,3-Dibutyl-5,6,7,8-tetrahydro-5-[2'-(1H-tetrazol-5-yl)[1,1'-biphenyl]-4-yl]imidazo[1,5-a]pyridin-8-yl]2,5-pyrrolidinedione Step 1: Preparation of Succinimidyl Imidazole A suspension of 727 mg (1.02 mmol) of impure biphenyl hydroxy imidazole (isolated from Step 1 of Example 5) and 7 g of active MnO2 in 10 mL of methylene chloride was stirred at room temperature for 3 h. The resulting mixture was filtered through a pad of celite, rinsed with IPA-methylene chloride, and concentrated in vacuo. The residue was purified by chromatography to give 316 mg (16% from Step 1 of Example 4) of ketone (the trityl-protected title compound of Example 5), and 130 mg (6% from Step 1 of Example 4) of the trityl-protected biphenyl succinimidyl imidazole: $^1$H NMR (CDCl3) δ 0.70 (t, J=7.31 Hz, 3H), 0.91 (t, J=7.19 Hz, 3H), 1.08 (septet, J=7.5 Hz, 2H), 1.2-1.70 (m, 6H), 1.8-1.9 (m, 1H), 2.1-2.4 (m, 7H), 2.72 (s, 4H), 5.13 (s, 1H), 5.35-5.5 (m, 1H), 6.94 (d, J=6.84 Hz, 6H), 7.09 (d, J=8.34 Hz, 2H), 7.16 (d, J=8.28 Hz, 2H), 7.20-7.55 (m, 12H), 7.86 (dd, J=6.8, 2.6 Hz, 1H).

Alternatively, the succinimide can be prepared from trityl protected title compound of Example 1 (Step 4). To a solution of 2.17 g (3.13 mmol) of biphenyl bicyclic imidazole (Example 1, Step 4) and 1.25 g (12.6 mmol) of succinimide in 20 mL of anhydrous acetonitrile is added 572 mg (3.21 mmol) of NBS in one portion. The resulting orange-red solution is stirred at room temperature for 30 min, then evaporated in vacuo. The residue is dissolved in ethyl acetate and washed with aqueous sodium bisulfite, water, and brine. The extracts are dried (MgSO4) and concentrated in vacuo. The residue is purified to give the trityl protected succinimidyl imidazole.

Step 2: Detritylation of Trityl Tetrazolyl Imidazole

A solution of 130 mg (0.16 mmol) of trityl-protected biphenyl succinimidyl imidazole (obtained from Step 1) in 0.2 mL of water and 1 mL of acetic acid was stirred at room temperature for 12 h and concentrated in vacuo. The residue was worked up as described in Step 5 of Example 1 and purified by chromatography to give 64 mg (79%) of the title compound as a solid: mp 166.8°-170.0° C. (decomposed); $^1$H NHR (CD$_3$OD) δ 1.10 (t, J=7.3 Hz, 3H), 1.22 (t, J=7.31 Hz, 3H), 1.50 (septet, J=7.4 Hz, 2H), 1.55-1.93 (m, 6H), 2.1-2.25 (m, 1H), 2.4-2.85 (m, 7H), 3.06 (s, 4H), 5.76 (dd, J=8.7, 7.8 Hz, 1H), 5.8-5.9 (m, 1H), 7.46 (d, J=8.35 Hz, 2H), 7.60 (d, J=8.28 Hz, 2H), 7.7-7.9 (m, 4H); HRMS. calcd for M+H: 552.3087. Found: 552.3067.

EXAMPLE 9

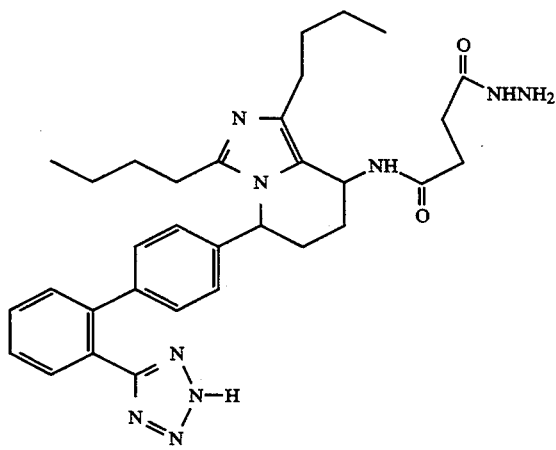

4-[1,3-Dibutyl-5,6,7,8-tetrahydro-5-[2'-(1H-tetrazol-5-yl) [1,1'-biphenyl]-4-yl]imidazo [1,5 -a]pyridin-8-yl]amino]-4-oxobutanoic acid, hydrazide A solution of 34.8 mg (0.06 mmol) of succinimidyl imidazole (the title compound of Example 8 and 11 μL (5.6 mmol) of hydrazine in 0.5 mL of ethanol was stirred at room temperature for 6 days and concentrated in vacuo to give the title compound as a solid: mp 136.5°-139.4° C. (decomposed); $^1$H NMR (CD$_3$OD) δ 0.68 (t, J=7.23 Hz, 3H), 0.83 (t, J=7.27 Hz, 3H), 1.00-1.43 (m, 6H), 1.40-1.57 (m, 2H), 1.58-1.75 (m, 1H), 1.80-1.93 (m, 1H), 1.98-2.12 (m, 1H), 2.20-2.65 (m, 9H), 5.10 (dd, J=8.77, 5.99 Hz, 1H), 5.54 (br s, 1H), 7.05 (qAB, J=8.35 Hz, 4H), 7.35-7.50 (m, 2H), 7.50-7.63 (m, 2H); HRMS. calcd for M+H: 584.3461. Found: 584.3525.

EXAMPLE 10

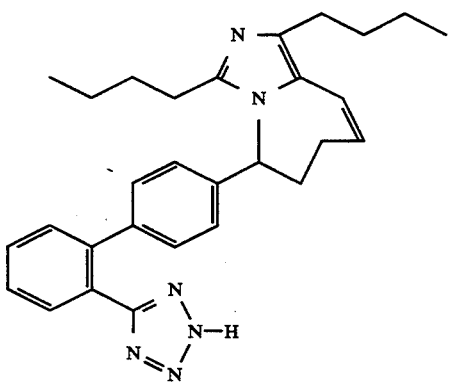

1,3-Dibutyl-6,7-dihydro-5-[2'-(1H-tetrazol-5-yl) [1,1'-biphenyl]-4-yl]-5H-imidazo[1,5-a]azepine Step 1: Alkylation of Biphenyl Imidazole To a solution of 100 mg (0.152 mmol) of biphenyl imidazole (obtained from Step 2 of Example 1) in 0.8 mL of DME cooled at −45° C. (acetonitrile-dry ice) was added 125 μL of 1.6M (0.2 mmol) of n-butyllithium in hexane over a 4-min period. The resulting dark red solution was stirred cold for another 15 min, followed by addition of 70 μL (0.37 mmol) of 2-(3-bromopropyl)-5,5-dimethyl-1,3-dioxane in one portion. The mixture was stirred cold for 40 min, then was warmed to −10° C. over a 40 min period. The reaction was quenched with aqueous NH$_4$Cl, extracted with three 20 mL portions of diethyl ether. The combined extracts were washed with brine, dried (MgSO$_4$) and concentrated in vacuo. The crude product was used directly in the subsequent Step 2 without purification. The $^1$H NMR spectrum (in CDCl$_3$) of the crude mixture indicated a >9:1 ratio of the desired alkylated product to the recovered starting material (based on the integration areas of singlet peaks at δ 6.55 and 6.3, respectively). HPLC analysis also agreed with the result from the $^1$H NMR study (C18 column, 60% acetonitrile in water containing 0.05% of TFA, flow rate 1.5 mL/min, retention time 13.5 min and 7.1 min, respectively).

Step 2: Preparation of the Bicyclic Imidazole

A solution of 135 mg (0.152 retool) of the crude biphenyl acetal imidazole (obtained from Step 1) and 255 mg (3 mmol) of NaOAc in 0.6 mL of water and 2 mL of glacial acetic acid was stirred at reflux for 22 h, cooled and concentrated in vacuo. The residue was dissolved in methylene chloride and filtered. The filtrate was stirred with 130 mg (0.46 mmol) of trityl chloride and 0.22 mL (1.6 mmol) of TEA at room temperature overnight (16 h) and concentrated in vacuo. The residue was purified by chromatography to give 25 mg (23%) of trityl-protected biphenyl bicyclic imidazole: $^1$H NMR (CDCl$_3$) δ 0.78 (t, J=7.5 Hz, 3H), 0.87 (t, J=7.4 Hz, 3H), 1.1-1.32 (m, 2H), 1.35-1.60 (m, 4H), 1.62-1.90 (m, 3H), 1.95-2.12 (m, 1H), 2.20-2.38 (m, 2H), 2.38-2.55 (m, 2H), 2.58-2.75 (m, 2H), 5.15-5.38 (m, 1H), 5.53 (br s, 1H), 6.27 (dd, J=17.5, 3 Hz, 1H), 6.68 (d, J=7.5 Hz, 2H), 6.93 (d, J=8.3 Hz, 6H), 7.08 (d, J=7.7 Hz, 2H), 7.20-7.38 (m, 10H), 7.40-7.55 (m, 2H), 7.9 (dd, J=7.5, 3.0 Hz, 1H).

Step 3: Detritylation of Trityl Tetrazole

A solution of 25 mg (0.035 mmol) of the bipenyl bicyclic imidazole (obtained from Step 2) was stirred with 0.4 mL of water and 2 mL of acetic acid at room temperature for 14 h. The solution was concentrated in vacuo. The residue was worked up as described in Step 5 of Example 1 to give 13 mg (80%) of the title compound of Example 10 as an oil which solidified as a glass: mp 125°-130° C. (decomposed); HRMS. calcd for M+H: 467.2923. Found: 467.2944.

EXAMPLE 11

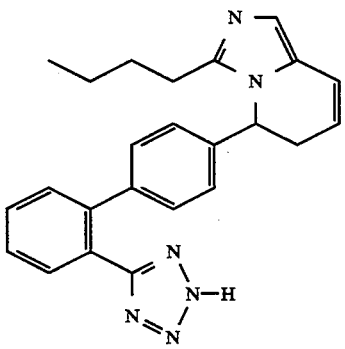

3-Butyl-5,6-dihydro-5-[2'-(1H-tetrazol-5-yl)[1,1'-biphenyl]-4-yl]imidazo[1,5-a]pyridine Step 1: Preparation of 2-Butylimidazole To a mixture of 72.4 g (0.56 mol) of ethyl valery imidate and 63 mL (0,433 mol) of aminoacetaldehyde diethyl acetal was added slowly 50 mL of glacial acetic acid over a 20 min period, and the resulting solution was stirred at reflux for 2.5 h. To the solution was added 144 mL of 5N HCl aqueous solution, and the resulting mixture was stirred at reflux for another 2 h. The mixture was cooled and concentrated to about 200 mL, washed with 200 mL of ethyl acetate, 200 mL of ether, then basified to pH 8 with 50% NaOH, and extracted with four 225 mL portions of chloroform. The combined extracts were dried (MgSO$_4$) and concentrated to give 30 g (56%) of 2-butyl imidazole as a light brown solid: $^1$H NMR (CDCl$_3$) δ 0.85 (t, J=7.31 Hz, 3H), 1.31 (septet, J=7.46 Hz, 2H), 1.73 (quintet, J=7.31 Hz, 2H), 2.86 (t, J=7.39 Hz, 2H), 6.99 (s, 2H), 11.09-12.4 (br s, 1H).

Step 2: Preparation of Biphenyl Imidazole

To a solution of 4.07 g (32.8 mmol) of 2-butylimidazole (obtained from step 1) in 110 mL of DMF was added 44.3 mL (44.3 mmol) of potassium tert-butoxide (1M in THF), and the resulting solution was stirred at room temperature for 15 min. To the dark brown mixture was added 20.1 g (36.1 mmol) of the bromomethyl biphenyl. The reaction mixture was stirred at room temperature for 16 h, and concentrated in vacuo. The residue was dissolved in chloroform and washed with water. The aqueous layer was extracted with fresh chloroform, and the combined extracts were dried (MgSO$_4$) and concentrated in vacuo. The residue was purified by chromatography to give 7.2 g (37%) of the biphenyl imidazole intermediate as a yellow oil which solidified as a glass: $^1$H NMR (CDCl$_3$) δ 0.90 (t, J=7.31 Hz, 3H), 1.35 (septet, J=7.5 Hz, 2H), 1.71 (quintet, J=7.74 Hz, 2H), 2.61 (t, J=7.58 Hz, 2H), 4.93 (s, 2H), 6.65 (d, J=1.35 Hz, 1H), 6.79 (d, J=8.31 Hz, 2H), 6.92 (d, J=7.3 Hz, 6H), 6.97 (d, J=1.32 Hz, 1H), 7.11 (d, J=8.2 Hz, 2H), 7.2-7.4 (m, 10H), 7.4-7.55 (m, 2H), 7.95 (dd, J=6.85, 2.08 Hz, 1H); MS(FAB) m/e (relative intensity) 607 (100, M+Li), 601 (90, M+H).

Step 3: Alkylation of the Biphenyl Imidazole

To a solution of 7.5 g (12.5 mmol) of the biphenyl imidazole (obtained from Step 2) in 49 mL of DME and 86 mL of THF cooled at −45° C. (acetonitrile-dry ice) was added 14.8 mL of 1.6M (24 mmol) of n-butyllithium in hexane over a 4 min period. The resulting dark red solution was stirred cold for another 15 min, followed by addition of 3.8 mL (25 mmol) of 3-bromo-proprionaldedyde dimethyl acetal in one portion. The mixture was stirred cold for 1 h, then was allowed to warm to −10° C. over a 1.5-h period. The reaction was quenched with aqueous NH$_4$Cl, extracted with methylene chloride. The combined extracts were washed with brine, dried (MgSO$_4$) and concentrated in vacuo to give the crude acetal biphenyl imidazole. The crude product was used directly in the subsequent Step 4 without purification. The $^1$H NMR spectrum of the crude mixture indicated a 9:1 ratio of the desired alkylated product to the recovered starting material [based on the integration areas of peaks at δ 5.13 (dd, 1H) and 4.93 (s, 2H), respectively].

Step 4: Preparation of the Bicyclic Imidazole

The crude mixture (12.5 mmol, obtained from Step 3) and 21 g (260 mol) of NaOAc in 52 mL of water and 160 mL of glacial acetic acid was stirred at reflux for 2 days, cooled and concentrated in vacuo. The residue was partitioned between chloroform and water. The combined extracts were dried (MgSO$_4$) and concentrated in vacuo. The residue was dissolved in 40 mL of chloroform and stirred with 8.0 g (28.7 mmol) of trityl chloride and 16 mL (0.115 mol) of TEA at room temperature overnight (16 h) and concentrated in vacuo. The residue was partitioned between chloroform and water. The combined extracts were dried (MgSO$_4$) and concentrated in vacuo. The residue was purified by chromatography (eluted with 2-propanol:hexane=1:10) to give 3.01 g (34%) of the trityl-protected biphenyl bicyclic imidazole: $^1$H NMR (CDCl$_3$) δ 0.76 (t, J=7.31 Hz, 3H), 1.18 (septet, J=7.4 Hz, 2H), 1.43-1.62 (m, 2H), 2.20-2.49 (m, 3H), 2.83-2.97 (m, 1H), 5.22-5.31 [m (with d at 5.24, J=7.0 Hz), 2H], 6.42 (dd, J=9.82, 3.05 Hz, 1H), 6.54 (d, J=8.2 Hz, 2H), 6.84 (d, J=7.81 Hz, 6H), 6.97 (d, J=6.07 Hz, 2H), 7.01 (s, 1H), 7.09-7.33 (m, 10H), 7.34-7.50 (m, 2H), 7.88 (dd, J=6.8, 2.16 Hz, 1H).

Step 5: Detritylation of the Trityl Tetrazole

A solution of 50 mg (0.078 mmol) of the trityl-protected biphenyl bicyclic imidazole (obtained from Step 4) was stirred with 0.5 mL of water and 2 mL of acetic acid at room temperature for 18 h. The solution was concentrated in vacuo. The residue was worked up as described in Step 5 of Example 1 to give 25 mg (80%) of the title compound of Example 11 as an oil which solidified as a glass: mp: 146°-156° C. (decomposed); $^1$H NMR (CD$_3$OD) δ 0.72 (t, J=7.27 Hz, 3H), 1.10-1.50 (m, 4H), 2.55-2.80 (m, 3H), 3.00-3.21 (m, 1H), 5.82 (d, J=7.66 Hz, 1H), 5.91-6.00 (m, 1H), 6.56 (dd, J=10.1, 3.06 Hz, 1H), 6.84 (d, J=8.19 Hz, 2H), 6.99 (d, J=8.35 Hz, 2H), 7.30-7.60 [m (with s at 7.36), 5H]; HRMS. calcd. for M+H: 397.2141. Found: 97.2181.

EXAMPLE 12

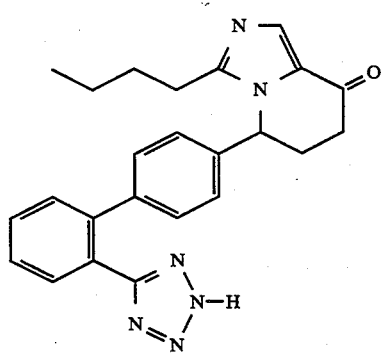

3-Butyl-5,6-dihydro-5-[2'-(1H-tetrazol-5-yl)[1,1'-biphenyl]-4-yl]imidazo[1,5-a]pyridin-8(5H) -one Step 1: Preparation of the Bromohydrin Intermediate To a solution of 2.0 g (3.13 mmol) of biphenyl olefin imidazole (obtained from Step 4 of Example 11) in 2.2 mL (0.122 mmol) of water and 22 mL of DMSO at room temperature was added 587 mg (3.30 mmol) of NBS in one portion. The resulting orange solution was stirred at room temperature for 40 min, quenched with 100 mL of water and 12 mL of saturated Na$_2$SO$_3$, extracted with two 100 mL portions of chloroform. The combined extracts were washed with two 60 mL portions of water, and the combined aqueous layer was extracted with 40 mL of chloroform. The combined extracts were washed with brine, dried (MgSO$_4$) and concentrated in vacuo to give a crude bromohydrin intermediate which was used directly in the subsequent Step 2 without further purification.

Step 2: Preparation of the Trityl Tetrazolyl Hydroxy Imidazole

To the crude bromohydrin intermediate (3.13 mmol, obtained from Step 1) in 42 mL of degassed dry benzene was added 4.3 mL (14.7 mmol) of n-Bu$_3$SnH and 456 mg (2.7 mmol) of AIBN in one portion and the resulting solution was stirred at reflux for 1 h. The mixture was concentrated in vacuo and partitioned between 20 mL of hexane and 80 mL of acetonitrile. The acetonitrile layer was washed with two fresh 20 mL portions of hexane, and the combined hexane layer was extracted with another 50 mL of acetonitrile. The combined acetonitrile extracts were concentrated in vacuo to give an isomeric mixture of both cis- and trans-hydroxy imidazole (relative to the biphenyl moiety). The $^1$H NMR spectrum of the crude mixture indicated a 1.8:1 ratio of the cis-hydroxy product to the trans-hydroxy product [based on the integration areas of peaks at δ 5.09 (t) and 5.28 (d), respectively]. The crude mixture was used directly in subsequent Step 3 without further purification. In one experiment, the mixture was used to prepare the biphenyl trans-hydroxy imidazole (the title compound of Example 14).

Step 3: Preparation of the Keto Imidazole

A suspension of the crude product (2.72 mmol, obtained from Step 2 and 13 g of active MnO$_2$ in 15 mL of methylene chloride was stirred at room temperature for 17 h. The mixture was filtered through a pad of celite, rinsed with IPA-methylene chloride, and concentrated in vacuo. The residue was purified by chromatography to give 0.24 g (12%) of olefinic starting material (the trityl protected title compound of Example 11 ), and 1.01 g (57% ) of trityl-protected keto imidazole as a solid: $^1$H NMR (CDCl$_3$) δ 0.72 (t, J=7.25 Hz, 3H), 1.13 (septet, J=7.26 Hz, 2H), 1.40–1.65 (m, 2H), 1.95–2.22 (m, 3H), 2.25–2.42 (m, 2H), 2.45–2.60 (m, 1H), 5.36 (br d, J=3.22 Hz, 1H), 6.54 (d, J=8.06 Hz, 2H), 6.83 (d, J=7.66 Hz, 6H), 7.08 (d, J=8.06 Hz, 2H), 7.13–7.35 (m, 10H), 7.42 (quintet, J=3.63 Hz, 2H), 7.86 (s, 1H), 7.92 (dd, J=6.85, 1.61 Hz, 1H).

Step 4: Detritylation of Trityl Tetrazolyl Imidazole

A solution of 86 mg (0.131 mmol of trityl-protected keto imidazole (obtained from Step 3) in 1.0 mL of water and 5.0 mL of acetic acid was stirred at room temperature for 20 h, and concentrated in vacuo. The residue was worked up as described in Step 5 of Example 1 to give 54 mg (quantitative) of the title compound of Example 12 as a solid: mp 128°–144° C. (decomposed); $^1$H NMR (CD$_3$OD) δ 0.82 (t, J=7.25 Hz, 3H), 1.15–1.35 (m, 2H), 1.35–1.65 (m, 2H), 2.3–2.8 (m, 6H), 5.84 (d, J=3.23 Hz, 1H), 6.88 (d, J=8.46 Hz, 2H), 7.13 (d, J=8.06 Hz, 2H), 7.49–7.60 (m, 2H), 7.60–7.70 (m, 2H), 7.80 (s, 1H); HRMS. calcd for M+H: 413.2090. Found: 413.2016.

EXAMPLE 13

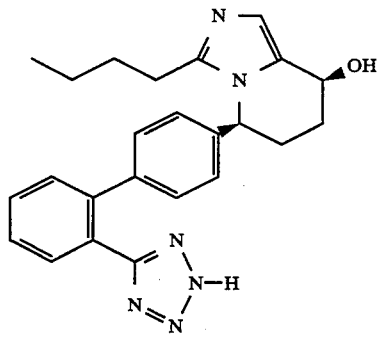

3-Butyl-5,6,7,8-tetrahydro-5-[2'-(1H-tetrazol-5-yl) [1,1'-biphenyl]-4-yl]imidazo[1,5-a]pyridin-cis-8-ol Step 1: Preparation of Biphenyl Cis-Hydroxy Imidazole To a solution of 298 mg (0.456 mmol) of ketone (obtained from Step 3 of Example 12) in 0.5 mL of methanol and 2.0 mL of THF at 0° C. was added in small portions 34 mg (0.899 mmol) of NaBH$_4$. The resulting solution was stirred at 0° C. and slowly warmed to room temperature for 17 h. The reaction was quenched with aqueous NH$_4$Cl, extracted with methylene chloride, dried (MgSO$_4$) and concentrated in vacuo. The residue was chromatography to give 273 mg (91%) of the biphenyl cis-hydroxy imidazole (relative to the biphenyl moiety) as a solid: $^1$H NMR (CDCl$_3$) δ 0.68 (t, J=7.46 Hz, 3H), 1.07 (septet, J=7.38 Hz, 2H), 1.25–1.64 (m, 3H), 1.68–1.82 (m, 2H), 1.82–1.96 (m, 2H), 1.96–2.15 [m (with t at 2.10, J=8.4 Hz,), 3H], 4.84 (dd, J=8.7, 5.57 Hz, 1H), 5.03 (t, J=5.06 Hz, 1H), 6.63 (d, J=8.27 Hz, 2H), 6.89 (d, J=7.08 Hz, 6H), 6.98–7.08 [m (with s at 7.03 and d at 7.03, J=8.27 Hz), 3H], 7.15–7.32 (m, 10H), 7.32–7.45 (m, 2H), 7.85 (dd, J=6.85, 2.17 Hz, 1H).

Step 2: Detritylation of Trityl Tetrazolyl Imidazole

A solution of 170 mg (0.259 mmol) of trityl-protected biphenyl hydroxy imidazole (obtained from Step 1) in 0.4 mL of water and 2.0 mL of acetic acid was stirred at room temperature for 16 h and concentrated in vacuo. The residue was dissolved in a minimum amount of methanol, diluted with methylene chloride, then triturated with ether to give 92 mg (86%) of the title compound of Example 13 as a solid: mp 175.5°–180° C.; $^1$H NMR (CD$_3$OD) δ 0.80 (t, J=7.26 Hz, 3H), 1.15–1.28 (m, 2H), 1.28–1.43 (m, 1H), 1.43 –1.60 (m, 1H), 1.69–1.86 (m, 1H), 1.92–2.05 (m, 1H), 2.13–2.28 (m 1H), 2.28–2.55 (m, 3H), 4.81–4.95 (m, 1H), 5.57 (t, J=4.80 Hz, 1H), 6.90 (d, J=8.46 Hz, 2H), 7.14 (d, J=8.06 Hz, 2H), 7.36 (s, 1H), 7.40–7.62 (m, 4H); HRMS. calcd for M+Li: 421.2328. Found: 421.2306.

EXAMPLE 14

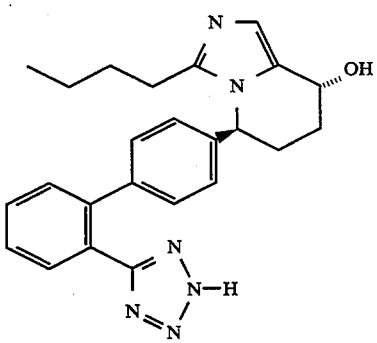

3-Butyl-5,6,7,8-tetrahydro-5-[2'-(1H-tetrazol-5-yl) [1,1'-biphenyl]-4-yl]imidazo[1,5-a]pyridin-trans-8-ol Step 1: Preparation of Biphenyl Trans-Hydroxy Imidazole A suspension of the crude biphenyl hydroxy imidazole (1.307 mmol, obtained from Step 2 of Example 12) and 3.0 g of active $MnO_2$ in 5.0 mL of methylene chloride was stirred at room temperature. The reaction was stopped before its completion (in this particular experiment, the reaction time was 14 h). The mixture was filtered through a pad of celite, rinsed with IPA-methylene chloride, and concentrated in vacuo. The residue was purified by chromatography to give 190 mg of olefinic starting material (23% from Step 1 of Example 12), 341 mg of trityl-protected ketone (40% from Step 1 of Example 12), and 74 mg of the trityl protected biphenyl trans-hydroxy imidazole (9% from Step 1 of Example 12) as a solid: $^1$H NMR ($CDCl_3$) δ 0.76 (t, J=7.25 Hz, 3H), 1.16 (septet, J=7.25 Hz, 2H), 1.23 –1.62 (m, 4H), 1.68 (br d, J=12.09 Hz, 1H), 2.07–2.34 (m, 2H), 2.56–2.73 (m, 1H), 2.73 –2.95 (br s, 1H). 4.94 (br s, 1H), 5.26 (br d, J=3.62 Hz, 1H), 6.47 (d, J=8.06 Hz, 2H), 6.90 (d, J=7.25 Hz, 6H), 7.05 (s, 1H), 7.07 (d, J=8.06 Hz, 2H), 7.17–7.38 (m, 10H), 7.40–7.55 (m, 2H), 7.93 (dd, J=7.25, 2.02 Hz, 1H).

Alternatively, the biphenyl trans-hydroxy imidazole can be prepared using the Mitsunobu reaction conditions. To a solution of diethyl azodicarboxylate (2.0 mmol) and 3-nitrobenzoic acid (2.0 mmol) in 2.0 mL of THF is added dropwise a solution of the biphenyl hydroxy imidazole (2.0 mmol, obtained from Step 1 of Example 13); and triphenylphosphine (2.0 mmol) in 1.0 mL of THF at room temperature. The resulting solution is stirred at room temperature until the reaction is complete. The resulting mixture is diluted with ether or ethyl acetate, and washed with water. The extracts are dried ($MgSO_4$) and concentrated in vacuo to give the biphenyl imidazolyl nitrobenzoate. The crude benzoate is hydrolyzed with LiOH in aqueous THF at room temperature and purified to give the biphenyl trans-hydroxy imidazole.

Step 2: Detritylation of Trityl Tetrazole

A solution of 52 mg 0.079 mmol) of biphenyl trans-hydroxy imidazole (obtained from Step 1) in 0.4 mL of water and 2.0 mL of acetic acid was stirred at room temperature for 17 h and concentrated in vacuo. The residue was dissolved in a minimum amount of methanol, diluted with methylene chloride, then triturated with ether to give 23 mg (70%) of the title compound of Example 14 as a solid: mp 185.2°–188.0° C. (decomposed); $^1$H NMR ($CD_3OD$) δ 0.82 (t, J=7.26 Hz, 3H), 1.15–1.62 (m, 4H), 1.72–1.87 (m, 1H), 1.90–2.10 (m, 2H), 2.35–2.60 (m, 2H), 2.63–2.80 (m, 1H), 5.01 (t, J=3.9 Hz, 1H), 5.65 (br t, J=5.1 Hz, 1H), 6.81 (d, J=8.40 Hz, 2H), 7.13 (d, J=8.4 Hz, 2H), 7.39 (s, 1H), 7.42–7.65 (m, 4H); MS (FAB) m/e (relative intensity): 415 (100, M+H), 372 (20), 359 (18); HRMS. calcd for M+Li: 421.2328. Found: 421.2373.

EXAMPLE 15

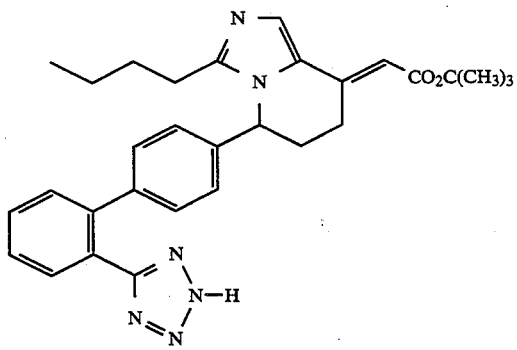

1,1-Dimethylethyl [3-butyl-6,7-dihydro-5-[2'-(1H-tetrazol-5-yl)[1,1'-biphenyl]-4-yl]imidazo[1,5-a]pyridin-8(5H)-ylidene]acetate Step 1: Preparation of Tert-Butyl Ester To a suspension of 64 mg (2.63 mmol) of magnesium in 3.0 mL of THF at 55° C. was added two 10 μL portions of 1,2-dibromoethane, 5 min apart. The resulting mixture was stirred at 45° C. for 10 min, followed by dropwise addition of a solution of 200 mg (0.306 mmol) of trityl-protected keto imidazole (obtained from Step 3 of Example 12) and 242 μL (1.50 mmol) of tert-butyl bromoacetate in 2.0 mL of THF at 55° C. over a 1 h period. The resulting solution was stirred for an additional 20 min, cooled and quenched with aqueous $NH_4Cl$. The mixture was extracted with ether, dried ($MgSO_4$) and concentrated in vacuo. The crude mixture was used directly in the subsequent Step 2 without further purification.

Step 2: Preparation of Unsaturated Butyl Ester

To a solution of the crude alcohol (0.306 mmol) (obtained from Step 1) and 200 μL (2.47 mmol) of pyridine in 2 mL of methylene chloride at 0° C. was added dropwise 80 μL (1.1 mmol) of thionyl chloride. The resulting dark brown solution was stirred an 0° C. for 1 h, diluted with water and extracted with methylene chloride. TLC analysis indicated that some product was detritylated. The methylene chloride solution was treated with 100 mg of trityl chloride and 200 μL of TEA, stirred at room temperature for 16 h, and concentrated in vacuo. The residue was purified by chromatography to give 164 mg (71%) of the biphenyl imidazolyl unsaturated ester as an oil which solidified as a glass: $^1$H NMR ($CDCl_3$) δ 0.77 (t, J=7.26 Hz, 3H), 1.17 (septet, J=7.25 Hz, 2H), 1.40–1.70 [m (with s at 1.47), 11H], 1.96–2.12 (m, 1H), 2.12–2.32 (m, 2H), 2.32 –2.52 (m, 2H), 3.50 (d, J=15.7 Hz, 1H), 5.28–5.40 (br s, 1H), 6.23 (s, 1H), 6.60 (d, J=8.47 Hz, 2H), 6.90 (d, J=7.25 Hz, 6H), 7.14 (d, J=8.06 Hz, 2H), 7.20–7.40 (m, 10H), 7.42–7.56 (m, 2H), 7.60 (s, 1H), 7.97 (dd, J=7.25, 2.01 Hz, 1H).

Step 3: Detritylation of Trityl Tetrazolyl Imidazole

A solution of 100 mg (0.133 mmol of trityl-protected imidazolyl butyl ester (obtained from Step 2) in 1.0 mL of water and 5.0 mL of acetic acid was stirred at room temperature for 20 h and concentrated in vacuo. The residue was worked up as described in Step 5 of Example 1 to give 66 mg (97%) of the title compound of Example 15 as a solid: mp 205°–212° C. (decomposed); $^1$H NMR (CD$_3$OD) δ 1.09 (t, J=7.31 Hz, 3H), 1.43–1.65 (m, 2H), 1.65–1.95 [m {with s at 1.76}, 11H], 2.45–2.65 (m, 3H), 2.68–2.95 (m, 2H), 3.73–3.92 (m, 1H), 5.95–6.02 (br s, 1H), 6.61 (s, 1H), 7.12 (d, J=8.09 Hz, 2H), 7.40 (d, J=8.28 Hz, 2H), 7.79 (t, J=7.58 Hz, 2H), 7.89 (t, J=7.81 Hz, 2H), 7.97 (s, 1H), 8.17 (s, 1H); HRMS. calcd for M+H: 511.2821. Found: 511.2793.

EXAMPLE 16

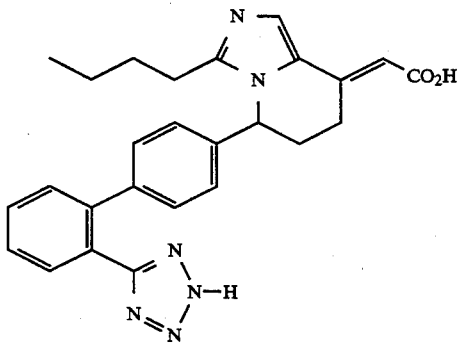

[3-Butyl-6,7-dihydro-5-[2'-(1H-tetrazol-5-yl) [1,1'-biphenyl]-4-yl]imidazo[1,5-a]pyridin-8(5H)-ylidene]acetic acid To a solution of 32 mg (0.0627 mmol) of tert-butyl ester (the title compound of Example 15) in 2 mL of CDCl$_3$ at room temperature was added 0.5 mL of TFA, and the progress of the reaction was monitored by $^1$H NMR. The resulting yellow solution was stirred at room temperature for 1 h and concentrated in vacuo. The crude product was dissolved in a minimum amount of methanol, diluted with methylene chloride, then triturated with ether and hexane at 5° C. to give 27 mg (96%) of the title compound of Example 16 as a solid: mp 154.0°–155.5° C. (decomposed); $^1$H NMR (CD$_3$OD) δ 0.84 (t, J=7.5 Hz, 3H), 1.2–1.45 (m, 2H), 1.45–1.63 (m, 2H), 2.25–2.55 (m, 3H), 2.60–2.9 (m, 2H), 3.52–3.7 (m, 1H), 5.95 (br s, 1H), 6.59 ( s, 1H), 6.99 (d, J=7.5 Hz, 2H), 7.19 (d, J=7.7 Hz, 2H), 7.50–7.62 (m, 2H, 7.67 (d, J=7.2 Hz, 2H), 8.16 (s, 1H); HRMS. calcd for M+H: 455.2195. Found: 455.2195.

EXAMPLE 17

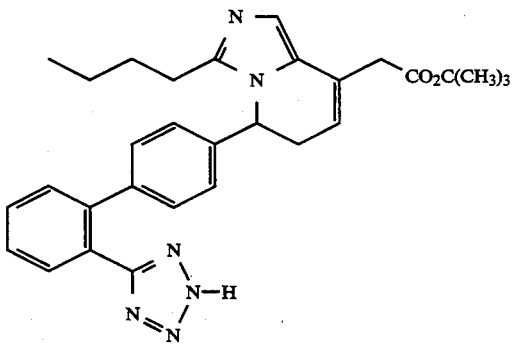

1,1-Dimethylethyl 3-butyl-5,6-dihydro-5-[2'-(1H-tetrazol-5-yl)[1,1'-biphenyl]-4-yl]imidazo[1,5-a]pyridin-8-acetate Step 1: Preparation of Deconjugated Ester To a solution of 178 mg (0,237 mmol) of conjugated butyl ester (obtained from Step 2 of Example 15) in 4 mL of THF at 0° C. was added 310 µL of 1.5M (0.467 mmol) LDA over a 2 min period, and the resulting solution was stirred at 0° C. for 10 min. The mixture was cooled to −78° C., stirred cold for 5 min, and quenched at −78° C. with dropwise addition of 100 µL of acetic acid in 1 mL of hexane. The mixture was stirred cold for 15 min, then warmed to room temperature and treated with aqueous NaHCO$_3$. The mixture was extracted with three 5 mL portions of methylene chloride. The combined extracts were washed with water, dried (MgSO$_4$) and concentrated in vacuo to give a crude biphenyl imidazolyl deconjugated ester. No starting material could be detected by the $^1$H NMR spectrum. The crude product was purified by chromatography to give 145 mg (81%) of the biphenyl imidazolyl deconjugated ester as a solid: $^1$H NMR (CDCl$_3$) δ 0.74 (t, J=7.23 Hz, 3H), 1.16 (septet, 7.39 Hz, 2H), 1.41 (s, 9H), 1.42–1.60 (m, 2H), 2.20 (dd, J=17.05, 6.61 Hz, 1H), 2.23–2.50 (m, 2H), 2.93 (ddd, J=17.3, 7.65, 1.74 Hz, 1H), 3.20 (s, 2H), 5.12–5.25 [m (with d at 5.17, J=7.66 Hz), 2H], 6.58 (d, J=8.0 Hz, 2H), 6.82 (d, J=7.84 Hz, 6H), 6.99 (d, J=8.27 Hz, 2H), 7.05 (s, 1H), 7.15–7.35 (m, 10H), 7.35–7.50 (m, 2H), 7.88 (dd, J=6.69, 2.24 Hz, 1H).

Step 2: Detritylation of Trityl Tetrazolyl Imidazole

A solution of 124 mg (0.165 mmol) of trityl biphenyl imidazole (obtained from Step 1) in 1 mL of water and 3 mL of acetic acid was stirred at room temperature for 2 days, and concentrated in vacuo. The residue was worked up as described in Step 5 of Example 1. The crude product was recrystallized from methylene chloride-ether to give 78 mg (93%) of the title compound of Example 17 as a solid: mp 221°–223° C. (decomposed); $^1$H NMR (CD$_3$OD) δ 0.83 (t, J=7.25 Hz, 3H), 1.15–1.60 [m (with s at 1.44), 13H], 2.72–2.97 (m, 3H), 3.19–3.3 (m, 1H), 3,40 (d, J=16.5 Hz, 1H), 3.49 (d, J=15.71 Hz, 1H), 5.88–6.0 [m (with d at 5.92, J=7.26 Hz), 2H], 7.11 (s, 4H), 7.51 (d, J=7.65 Hz, 1H), 7.55–7.62 (m, 2H), 7.62–7.73 (m, 2H); HRMS. calcd for M+H: 511.2821. Found: 511.2847.

EXAMPLE 18

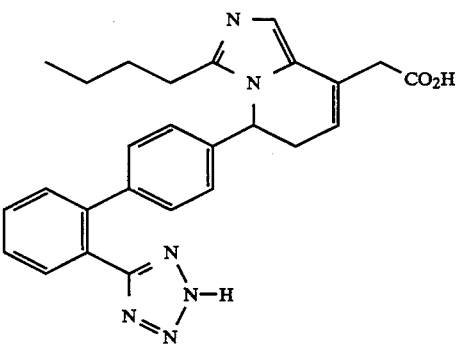

3-Butyl-5,6-dihydro-5-[2'-(1H-tetrazol-5-yl)[1,1'-biphenyl]-4-yl]imidazo[1,5-a]pyridin-8-acetic acid To a solution of 20 mg (0.039 mmol) of biphenyl imidazolyl tert-butyl ester (the title compound of Example 17) in 0.5 mL of chloroform was added 0.25 mL of TFA, and the progress of the reaction was monitored by $^1$H NMR. The resulting solution was stirred at room temperature for 75 min. The mixture was quenched with methanol and concentrated in vacuo. The residue was dissolved in a minimum amount of methanol and triturated with dropwise addition of methylene chloride-ether-hexane to give 15 mg (84%) of the title compound of Example 18 as a solid: mp 148°-171° C. (decomposed); $^1$H NMR (CD$_3$OD) δ 0.83 (t, J=7.25 Hz, 3H), 1.10-1.60 (m, 4H), 2.68-2.95 (m, 3H), 3.13 -3.35 (m, 1H), 3.48-3.60 (m, 2H), 5.80-6.0 [m (with d at 5.87, J=7.66 Hz), 2H], 7.10 (br s, 4H), 7.40-7.75 (m, 5H); HRMS. calcd for M+H: 455.2195. Found: 455.2215.

EXAMPLE 19

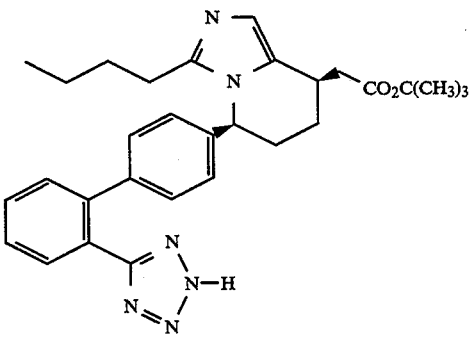

1,1-Dimethylethyl 3-butyl-5,6,7,8-tetrahydro-5-[2'-(1H-tetrazol-5-yl)[1,1'-biphenyl]-4-yl]imidazo[1,5-a]pyridin-cis-8-acetate A suspension of 30 mg (0.059 mmol) of the imidazolyl unsaturated butyl ester (the title compound of Example 17) and 20 mg (0.0188 mmol) of 10% palladium on charcoal in 1.5 mL of methanol was stirred at room temperature under an atmosphere of hydrogen gas for 4 h. The mixture was filtered through a pad of celite and concentrated in vacuo. The residue was recrystallized from methanol, ether and hexane to give 28 mg (93%) of the title compound as a solid: mp 194°-203° C. (decomposed); $^1$H NMR (CD$_3$OD) δ 0.84 (t, J=7.25 Hz, 3H), 1.15-1.75 (m, 15H), 1.82-2.00 (m, 1H), 2.20 (br d, J=14.1 Hz, 1H), 2.38-2.59 (m, 2H), 2.59-2.78 [m (with dd at 2.68, J=16.5, 6.85 Hz), 2H], 2.86 (br dd, J=16.1, 4.84 Hz, 1H), 5.80 (br d, J=4.03 Hz, 1H), 6.95 (d, J=7.65 Hz, 2H), 7.16 (d, J=7.66 Hz, 2H), 7.40 (s, 1H), 7.46-7.63 (m, 2H), 7.63-7.75 (m, 2H); HRMS. calcd for M+H: 513.2978. Found: 513.2992.

EXAMPLE 20

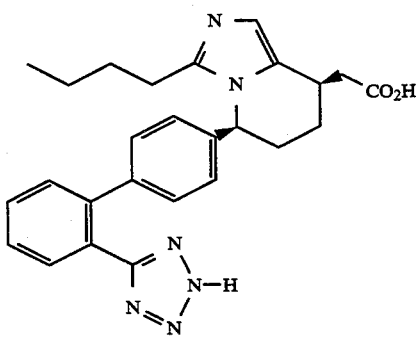

3-Butyl-5,6,7,8-tetrahydro-5-[2'-(1H-tetrazol-5-yl) [1,1'-biphenyl]-4-yl]imidazo[1,5-a]pyridin-cis-8-acetic acid To a solution of 17 mg (0.0332 mmol) of biphenyl imidazolyl tert-butyl ester (the title compound of Example 19) in 0.4 mL of CDCl$_3$ was added 0.2 mL of TFA, and the progress of the reaction was monitored by $^1$H NMR. The resulting solution was allowed to stand at room temperature for 1.5 h. The reaction mixture was diluted with methanol and concentrated. The residue was recrystallized from methanol, methylene chloride and ether to give 13 mg (87%) of the title compound of Example 20 as a solid: mp 119.5°-122° C.; $^1$H NMR (CD$_3$OD) δ 0.84 (t, J=7.25 Hz, 3H), 1.13-1.73 (m, 6H), 1.87-2.00 (m, 1H), 2.20 (br d, J=14.1 Hz, 1H), 2.40 -2.57 (m, 2H), 2.57-2.70 (m, 1H), 2.7 6 (dd, J=16.5, 6.45 Hz, 1H), 2.90 (dd, J=16.51, 5.23 Hz, 1H), 5.78 (d, J=4.43 Hz, 1H), 6.96 (d, J=8.05 Hz, 2H), 7.16 (d, J=8.46 Hz, 2H), 7.42 (s, 1H), 7.48-7.62 (m, 2H), 7.62-7.72 (m, 2H); HRMS. calcd for M+H: 457.2352. Found: 457.2371.

EXAMPLE 21

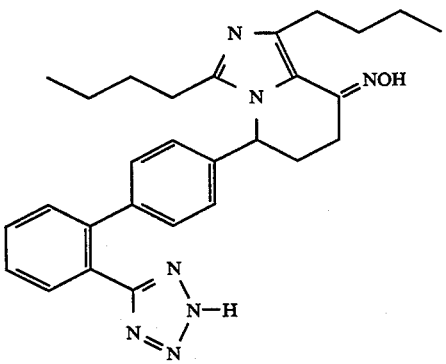

1,3-Dibutyl-5,6-dihydro-N-hydroxy-5-[2'-(1H-tetrazol-5-yl) [1.1'-biphenyl]-4-yl]imidazol[1,5-a]pyridin-8(7H)-imine A mixture of 44 mg (0.094 mmol) of biphenyl keto imidazole (the title compound of Example 5), 20 mg (0.29 mmol) of N-hydroxyamine (hydrochloride salt) and 30 mg of NaOAc in 2 mL of methanol was stirred at 60° C. for 16 h. The mixture was diluted with chloroform and filtered. The solid was washed with methanol. The filtrate was concentrated in vacuo and recrystallized from methanol and chloroform at 5° C. to give 33 mg of the oxime as a solid: $^1$H NMR (CD$_3$OD) δ 0.68 (t, J=7.31 Hz, 3H), 0.82 (t, J=7.30 Hz, 3H), 1.11 (quintet, J=7.65 Hz, 2H), 1.19-1.45 (m, 4H), 1.53 (quintet, J=7.66 Hz, 2H), 1.85-2.07 (m, 1H), 2.12-2.35 (br s, 2H), 2.56 (t, J=7.85 Hz, 2H), 2.83 (septet, J=8.28 Hz, 2H), 2.95 (d, J=17.50 Hz, 1H), 5.68 (s, 1H), 6.70 (d, J=8.00 Hz, 2H), 6.99 (d, J=8.20 Hz, 2H), 7.25-7.55 [m (with t at 7.33, J=7.38 Hz), 5H]; $^{13}$C NMR (CD$_3$OD) δ 12.22, 12.59, 15.93, 21.51, 21.85, 24.05, 25.34, 27.70, 28.42, 30.15, 55.53, 121.60, 124.73, 127.01, 127.07, 127.44, 127.67, 129.24, 129.40, 129.74, 130.19, 132.79, 136.43, 140.60, 140.80, 145.59, 145.86, 159.37; MS (FAB) m/e (relative intensity): 484 (100, M+H), 456 (60), 427 (30); HRMS. calcd for M+H: 484.2825. Found: 484.2837.

EXAMPLE 22

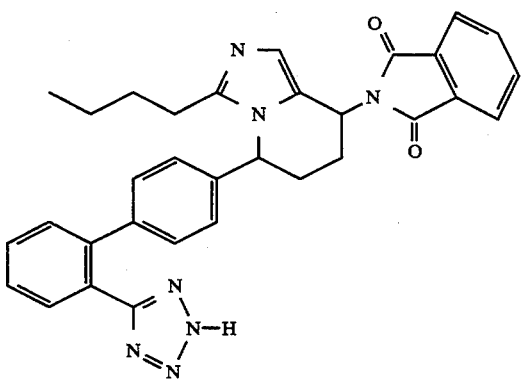

1-[3-Butyl-5,6,7,8-tetrahydro-5-[2'-(1H-tetrazol-5-yl)[1,1'-biphenyl]-4-yl]imidazo[1,5-a]pyridin-8-yl]phthalimide Step 1: Preparation of Biphenyl Phthalimidyl Imidazole To a solution of the biphenyl hydroxy imidazole (2.0 mmol, obtained from Step 1 of Example 13 or 14), phthalimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (MgSO$_4$) and concentrated in vacuo. The residue is purified to give the trityl protected phthalimidyl imidazole.

Step 2: Detritylation of Trityl Tetrazole

A solution of trityl-protected biphenyl phthalimidyl imidazole (2.0 mmol, obtained from Step 1) in 2 mL of water and 10 mL of acetic acid is stirred at room temperature until the reaction is complete. The mixture is concentrated in vacuo. The residue is worked up as described in Step 5 of Example 1 and purified give the title compound of Example 22.

EXAMPLE 23

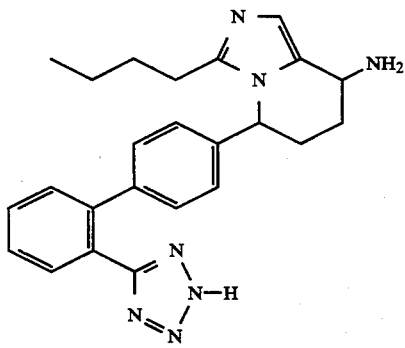

3-Butyl-5,6,7,8-tetrahydro-8-amino-5-[2'-(1H-tetrazol-5-yl)[1,1'-biphenyl]-4-yl]imidazo[1,5-a]pyridine A solution of phthalimidyl imidazole (0.6 mmol, the title compound of Example 22) and 3 μL (1.5 mmol) of hydrazine in 1.0 mL of ethanol is stirred at room temperature until the reaction is complete. The mixture is concentrated in vacuo, and purified to give the title compound of Example 23.

Alternatively, the title compound of Example 23 can be prepared from the corresponding oxime. A suspension of the biphenyl imidazolyl oxime (0.059 mmol, can be prepared from biphenyl ketone imidazole, the title compound of Example 12, according to the procedure described in Example 21) and 20 mg (0.0188 mmol) of 10% palladium on charcoal in 1.5 mL of methanol is stirred at room temperature under 50 psi of hydrogen gas until the reaction is complete. The mixture is filtered through a pad of celite, concentrated in vacuo and purified to give the title compound of Example 23.

The following examples, 24–1433, located in Tables I–XXIV, are further conformationally restricted angiotensin II antagonists embraced by Formula II above.

TABLE I

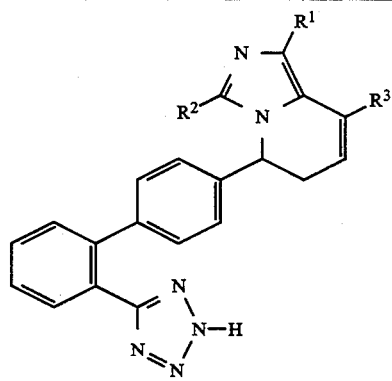

| EX. # | R$^1$ | R$^2$ | R$^3$ |
|---|---|---|---|
| 24 | H | C$_3$H$_7$(n) | H |
| 25 | H | C$_3$H$_7$(n) | C$_2$H$_5$ |
| 26 | H | C$_3$H$_7$(n) | CH$_2$OH |
| 27 | H | C$_3$H$_7$(n) | CO$_2$H |
| 28 | H | C$_3$H$_7$(n) | CH$_2$CO$_2$H |
| 29 | H | C$_3$H$_7$(n) | CH$_2$CO$_2$C(CH$_3$)$_3$ |
| 30 | H | C$_3$H$_7$(n) | CH(C$_2$H$_5$)CO$_2$H |
| 31 | H | C$_3$H$_7$(n) | CH(C$_2$H$_5$)CO$_2$C(CH$_3$)$_3$ |
| 32 | H | C$_3$H$_7$(n) | phenyl |
| 33 | H | C$_3$H$_7$(n) | benzyl |
| 34 | H | C$_3$H$_7$(n) | phenylethyl |
| 35 | H | C$_4$H$_9$(n) | C$_2$H$_5$ |
| 36 | H | C$_4$H$_9$(n) | CH$_2$OH |
| 37 | H | C$_4$H$_9$(n) | CO$_2$H |
| 38 | H | C$_4$H$_9$(n) | CH(C$_2$H$_5$)CO$_2$H |
| 39 | H | C$_4$H$_9$(n) | CH(C$_2$H$_5$)CO$_2$C(CH$_3$)$_3$ |
| 40 | H | C$_4$H$_9$(n) | phenyl |
| 41 | H | C$_4$H$_9$(n) | benzyl |
| 42 | H | C$_4$H$_9$(n) | phenylethyl |
| 43 | Cl | C$_3$H$_7$(n) | H |
| 44 | Cl | C$_3$H$_7$(n) | C$_2$H$_5$ |
| 45 | Cl | C$_3$H$_7$(n) | CH$_2$OH |
| 46 | Cl | C$_3$H$_7$(n) | CO$_2$H |
| 47 | Cl | C$_3$H$_7$(n) | CH$_2$CO$_2$H |
| 48 | Cl | C$_3$H$_7$(n) | CH$_2$CO$_2$C(CH$_3$)$_3$ |
| 49 | Cl | C$_3$H$_7$(n) | CH(C$_2$H$_5$)CO$_2$H |
| 50 | Cl | C$_3$H$_7$(n) | CH(C$_2$H$_5$)CO$_2$C(CH$_3$)$_3$ |
| 51 | Cl | C$_4$H$_9$(n) | H |
| 52 | Cl | C$_4$H$_9$(n) | C$_2$H$_5$ |
| 53 | Cl | C$_4$H$_9$(n) | CH$_2$OH |
| 54 | Cl | C$_4$H$_9$(n) | CO$_2$H |
| 55 | Cl | C$_4$H$_9$(n) | CH$_2$CO$_2$H |
| 56 | Cl | C$_4$H$_9$(n) | CH$_2$CO$_2$C(CH$_3$)$_3$ |
| 57 | Cl | C$_4$H$_9$(n) | CH(C$_2$H$_5$)CO$_2$H |
| 58 | Cl | C$_4$H$_9$(n) | CH(C$_2$H$_5$)CO$_2$C(CH$_3$)$_3$ |
| 59 | ethyl | C$_3$H$_7$(n) | H |
| 60 | ethyl | C$_3$H$_7$(n) | C$_2$H$_5$ |
| 61 | ethyl | C$_3$H$_7$(n) | CH$_2$OH |
| 62 | ethyl | C$_3$H$_7$(n) | CO$_2$H |
| 63 | ethyl | C$_3$H$_7$(n) | CH$_2$CO$_2$H |
| 64 | ethyl | C$_3$H$_7$(n) | CH$_2$CO$_2$C(CH$_3$)$_3$ |
| 65 | ethyl | C$_4$H$_9$(n) | H |
| 66 | ethyl | C$_4$H$_9$(n) | C$_2$H$_5$ |
| 67 | ethyl | C$_4$H$_9$(n) | CH$_2$OH |

TABLE I-continued

| EX. # | R¹ | R² | R³ |
|---|---|---|---|
| 68 | ethyl | $C_4H_9(n)$ | $CO_2H$ |
| 69 | ethyl | $C_4H_9(n)$ | $CH_2CO_2H$ |
| 70 | ethyl | $C_4H_9(n)$ | $CH_2CO_2C(CH_3)_3$ |
| 71 | n-butyl | $C_3H_7(n)$ | H |
| 72 | n-butyl | $C_3H_7(n)$ | $C_2H_5$ |
| 73 | n-butyl | $C_3H_7(n)$ | $CH_2OH$ |
| 74 | n-butyl | $C_3H_7(n)$ | $CO_2H$ |
| 75 | n-butyl | $C_3H_7(n)$ | $CH_2CO_2H$ |
| 76 | n-butyl | $C_3H_7(n)$ | $CH_2CO_2C(CH_3)_3$ |
| 77 | n-butyl | $C_4H_9(n)$ | $C_2H_5$ |
| 78 | n-butyl | $C_4H_9(n)$ | $CH_2OH$ |
| 79 | n-butyl | $C_4H_9(n)$ | $CO_2H$ |
| 80 | n-butyl | $C_4H_9(n)$ | $CH_2CO_2H$ |
| 81 | n-butyl | $C_4H_9(n)$ | $CH_2CO_2C(CH_3)_3$ |
| 82 | (2-ethylphenyl) | $C_3H_7(n)$ | H |
| 83 | (2-ethylphenyl) | $C_3H_7(n)$ | $C_2H_5$ |
| 84 | (2-ethylphenyl) | $C_3H_7(n)$ | $CH_2OH$ |
| 85 | (2-ethylphenyl) | $C_3H_7(n)$ | $CO_2H$ |
| 86 | (2-ethylphenyl) | $C_3H_7(n)$ | $CH_2CO_2H$ |
| 87 | (2-ethylphenyl) | $C_3H_7(n)$ | $CH_2CO_2C(CH_3)_3$ |
| 88 | (2-ethylphenyl) | $C_4H_9(n)$ | H |
| 89 | (2-ethylphenyl) | $C_4H_9(n)$ | $C_2H_5$ |
| 90 | (2-ethylphenyl) | $C_4H_9(n)$ | $CH_2OH$ |
| 91 | (2-ethylphenyl) | $C_4H_9(n)$ | $CO_2H$ |
| 92 | (2-ethylphenyl) | $C_4H_9(n)$ | $CH_2CO_2H$ |
| 93 | (2-ethylphenyl) | $C_4H_9(n)$ | $CH_2CO_2C(CH_3)_3$ |
| 94 | (2,6-dimethylphenyl) | $C_3H_7(n)$ | H |
| 95 | (2,6-dimethylphenyl) | $C_3H_7(n)$ | $C_2H_5$ |
| 96 | (2,6-dimethylphenyl) | $C_3H_7(n)$ | $CH_2OH$ |
| 97 | (2,6-dimethylphenyl) | $C_3H_7(n)$ | $CO_2H$ |
| 98 | (2,6-dimethylphenyl) | $C_3H_7(n)$ | $CH_2CO_2H$ |
| 99 | (2,6-dimethylphenyl) | $C_3H_7(n)$ | $CH_2CO_2C(CH_3)_3$ |
| 100 | (2,6-dimethylphenyl) | $C_4H_9(n)$ | H |
| 101 | (2,6-dimethylphenyl) | $C_4H_9(n)$ | $C_2H_5$ |
| 102 | (2,6-dimethylphenyl) | $C_4H_9(n)$ | $CH_2OH$ |
| 103 | (2,6-dimethylphenyl) | $C_4H_9(n)$ | $CO_2H$ |
| 104 | (2,6-dimethylphenyl) | $C_4H_9(n)$ | $CH_2CO_2H$ |
| 105 | (2,6-dimethylphenyl) | $C_4H_9(n)$ | $CH_2CO_2C(CH_3)_3$ |

TABLE II

| EX. # | R⁴ | R⁵ | R⁶ |
|---|---|---|---|
| 106 | H | $C_3H_7(n)$ | O |
| 107 | H | $C_3H_7(n)$ | S |
| 108 | H | $C_3H_7(n)$ | $CHCO_2H$ |
| 109 | H | $C_3H_7(n)$ | $CHCO_2C(CH_3)_3$ |
| 110 | H | $C_3H_7(n)$ | NOH |
| 111 | H | $C_4H_9(n)$ | S |
| 112 | H | $C_4H_9(n)$ | NOH |
| 113 | Cl | $C_3H_7(n)$ | O |
| 114 | Cl | $C_3H_7(n)$ | S |
| 115 | Cl | $C_3H_7(n)$ | $CHCO_2H$ |
| 116 | Cl | $C_3H_7(n)$ | $CHCO_2C(CH_3)_3$ |
| 117 | Cl | $C_3H_7(n)$ | NOH |
| 118 | Cl | $C_4H_9(n)$ | O |
| 119 | Cl | $C_4H_9(n)$ | S |
| 120 | Cl | $C_4H_9(n)$ | $CHCO_2H$ |
| 121 | Cl | $C_4H_9(n)$ | $CHCO_2C(CH_3)_3$ |
| 122 | Cl | $C_4H_9(n)$ | NOH |
| 123 | $C_2H_5$ | $C_3H_7(n)$ | O |
| 124 | $C_2H_5$ | $C_3H_7(n)$ | S |
| 125 | $C_2H_5$ | $C_3H_7(n)$ | $CHCO_2H$ |
| 126 | $C_2H_5$ | $C_3H_7(n)$ | $CHCO_2C(CH_3)_3$ |
| 127 | $C_2H_5$ | $C_3H_7(n)$ | NOH |
| 128 | $C_2H_5$ | $C_4H_9(n)$ | O |
| 129 | $C_2H_5$ | $C_4H_9(n)$ | S |
| 130 | $C_2H_5$ | $C_4H_9(n)$ | $CHCO_2H$ |
| 131 | $C_2H_5$ | $C_4H_9(n)$ | $CHCO_2C(CH_3)_3$ |
| 132 | $C_2H_5$ | $C_4H_9(n)$ | NOH |
| 133 | $C_4H_9(n)$ | $C_3H_7(n)$ | O |
| 134 | $C_4H_9(n)$ | $C_3H_7(n)$ | S |
| 135 | $C_4H_9(n)$ | $C_3H_7(n)$ | $CHCO_2H$ |
| 136 | $C_4H_9(n)$ | $C_3H_7(n)$ | $CHCO_2C(CH_3)_3$ |
| 137 | $C_4H_9(n)$ | $C_4H_9(n)$ | S |
| 138 | $C_4H_9(n)$ | $C_4H_9(n)$ | $CHCO_2C(CH_3)_3$ |
| 139 | $C_4H_9(n)$ | $C_4H_9(n)$ | NOH |
| 140 | (2-ethylphenyl) | $C_3H_7(n)$ | O |
| 141 | (2-ethylphenyl) | $C_3H_7(n)$ | S |
| 142 | (2-ethylphenyl) | $C_3H_7(n)$ | $CHCO_2H$ |
| 143 | (2-ethylphenyl) | $C_3H_7(n)$ | NOH |
| 144 | (2-ethylphenyl) | $C_4H_9(n)$ | O |
| 145 | (2-ethylphenyl) | $C_4H_9(n)$ | S |
| 146 | (2-ethylphenyl) | $C_4H_9(n)$ | $CHCO_2H$ |
| 147 | (2-ethylphenyl) | $C_4H_9(n)$ | NOH |
| 148 | (2,6-dimethylphenyl) | $C_3H_7(n)$ | O |
| 149 | (2,6-dimethylphenyl) | $C_3H_7(n)$ | S |
| 150 | (2,6-dimethylphenyl) | $C_3H_7(n)$ | $CHCO_2H$ |
| 151 | (2,6-dimethylphenyl) | $C_3H_7(n)$ | NOH |
| 152 | (2,6-dimethylphenyl) | $C_4H_9(n)$ | O |
| 153 | (2,6-dimethylphenyl) | $C_4H_9(n)$ | S |
| 154 | (2,6-dimethylphenyl) | $C_4H_9(n)$ | $CHCO_2H$ |
| 155 | (2,6-dimethylphenyl) | $C_4H_9(n)$ | NOH |

TABLE III

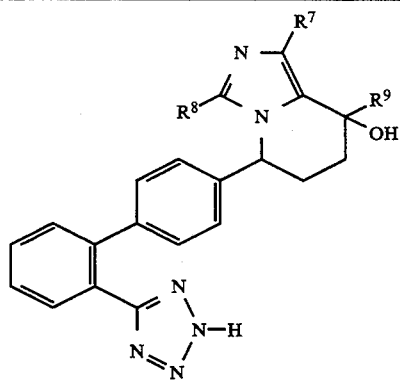

| EX. # | R⁷ | R⁸ | R⁹ |
|---|---|---|---|
| 156 | H | $C_3H_7(n)$ | $C_2H_5$ |
| 157 | H | $C_3H_7(n)$ | $C_3H_7(n)$ |
| 158 | H | $C_4H_9(n)$ | $C_2H_5$ |
| 159 | H | $C_4H_9(n)$ | $C_3H_7(n)$ |
| 160 | Cl | $C_3H_7(n)$ | $C_2H_5$ |
| 161 | Cl | $C_3H_7(n)$ | $C_3H_7(n)$ |
| 162 | Cl | $C_4H_9(n)$ | $C_2H_5$ |
| 163 | Cl | $C_4H_9(n)$ | $C_3H_7(n)$ |
| 164 | $C_2H_5$ | $C_3H_7(n)$ | $C_2H_5$ |
| 165 | $C_2H_5$ | $C_3H_7(n)$ | $C_3H_7(n)$ |
| 166 | $C_2H_5$ | $C_4H_9(n)$ | $C_2H_5$ |
| 167 | $C_2H_5$ | $C_4H_9(n)$ | $C_3H_7(n)$ |
| 168 | $C_4H_9(n)$ | $C_3H_7(n)$ | $C_2H_5$ |
| 169 | $C_4H_9(n)$ | $C_4H_9(n)$ | $C_2H_5$ |
| 170 | (2-ethylphenyl) | $C_3H_7(n)$ | $C_2H_5$ |
| 171 | (2-ethylphenyl) | $C_4H_9(n)$ | $C_2H_5$ |
| 172 | (2,6-dimethylphenyl) | $C_3H_7(n)$ | $C_2H_5$ |
| 173 | (2,6-dimethylphenyl) | $C_4H_9(n)$ | $C_2H_5$ |

TABLE IV

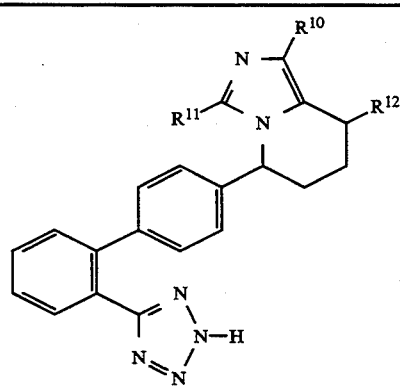

| EX. # | R¹⁰ | R¹¹ | R¹² |
|---|---|---|---|
| 174 | H | $C_3H_7(n)$ | H |
| 175 | H | $C_3H_7(n)$ | $NH_2$ |
| 176 | H | $C_3H_7(n)$ | OH |
| 177 | H | $C_3H_7(n)$ | $CH_2OH$ |
| 178 | H | $C_3H_7(n)$ | $CO_2H$ |
| 179 | H | $C_3H_7(n)$ | $CO_2C(CH_3)_3$ |
| 180 | H | $C_3H_7(n)$ | $C_2H_5$ |
| 181 | H | $C_3H_7(n)$ | $C_3H_7(n)$ |
| 182 | H | $C_3H_7(n)$ | $C_6H_5$ |
| 183 | H | $C_3H_7(n)$ | $C_6H_5CH_2$ |
| 184 | H | $C_3H_7(n)$ | (2-ethylphenyl) |
| 185 | H | $C_4H_9(n)$ | H |
| 186 | H | $C_4H_9(n)$ | $CH_2OH$ |
| 187 | H | $C_4H_9(n)$ | $CO_2H$ |
| 188 | H | $C_4H_9(n)$ | $CO_2C(CH_3)_3$ |
| 189 | H | $C_4H_9(n)$ | $C_2H_5$ |
| 190 | H | $C_4H_9(n)$ | $C_3H_7(n)$ |
| 191 | H | $C_4H_9(n)$ | $C_6H_5$ |
| 192 | H | $C_4H_9(n)$ | $C_6H_5CH_2$ |
| 193 | H | $C_4H_9(n)$ | (2-ethylphenyl) |

TABLE IV-continued

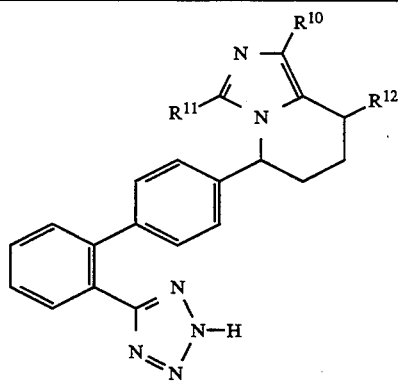

| EX. # | R¹⁰ | R¹¹ | R¹² |
|---|---|---|---|
| 194 | Cl | $C_3H_7(n)$ | H |
| 195 | Cl | $C_3H_7(n)$ | $NH_2$ |
| 196 | Cl | $C_3H_7(n)$ | OH |
| 197 | Cl | $C_3H_7(n)$ | $CH_2OH$ |
| 198 | Cl | $C_3H_7(n)$ | $CO_2H$ |
| 199 | Cl | $C_3H_7(n)$ | $CO_2C(CH_3)_3$ |
| 200 | Cl | $C_3H_7(n)$ | $C_2H_5$ |
| 201 | Cl | $C_3H_7(n)$ | $C_3H_7(n)$ |
| 202 | Cl | $C_3H_7(n)$ | $C_6H_5$ |
| 203 | Cl | $C_3H_7(n)$ | $C_6H_5CH_2$ |
| 204 | Cl | $C_3H_7(n)$ | (2-ethylphenyl) |
| 205 | Cl | $C_4H_9(n)$ | H |
| 206 | Cl | $C_4H_9(n)$ | $NH_2$ |
| 207 | Cl | $C_4H_9(n)$ | OH |
| 208 | Cl | $C_4H_9(n)$ | $CH_2OH$ |
| 209 | Cl | $C_4H_9(n)$ | $CO_2H$ |
| 210 | Cl | $C_4H_9(n)$ | $CO_2C(CH_3)_3$ |
| 211 | Cl | $C_4H_9(n)$ | $C_2H_5$ |
| 212 | Cl | $C_4H_9(n)$ | $C_3H_7(n)$ |
| 213 | Cl | $C_4H_9(n)$ | $C_6H_5$ |
| 214 | Cl | $C_4H_9(n)$ | $C_6H_5CH_2$ |
| 215 | Cl | $C_4H_9(n)$ | (2-ethylphenyl) |
| 216 | $C_2H_5$ | $C_3H_7(n)$ | H |
| 217 | $C_2H_5$ | $C_3H_7(n)$ | $NH_2$ |
| 218 | $C_2H_5$ | $C_3H_7(n)$ | OH |
| 219 | $C_2H_5$ | $C_3H_7(n)$ | $CH_2OH$ |
| 220 | $C_2H_5$ | $C_3H_7(n)$ | $CO_2H$ |
| 221 | $C_2H_5$ | $C_3H_7(n)$ | $CO_2C(CH_3)_3$ |
| 222 | $C_2H_5$ | $C_3H_7(n)$ | $C_2H_5$ |
| 223 | $C_2H_5$ | $C_4H_9(n)$ | H |
| 224 | $C_2H_5$ | $C_4H_9(n)$ | $NH_2$ |
| 225 | $C_2H_5$ | $C_4H_9(n)$ | OH |
| 226 | $C_2H_5$ | $C_4H_9(n)$ | $CH_2OH$ |
| 227 | $C_2H_5$ | $C_4H_9(n)$ | $CO_2H$ |
| 228 | $C_2H_5$ | $C_4H_9(n)$ | $CO_2C(CH_3)_3$ |
| 229 | $C_2H_5$ | $C_4H_9(n)$ | $C_2H_5$ |
| 230 | $C_4H_9(n)$ | $C_3H_7(n)$ | H |
| 231 | $C_4H_9(n)$ | $C_3H_7(n)$ | $NH_2$ |
| 232 | $C_4H_9(n)$ | $C_3H_7(n)$ | OH |
| 233 | $C_4H_9(n)$ | $C_3H_7(n)$ | $CH_2OH$ |
| 234 | $C_4H_9$ | $C_3H_7(n)$ | $CO_2H$ |
| 235 | $C_4H_9$ | $C_3H_7(n)$ | $CO_2C(CH_3)_3$ |
| 236 | $C_4H_9(n)$ | $C_3H_7(n)$ | $C_2H_5$ |
| 237 | $C_4H_9(n)$ | $C_3H_7(n)$ | $C_6H_5CH_2$ |
| 238 | $C_4H_9(n)$ | $C_4H_9(n)$ | $NH_2$ |
| 239 | $C_4H_9(n)$ | $C_4H_9(n)$ | $CH_2OH$ |
| 240 | $C_4H_9$ | $C_4H_9(n)$ | $CO_2H$ |
| 241 | $C_4H_9$ | $C_4H_9(n)$ | $CO_2C(CH_3)_3$ |
| 242 | $C_4H_9(n)$ | $C_4H_9(n)$ | $C_2H_5$ |
| 243 | (2-ethylphenyl) | $C_3H_7(n)$ | H |
| 244 | (2-ethylphenyl) | $C_3H_7(n)$ | $NH_2$ |
| 245 | (2-ethylphenyl) | $C_3H_7(n)$ | OH |
| 246 | (2-ethylphenyl) | $C_3H_7(n)$ | $CH_2OH$ |
| 247 | (2-ethylphenyl) | $C_3H_7(n)$ | $CO_2H$ |
| 248 | (2-ethylphenyl) | $C_3H_7(n)$ | $CO_2C(CH_3)_3$ |
| 249 | (2-ethylphenyl) | $C_3H_7(n)$ | $C_2H_5$ |
| 250 | (2-ethylphenyl) | $C_4H_9(n)$ | H |
| 251 | (2-ethylphenyl) | $C_4H_9(n)$ | $NH_2$ |
| 252 | (2-ethylphenyl) | $C_4H_9(n)$ | OH |
| 253 | (2-ethylphenyl) | $C_4H_9(n)$ | $CH_2OH$ |
| 254 | (2-ethylphenyl) | $C_4H_9(n)$ | $CO_2H$ |
| 255 | (2-ethylphenyl) | $C_4H_9(n)$ | $CO_2C(CH_3)_3$ |

TABLE IV-continued

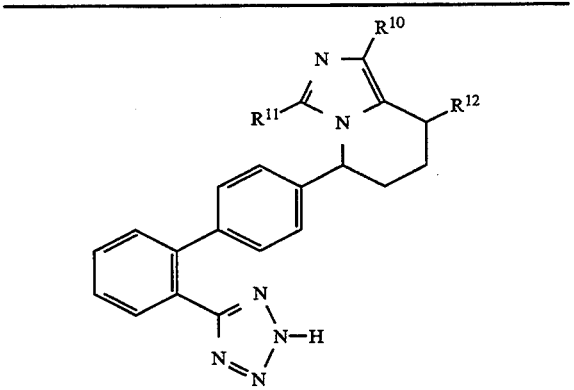

| EX. # | R10 | R11 | R12 |
|---|---|---|---|
| 256 | (2-ethylphenyl) | C4H9(n) | C2H5 |
| 257 | (2,6-dimethylphenyl) | C3H7(n) | H |
| 258 | (2,6-dimethylphenyl) | C3H7(n) | NH2 |
| 259 | (2,6-dimethylphenyl) | C3H7(n) | OH |
| 260 | (2,6-dimethylphenyl) | C3H7(n) | CH2OH |
| 261 | (2,6-dimethylphenyl) | C3H7(n) | CO2H |
| 262 | (2,6-dimethylphenyl) | C3H7(n) | CO2C(CH3)3 |
| 263 | (2,6-dimethylphenyl) | C3H7(n) | C2H5 |
| 264 | (2,6-dimethylphenyl) | C4H9(n) | H |
| 265 | (2,6-dimethylphenyl) | C4H9(n) | NH2 |
| 266 | (2,6-dimethylphenyl) | C4H9(n) | OH |
| 267 | (2,6-dimethylphenyl) | C4H9(n) | CH2OH |
| 268 | (2,6-dimethylphenyl) | C4H9(n) | CO2H |
| 269 | (2,6-dimethylphenyl) | C4H9(n) | CO2C(CH3)3 |
| 270 | (2,6-dimethylphenyl) | C4H9(n) | C2H5 |

TABLE V

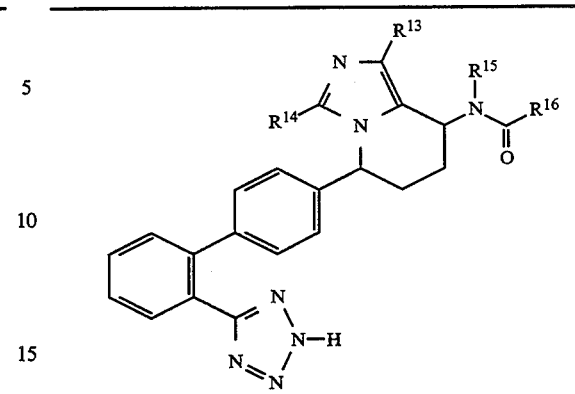

| EX. # | R13 | R14 | R15 | R16 |
|---|---|---|---|---|
| 271 | H | C3H7(n) | H | CH3 |
| 272 | H | C3H7(n) | CH3 | CH3 |
| 273 | H | C3H7(n) | C6H5CH2 | CH3 |
| 274 | H | C4H9(n) | H | CH3 |
| 275 | H | C4H9(n) | CH3 | CH3 |
| 276 | H | C4H9(n) | C6H5CH2 | CH3 |
| 277 | Cl | C3H7(n) | H | CH3 |
| 278 | Cl | C3H7(n) | CH3 | CH3 |
| 279 | Cl | C3H7(n) | C6H5CH2 | CH3 |
| 280 | Cl | C4H9(n) | H | CH3 |
| 281 | Cl | C4H9(n) | CH3 | CH3 |
| 282 | Cl | C4H9(n) | C6H5CH2 | CH3 |
| 283 | C2H5 | C3H7(n) | H | CH3 |
| 284 | C2H5 | C3H7(n) | CH3 | CH3 |
| 285 | C2H5 | C4H9(n) | H | CH3 |
| 286 | C2H5 | C4H9(n) | CH3 | CH3 |
| 287 | C4H9(n) | C3H7(n) | H | CH3 |
| 288 | C4H9(n) | C3H7(n) | CH3 | CH3 |
| 289 | C4H9(n) | C4H9(n) | H | CH3 |
| 290 | C4H9(n) | C4H9(n) | CH3 | CH3 |
| 291 | (2-ethylphenyl) | C3H7(n) | H | CH3 |
| 292 | (2-ethylphenyl) | C3H7(n) | CH3 | CH3 |
| 293 | (2-ethylphenyl) | C4H9(n) | H | CH3 |

TABLE V-continued

| EX. # | R13 | R14 | R15 | R16 |
|---|---|---|---|---|
| 294 | (2-ethylphenyl) | C4H9(n) | CH3 | CH3 |
| 295 | (2,6-dimethylphenyl) | C3H7(n) | H | CH3 |
| 296 | (2,6-dimethylphenyl) | C3H7(n) | CH3 | CH3 |
| 297 | (2,6-dimethylphenyl) | C4H9(n) | H | CH3 |
| 298 | (2,6-dimethylphenyl) | C4H9(n) | CH3 | CH3 |
| 299 | H | C3H7(n) | H | C2H5 |
| 300 | H | C3H7(n) | CH3 | C2H5 |
| 301 | H | C3H7(n) | C2H5 | C2H5 |
| 302 | H | C4H9(n) | H | C2H5 |
| 303 | H | C4H9(n) | CH3 | C2H5 |
| 304 | H | C4H9(n) | C2H5 | C2H5 |
| 305 | Cl | C3H7(n) | H | C2H5 |
| 306 | Cl | C3H7(n) | CH3 | C2H5 |
| 307 | Cl | C3H7(n) | C2H5 | C2H5 |
| 308 | Cl | C4H9(n) | H | C2H5 |
| 309 | Cl | C4H9(n) | CH3 | C2H5 |
| 310 | Cl | C4H9(n) | C2H5 | C2H5 |
| 311 | C2H5 | C3H7(n) | H | C2H5 |
| 312 | C2H5 | C3H7(n) | CH3 | C2H5 |
| 313 | C2H5 | C4H9(n) | H | C2H5 |
| 314 | C2H5 | C4H9(n) | CH3 | C2H5 |
| 315 | (2-ethylphenyl) | C3H7(n) | H | C2H5 |
| 316 | (2-ethylphenyl) | C4H9(n) | H | C2H5 |
| 317 | (2,6-dimethylphenyl) | C3H7(n) | H | C2H5 |
| 318 | (2,6-dimethylphenyl) | C4H9(n) | H | C2H5 |
| 319 | H | C3H7(n) | H | C6H5 |
| 320 | H | C3H7(n) | CH3 | C6H5 |
| 321 | H | C4H9(n) | H | C6H5 |
| 322 | H | C4H9(n) | CH3 | C6H5 |
| 323 | Cl | C3H7(n) | H | C6H5 |
| 324 | Cl | C3H7(n) | CH3 | C6H5 |
| 325 | Cl | C4H9(n) | H | C6H5 |
| 326 | Cl | C4H9(n) | CH3 | C6H5 |
| 327 | C2H5 | C3H7(n) | H | C6H5 |
| 328 | C2H5 | C3H7(n) | CH3 | C6H5 |
| 329 | C2H5 | C4H9(n) | H | C6H5 |
| 330 | C2H5 | C4H9(n) | CH3 | C6H5 |
| 331 | C4H9(n) | C3H7(n) | H | C6H5 |
| 332 | C4H9(n) | C3H7(n) | CH3 | C6H5 |
| 333 | C4H9(n) | C4H9(n) | H | C6H5 |
| 334 | C4H9(n) | C4H9(n) | CH3 | C6H5 |
| 335 | C4H9(n) | C4H9(n) | H | CH2CH2CO2H |
| 336 | C4H9(n) | C4H9(n) | CH3 | CH2CH2CO2H |
| 337 | (2-ethylphenyl) | C3H7(n) | H | CH2CH2CO2H |
| 338 | (2-ethylphenyl) | C3H7(n) | CH3 | CH2CH2CO2H |
| 339 | (2-ethylphenyl) | C4H9(n) | H | CH2CH2CO2H |
| 340 | (2-ethylphenyl) | C4H9(n) | CH3 | CH2CH2CO2H |
| 341 | (2,6-dimethylphenyl) | C3H7(n) | H | CH2CH2CO2H |
| 342 | (2,6-dimethylphenyl) | C3H7(n) | CH3 | CH2CH2CO2H |
| 343 | (2,6-dimethylphenyl) | C4H9(n) | H | CH2CH2CO2H |
| 344 | (2,6-dimethyl- | C4H9(n) | CH3 | CH2CH2CO2H |

TABLE V-continued

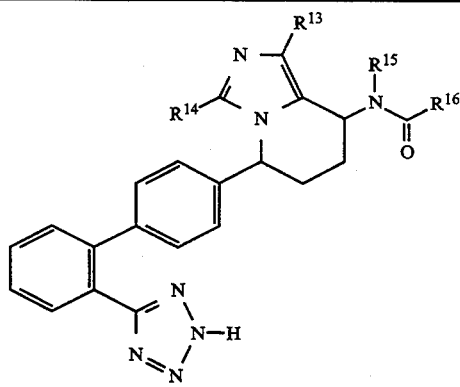

| EX. # | R¹³ | R¹⁴ | R¹⁵ | R¹⁶ |
|---|---|---|---|---|
| | phenyl) | | | |

TABLE VI

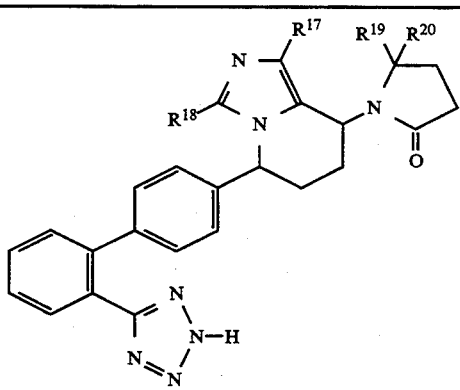

| EX. # | R¹⁷ | R¹⁸ | R¹⁹, R²⁰ |
|---|---|---|---|
| 345 | H | $C_3H_7(n)$ | O |
| 346 | H | $C_3H_7(n)$ | H, H |
| 347 | H | $C_3H_7(n)$ | H, $CH_3$ |
| 348 | H | $C_3H_7(n)$ | H, $C_2H_5$ |
| 349 | H | $C_3H_7(n)$ | H, $CH_2OH$ |
| 350 | H | $C_3H_7(n)$ | H, $CO_2H$ |
| 351 | H | $C_4H_9(n)$ | O |
| 352 | H | $C_4H_9(n)$ | H, H |
| 353 | H | $C_4H_9(n)$ | H, $CH_3$ |
| 354 | H | $C_4H_9(n)$ | H, $C_2H_5$ |
| 355 | H | $C_4H_9(n)$ | H, $CH_2OH$ |
| 356 | H | $C_4H_9(n)$ | H, $CO_2H$ |
| 357 | Cl | $C_3H_7(n)$ | O |
| 358 | Cl | $C_3H_7(n)$ | H, H |
| 359 | Cl | $C_3H_7(n)$ | H, $CH_3$ |
| 360 | Cl | $C_3H_7(n)$ | H, $C_2H_5$ |
| 361 | Cl | $C_3H_7(n)$ | H, $CH_2OH$ |
| 362 | Cl | $C_3H_7(n)$ | H, $CO_2H$ |
| 363 | Cl | $C_4H_9(n)$ | O |
| 364 | Cl | $C_4H_9(n)$ | H, H |
| 365 | Cl | $C_4H_9(n)$ | H, $CH_3$ |
| 366 | Cl | $C_4H_9(n)$ | H, $C_2H_5$ |
| 367 | Cl | $C_4H_9(n)$ | H, $CH_2OH$ |
| 368 | Cl | $C_4H_9(n)$ | H, $CO_2H$ |
| 369 | $C_2H_5$ | $C_3H_7(n)$ | O |
| 370 | $C_2H_5$ | $C_3H_7(n)$ | H, H |
| 371 | $C_2H_5$ | $C_3H_7(n)$ | H, $CH_3$ |
| 372 | $C_2H_5$ | $C_3H_7(n)$ | H, $C_2H_5$ |
| 373 | $C_2H_5$ | $C_3H_7(n)$ | H, $CH_2OH$ |
| 374 | $C_2H_5$ | $C_3H_7(n)$ | H, $CO_2H$ |
| 375 | $C_2H_5$ | $C_4H_9(n)$ | O |
| 376 | $C_2H_5$ | $C_4H_9(n)$ | H, H |
| 377 | $C_2H_5$ | $C_4H_9(n)$ | H, $CH_3$ |
| 378 | $C_2H_5$ | $C_4H_9(n)$ | H, $C_2H_5$ |
| 379 | $C_2H_5$ | $C_4H_9(n)$ | H, $CH_2OH$ |
| 380 | $C_2H_5$ | $C_4H_9(n)$ | H, $CO_2H$ |
| 381 | $C_4H_9(n)$ | $C_3H_7(n)$ | O |

TABLE VI-continued

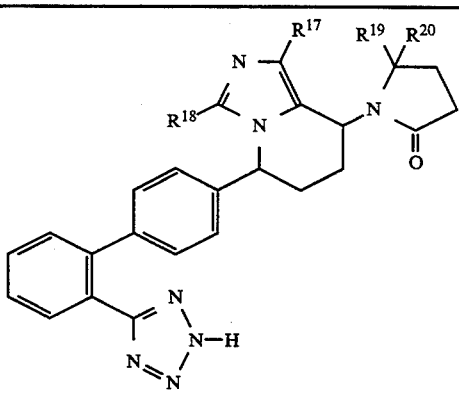

| EX. # | R¹⁷ | R¹⁸ | R¹⁹, R²⁰ |
|---|---|---|---|
| 382 | $C_4H_9(n)$ | $C_3H_7(n)$ | H, H |
| 383 | $C_4H_9(n)$ | $C_3H_7(n)$ | H, $CH_3$ |
| 384 | $C_4H_9(n)$ | $C_3H_7(n)$ | H, $CH_2OH$ |
| 385 | $C_4H_9(n)$ | $C_3H_7(n)$ | H, $CO_2H$ |
| 386 | $C_4H_9(n)$ | $C_4H_9(n)$ | H, H |
| 387 | $C_4H_9(n)$ | $C_4H_9(n)$ | H, $CH_3$ |
| 388 | $C_4H_9(n)$ | $C_4H_9(n)$ | H, $CH_2OH$ |
| 389 | $C_4H_9(n)$ | $C_4H_9(n)$ | H, $CO_2H$ |
| 390 | (2-ethylphenyl) | $C_3H_7(n)$ | O |
| 391 | (2-ethylphenyl) | $C_3H_7(n)$ | H, H |
| 392 | (2-ethylphenyl) | $C_3H_7(n)$ | H, $CH_3$ |
| 393 | (2-ethylphenyl) | $C_3H_7(n)$ | $CH_3$, $CH_3$ |
| 394 | (2-ethylphenyl) | $C_3H_7(n)$ | H, $CH_2OH$ |
| 395 | (2-ethylphenyl) | $C_3H_7(n)$ | H, $CO_2H$ |
| 396 | (2-ethylphenyl) | $C_4H_9(n)$ | O |
| 397 | (2-ethylphenyl) | $C_4H_9(n)$ | H, H |
| 398 | (2-ethylphenyl) | $C_4H_9(n)$ | H, $CH_3$ |
| 399 | (2-ethylphenyl) | $C_4H_9(n)$ | $CH_3$, $CH_3$ |
| 400 | (2-ethylphenyl) | $C_4H_9(n)$ | H, $CH_2OH$ |
| 401 | (2-ethylphenyl) | $C_4H_9(n)$ | H, $CO_2H$ |

TABLE VII

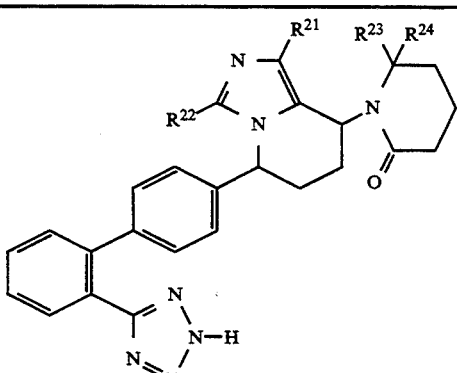

| EX. # | R²¹ | R²² | R²³, R²⁴ |
|---|---|---|---|
| 402 | H | $C_3H_7(n)$ | O |
| 403 | H | $C_3H_7(n)$ | H, H |
| 404 | H | $C_3H_7(n)$ | H, $CH_3$ |
| 405 | H | $C_3H_7(n)$ | H, $C_2H_5$ |
| 406 | H | $C_3H_7(n)$ | H, $CH_2OH$ |
| 407 | H | $C_3H_7(n)$ | H, $CO_2H$ |
| 408 | H | $C_4H_9(n)$ | O |
| 409 | H | $C_4H_9(n)$ | H, H |
| 410 | H | $C_4H_9(n)$ | H, $CH_3$ |
| 411 | H | $C_4H_9(n)$ | H, $C_2H_5$ |
| 412 | H | $C_4H_9(n)$ | H, $CH_2OH$ |
| 413 | H | $C_4H_9(n)$ | H, $CO_2H$ |
| 414 | Cl | $C_3H_7(n)$ | O |
| 415 | Cl | $C_3H_7(n)$ | H, H |
| 416 | Cl | $C_3H_7(n)$ | H, $CH_3$ |
| 417 | Cl | $C_3H_7(n)$ | $CH_3$, $CH_3$ |
| 418 | Cl | $C_3H_7(n)$ | H, $CH_2OH$ |
| 419 | Cl | $C_3H_7(n)$ | H, $CO_2H$ |

TABLE VII-continued

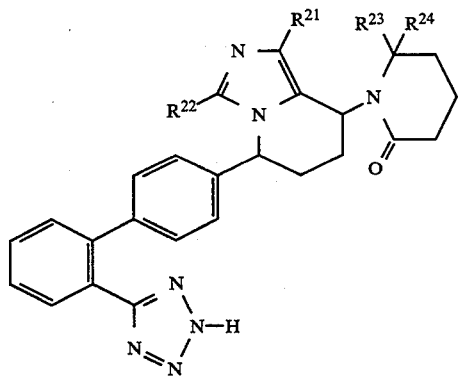

| EX. # | R²¹ | R²² | R²³, R²⁴ |
|---|---|---|---|
| 420 | Cl | C₄H₉(n) | O |
| 421 | Cl | C₄H₉(n) | H, H |
| 422 | Cl | C₄H₉(n) | H, CH₃ |
| 423 | Cl | C₄H₉(n) | H, C₂H₅ |
| 424 | Cl | C₄H₉(n) | H, CH₂OH |
| 425 | Cl | C₄H₉(n) | H, CO₂H |
| 426 | C₂H₅ | C₃H₇(n) | O |
| 427 | C₂H₅ | C₃H₇(n) | H, H |
| 428 | C₂H₅ | C₃H₇(n) | H, CH₃ |
| 429 | C₂H₅ | C₃H₇(n) | H, C₂H₅ |
| 430 | C₂H₅ | C₃H₇(n) | H, CH₂OH |
| 431 | C₂H₅ | C₃H₇(n) | H, CO₂H |
| 432 | C₂H₅ | C₄H₉(n) | O |
| 433 | C₂H₅ | C₄H₉(n) | H, H |
| 434 | C₂H₅ | C₄H₉(n) | H, CH₃ |
| 435 | C₂H₅ | C₄H₉(n) | H, C₂H₅ |
| 436 | C₂H₅ | C₄H₉(n) | H, CH₂OH |
| 437 | C₂H₅ | C₄H₉(n) | H, CO₂H |
| 438 | C₄H₉(n) | C₃H₇(n) | O |
| 439 | C₄H₉(n) | C₃H₇(n) | H, H |
| 440 | C₄H₉(n) | C₃H₇(n) | H, CH₃ |
| 441 | C₄H₉(n) | C₃H₇(n) | H, CH₂OH |
| 442 | C₄H₉(n) | C₃H₇(n) | H, CO₂H |
| 443 | C₄H₉(n) | C₄H₉(n) | O |
| 444 | C₄H₉(n) | C₄H₉(n) | H, H |
| 445 | C₄H₉(n) | C₄H₉(n) | H, CH₃ |
| 446 | C₄H₉(n) | C₄H₉(n) | H, CH₂OH |
| 447 | C₄H₉(n) | C₄H₉(n) | H, CO₂H |
| 448 | (2-ethylphenyl) | C₃H₇(n) | O |
| 449 | (2-ethylphenyl) | C₃H₇(n) | H, H |
| 450 | (2-ethylphenyl) | C₃H₇(n) | H, CH₃ |
| 451 | (2-ethylphenyl) | C₃H₇(n) | CH₃, CH₃ |
| 452 | (2-ethylphenyl) | C₃H₇(n) | H, CH₂OH |
| 453 | (2-ethylphenyl) | C₃H₇(n) | H, CO₂H |
| 454 | (2-ethylphenyl) | C₄H₉(n) | O |
| 455 | (2-ethylphenyl) | C₄H₉(n) | H, H |
| 456 | (2-ethylphenyl) | C₄H₉(n) | H, CH₃ |
| 457 | (2-ethylphenyl) | C₄H₉(n) | CH₃, CH₃ |
| 458 | (2-ethylphenyl) | C₄H₉(n) | H, CH₂OH |
| 459 | (2-ethylphenyl) | C₄H₉(n) | H, CO₂H |

TABLE VIII

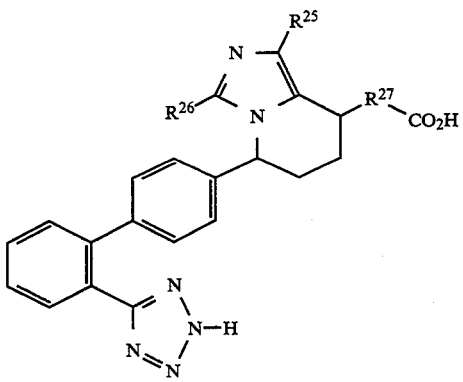

| EX. # | R²⁵ | R²⁶ | R²⁷ |
|---|---|---|---|
| 460 | H | C₃H₇(n) | CH₂ |
| 461 | H | C₃H₇(n) | CH(C₂H₅) |
| 462 | H | C₃H₇(n) | CH(CH₂C₆H₅) |
| 463 | H | C₃H₇(n) | CH₂CH₂ |
| 464 | H | C₃H₇(n) | CH(C₂H₅)CH₂ |
| 465 | H | C₃H₇(n) | CH(CH₂C₆H₅)CH₂ |
| 466 | H | C₄H₉(n) | CH(C₂H₅) |
| 467 | H | C₄H₉(n) | CH(CH₂C₆H₅) |
| 468 | H | C₄H₉(n) | CH₂CH₂ |
| 469 | H | C₄H₉(n) | CH(C₂H₅)CH₂ |
| 470 | H | C₄H₉(n) | CH(CH₂C₆H₅)CH₂ |
| 471 | Cl | C₃H₇(n) | CH₂ |
| 472 | Cl | C₃H₇(n) | CH(C₂H₅) |
| 473 | Cl | C₃H₇(n) | CH(CH₂C₆H₅) |
| 474 | Cl | C₃H₇(n) | CH₂CH₂ |
| 475 | Cl | C₃H₇(n) | CH(C₂H₅)CH₂ |
| 476 | Cl | C₃H₇(n) | CH(CH₂C₆H₅)CH₂ |
| 477 | Cl | C₄H₉(n) | CH₂ |
| 478 | Cl | C₄H₉(n) | CH(C₂H₅) |
| 479 | Cl | C₄H₉(n) | CH(CH₂C₆H₅) |
| 480 | Cl | C₄H₉(n) | CH₂CH₂ |
| 481 | Cl | C₄H₉(n) | CH(C₂H₅)CH₂ |
| 482 | Cl | C₄H₉(n) | CH(CH₂C₆H₅)CH₂ |
| 483 | C₂H₅ | C₃H₇(n) | CH₂ |
| 484 | C₂H₅ | C₃H₇(n) | CH(C₂H₅) |
| 485 | C₂H₅ | C₃H₇(n) | CH(CH₂C₆H₅) |
| 486 | C₂H₅ | C₃H₇(n) | CH₂CH₂ |
| 487 | C₂H₅ | C₃H₇(n) | CH(C₂H₅)CH₂ |
| 488 | C₂H₅ | C₃H₇(n) | CH(CH₂C₆H₅)CH₂ |
| 489 | C₂H₅ | C₄H₉(n) | CH₂ |
| 490 | C₂H₅ | C₄H₉(n) | CH(C₂H₅) |
| 491 | C₂H₅ | C₄H₉(n) | CH(CH₂C₆H₅) |
| 492 | C₂H₅ | C₄H₉(n) | CH₂CH₂ |
| 493 | C₂H₅ | C₄H₉(n) | CH(C₂H₅)CH₂ |
| 494 | C₂H₅ | C₄H₉(n) | CH(CH₂C₆H₅)CH₂ |
| 495 | C₄H₉(n) | C₃H₇(n) | CH₂ |
| 496 | C₄H₉(n) | C₃H₇(n) | CH₂CH₂ |
| 497 | C₄H₉(n) | C₄H₉(n) | CH₂ |
| 498 | C₄H₉(n) | C₄H₉(n) | CH₂CH₂ |
| 499 | (2-ethylphenyl) | C₃H₇(n) | CH₂ |
| 500 | (2-ethylphenyl) | C₃H₇(n) | CH₂CH₂ |
| 501 | (2-ethylphenyl) | C₄H₉(n) | CH₂ |
| 502 | (2-ethylphenyl) | C₄H₉(n) | CH₂CH₂ |
| 503 | (2,6-dimethylphenyl) | C₃H₇(n) | CH₂ |
| 504 | (2,6-dimethylphenyl) | C₃H₇(n) | CH₂CH₂ |
| 505 | (2,6-dimethylphenyl) | C₄H₉(n) | CH₂ |
| 506 | (2,6-dimethylphenyl) | C₄H₉(n) | CH₂CH₂ |

TABLE IX

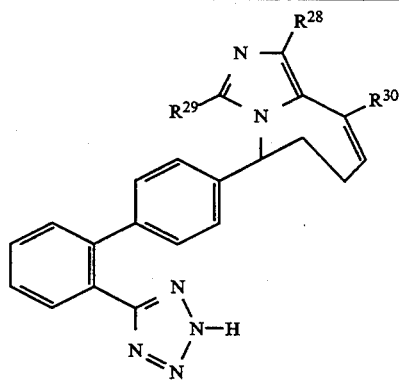

| EX. # | R28 | R29 | R30 |
|---|---|---|---|
| 507 | H | $C_3H_7(n)$ | H |
| 508 | H | $C_3H_7(n)$ | $C_2H_5$ |
| 509 | H | $C_3H_7(n)$ | $CH_2OH$ |
| 510 | H | $C_3H_7(n)$ | $CO_2H$ |
| 511 | H | $C_3H_7(n)$ | $CH_2CO_2H$ |
| 512 | H | $C_3H_7(n)$ | $CH_2CO_2C(CH_3)_3$ |
| 513 | H | $C_3H_7(n)$ | $CH(C_2H_5)CO_2H$ |
| 514 | H | $C_3H_7(n)$ | $CH(C_2H_5)CO_2C(CH_3)_3$ |
| 515 | H | $C_3H_7(n)$ | phenyl |
| 516 | H | $C_3H_7(n)$ | benzyl |
| 517 | H | $C_3H_7(n)$ | phenylethyl |
| 518 | H | $C_4H_9(n)$ | H |
| 519 | H | $C_4H_9(n)$ | $C_2H_5$ |
| 520 | H | $C_4H_9(n)$ | $CH_2OH$ |
| 521 | H | $C_4H_9(n)$ | $CO_2H$ |
| 522 | H | $C_4H_9(n)$ | $CH_2CO_2H$ |
| 523 | H | $C_4H_9(n)$ | $CH_2CO_2C(CH_3)_3$ |
| 524 | H | $C_4H_9(n)$ | $CH(C_2H_5)CO_2H$ |
| 525 | H | $C_4H_9(n)$ | $CH(C_2H_5)CO_2C(CH_3)_3$ |
| 526 | H | $C_4H_9(n)$ | phenyl |
| 527 | H | $C_4H_9(n)$ | benzyl |
| 528 | H | $C_4H_9(n)$ | phenylethyl |
| 529 | Cl | $C_3H_7(n)$ | H |
| 530 | Cl | $C_3H_7(n)$ | $C_2H_5$ |
| 531 | Cl | $C_3H_7(n)$ | $CH_2OH$ |
| 532 | Cl | $C_3H_7(n)$ | $CO_2H$ |
| 533 | Cl | $C_3H_7(n)$ | $CH_2CO_2H$ |
| 534 | Cl | $C_3H_7(n)$ | $CH_2CO_2C(CH_3)_3$ |
| 535 | Cl | $C_3H_7(n)$ | $CH(C_2H_5)CO_2H$ |
| 536 | Cl | $C_3H_7(n)$ | $CH(C_2H_5)CO_2C(CH_3)_3$ |
| 537 | Cl | $C_4H_9(n)$ | H |
| 538 | Cl | $C_4H_9(n)$ | $C_2H_5$ |
| 539 | Cl | $C_4H_9(n)$ | $CH_2OH$ |
| 540 | Cl | $C_4H_9(n)$ | $CO_2H$ |
| 541 | Cl | $C_4H_9(n)$ | $CH_2CO_2H$ |
| 542 | Cl | $C_4H_9(n)$ | $CH_2CO_2C(CH_3)_3$ |
| 543 | Cl | $C_4H_9(n)$ | $CH(C_2H_5)CO_2H$ |
| 544 | Cl | $C_4H_9(n)$ | $CH(C_2H_5)CO_2C(CH_3)_3$ |
| 545 | ethyl | $C_3H_7(n)$ | H |
| 546 | ethyl | $C_3H_7(n)$ | $C_2H_5$ |
| 547 | ethyl | $C_3H_7(n)$ | $CH_2OH$ |
| 548 | ethyl | $C_3H_7(n)$ | $CO_2H$ |
| 549 | ethyl | $C_3H_7(n)$ | $CH_2CO_2H$ |
| 550 | ethyl | $C_3H_7(n)$ | $CH_2CO_2C(CH_3)_3$ |
| 551 | ethyl | $C_4H_9(n)$ | H |
| 552 | ethyl | $C_4H_9(n)$ | $C_2H_5$ |
| 553 | ethyl | $C_4H_9(n)$ | $CH_2OH$ |
| 554 | ethyl | $C_4H_9(n)$ | $CO_2H$ |
| 555 | ethyl | $C_4H_9(n)$ | $CH_2CO_2H$ |
| 556 | ethyl | $C_4H_9(n)$ | $CH_2CO_2C(CH_3)_3$ |
| 557 | n-butyl | $C_3H_7(n)$ | H |
| 558 | n-butyl | $C_3H_7(n)$ | $C_2H_5$ |
| 559 | n-butyl | $C_3H_7(n)$ | $CH_2OH$ |
| 560 | n-butyl | $C_3H_7(n)$ | $CO_2H$ |
| 561 | n-butyl | $C_3H_7(n)$ | $CH_2CO_2H$ |
| 562 | n-butyl | $C_3H_7(n)$ | $CH_2CO_2C(CH_3)_3$ |
| 563 | n-butyl | $C_4H_9(n)$ | $C_2H_5$ |
| 564 | n-butyl | $C_4H_9(n)$ | $CH_2OH$ |
| 565 | n-butyl | $C_4H_9(n)$ | $CH_2CO_2H$ |
| 566 | n-butyl | $C_4H_9(n)$ | $CH_2CO_2C(CH_3)_3$ |
| 567 | (2-ethylphenyl) | $C_3H_7(n)$ | H |
| 568 | (2-ethylphenyl) | $C_3H_7(n)$ | $C_2H_5$ |

TABLE IX-continued

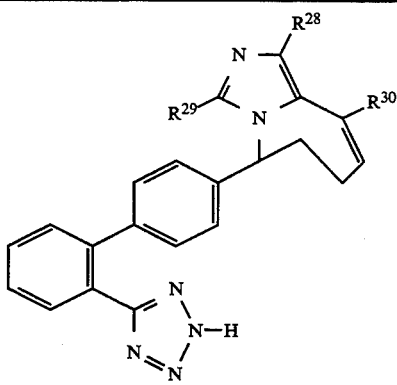

| EX. # | R28 | R29 | R30 |
|---|---|---|---|
| 569 | (2-ethylphenyl) | $C_3H_7(n)$ | $CH_2OH$ |

TABLE X

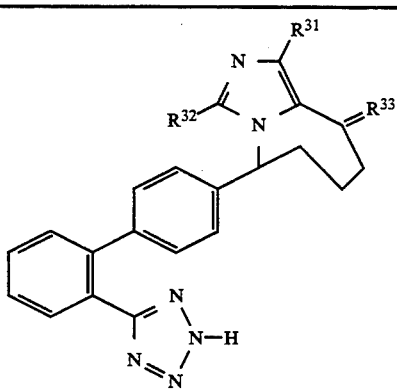

| EX. # | R31 | R32 | R33 |
|---|---|---|---|
| 570 | H | $C_3H_7(n)$ | O |
| 571 | H | $C_3H_7(n)$ | S |
| 572 | H | $C_3H_7(n)$ | $CHCO_2H$ |
| 573 | H | $C_3H_7(n)$ | $CHCO_2C(CH_3)_3$ |
| 574 | H | $C_3H_7(n)$ | NOH |
| 575 | H | $C_4H_9(n)$ | O |
| 576 | H | $C_4H_9(n)$ | S |
| 577 | H | $C_4H_9(n)$ | $CHCO_2H$ |
| 578 | H | $C_4H_9(n)$ | $CHCO_2C(CH_3)_3$ |
| 579 | H | $C_4H_9(n)$ | NOH |
| 580 | Cl | $C_3H_7(n)$ | O |
| 581 | Cl | $C_3H_7(n)$ | S |
| 582 | Cl | $C_3H_7(n)$ | $CHCO_2H$ |
| 583 | Cl | $C_3H_7(n)$ | $CHCO_2C(CH_3)_3$ |
| 584 | Cl | $C_3H_7(n)$ | NOH |
| 585 | Cl | $C_4H_9(n)$ | O |
| 586 | Cl | $C_4H_9(n)$ | S |
| 587 | Cl | $C_4H_9(n)$ | $CHCO_2H$ |
| 588 | Cl | $C_4H_9(n)$ | $CHCO_2C(CH_3)_3$ |
| 589 | Cl | $C_4H_9(n)$ | NOH |
| 590 | $C_2H_5$ | $C_3H_7(n)$ | O |
| 591 | $C_2H_5$ | $C_3H_7(n)$ | S |
| 592 | $C_2H_5$ | $C_3H_7(n)$ | $CHCO_2H$ |
| 593 | $C_2H_5$ | $C_3H_7(n)$ | $CHCO_2C(CH_3)_3$ |
| 594 | $C_2H_5$ | $C_3H_7(n)$ | NOH |
| 595 | $C_2H_5$ | $C_4H_9(n)$ | O |
| 596 | $C_2H_5$ | $C_4H_9(n)$ | S |
| 597 | $C_2H_5$ | $C_4H_9(n)$ | $CHCO_2H$ |
| 598 | $C_2H_5$ | $C_4H_9(n)$ | $CHCO_2C(CH_3)_3$ |
| 599 | $C_2H_5$ | $C_4H_9(n)$ | NOH |
| 600 | $C_4H_9(n)$ | $C_3H_7(n)$ | O |
| 601 | $C_4H_9(n)$ | $C_3H_7(n)$ | S |
| 602 | $C_4H_9(n)$ | $C_3H_7(n)$ | $CHCO_2H$ |
| 603 | $C_4H_9(n)$ | $C_3H_7(n)$ | $CHCO_2C(CH_3)_3$ |
| 604 | $C_4H_9(n)$ | $C_3H_7(n)$ | NOH |
| 605 | $C_4H_9(n)$ | $C_4H_9(n)$ | O |
| 606 | $C_4H_9(n)$ | $C_4H_9(n)$ | S |

TABLE X-continued

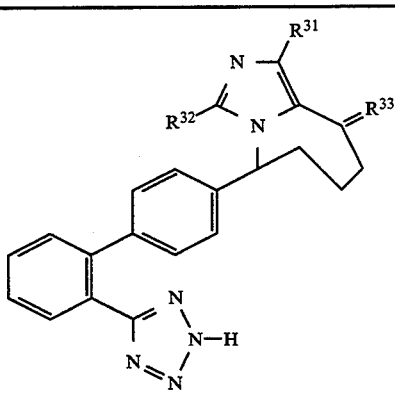

| EX. # | R³¹ | R³² | R³³ |
|---|---|---|---|
| 607 | C₄H₉(n) | C₄H₉(n) | CHCO₂H |
| 608 | C₄H₉(n) | C₄H₉(n) | CHCO₂C(CH₃)₃ |
| 609 | C₄H₉(n) | C₄H₉(n) | NOH |
| 610 | (2-ethylphenyl) | C₃H₇(n) | O |
| 611 | (2-ethylphenyl) | C₃H₇(n) | S |
| 612 | (2-ethylphenyl) | C₃H₇(n) | CHCO₂H |
| 613 | (2-ethylphenyl) | C₃H₇(n) | NOH |
| 614 | (2-ethylphenyl) | C₄H₉(n) | O |
| 615 | (2-ethylphenyl) | C₄H₉(n) | S |
| 616 | (2-ethylphenyl) | C₄H₉(n) | CHCO₂H |
| 617 | (2-ethylphenyl) | C₄H₉(n) | NOH |
| 618 | (2,6-dimethylphenyl) | C₃H₇(n) | O |
| 619 | (2,6-dimethylphenyl) | C₃H₇(n) | S |
| 620 | (2,6-dimethylphenyl) | C₃H₇(n) | CHCO₂H |
| 621 | (2,6-dimethylphenyl) | C₃H₇(n) | NOH |
| 622 | (2,6-dimethylphenyl) | C₄H₉(n) | O |
| 623 | (2,6-dimethylphenyl) | C₄H₉(n) | S |
| 624 | (2,6-dimethylphenyl) | C₄H₉(n) | CHCO₂H |
| 625 | (2,6-dimethylphenyl) | C₄H₉(n) | NOH |

TABLE XI

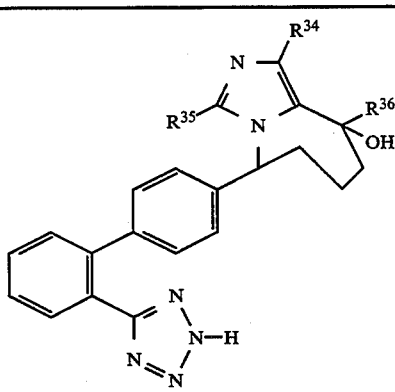

| EX. # | R³⁴ | R³⁵ | R³⁶ |
|---|---|---|---|
| 626 | H | C₃H₇(n) | C₂H₅ |
| 627 | H | C₃H₇(n) | C₃H₇(n) |
| 628 | H | C₄H₉(n) | C₂H₅ |
| 629 | H | C₄H₉(n) | C₃H₇(n) |
| 630 | Cl | C₃H₇(n) | C₂H₅ |
| 631 | Cl | C₃H₇(n) | C₃H₇(n) |
| 632 | Cl | C₄H₉(n) | C₂H₅ |
| 633 | Cl | C₄H₉(n) | C₃H₇(n) |
| 634 | C₂H₅ | C₃H₇(n) | C₂H₅ |
| 635 | C₂H₅ | C₃H₇(n) | C₃H₇(n) |
| 636 | C₂H₅ | C₄H₉(n) | C₂H₅ |
| 637 | C₂H₅ | C₄H₉(n) | C₃H₇(n) |
| 638 | C₄H₉(n) | C₃H₇(n) | C₂H₅ |
| 639 | C₄H₉(n) | C₄H₉(n) | C₂H₅ |
| 640 | (2-ethylphenyl) | C₃H₇(n) | C₂H₅ |
| 641 | (2-ethylphenyl) | C₄H₉(n) | C₂H₅ |
| 642 | (2,6-dimethylphenyl) | C₃H₇(n) | C₂H₅ |

TABLE XI-continued

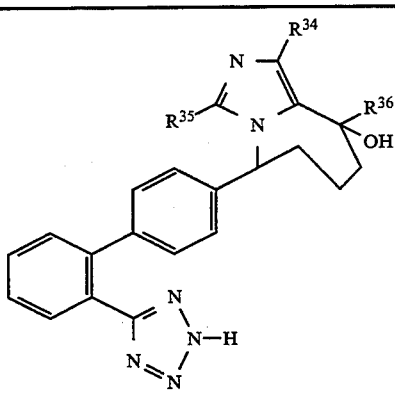

| EX. # | R³⁴ | R³⁵ | R³⁶ |
|---|---|---|---|
| 643 | (2,6-dimethylphenyl) | C₄H₉(n) | C₂H₅ |

TABLE XII

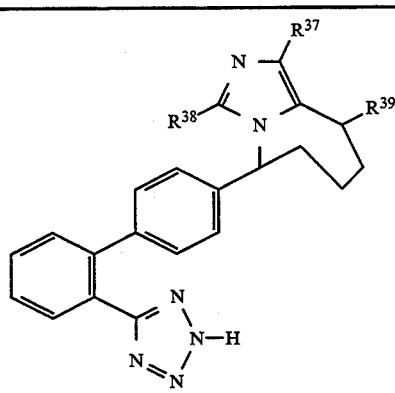

| EX. # | R³⁷ | R³⁸ | R³⁹ |
|---|---|---|---|
| 644 | H | C₃H₇(n) | H |
| 645 | H | C₃H₇(n) | NH₂ |
| 646 | H | C₃H₇(n) | OH |
| 647 | H | C₃H₇(n) | CH₂OH |
| 648 | H | C₃H₇(n) | C₂H₅ |
| 649 | H | C₃H₇(n) | C₃H₇(n) |
| 650 | H | C₃H₇(n) | C₆H₅ |
| 651 | H | C₃H₇(n) | C₆H₅CH₂ |
| 652 | H | C₃H₇(n) | (2-ethylphenyl) |
| 653 | H | C₄H₉(n) | H |
| 654 | H | C₄H₉(n) | NH₂ |
| 655 | H | C₄H₉(n) | OH |
| 656 | H | C₄H₉(n) | CH₂OH |
| 657 | H | C₄H₉(n) | C₂H₅ |
| 658 | H | C₄H₉(n) | C₃H₇(n) |
| 659 | H | C₄H₉(n) | C₆H₅ |
| 660 | H | C₄H₉(n) | C₆H₅CH₂ |
| 661 | H | C₄H₉(n) | (2-ethylphenyl) |
| 662 | Cl | C₃H₇(n) | H |
| 663 | Cl | C₃H₇(n) | NH₂ |
| 664 | Cl | C₃H₇(n) | OH |
| 665 | Cl | C₃H₇(n) | CH₂OH |
| 666 | Cl | C₃H₇(n) | C₂H₅ |
| 667 | Cl | C₃H₇(n) | C₃H₇(n) |
| 668 | Cl | C₃H₇(n) | C₆H₅ |
| 669 | Cl | C₃H₇(n) | C₆H₅CH₂ |
| 670 | Cl | C₃H₇(n) | (2-ethylphenyl) |
| 671 | Cl | C₄H₉(n) | H |
| 672 | Cl | C₄H₉(n) | NH₂ |
| 673 | Cl | C₄H₉(n) | OH |
| 674 | Cl | C₄H₉(n) | CH₂OH |
| 675 | Cl | C₄H₉(n) | C₂H₅ |
| 676 | Cl | C₄H₉(n) | C₃H₇(n) |
| 677 | Cl | C₄H₉(n) | C₆H₅ |
| 678 | Cl | C₄H₉(n) | C₆H₅CH₂ |
| 679 | Cl | C₄H₉(n) | (2-ethylphenyl) |
| 680 | C₂H₅ | C₃H₇(n) | H |

TABLE XII-continued

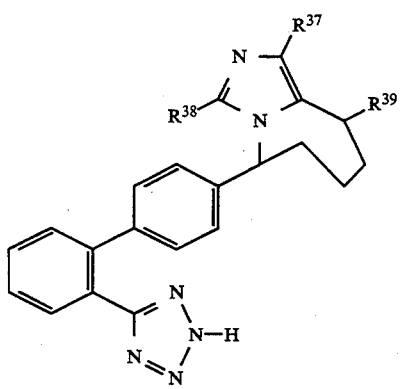

| EX. # | $R^{37}$ | $R^{38}$ | $R^{39}$ |
|---|---|---|---|
| 681 | $C_2H_5$ | $C_3H_7(n)$ | $NH_2$ |
| 682 | $C_2H_5$ | $C_3H_7(n)$ | OH |
| 683 | $C_2H_5$ | $C_3H_7(n)$ | $CH_2OH$ |
| 684 | $C_2H_5$ | $C_3H_7(n)$ | $C_2H_5$ |
| 685 | $C_2H_5$ | $C_4H_9(n)$ | H |
| 686 | $C_2H_5$ | $C_4H_9(n)$ | $NH_2$ |
| 687 | $C_2H_5$ | $C_4H_9(n)$ | OH |
| 688 | $C_2H_5$ | $C_4H_9(n)$ | $CH_2OH$ |
| 689 | $C_2H_5$ | $C_4H_9(n)$ | $C_2H_5$ |
| 690 | $C_4H_9(n)$ | $C_3H_7(n)$ | H |
| 691 | $C_4H_9(n)$ | $C_3H_7(n)$ | $NH_2$ |
| 692 | $C_4H_9(n)$ | $C_3H_7(n)$ | OH |
| 693 | $C_4H_9(n)$ | $C_3H_7(n)$ | $CH_2OH$ |
| 694 | $C_4H_9(n)$ | $C_3H_7(n)$ | $C_2H_5$ |
| 695 | $C_4H_9(n)$ | $C_3H_7(n)$ | $C_6H_5CH_2$ |
| 696 | $C_4H_9(n)$ | $C_4H_9(n)$ | H |
| 697 | $C_4H_9(n)$ | $C_4H_9(n)$ | $NH_2$ |
| 698 | $C_4H_9(n)$ | $C_4H_9(n)$ | OH |
| 699 | $C_4H_9(n)$ | $C_4H_9(n)$ | $CH_2OH$ |
| 700 | $C_4H_9(n)$ | $C_4H_9(n)$ | $C_2H_5$ |
| 701 | (2-ethylphenyl) | $C_3H_7(n)$ | H |
| 702 | (2-ethylphenyl) | $C_3H_7(n)$ | $NH_2$ |
| 703 | (2-ethylphenyl) | $C_3H_7(n)$ | OH |
| 704 | (2-ethylphenyl) | $C_3H_7(n)$ | $CH_2OH$ |
| 705 | (2-ethylphenyl) | $C_3H_7(n)$ | $C_2H_5$ |
| 706 | (2-ethylphenyl) | $C_4H_9(n)$ | H |
| 707 | (2-ethylphenyl) | $C_4H_9(n)$ | $NH_2$ |
| 708 | (2-ethylphenyl) | $C_4H_9(n)$ | OH |
| 709 | (2-ethylphenyl) | $C_4H_9(n)$ | $CH_2OH$ |
| 710 | (2-ethylphenyl) | $C_4H_9(n)$ | $C_2H_5$ |
| 711 | (2,6-dimethylphenyl) | $C_3H_7(n)$ | H |
| 712 | (2,6-dimethylphenyl) | $C_3H_7(n)$ | $NH_2$ |
| 713 | (2,6-dimethylphenyl) | $C_3H_7(n)$ | OH |
| 714 | (2,6-dimethylphenyl) | $C_3H_7(n)$ | $CH_2OH$ |
| 715 | (2,6-dimethylphenyl) | $C_3H_7(n)$ | $C_2H_5$ |
| 716 | (2,6-dimethylphenyl) | $C_4H_9(n)$ | H |
| 717 | (2,6-dimethylphenyl) | $C_4H_9(n)$ | $NH_2$ |
| 718 | (2,6-dimethylphenyl) | $C_4H_9(n)$ | OH |
| 719 | (2,6-dimethylphenyl) | $C_4H_9(n)$ | $CH_2OH$ |
| 720 | (2,6-dimethylphenyl) | $C_4H_9(n)$ | $C_2H_5$ |

TABLE XIII

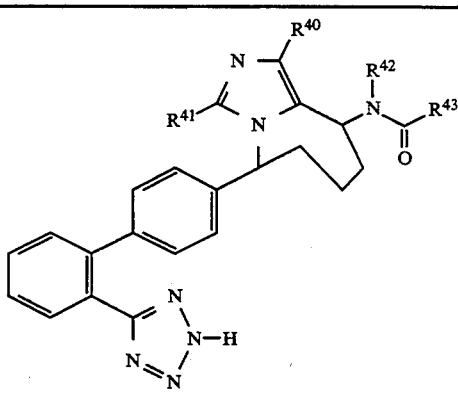

| EX. # | $R^{40}$ | $R^{41}$ | $R^{42}$ | $R^{43}$ |
|---|---|---|---|---|
| 721 | H | $C_3H_7(n)$ | H | $CH_3$ |
| 722 | H | $C_3H_7(n)$ | $CH_3$ | $CH_3$ |
| 723 | H | $C_3H_7(n)$ | $C_6H_5CH_2$ | $CH_3$ |
| 724 | H | $C_4H_9(n)$ | H | $CH_3$ |
| 725 | H | $C_4H_9(n)$ | $CH_3$ | $CH_3$ |
| 726 | H | $C_4H_9(n)$ | $C_6H_5CH_2$ | $CH_3$ |
| 727 | Cl | $C_3H_7(n)$ | H | $CH_3$ |
| 728 | Cl | $C_3H_7(n)$ | $CH_3$ | $CH_3$ |
| 729 | Cl | $C_3H_7(n)$ | $C_6H_5CH_2$ | $CH_3$ |
| 730 | Cl | $C_4H_9(n)$ | H | $CH_3$ |
| 731 | Cl | $C_4H_9(n)$ | $CH_3$ | $CH_3$ |
| 732 | Cl | $C_4H_9(n)$ | $C_6H_5CH_2$ | $CH_3$ |
| 733 | $C_2H_5$ | $C_3H_7(n)$ | H | $CH_3$ |
| 734 | $C_2H_5$ | $C_3H_7(n)$ | $CH_3$ | $CH_3$ |
| 735 | $C_2H_5$ | $C_4H_9(n)$ | H | $CH_3$ |
| 736 | $C_2H_5$ | $C_4H_9(n)$ | $CH_3$ | $CH_3$ |
| 737 | $C_4H_9(n)$ | $C_3H_7(n)$ | H | $CH_3$ |
| 738 | $C_4H_9(n)$ | $C_3H_7(n)$ | $CH_3$ | $CH_3$ |
| 739 | $C_4H_9(n)$ | $C_4H_9(n)$ | H | $CH_3$ |
| 740 | $C_4H_9(n)$ | $C_4H_9(n)$ | $CH_3$ | $CH_3$ |
| 741 | (2-ethylphenyl) | $C_3H_7(n)$ | H | $CH_3$ |
| 742 | (2-ethylphenyl) | $C_3H_7(n)$ | $CH_3$ | $CH_3$ |
| 743 | (2-ethylphenyl) | $C_4H_9(n)$ | H | $CH_3$ |
| 744 | (2-ethylphenyl) | $C_4H_9(n)$ | $CH_3$ | $CH_3$ |
| 745 | (2,6-dimethylphenyl) | $C_3H_7(n)$ | H | $CH_3$ |
| 746 | (2,6-dimethylphenyl) | $C_3H_7(n)$ | $CH_3$ | $CH_3$ |
| 747 | (2,6-dimethylphenyl) | $C_4H_9(n)$ | H | $CH_3$ |
| 748 | (2,6-dimethylphenyl) | $C_4H_9(n)$ | $CH_3$ | $CH_3$ |
| 749 | H | $C_3H_7(n)$ | H | $C_2H_5$ |
| 750 | H | $C_3H_7(n)$ | $CH_3$ | $C_2H_5$ |
| 751 | H | $C_3H_7(n)$ | $C_2H_5$ | $C_2H_5$ |
| 752 | H | $C_4H_9(n)$ | H | $C_2H_5$ |
| 753 | H | $C_4H_9(n)$ | $CH_3$ | $C_2H_5$ |
| 754 | H | $C_4H_9(n)$ | $C_2H_5$ | $C_2H_5$ |
| 755 | Cl | $C_3H_7(n)$ | H | $C_2H_5$ |
| 756 | Cl | $C_3H_7(n)$ | $CH_3$ | $C_2H_5$ |
| 757 | Cl | $C_3H_7(n)$ | $C_2H_5$ | $C_2H_5$ |
| 758 | Cl | $C_4H_9(n)$ | H | $C_2H_5$ |
| 759 | Cl | $C_4H_9(n)$ | $CH_3$ | $C_2H_5$ |
| 760 | Cl | $C_4H_9(n)$ | $C_2H_5$ | $C_2H_5$ |
| 761 | $C_2H_5$ | $C_3H_7(n)$ | H | $C_2H_5$ |
| 762 | $C_2H_5$ | $C_3H_7(n)$ | $CH_3$ | $C_2H_5$ |
| 763 | $C_2H_5$ | $C_4H_9(n)$ | H | $C_2H_5$ |
| 764 | $C_2H_5$ | $C_4H_9(n)$ | $CH_3$ | $C_2H_5$ |
| 765 | (2-ethylphenyl) | $C_3H_7(n)$ | H | $C_2H_5$ |
| 766 | (2-ethylphenyl) | $C_4H_9(n)$ | H | $C_2H_5$ |
| 767 | (2,6-dimethylphenyl) | $C_3H_7(n)$ | H | $C_2H_5$ |
| 768 | (2,6-dimethylphenyl) | $C_4H_9(n)$ | H | $C_2H_5$ |
| 769 | H | $C_3H_7(n)$ | H | $C_6H_5$ |
| 770 | H | $C_3H_7(n)$ | $CH_3$ | $C_6H_5$ |
| 771 | H | $C_4H_9(n)$ | H | $C_6H_5$ |
| 772 | H | $C_4H_9(n)$ | $CH_3$ | $C_6H_5$ |
| 773 | Cl | $C_3H_7(n)$ | H | $C_6H_5$ |
| 774 | Cl | $C_3H_7(n)$ | $CH_3$ | $C_6H_5$ |
| 775 | Cl | $C_4H_9(n)$ | H | $C_6H_5$ |
| 776 | Cl | $C_4H_9(n)$ | $CH_3$ | $C_6H_5$ |
| 777 | $C_2H_5$ | $C_3H_7(n)$ | H | $C_6H_5$ |
| 778 | $C_2H_5$ | $C_3H_7(n)$ | $CH_3$ | $C_6H_5$ |
| 779 | $C_2H_5$ | $C_4H_9(n)$ | H | $C_6H_5$ |
| 780 | $C_2H_5$ | $C_4H_9(n)$ | $CH_3$ | $C_6H_5$ |
| 781 | $C_4H_9(n)$ | $C_3H_7(n)$ | H | $C_6H_5$ |

TABLE XIII-continued

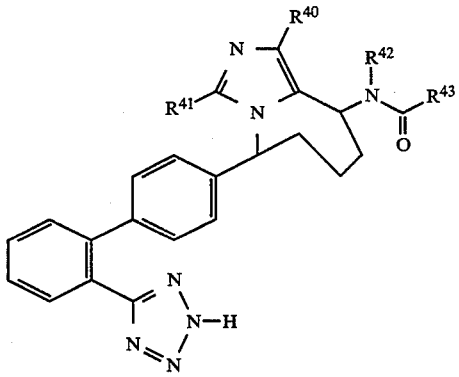

| EX. # | $R^{40}$ | $R^{41}$ | $R^{42}$ | $R^{43}$ |
|---|---|---|---|---|
| 782 | $C_4H_9(n)$ | $C_3H_7(n)$ | $CH_3$ | $C_6H_5$ |
| 783 | $C_4H_9(n)$ | $C_4H_9(n)$ | H | $C_6H_5$ |
| 784 | $C_4H_9(n)$ | $C_4H_9(n)$ | $CH_3$ | $C_6H_5$ |
| 785 | $C_4H_9(n)$ | $C_4H_9(n)$ | H | $CH_2CH_2CO_2H$ |
| 786 | $C_4H_9(n)$ | $C_4H_9(n)$ | $CH_3$ | $CH_2CH_2CO_2H$ |
| 787 | (2-ethylphenyl) | $C_3H_7(n)$ | H | $CH_2CH_2CO_2H$ |
| 788 | (2-ethylphenyl) | $C_3H_7(n)$ | $CH_3$ | $CH_2CH_2CO_2H$ |
| 789 | (2-ethylphenyl) | $C_4H_9(n)$ | H | $CH_2CH_2CO_2H$ |
| 790 | (2-ethylphenyl) | $C_4H_9(n)$ | $CH_3$ | $CH_2CH_2CO_2H$ |
| 791 | (2,6-dimethylphenyl) | $C_3H_7(n)$ | H | $CH_2CH_2CO_2H$ |
| 792 | (2,6-dimethylphenyl) | $C_3H_7(n)$ | $CH_3$ | $CH_2CH_2CO_2H$ |
| 793 | (2,6-dimethylphenyl) | $C_4H_9(n)$ | H | $CH_2CH_2CO_2H$ |
| 794 | (2,6-dimethylphenyl) | $C_4H_9(n)$ | $CH_3$ | $CH_2CH_2CO_2H$ |

TABLE XIV

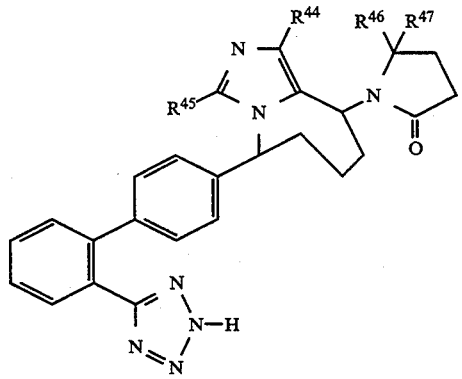

| EX. # | $R^{44}$ | $R^{45}$ | $R^{46}, R^{47}$ |
|---|---|---|---|
| 795 | H | $C_3H_7(n)$ | O |
| 796 | H | $C_3H_7(n)$ | H,H |
| 797 | H | $C_3H_7(n)$ | H,$CH_3$ |
| 798 | H | $C_3H_7(n)$ | H,$C_2H_5$ |
| 799 | H | $C_3H_7(n)$ | H,$CH_2OH$ |
| 800 | H | $C_3H_7(n)$ | H,$CO_2H$ |
| 801 | H | $C_4H_9(n)$ | O |
| 802 | H | $C_4H_9(n)$ | H,H |
| 803 | H | $C_4H_9(n)$ | H,$CH_3$ |
| 804 | H | $C_4H_9(n)$ | H,$C_2H_5$ |
| 805 | H | $C_4H_9(n)$ | H,$CH_2OH$ |
| 806 | H | $C_4H_9(n)$ | H,$CO_2H$ |
| 807 | Cl | $C_3H_7(n)$ | O |
| 808 | Cl | $C_3H_7(n)$ | H,H |
| 809 | Cl | $C_3H_7(n)$ | H,$CH_3$ |
| 810 | Cl | $C_3H_7(n)$ | H,$C_2H_5$ |
| 811 | Cl | $C_3H_7(n)$ | H,$CH_2OH$ |
| 812 | Cl | $C_3H_7(n)$ | H,$CO_2H$ |
| 813 | Cl | $C_4H_9(n)$ | O |
| 814 | Cl | $C_4H_9(n)$ | H,H |
| 815 | Cl | $C_4H_9(n)$ | H,$CH_3$ |
| 816 | Cl | $C_4H_9(n)$ | H,$C_2H_5$ |
| 817 | Cl | $C_4H_9(n)$ | H,$CH_2OH$ |
| 818 | Cl | $C_4H_9(n)$ | H,$CO_2H$ |

TABLE XIV-continued

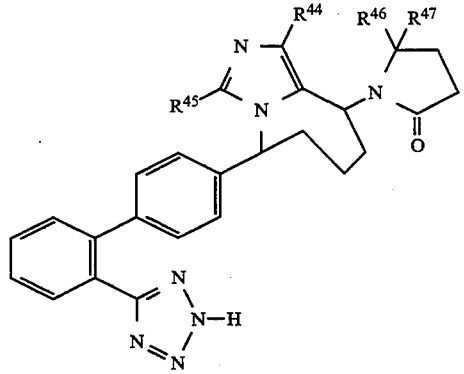

| EX. # | $R^{44}$ | $R^{45}$ | $R^{46}, R^{47}$ |
|---|---|---|---|
| 819 | $C_2H_5$ | $C_3H_7(n)$ | O |
| 820 | $C_2H_5$ | $C_3H_7(n)$ | H,H |
| 821 | $C_2H_5$ | $C_3H_7(n)$ | H,$CH_3$ |
| 822 | $C_2H_5$ | $C_3H_7(n)$ | H,$C_2H_5$ |
| 823 | $C_2H_5$ | $C_3H_7(n)$ | H,$CH_2OH$ |
| 824 | $C_2H_5$ | $C_3H_7(n)$ | H,$CO_2H$ |
| 825 | $C_2H_5$ | $C_4H_9(n)$ | O |
| 826 | $C_2H_5$ | $C_4H_9(n)$ | H,H |
| 827 | $C_2H_5$ | $C_4H_9(n)$ | H,$CH_3$ |
| 828 | $C_2H_5$ | $C_4H_9(n)$ | H,$C_2H_5$ |
| 829 | $C_2H_5$ | $C_4H_9(n)$ | H,$CH_2OH$ |
| 830 | $C_2H_5$ | $C_4H_9(n)$ | H,$CO_2H$ |
| 831 | $C_4H_9(n)$ | $C_3H_7(n)$ | O |
| 832 | $C_4H_9(n)$ | $C_3H_7(n)$ | H,H |
| 833 | $C_4H_9(n)$ | $C_3H_7(n)$ | H,$CH_3$ |
| 834 | $C_4H_9(n)$ | $C_3H_7(n)$ | H,$CH_2OH$ |
| 835 | $C_4H_9(n)$ | $C_3H_7(n)$ | H,$CO_2H$ |
| 836 | $C_4H_9(n)$ | $C_4H_9(n)$ | O |
| 837 | $C_4H_9(n)$ | $C_4H_9(n)$ | H,H |
| 838 | $C_4H_9(n)$ | $C_4H_9(n)$ | H,$CH_3$ |
| 839 | $C_4H_9(n)$ | $C_4H_9(n)$ | H,$CH_2OH$ |
| 840 | $C_4H_9(n)$ | $C_4H_9(n)$ | H,$CO_2H$ |
| 841 | (2-ethylphenyl) | $C_3H_7(n)$ | O |
| 842 | (2-ethylphenyl) | $C_3H_7(n)$ | H,H |
| 843 | (2-ethylphenyl) | $C_3H_7(n)$ | H,$CH_3$ |
| 844 | (2-ethylphenyl) | $C_3H_7(n)$ | $CH_3,CH_3$ |
| 845 | (2-ethylphenyl) | $C_3H_7(n)$ | H,$CH_2OH$ |
| 846 | (2-ethylphenyl) | $C_3H_7(n)$ | H,$CO_2H$ |
| 847 | (2-ethylphenyl) | $C_4H_9(n)$ | O |
| 848 | (2-ethylphenyl) | $C_4H_9(n)$ | H,H |
| 849 | (2-ethylphenyl) | $C_4H_9(n)$ | H,$CH_3$ |
| 850 | (2-ethylphenyl) | $C_4H_9(n)$ | $CH_3,CH_3$ |
| 851 | (2-ethylphenyl) | $C_4H_9(n)$ | H,$CH_2OH$ |
| 852 | (2-ethylphenyl) | $C_4H_9(n)$ | H,$CO_2H$ |

TABLE XV

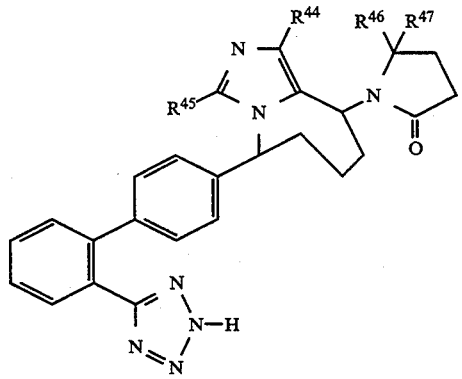

| EX. # | $R^{48}$ | $R^{49}$ | $R^{50}, R^{51}$ |
|---|---|---|---|
| 853 | H | $C_3H_7(n)$ | O |
| 854 | H | $C_3H_7(n)$ | H,H |
| 855 | H | $C_3H_7(n)$ | H,$CH_3$ |
| 856 | H | $C_3H_7(n)$ | H,$C_2H_5$ |

TABLE XV-continued

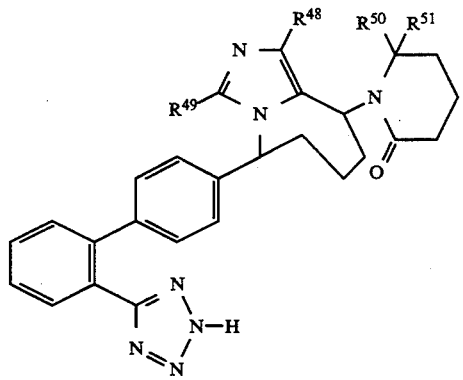

| EX. # | R⁴⁸ | R⁴⁹ | R⁵⁰, R⁵¹ |
|---|---|---|---|
| 857 | H | C₃H₇(n) | H,CH₂OH |
| 858 | H | C₃H₇(n) | H,CO₂H |
| 859 | H | C₄H₉(n) | O |
| 860 | H | C₄H₉(n) | H,H |
| 861 | H | C₄H₉(n) | H,CH₃ |
| 862 | H | C₄H₉(n) | H,C₂H₅ |
| 863 | H | C₄H₉(n) | H,CH₂OH |
| 864 | H | C₄H₉(n) | H,CO₂H |
| 865 | Cl | C₃H₇(n) | O |
| 866 | Cl | C₃H₇(n) | H,H |
| 867 | Cl | C₃H₇(n) | H,CH₃ |
| 868 | Cl | C₃H₇(n) | CH₃,CH₃ |
| 869 | Cl | C₃H₇(n) | H,CH₂OH |
| 870 | Cl | C₃H₇(n) | H,CO₂H |
| 871 | Cl | C₄H₉(n) | O |
| 872 | Cl | C₄H₉(n) | H,H |
| 873 | Cl | C₄H₉(n) | H,CH₃ |
| 874 | Cl | C₄H₉(n) | H,C₂H₅ |
| 875 | Cl | C₄H₉(n) | H,CH₂OH |
| 876 | Cl | C₄H₉(n) | H,CO₂H |
| 877 | C₂H₅ | C₃H₇(n) | O |
| 878 | C₂H₅ | C₃H₇(n) | H,H |
| 879 | C₂H₅ | C₃H₇(n) | H,CH₃ |
| 880 | C₂H₅ | C₃H₇(n) | H,C₂H₅ |
| 881 | C₂H₅ | C₃H₇(n) | H,CH₂OH |
| 882 | C₂H₅ | C₃H₇(n) | H,CO₂H |
| 883 | C₂H₅ | C₄H₉(n) | O |
| 884 | C₂H₅ | C₄H₉(n) | H,H |
| 885 | C₂H₅ | C₄H₉(n) | H,CH₃ |
| 886 | C₂H₅ | C₄H₉(n) | H,C₂H₅ |
| 887 | C₂H₅ | C₄H₉(n) | H,CH₂OH |
| 888 | C₂H₅ | C₄H₉(n) | H,CO₂H |
| 889 | C₄H₉(n) | C₃H₇(n) | O |
| 890 | C₄H₉(n) | C₃H₇(n) | H,H |
| 891 | C₄H₉(n) | C₃H₇(n) | H,CH₃ |
| 892 | C₄H₉(n) | C₃H₇(n) | H,CH₂OH |
| 893 | C₄H₉(n) | C₃H₇(n) | H,CO₂H |
| 894 | C₄H₉(n) | C₄H₉(n) | O |
| 895 | C₄H₉(n) | C₄H₉(n) | H,H |
| 896 | C₄H₉(n) | C₄H₉(n) | H,CH₃ |
| 897 | C₄H₉(n) | C₄H₉(n) | H,CH₂OH |
| 898 | C₄H₉(n) | C₄H₉(n) | H,CO₂H |
| 899 | (2-ethylphenyl) | C₃H₇(n) | O |
| 900 | (2-ethylphenyl) | C₃H₇(n) | H,H |
| 901 | (2-ethylphenyl) | C₃H₇(n) | H,CH₃ |
| 902 | (2-ethylphenyl) | C₃H₇(n) | CH₃,CH₃ |
| 903 | (2-ethylphenyl) | C₃H₇(n) | H,CH₂OH |
| 904 | (2-ethylphenyl) | C₃H₇(n) | H,CO₂H |
| 905 | (2-ethylphenyl) | C₄H₉(n) | O |
| 906 | (2-ethylphenyl) | C₄H₉(n) | H,H |
| 907 | (2-ethylphenyl) | C₄H₉(n) | H,CH₃ |
| 908 | (2-ethylphenyl) | C₄H₉(n) | CH₃,CH₃ |
| 909 | (2-ethylphenyl) | C₄H₉(n) | H,CH₂OH |
| 910 | (2-ethylphenyl) | C₄H₉(n) | H,CO₂H |

TABLE XVI

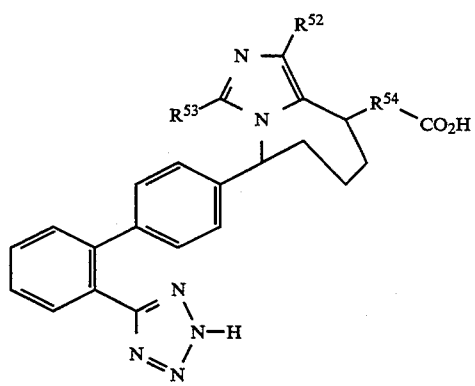

| EX. # | R⁵² | R⁵³ | R⁵⁴ |
|---|---|---|---|
| 911 | H | C₃H₇(n) | CH₂ |
| 912 | H | C₃H₇(n) | CH(C₂H₅) |
| 913 | H | C₃H₇(n) | CH(CH₂C₆H₅) |
| 914 | H | C₃H₇(n) | CH₂CH₂ |
| 915 | H | C₃H₇(n) | CH(C₂H₅)CH₂ |
| 916 | H | C₃H₇(n) | CH(CH₂C₆H₅)CH₂ |
| 917 | H | C₄H₉(n) | CH₂ |
| 918 | H | C₄H₉(n) | CH(C₂H₅) |
| 919 | H | C₄H₉(n) | CH(CH₂C₆H₅) |
| 920 | H | C₄H₉(n) | CH₂CH₂ |
| 921 | H | C₄H₉(n) | CH(C₂H₅)CH₂ |
| 922 | H | C₄H₉(n) | CH(CH₂C₆H₅)CH₂ |
| 923 | Cl | C₃H₇(n) | CH₂ |
| 924 | Cl | C₃H₇(n) | CH(C₂H₅) |
| 925 | Cl | C₃H₇(n) | CH(CH₂C₆H₅) |
| 926 | Cl | C₃H₇(n) | CH₂CH₂ |
| 927 | Cl | C₃H₇(n) | CH(C₂H₅)CH₂ |
| 928 | Cl | C₃H₇(n) | CH(CH₂C₆H₅)CH₂ |
| 929 | Cl | C₄H₉(n) | CH₂ |
| 930 | Cl | C₄H₉(n) | CH(C₂H₅) |
| 931 | Cl | C₄H₉(n) | CH(CH₂C₆H₅) |
| 932 | Cl | C₄H₉(n) | CH₂CH₂ |
| 933 | Cl | C₄H₉(n) | CH(C₂H₅)CH₂ |
| 934 | Cl | C₄H₉(n) | CH(CH₂C₆H₅)CH₂ |
| 935 | C₂H₅ | C₃H₇(n) | CH₂ |
| 936 | C₂H₅ | C₃H₇(n) | CH(C₂H₅) |
| 937 | C₂H₅ | C₃H₇(n) | CH(CH₂C₆H₅) |
| 938 | C₂H₅ | C₃H₇(n) | CH₂CH₂ |
| 939 | C₂H₅ | C₃H₇(n) | CH(C₂H₅)CH₂ |
| 940 | C₂H₅ | C₃H₇(n) | CH(CH₂C₆H₅)CH₂ |
| 941 | C₂H₅ | C₄H₉(n) | CH₂ |
| 942 | C₂H₅ | C₄H₉(n) | CH(C₂H₅) |
| 943 | C₂H₅ | C₄H₉(n) | CH(CH₂C₆H₅) |
| 944 | C₂H₅ | C₄H₉(n) | CH₂CH₂ |
| 945 | C₂H₅ | C₄H₉(n) | CH(C₂H₅)CH₂ |
| 946 | C₂H₅ | C₄H₉(n) | CH(CH₂C₆H₅)CH₂ |
| 947 | C₄H₉(n) | C₃H₇(n) | CH₂ |
| 948 | C₄H₉(n) | C₃H₇(n) | CH₂CH₂ |
| 949 | C₄H₉(n) | C₄H₉(n) | CH₂ |
| 950 | C₄H₉(n) | C₄H₉(n) | CH₂CH₂ |
| 951 | (2-ethylphenyl) | C₃H₇(n) | CH₂ |
| 952 | (2-ethylphenyl) | C₃H₇(n) | CH₂CH₂ |
| 953 | (2-ethylphenyl) | C₄H₉(n) | CH₂ |
| 954 | (2-ethylphenyl) | C₄H₉(n) | CH₂CH₂ |
| 955 | (2,6-dimethylphenyl) | C₃H₇(n) | CH₂ |
| 956 | (2,6-dimethylphenyl) | C₃H₇(n) | CH₂CH₂ |
| 957 | (2,6-dimethylphenyl) | C₄H₉(n) | CH₂ |
| 958 | (2,6-dimethylphenyl) | C₄H₉(n) | CH₂CH₂ |

TABLE XVII

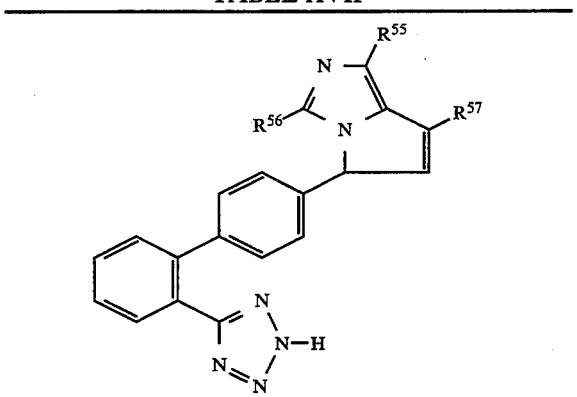

| EX. # | R55 | R56 | R57 |
|---|---|---|---|
| 959 | H | C3H7(n) | H |
| 960 | H | C3H7(n) | C2H5 |
| 961 | H | C3H7(n) | CH2OH |
| 962 | H | C3H7(n) | CO2H |
| 963 | H | C3H7(n) | CH2CO2H |
| 964 | H | C3H7(n) | CH2CO2C(CH3)3 |
| 965 | H | C3H7(n) | CH(C2H5)CO2H |
| 966 | H | C3H7(n) | CH(C2H5)CO2C(CH3)3 |
| 967 | H | C3H7(n) | phenyl |
| 968 | H | C3H7(n) | benzyl |
| 969 | H | C3H7(n) | phenylethyl |
| 970 | H | C4H9(n) | H |
| 971 | H | C4H9(n) | C2H5 |
| 972 | H | C4H9(n) | CH2OH |
| 973 | H | C4H9(n) | CO2H |
| 974 | H | C4H9(n) | CH2CO2H |
| 975 | H | C4H9(n) | CH2CO2C(CH3)3 |
| 976 | H | C4H9(n) | CH(C2H5)CO2H |
| 977 | H | C4H9(n) | CH(C2H5)CO2C(CH3)3 |
| 978 | H | C4H9(n) | phenyl |
| 979 | H | C4H9(n) | benzyl |
| 980 | H | C4H9(n) | phenylethyl |
| 981 | Cl | C3H7(n) | H |
| 982 | Cl | C3H7(n) | C2H5 |
| 983 | Cl | C3H7(n) | CH2OH |
| 984 | Cl | C3H7(n) | CO2H |
| 985 | Cl | C3H7(n) | CH2CO2H |
| 986 | Cl | C3H7(n) | CH2CO2C(CH3)3 |
| 987 | Cl | C3H7(n) | CH(C2H5)CO2H |
| 988 | Cl | C3H7(n) | CH(C2H5)CO2C(CH3)3 |
| 989 | Cl | C4H9(n) | H |
| 990 | Cl | C4H9(n) | C2H5 |
| 991 | Cl | C4H9(n) | CH2OH |
| 992 | Cl | C4H9(n) | CO2H |
| 993 | Cl | C4H9(n) | CH2CO2H |
| 994 | Cl | C4H9(n) | CH2CO2C(CH3)3 |
| 995 | Cl | C4H9(n) | CH(C2H5)CO2H |
| 996 | Cl | C4H9(n) | CH(C2H5)CO2C(CH3)3 |
| 997 | ethyl | C3H7(n) | H |
| 998 | ethyl | C3H7(n) | C2H5 |
| 999 | ethyl | C3H7(n) | CH2OH |
| 1000 | ethyl | C3H7(n) | CO2H |
| 1001 | ethyl | C3H7(n) | CH2CO2H |
| 1002 | ethyl | C3H7(n) | CH2CO2C(CH3)3 |
| 1003 | ethyl | C4H9(n) | H |
| 1004 | ethyl | C4H9(n) | C2H5 |
| 1005 | ethyl | C4H9(n) | CH2OH |
| 1006 | ethyl | C4H9(n) | CO2H |
| 1007 | ethyl | C4H9(n) | CH2CO2H |
| 1008 | ethyl | C4H9(n) | CH2CO2C(CH3)3 |
| 1009 | n-butyl | C3H7(n) | H |
| 1010 | n-butyl | C3H7(n) | C2H5 |
| 1011 | n-butyl | C3H7(n) | CH2OH |
| 1012 | n-butyl | C3H7(n) | CO2H |
| 1013 | n-butyl | C3H7(n) | CH2CO2H |
| 1014 | n-butyl | C3H7(n) | CH2CO2C(CH3)3 |
| 1015 | n-butyl | C4H9(n) | H |
| 1016 | n-butyl | C4H9(n) | C2H5 |
| 1017 | n-butyl | C4H9(n) | CH2OH |
| 1018 | n-butyl | C4H9(n) | CO2H |
| 1019 | n-butyl | C4H9(n) | CH2CO2H |
| 1020 | n-butyl | C4H9(n) | CH2CO2C(CH3)3 |

TABLE XVII-continued

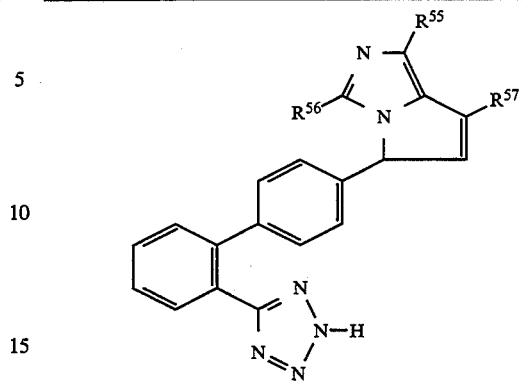

| EX. # | R55 | R56 | R57 |
|---|---|---|---|
| 1021 | (2-ethylphenyl) | C3H7(n) | H |
| 1022 | (2-ethylphenyl) | C3H7(n) | C2H5 |
| 1023 | (2-ethylphenyl) | C3H7(n) | CH2OH |
| 1024 | (2-ethylphenyl) | C3H7(n) | CO2H |
| 1025 | (2-ethylphenyl) | C3H7(n) | CH2CO2H |
| 1026 | (2-ethylphenyl) | C3H7(n) | CH2CO2C(CH3)3 |
| 1027 | (2-ethylphenyl) | C4H9(n) | H |
| 1028 | (2-ethylphenyl) | C4H9(n) | C2H5 |
| 1029 | (2-ethylphenyl) | C4H9(n) | CH2OH |
| 1030 | (2-ethylphenyl) | C4H9(n) | CO2H |
| 1031 | (2-ethylphenyl) | C4H9(n) | CH2CO2H |
| 1032 | (2-ethylphenyl) | C4H9(n) | CH2CO2C(CH3)3 |
| 1033 | (2,6-dimethylphenyl) | C3H7(n) | H |
| 1034 | (2,6-dimethylphenyl) | C3H7(n) | C2H5 |
| 1035 | (2,6-dimethylphenyl) | C3H7(n) | CH2OH |
| 1036 | (2,6-dimethylphenyl) | C3H7(n) | CO2H |
| 1037 | (2,6-dimethylphenyl) | C3H7(n) | CH2CO2H |
| 1038 | (2,6-dimethylphenyl) | C3H7(n) | CH2CO2C(CH3)3 |
| 1039 | (2,6-dimethylphenyl) | C4H9(n) | H |
| 1040 | (2,6-dimethylphenyl) | C4H9(n) | C2H5 |
| 1041 | (2,6-dimethylphenyl) | C4H9(n) | CH2OH |
| 1042 | (2,6-dimethylphenyl) | C4H9(n) | CO2H |
| 1043 | (2,6-dimethylphenyl) | C4H9(n) | CH2CO2H |
| 1044 | (2,6-dimethylphenyl) | C4H9(n) | CH2CO2C(CH3)3 |

TABLE XVIII

| EX. # | R58 | R59 | R60 |
|---|---|---|---|
| 1045 | H | C3H7(n) | O |
| 1046 | H | C3H7(n) | S |
| 1047 | H | C3H7(n) | CHCO2H |
| 1048 | H | C3H7(n) | CHCO2C(CH3)3 |
| 1049 | H | C3H7(n) | NOH |
| 1050 | H | C4H9(n) | O |
| 1051 | H | C4H9(n) | S |
| 1052 | H | C4H9(n) | CHCO2H |
| 1053 | H | C4H9(n) | CHCO2C(CH3)3 |
| 1054 | H | C4H9(n) | NOH |
| 1055 | Cl | C3H7(n) | O |
| 1056 | Cl | C3H7(n) | S |
| 1057 | Cl | C3H7(n) | CHCO2H |
| 1058 | Cl | C3H7(n) | CHCO2C(CH3)3 |

TABLE XVIII-continued

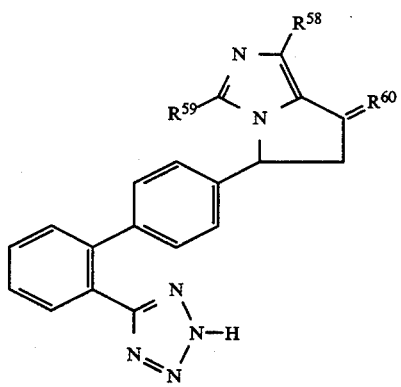

| EX. # | R58 | R59 | R60 |
|---|---|---|---|
| 1059 | Cl | $C_3H_7(n)$ | NOH |
| 1060 | Cl | $C_4H_9(n)$ | O |
| 1061 | Cl | $C_4H_9(n)$ | S |
| 1062 | Cl | $C_4H_9(n)$ | $CHCO_2H$ |
| 1063 | Cl | $C_4H_9(n)$ | $CHCO_2C(CH_3)_3$ |
| 1064 | Cl | $C_4H_9(n)$ | NOH |
| 1065 | $C_2H_5$ | $C_3H_7(n)$ | O |
| 1066 | $C_2H_5$ | $C_3H_7(n)$ | S |
| 1067 | $C_2H_5$ | $C_3H_7(n)$ | $CHCO_2H$ |
| 1068 | $C_2H_5$ | $C_3H_7(n)$ | $CHCO_2C(CH_3)_3$ |
| 1069 | $C_2H_5$ | $C_3H_7(n)$ | NOH |
| 1070 | $C_2H_5$ | $C_4H_9(n)$ | O |
| 1071 | $C_2H_5$ | $C_4H_9(n)$ | S |
| 1072 | $C_2H_5$ | $C_4H_9(n)$ | $CHCO_2H$ |
| 1073 | $C_2H_5$ | $C_4H_9(n)$ | $CHCO_2C(CH_3)_3$ |
| 1074 | $C_2H_5$ | $C_4H_9(n)$ | NOH |
| 1075 | $C_4H_9(n)$ | $C_3H_7(n)$ | O |
| 1076 | $C_4H_9(n)$ | $C_3H_7(n)$ | S |
| 1077 | $C_4H_9(n)$ | $C_3H_7(n)$ | $CHCO_2H$ |
| 1078 | $C_4H_9(n)$ | $C_3H_7(n)$ | $CHCO_2C(CH_3)_3$ |
| 1079 | $C_4H_9(n)$ | $C_3H_7(n)$ | NOH |
| 1080 | $C_4H_9(n)$ | $C_4H_9(n)$ | O |
| 1081 | $C_4H_9(n)$ | $C_4H_9(n)$ | S |
| 1082 | $C_4H_9(n)$ | $C_4H_9(n)$ | $CHCO_2H$ |
| 1083 | $C_4H_9(n)$ | $C_4H_9(n)$ | $CHCO_2C(CH_3)_3$ |
| 1084 | $C_4H_9(n)$ | $C_4H_9(n)$ | NOH |
| 1085 | (2-ethylphenyl) | $C_3H_7(n)$ | O |
| 1086 | (2-ethylphenyl) | $C_3H_7(n)$ | S |
| 1087 | (2-ethylphenyl) | $C_3H_7(n)$ | $CHCO_2H$ |
| 1088 | (2-ethylphenyl) | $C_3H_7(n)$ | NOH |
| 1089 | (2-ethylphenyl) | $C_4H_9(n)$ | O |
| 1090 | (2-ethylphenyl) | $C_4H_9(n)$ | S |
| 1091 | (2-ethylphenyl) | $C_4H_9(n)$ | $CHCO_2H$ |
| 1092 | (2-ethylphenyl) | $C_4H_9(n)$ | NOH |
| 1093 | (2,6-dimethylphenyl) | $C_3H_7(n)$ | O |
| 1094 | (2,6-dimethylphenyl) | $C_3H_7(n)$ | S |
| 1095 | (2,6-dimethylphenyl) | $C_3H_7(n)$ | $CHCO_2H$ |
| 1096 | (2,6-dimethylphenyl) | $C_3H_7(n)$ | NOH |
| 1097 | (2,6-dimethylphenyl) | $C_4H_9(n)$ | O |
| 1098 | (2,6-dimethylphenyl) | $C_4H_9(n)$ | S |
| 1099 | (2,6-dimethylphenyl) | $C_4H_9(n)$ | $CHCO_2H$ |
| 1100 | (2,6-dimethylphenyl) | $C_4H_9(n)$ | NOH |

TABLE XIX

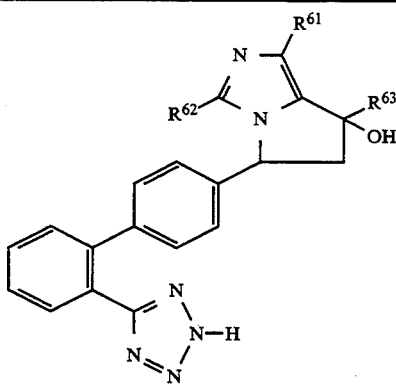

| EX. # | R61 | R62 | R63 |
|---|---|---|---|
| 1101 | H | $C_3H_7(n)$ | $C_2H_5$ |
| 1102 | H | $C_3H_7(n)$ | $C_3H_7(n)$ |
| 1103 | H | $C_4H_9(n)$ | $C_2H_5$ |
| 1104 | H | $C_4H_9(n)$ | $C_3H_7(n)$ |
| 1105 | Cl | $C_3H_7(n)$ | $C_2H_5$ |
| 1106 | Cl | $C_3H_7(n)$ | $C_3H_7(n)$ |
| 1107 | Cl | $C_4H_9(n)$ | $C_2H_5$ |
| 1108 | Cl | $C_4H_9(n)$ | $C_3H_7(n)$ |
| 1109 | $C_2H_5$ | $C_3H_7(n)$ | $C_2H_5$ |
| 1110 | $C_2H_5$ | $C_3H_7(n)$ | $C_3H_7(n)$ |
| 1111 | $C_2H_5$ | $C_4H_9(n)$ | $C_2H_5$ |
| 1112 | $C_2H_5$ | $C_4H_9(n)$ | $C_3H_7(n)$ |
| 1113 | $C_4H_9(n)$ | $C_3H_7(n)$ | $C_2H_5$ |
| 1114 | $C_4H_9(n)$ | $C_4H_9(n)$ | $C_2H_5$ |
| 1115 | (2-ethylphenyl) | $C_3H_7(n)$ | $C_2H_5$ |
| 1116 | (2-ethylphenyl) | $C_4H_9(n)$ | $C_2H_5$ |
| 1117 | (2,6-dimethylphenyl) | $C_3H_7(n)$ | $C_2H_5$ |
| 1118 | (2,6-dimethylphenyl) | $C_4H_9(n)$ | $C_2H_5$ |

TABLE XX

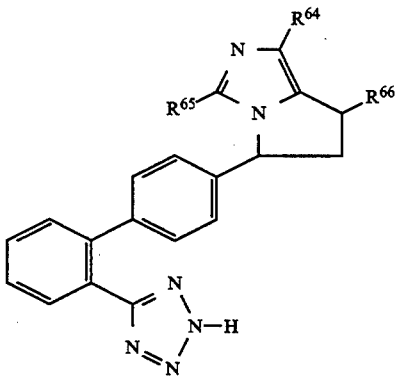

| EX. # | R64 | R65 | R66 |
|---|---|---|---|
| 1119 | H | $C_3H_7(n)$ | H |
| 1120 | H | $C_3H_7(n)$ | $NH_2$ |
| 1121 | H | $C_3H_7(n)$ | OH |
| 1122 | H | $C_3H_7(n)$ | $CH_2OH$ |
| 1123 | H | $C_3H_7(n)$ | $C_2H_5$ |
| 1124 | H | $C_3H_7(n)$ | $C_3H_7(n)$ |
| 1125 | H | $C_3H_7(n)$ | $C_6H_5$ |
| 1126 | H | $C_3H_7(n)$ | $C_6H_5CH_2$ |
| 1127 | H | $C_3H_7(n)$ | (2-ethylphenyl) |
| 1128 | H | $C_4H_9(n)$ | H |
| 1129 | H | $C_4H_9(n)$ | $NH_2$ |
| 1130 | H | $C_4H_9(n)$ | OH |
| 1131 | H | $C_4H_9(n)$ | $CH_2OH$ |
| 1132 | H | $C_4H_9(n)$ | $C_2H_5$ |
| 1133 | H | $C_4H_9(n)$ | $C_3H_7(n)$ |
| 1134 | H | $C_4H_9(n)$ | $C_6H_5$ |
| 1135 | H | $C_4H_9(n)$ | $C_6H_5CH_2$ |
| 1136 | H | $C_4H_9(n)$ | (2-ethylphenyl) |
| 1137 | Cl | $C_3H_7(n)$ | H |
| 1138 | Cl | $C_3H_7(n)$ | $NH_2$ |

TABLE XX-continued

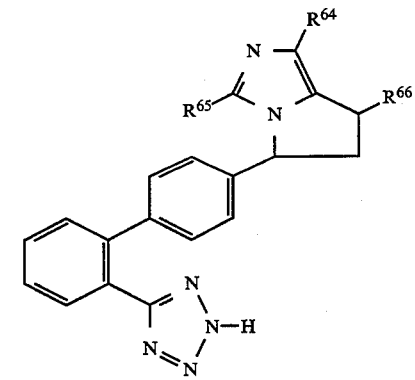

| EX. # | R64 | R65 | R66 |
|---|---|---|---|
| 1139 | Cl | C3H7(n) | OH |
| 1140 | Cl | C3H7(n) | CH2OH |
| 1141 | Cl | C3H7(n) | C2H5 |
| 1142 | Cl | C3H7(n) | C3H7(n) |
| 1143 | Cl | C3H7(n) | C6H5 |
| 1144 | Cl | C3H7(n) | C6H5CH2 |
| 1145 | Cl | C3H7(n) | (2-ethylphenyl) |
| 1146 | Cl | C4H9(n) | H |
| 1147 | Cl | C4H9(n) | NH2 |
| 1148 | Cl | C4H9(n) | OH |
| 1149 | Cl | C4H9(n) | CH2OH |
| 1150 | Cl | C4H9(n) | C2H5 |
| 1151 | Cl | C4H9(n) | C3H7(n) |
| 1152 | Cl | C4H9(n) | C6H5 |
| 1153 | Cl | C4H9(n) | C6H5CH2 |
| 1154 | Cl | C4H9(n) | (2-ethylphenyl) |
| 1155 | C2H5 | C3H7(n) | H |
| 1156 | C2H5 | C3H7(n) | NH2 |
| 1157 | C2H5 | C3H7(n) | OH |
| 1158 | C2H5 | C3H7(n) | CH2OH |
| 1159 | C2H5 | C3H7(n) | C2H5 |
| 1160 | C2H5 | C4H9(n) | H |
| 1161 | C2H5 | C4H9(n) | NH2 |
| 1162 | C2H5 | C4H9(n) | OH |
| 1163 | C2H5 | C4H9(n) | CH2OH |
| 1164 | C2H5 | C4H9(n) | C2H5 |
| 1165 | C4H9(n) | C3H7(n) | H |
| 1166 | C4H9(n) | C3H7(n) | NH2 |
| 1167 | C4H9(n) | C3H7(n) | OH |
| 1168 | C4H9(n) | C3H7(n) | CH2OH |
| 1169 | C4H9(n) | C3H7(n) | C2H5 |
| 1170 | C4H9(n) | C3H7(n) | C6H5CH2 |
| 1171 | C4H9(n) | C4H9(n) | H |
| 1172 | C4H9(n) | C4H9(n) | NH2 |
| 1173 | C4H9(n) | C4H9(n) | OH |
| 1174 | C4H9(n) | C4H9(n) | CH2OH |
| 1175 | C4H9(n) | C4H9(n) | C2H5 |
| 1176 | (2-ethylphenyl) | C3H7(n) | H |
| 1177 | (2-ethylphenyl) | C3H7(n) | NH2 |
| 1178 | (2-ethylphenyl) | C3H7(n) | OH |
| 1179 | (2-ethylphenyl) | C3H7(n) | CH2OH |
| 1180 | (2-ethylphenyl) | C3H7(n) | C2H5 |
| 1181 | (2-ethylphenyl) | C4H9(n) | H |
| 1182 | (2-ethylphenyl) | C4H9(n) | NH2 |
| 1183 | (2-ethylphenyl) | C4H9(n) | OH |
| 1184 | (2-ethylphenyl) | C4H9(n) | CH2OH |
| 1185 | (2-ethylphenyl) | C4H9(n) | C2H5 |
| 1186 | (2,6-dimethylphenyl) | C3H7(n) | H |
| 1187 | (2,6-dimethylphenyl) | C3H7(n) | NH2 |
| 1188 | (2,6-dimethylphenyl) | C3H7(n) | OH |
| 1189 | (2,6-dimethylphenyl) | C3H7(n) | CH2OH |
| 1190 | (2,6-dimethylphenyl) | C3H7(n) | C2H5 |
| 1191 | (2,6-dimethylphenyl) | C4H9(n) | H |
| 1192 | (2,6-dimethylphenyl) | C4H9(n) | NH2 |
| 1193 | (2,6-dimethylphenyl) | C4H9(n) | OH |
| 1194 | (2,6-dimethylphenyl) | C4H9(n) | CH2OH |
| 1195 | (2,6-dimethylphenyl) | C4H9(n) | C2H5 |

TABLE XXI

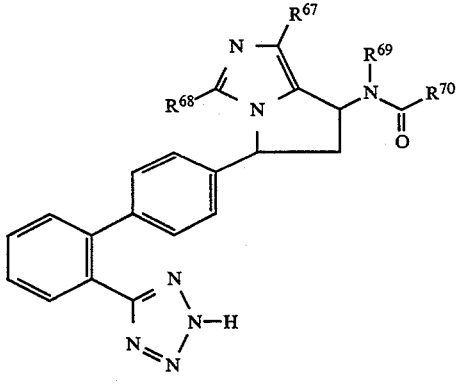

| EX. # | R67 | R68 | R69 | R70 |
|---|---|---|---|---|
| 1196 | H | C3H7(n) | H | CH3 |
| 1197 | H | C3H7(n) | CH3 | CH3 |
| 1198 | H | C3H7(n) | C6H5CH2 | CH3 |
| 1199 | H | C4H9(n) | H | CH3 |
| 1200 | H | C4H9(n) | CH3 | CH3 |
| 1201 | H | C4H9(n) | C6H5CH2 | CH3 |
| 1202 | Cl | C3H7(n) | H | CH3 |
| 1203 | Cl | C3H7(n) | CH3 | CH3 |
| 1204 | Cl | C3H7(n) | C6H5CH2 | CH3 |
| 1205 | Cl | C4H9(n) | H | CH3 |
| 1206 | Cl | C4H9(n) | CH3 | CH3 |
| 1207 | Cl | C4H9(n) | C6H5CH2 | CH3 |
| 1208 | C2H5 | C3H7(n) | H | CH3 |
| 1209 | C2H5 | C3H7(n) | CH3 | CH3 |
| 1210 | C2H5 | C4H9(n) | H | CH3 |
| 1211 | C2H5 | C4H9(n) | CH3 | CH3 |
| 1212 | C4H9(n) | C3H7(n) | H | CH3 |
| 1213 | C4H9(n) | C3H7(n) | CH3 | CH3 |
| 1214 | C4H9(n) | C4H9(n) | H | CH3 |
| 1215 | C4H9(n) | C4H9(n) | CH3 | CH3 |
| 1216 | (2-ethylphenyl) | C3H7(n) | H | CH3 |
| 1217 | (2-ethylphenyl) | C3H7(n) | CH3 | CH3 |
| 1218 | (2-ethylphenyl) | C4H9(n) | H | CH3 |
| 1219 | (2-ethylphenyl) | C4H9(n) | CH3 | CH3 |
| 1220 | (2,6-dimethyl-phenyl) | C3H7(n) | H | CH3 |
| 1221 | (2,6-dimethyl-phenyl) | C3H7(n) | CH3 | CH3 |
| 1222 | (2,6-dimethyl-phenyl) | C4H9(n) | H | CH3 |
| 1223 | (2,6-dimethyl-phenyl) | C4H9(n) | CH3 | CH3 |
| 1224 | H | C3H7(n) | H | C2H5 |
| 1225 | H | C3H7(n) | CH3 | C2H5 |
| 1226 | H | C3H7(n) | C2H5 | C2H5 |
| 1227 | H | C4H9(n) | H | C2H5 |
| 1228 | H | C4H9(n) | CH3 | C2H5 |
| 1229 | H | C4H9(n) | C2H5 | C2H5 |
| 1230 | Cl | C3H7(n) | H | C2H5 |
| 1231 | Cl | C3H7(n) | CH3 | C2H5 |
| 1232 | Cl | C3H7(n) | C2H5 | C2H5 |
| 1233 | Cl | C4H9(n) | H | C2H5 |
| 1234 | Cl | C4H9(n) | CH3 | C2H5 |
| 1235 | Cl | C4H9(n) | C2H5 | C2H5 |
| 1236 | C2H5 | C3H7(n) | H | C2H5 |
| 1237 | C2H5 | C3H7(n) | CH3 | C2H5 |
| 1238 | C2H5 | C4H9(n) | H | C2H5 |
| 1239 | C2H5 | C4H9(n) | CH3 | C2H5 |
| 1240 | (2-ethylphenyl) | C3H7(n) | H | C2H5 |
| 1241 | (2-ethylphenyl) | C4H9(n) | H | C2H5 |
| 1242 | (2,6-dimethyl-phenyl) | C3H7(n) | H | C2H5 |
| 1243 | (2,6-dimethyl-phenyl) | C4H9(n) | H | C2H5 |
| 1244 | H | C3H7(n) | H | C6H5 |
| 1245 | H | C3H7(n) | CH3 | C6H5 |
| 1246 | H | C4H9(n) | H | C6H5 |
| 1247 | H | C4H9(n) | CH3 | C6H5 |
| 1248 | Cl | C3H7(n) | H | C6H5 |
| 1249 | Cl | C3H7(n) | CH3 | C6H5 |
| 1250 | Cl | C4H9(n) | H | C6H5 |
| 1251 | Cl | C4H9(n) | CH3 | C6H5 |

TABLE XXI-continued

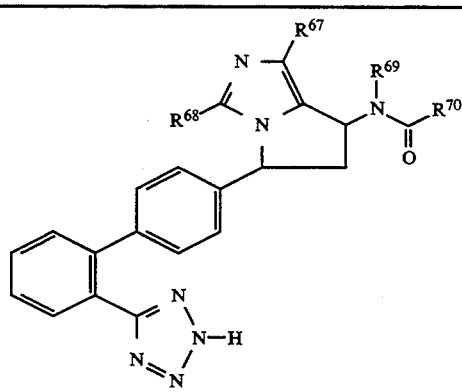

| EX. # | R67 | R68 | R69 | R70 |
|---|---|---|---|---|
| 1252 | C2H5 | C3H7(n) | H | C6H5 |
| 1253 | C2H5 | C3H7(n) | CH3 | C6H5 |
| 1254 | C2H5 | C4H9(n) | H | C6H5 |
| 1255 | C2H5 | C4H9(n) | CH3 | C6H5 |
| 1256 | C4H9(n) | C3H7(n) | H | C6H5 |
| 1257 | C4H9(n) | C3H7(n) | CH3 | C6H5 |
| 1258 | C4H9(n) | C4H9(n) | H | C6H5 |
| 1259 | C4H9(n) | C4H9(n) | CH3 | C6H5 |
| 1260 | C4H9(n) | C4H9(n) | H | CH2CH2CO2H |
| 1261 | C4H9(n) | C4H9(n) | CH3 | CH2CH2CO2H |
| 1262 | (2-ethylphenyl) | C3H7(n) | H | CH2CH2CO2H |
| 1263 | (2-ethylphenyl) | C3H7(n) | CH3 | CH2CH2CO2H |
| 1264 | (2-ethylphenyl) | C4H9(n) | H | CH2CH2CO2H |
| 1265 | (2-ethylphenyl) | C4H9(n) | CH3 | CH2CH2CO2H |
| 1266 | (2,6-dimethyl-phenyl) | C3H7(n) | H | CH2CH2CO2H |
| 1267 | (2,6-dimethyl-phenyl) | C3H7(n) | CH3 | CH2CH2CO2H |
| 1268 | (2,6-dimethyl-phenyl) | C4H9(n) | H | CH2CH2CO2H |
| 1269 | (2,6-dimethyl-phenyl) | C4H9(n) | CH3 | CH2CH2CO2H |

TABLE XXII

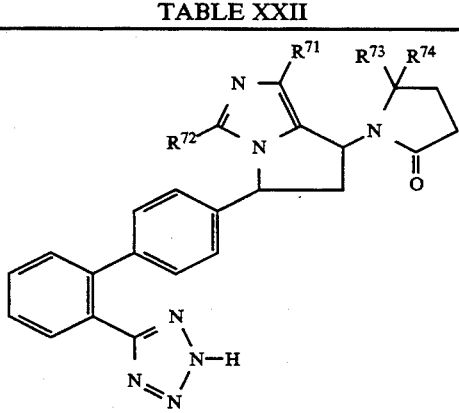

| EX. # | R71 | R72 | R73, R74 |
|---|---|---|---|
| 1270 | H | C3H7(n) | O |
| 1271 | H | C3H7(n) | H, H |
| 1272 | H | C3H7(n) | H, CH3 |
| 1273 | H | C3H7(n) | H, C2H5 |
| 1274 | H | C3H7(n) | H, CH2OH |
| 1275 | H | C3H7(n) | H, CO2H |
| 1276 | H | C4H9(n) | O |
| 1277 | H | C4H9(n) | H, H |
| 1278 | H | C4H9(n) | H, CH3 |
| 1279 | H | C4H9(n) | H, C2H5 |
| 1280 | H | C4H9(n) | H, CH2OH |
| 1281 | H | C4H9(n) | H, CO2H |
| 1282 | Cl | C3H7(n) | O |
| 1283 | Cl | C3H7(n) | H, H |
| 1284 | Cl | C3H7(n) | H, CH3 |
| 1285 | Cl | C3H7(n) | H, C2H5 |

TABLE XXII-continued

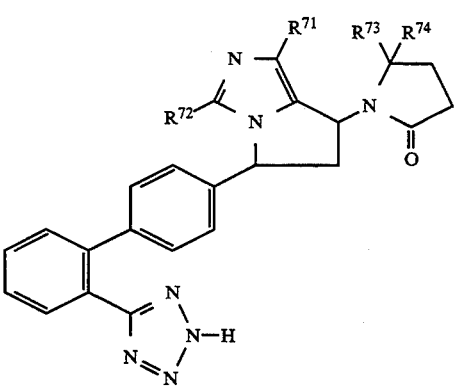

| EX. # | R71 | R72 | R73, R74 |
|---|---|---|---|
| 1286 | Cl | C3H7(n) | H, CH2OH |
| 1287 | Cl | C3H7(n) | H, CO2H |
| 1288 | Cl | C4H9(n) | O |
| 1289 | Cl | C4H9(n) | H, H |
| 1290 | Cl | C4H9(n) | H, CH3 |
| 1291 | Cl | C4H9(n) | H, C2H5 |
| 1292 | Cl | C4H9(n) | H, CH2OH |
| 1293 | Cl | C4H9(n) | H, CO2H |
| 1294 | C2H5 | C3H7(n) | O |
| 1295 | C2H5 | C3H7(n) | H, H |
| 1296 | C2H5 | C3H7(n) | H, CH3 |
| 1297 | C2H5 | C3H7(n) | H, C2H5 |
| 1298 | C2H5 | C3H7(n) | H, CH2OH |
| 1299 | C2H5 | C3H7(n) | H, CO2H |
| 1300 | C2H5 | C4H9(n) | O |
| 1301 | C2H5 | C4H9(n) | H, H |
| 1302 | C2H5 | C4H9(n) | H, CH3 |
| 1303 | C2H5 | C4H9(n) | H, C2H5 |
| 1304 | C2H5 | C4H9(n) | H, CH2OH |
| 1305 | C2H5 | C4H9(n) | H, CO2H |
| 1306 | C4H9(n) | C3H7(n) | O |
| 1307 | C4H9(n) | C3H7(n) | H, H |
| 1308 | C4H9(n) | C3H7(n) | H, CH3 |
| 1309 | C4H9(n) | C3H7(n) | H, CH2OH |
| 1310 | C4H9(n) | C3H7(n) | H, CO2H |
| 1311 | C4H9(n) | C4H9(n) | O |
| 1312 | C4H9(n) | C4H9(n) | H, H |
| 1313 | C4H9(n) | C4H9(n) | H, CH3 |
| 1314 | C4H9(n) | C4H9(n) | H, CH2OH |
| 1315 | C4H9(n) | C4H9(n) | H, CO2H |
| 1316 | (2-ethylphenyl) | C3H7(n) | O |
| 1317 | (2-ethylphenyl) | C3H7(n) | H, H |
| 1318 | (2-ethylphenyl) | C3H7(n) | H, CH3 |
| 1319 | (2-ethylphenyl) | C3H7(n) | CH3, CH3 |
| 1320 | (2-ethylphenyl) | C3H7(n) | H, CH2OH |
| 1321 | (2-ethylphenyl) | C3H7(n) | H, CO2H |
| 1322 | (2-ethylphenyl) | C4H9(n) | O |
| 1323 | (2-ethylphenyl) | C4H9(n) | H, H |
| 1324 | (2-ethylphenyl) | C4H9(n) | H, CH3 |
| 1325 | (2-ethylphenyl) | C4H9(n) | CH3, CH3 |
| 1326 | (2-ethylphenyl) | C4H9(n) | H, CH2OH |
| 1327 | (2-ethylphenyl) | C4H9(n) | H, CO2H |

TABLE XXIII

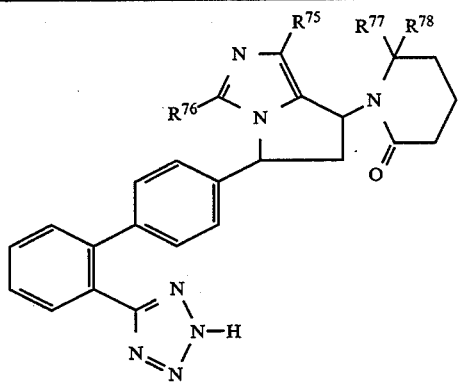

| EX. # | $R^{75}$ | $R^{76}$ | $R^{77}, R^{78}$ |
|---|---|---|---|
| 1328 | H | $C_3H_7(n)$ | O |
| 1329 | H | $C_3H_7(n)$ | H, H |
| 1330 | H | $C_3H_7(n)$ | H, $CH_3$ |
| 1331 | H | $C_3H_7(n)$ | H, $C_2H_5$ |
| 1332 | H | $C_3H_7(n)$ | H, $CH_2OH$ |
| 1333 | H | $C_3H_7(n)$ | H, $CO_2H$ |
| 1334 | H | $C_4H_9(n)$ | O |
| 1335 | H | $C_4H_9(n)$ | H, H |
| 1336 | H | $C_4H_9(n)$ | H, $CH_3$ |
| 1337 | H | $C_4H_9(n)$ | H, $C_2H_5$ |
| 1338 | H | $C_4H_9(n)$ | H, $CH_2OH$ |
| 1339 | H | $C_4H_9(n)$ | H, $CO_2H$ |
| 1340 | Cl | $C_3H_7(n)$ | O |
| 1341 | Cl | $C_3H_7(n)$ | H, H |
| 1342 | Cl | $C_3H_7(n)$ | H, $CH_3$ |
| 1343 | Cl | $C_3H_7(n)$ | $CH_3$, $CH_3$ |
| 1344 | Cl | $C_3H_7(n)$ | H, $CH_2OH$ |
| 1345 | Cl | $C_3H_7(n)$ | H, $CO_2H$ |
| 1346 | Cl | $C_4H_9(n)$ | O |
| 1347 | Cl | $C_4H_9(n)$ | H, H |
| 1348 | Cl | $C_4H_9(n)$ | H, $CH_3$ |
| 1349 | Cl | $C_4H_9(n)$ | H, $C_2H_5$ |
| 1350 | Cl | $C_4H_9(n)$ | H, $CH_2OH$ |
| 1351 | Cl | $C_4H_9(n)$ | H, $CO_2H$ |
| 1352 | $C_2H_5$ | $C_3H_7(n)$ | O |
| 1353 | $C_2H_5$ | $C_3H_7(n)$ | H, H |
| 1354 | $C_2H_5$ | $C_3H_7(n)$ | H, $CH_3$ |
| 1355 | $C_2H_5$ | $C_3H_7(n)$ | H, $C_2H_5$ |
| 1356 | $C_2H_5$ | $C_3H_7(n)$ | H, $CH_2OH$ |
| 1357 | $C_2H_5$ | $C_3H_7(n)$ | H, $CO_2H$ |
| 1358 | $C_2H_5$ | $C_4H_9(n)$ | O |
| 1359 | $C_2H_5$ | $C_4H_9(n)$ | H, H |
| 1360 | $C_2H_5$ | $C_4H_9(n)$ | H, $CH_3$ |
| 1361 | $C_2H_5$ | $C_4H_9(n)$ | H, $C_2H_5$ |
| 1362 | $C_2H_5$ | $C_4H_9(n)$ | H, $CH_2OH$ |
| 1363 | $C_2H_5$ | $C_4H_9(n)$ | H, $CO_2H$ |
| 1364 | $C_4H_9(n)$ | $C_3H_7(n)$ | O |
| 1365 | $C_4H_9(n)$ | $C_3H_7(n)$ | H, H |
| 1366 | $C_4H_9(n)$ | $C_3H_7(n)$ | H, $CH_3$ |
| 1367 | $C_4H_9(n)$ | $C_3H_7(n)$ | H, $CH_2OH$ |
| 1368 | $C_4H_9(n)$ | $C_3H_7(n)$ | H, $CO_2H$ |
| 1369 | $C_4H_9(n)$ | $C_4H_9(n)$ | O |
| 1370 | $C_4H_9(n)$ | $C_4H_9(n)$ | H, H |
| 1371 | $C_4H_9(n)$ | $C_4H_9(n)$ | H, $CH_3$ |
| 1372 | $C_4H_9(n)$ | $C_4H_9(n)$ | H, $CH_2OH$ |
| 1373 | $C_4H_9(n)$ | $C_4H_9(n)$ | H, $CO_2H$ |
| 1374 | (2-ethylphenyl) | $C_3H_7(n)$ | O |
| 1375 | (2-ethylphenyl) | $C_3H_7(n)$ | H, H |
| 1376 | (2-ethylphenyl) | $C_3H_7(n)$ | H, $CH_3$ |
| 1377 | (2-ethylphenyl) | $C_3H_7(n)$ | $CH_3$, $CH_3$ |
| 1378 | (2-ethylphenyl) | $C_3H_7(n)$ | H, $CH_2OH$ |
| 1379 | (2-ethylphenyl) | $C_3H_7(n)$ | H, $CO_2H$ |
| 1380 | (2-ethylphenyl) | $C_4H_9(n)$ | O |
| 1381 | (2-ethylphenyl) | $C_4H_9(n)$ | H, H |
| 1382 | (2-ethylphenyl) | $C_4H_9(n)$ | H, $CH_3$ |
| 1383 | (2-ethylphenyl) | $C_4H_9(n)$ | $CH_3$, $CH_3$ |
| 1384 | (2-ethylphenyl) | $C_4H_9(n)$ | H, $CH_2OH$ |
| 1385 | (2-ethylphenyl) | $C_4H_9(n)$ | H, $CO_2H$ |

TABLE XXIV

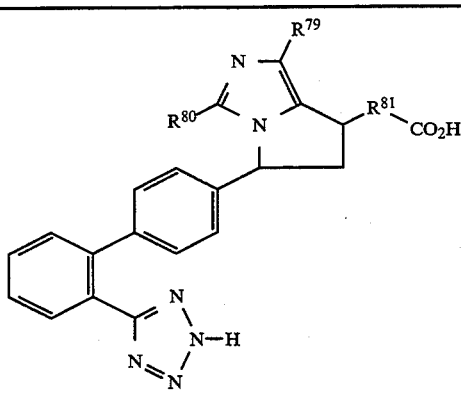

| EX. # | $R^{79}$ | $R^{80}$ | $R^{81}$ |
|---|---|---|---|
| 1386 | H | $C_3H_7(n)$ | $CH_2$ |
| 1387 | H | $C_3H_7(n)$ | $CH(C_2H_5)$ |
| 1388 | H | $C_3H_7(n)$ | $CH(CH_2C_6H_5)$ |
| 1389 | H | $C_3H_7(n)$ | $CH_2CH_2$ |
| 1390 | H | $C_3H_7(n)$ | $CH(C_2H_5)CH_2$ |
| 1391 | H | $C_3H_7(n)$ | $CH(CH_2C_6H_5)CH_2$ |
| 1392 | H | $C_4H_9(n)$ | $CH_2$ |
| 1393 | H | $C_4H_9(n)$ | $CH(C_2H_5)$ |
| 1394 | H | $C_4H_9(n)$ | $CH(CH_2C_6H_5)$ |
| 1395 | H | $C_4H_9(n)$ | $CH_2CH_2$ |
| 1396 | H | $C_4H_9(n)$ | $CH(C_2H_5)CH_2$ |
| 1397 | H | $C_4H_9(n)$ | $CH(CH_2C_6H_5)CH_2$ |
| 1398 | Cl | $C_3H_7(n)$ | $CH_2$ |
| 1399 | Cl | $C_3H_7(n)$ | $CH(C_2H_5)$ |
| 1400 | Cl | $C_3H_7(n)$ | $CH(CH_2C_6H_5)$ |
| 1401 | Cl | $C_3H_7(n)$ | $CH_2CH_2$ |
| 1402 | Cl | $C_3H_7(n)$ | $CH(C_2H_5)CH_2$ |
| 1403 | Cl | $C_3H_7(n)$ | $CH(CH_2C_6H_5)CH_2$ |
| 1404 | Cl | $C_4H_9(n)$ | $CH_2$ |
| 1405 | Cl | $C_4H_9(n)$ | $CH(C_2H_5)$ |
| 1406 | Cl | $C_4H_9(n)$ | $CH(CH_2C_6H_5)$ |
| 1407 | Cl | $C_4H_9(n)$ | $CH_2CH_2$ |
| 1408 | Cl | $C_4H_9(n)$ | $CH(C_2H_5)CH_2$ |
| 1409 | Cl | $C_4H_9(n)$ | $CH(CH_2C_6H_5)CH_2$ |
| 1410 | $C_2H_5$ | $C_3H_7(n)$ | $CH_2$ |
| 1411 | $C_2H_5$ | $C_3H_7(n)$ | $CH(C_2H_5)$ |
| 1412 | $C_2H_5$ | $C_3H_7(n)$ | $CH(CH_2C_6H_5)$ |
| 1413 | $C_2H_5$ | $C_3H_7(n)$ | $CH_2CH_2$ |
| 1414 | $C_2H_5$ | $C_3H_7(n)$ | $CH(C_2H_5)CH_2$ |
| 1415 | $C_2H_5$ | $C_3H_7(n)$ | $CH(CH_2C_6H_5)CH_2$ |
| 1416 | $C_2H_5$ | $C_4H_9(n)$ | $CH_2$ |
| 1417 | $C_2H_5$ | $C_4H_9(n)$ | $CH(C_2H_5)$ |
| 1418 | $C_2H_5$ | $C_4H_9(n)$ | $CH(CH_2C_6H_5)$ |
| 1419 | $C_2H_5$ | $C_4H_9(n)$ | $CH_2CH_2$ |
| 1420 | $C_2H_5$ | $C_4H_9(n)$ | $CH(C_2H_5)CH_2$ |
| 1421 | $C_2H_5$ | $C_4H_9(n)$ | $CH(CH_2C_6H_5)CH_2$ |
| 1422 | $C_4H_9(n)$ | $C_3H_7(n)$ | $CH_2$ |
| 1423 | $C_4H_9(n)$ | $C_3H_7(n)$ | $CH_2CH_2$ |
| 1424 | $C_4H_9(n)$ | $C_4H_9(n)$ | $CH_2$ |
| 1425 | $C_4H_9(n)$ | $C_4H_9(n)$ | $CH_2CH_2$ |
| 1426 | (2-ethylphenyl) | $C_3H_7(n)$ | $CH_2$ |
| 1427 | (2-ethylphenyl) | $C_3H_7(n)$ | $CH_2CH_2$ |
| 1428 | (2-ethylphenyl) | $C_4H_9(n)$ | $CH_2$ |
| 1429 | (2-ethylphenyl) | $C_4H_9(n)$ | $CH_2CH_2$ |
| 1430 | (2,6-dimethylphenyl) | $C_3H_7(n)$ | $CH_2$ |
| 1431 | (2,6-dimethylphenyl) | $C_3H_7(n)$ | $CH_2CH_2$ |
| 1432 | (2,6-dimethylphenyl) | $C_4H_9(n)$ | $CH_2$ |
| 1433 | (2,6-dimethylphenyl) | $C_4H_9(n)$ | $CH_2CH_2$ |

An appropriately substituted imidazole 31, the heterocyclic starting material, may be prepared as described in the literature [Klaus Hofmann, in "Imidazole and its Derivatives" of *The Chemistry of Heterocyclic Compounds,* Arnold Weissberger Ed., Wiley Interscience New York, 1953]. The imidazole 31 in N,N-dimethylformamide (DMF) is treated with base, such as potassium tert-butoxide, followed by addition of appropriate alkylating agent 32 to give the coupled product 33 (Scheme V). For compounds where X is a substituted phenyl group, several procedures have been published for the preparations of the alkylating agent 32 [see references for compound 2].

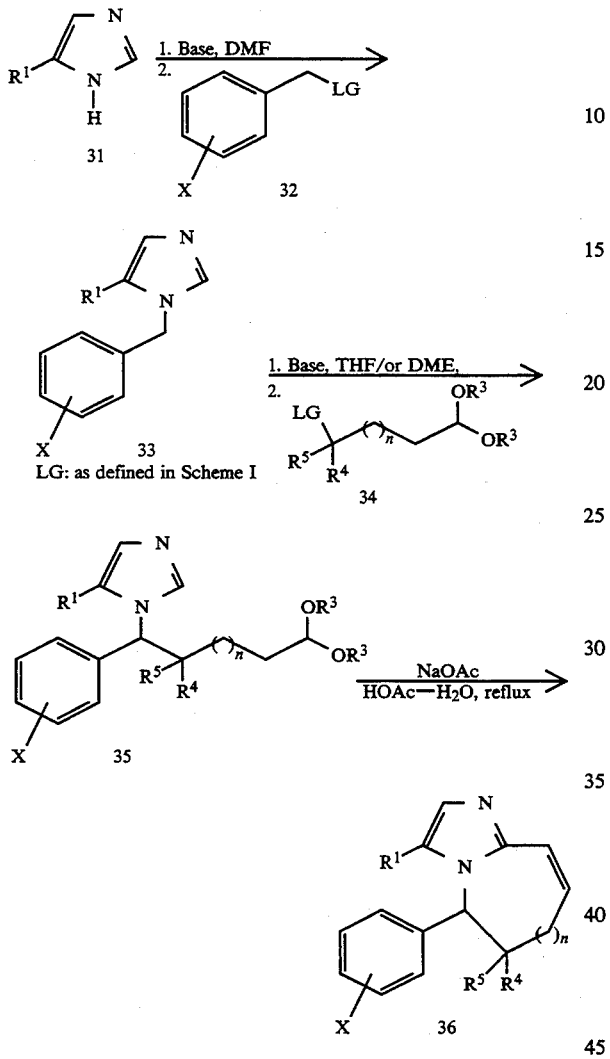

The arylated imidazole 33 itself may be an angiotensin II receptor antagonist, but it may also be used as a key intermediate in the preparation of the compounds of the invention. Imidazole 33 in THF (or DME) is treated with base (such as n-BuLi or LDA) at −78° C. (or −65° C.), followed by addition of an appropriate alkylating agent or other electrophiles 34 (the acetal shown in Scheme V may be other aldehyde masking group or equivalent, and LG is a leaving group such as halide, triflate or rosylate). The resulting masked aldehyde 35 was stirred with NaOAc in aqueous acetic acid at reflux for a few days (1 to 5 days) to give one of the described invention compounds, a cyclized imidazole 36.

The imidazole 36 may be used as an intermediate to prepare other substituted compounds with appropriate functional group transformations and preparations of some of those compounds are illustrated in Scheme VI (all of the intermediates shown in the sequences are also angiotensin II receptor antagonists). For example, The unsaturated imidazole 36 and NBS in CCl4 is stirred at reflux to give a bromide 37. The bromide 37 may be treated with organolithium, such as n-BuLi or tert-BuLi, followed by addition of an appropriate electrophile, (such as alkyl halide, carbon dioxide, aldehyde, ketone and others) to give the addition product 38. The olefin 38 may be hydrogenated to give its saturated product 39.

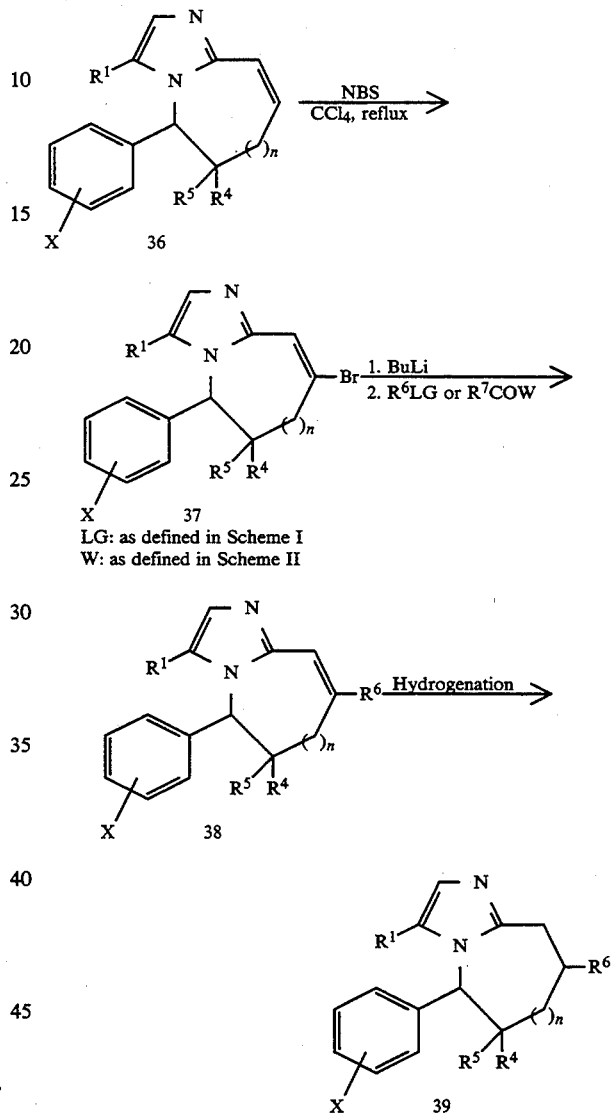

Alternatively, as illustrated in Scheme VII, the unsaturated imidazole 36 may be treated with NBS in wet DMSO to give a bromohydrin which may be reduced with nBu3SnH to an alcohol 40 and the oxidation of the alcohol with MnO2 will afford a ketone 41. The ketone 41 may be condensed with appropriately substituted amine, then reduced to an amine 42 with an appropriate reducing agent (e.g. NaBH4, or hydrogen over catalyst). The amine 42 may also be prepared directly from olefin 36 under bromination condition (NBS, CH3CN) with a large excess of succinimide. The amine 42 may be used to prepare other derivatives. Alternatively, the alcohol 40 may be treated with triphenylphosphine, diethoxyazo dicarboxylate and an imide (e.g. phthalimide) to give an imide analogue which may be converted to an amine 42.

The ketone 41 may be treated with appropriate organometallic reagents (such as Grignard, organolithium, organocerium or organozinc reagents) to give the additional product, a tertiary alcohol. The alcohol may be dehydrated to give an olefin 43 or an isomeric mixture of olefins 43. The olefin 43 may be treated with base, such as LDA and kinetically quenched with either organic acid or appropriate electrophile at low temperature to give the isomerized olefin 44. The olefins 43 or 44 may be hydrogenated to its saturated analogue 45.

another equivalent of base followed by addition of electrophile 46 or 47. If necessary, the resulting lithium anion obtained from the procedure described above may be converted to other organometallic reagents according to well-established procedures. Electrophiles 47 and 48 can be prepared from $HC(=O)(CR^4R^5)(CH_2)_nC(=O)LG$ and an appropriate organometallic reagent such as $XC_6H_4MgBr$.

SCHEME VII

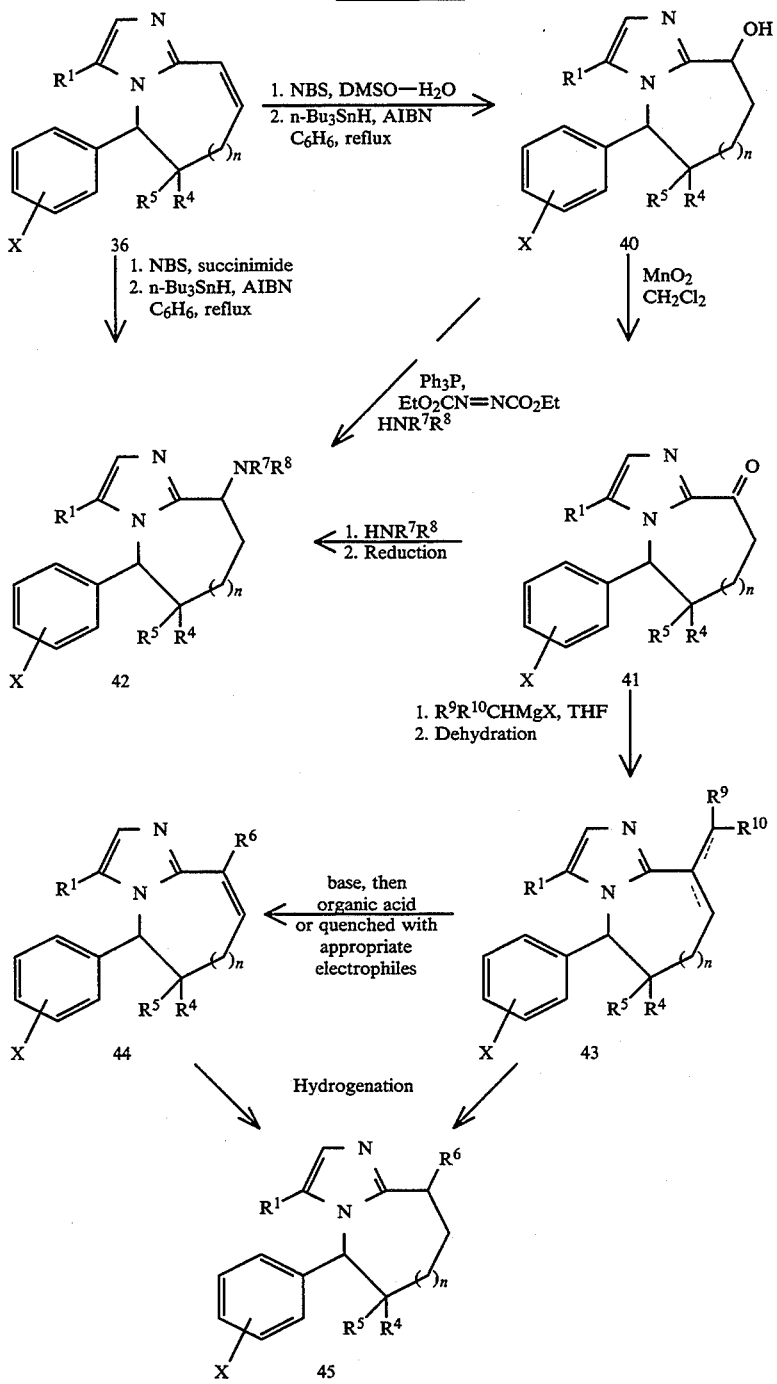

In Scheme VIII, an alternative preparation for the compounds of the invention is described. An appropriately substituted imidazole 31 may be treated with one equivalent of base, then protected as SEM or BOC derivative. The protected imidazole then is treated with If PLG is an hydroxyl group and Z is a proton, the resulting addition product 49, may be cyclized with triphenylphosphine and diethyl azodicarboxylate (Mitsunobu reaction or other modified conditions). If PLG is or is converted to a leaving group, such as halides, rosylate, and Z is a proton, the cyclization may be achieved with a weak base in DMF (e.g. K$_2$CO$_3$, CsCO$_3$) to give a ketone 41. The ketone 41 may be reduced to an alcohol 40 with NaBH$_4$ in methanol. The alcohol 40 may be dehydrated to olefin 36 with acid (e.g. HOAc and heat) or thionyl chloride and pyridine. Other compounds may be prepared from compounds 36, 40, or 41 as described in Scheme VI and VII.

SCHEME VIII

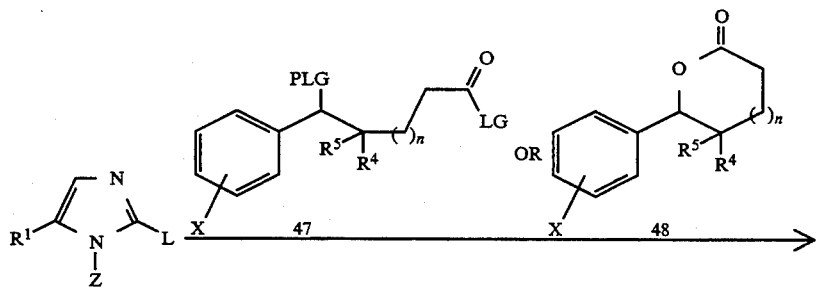

31 Z, L = H
46 Z = protecting group,
 e.g. SEM, or BOC
L = Mg, Ce, Cd, Zn halide or Li

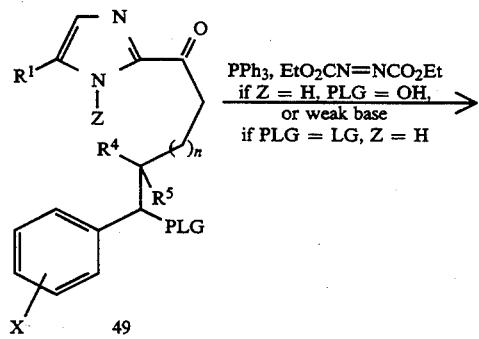

PPh$_3$, EtO$_2$CN=NCO$_2$Et
if Z = H, PLG = OH,
or weak base
if PLG = LG, Z = H PLG = a leaving group or a group that can be easily converted to a leaving group

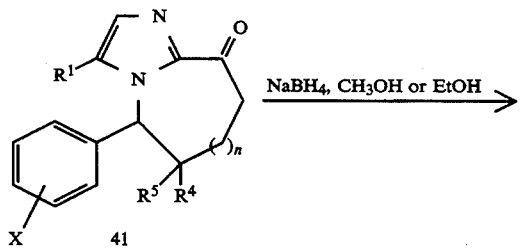

NaBH$_4$, CH$_3$OH or EtOH

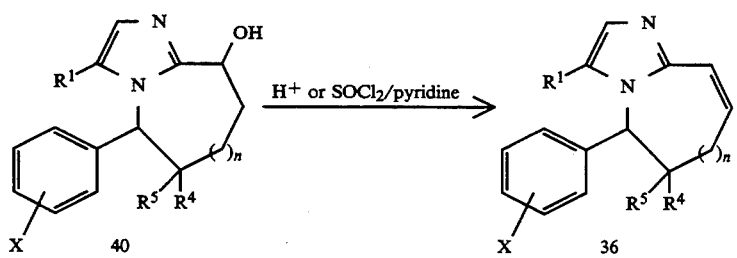

H$^+$ or SOCl$_2$/pyridine

EXAMPLE 1434

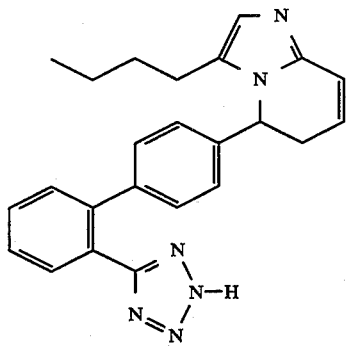

3-Butyl-5,6-dihydro-5-[2'-(1H-tetrazol-5-yl)[1,1'-biphenyl]-4-yl]imidazo[1,2-a]pyridine Step 1: Preparation of Biphenyl Imidazole To a solution of 4-butylimidazole (2.65 mmol) in 5.3 ml of DMF is added 3.45 ml (3.45 mmol) of potassium tert-butoxide (1M in THF), and the resulting solution is stirred at room temperature for 30 min. To the dark brown mixture is added 2.75 g (3.45 mmol) of the bromomethyl biphenyl. The reaction mixture is stirred at room temperature until the reaction is complete. The mixture is concentrated in vacuo. The residue is purified to give the trityl-protected biphenyl imidazole.

Step 2: Preparation of Dimethyl Acetal Imidazole

To a solution of biphenyl imidazole (3.18 mmol, obtained from Step 1) in 16 mL of THF cooled at −45° C. (acetonitrile-dry ice) is added 2.8 mL (4.06 mmol) of n-butyllithium (1.45M in hexane) over a 4 minute period. The resulting dark purple solution is stirred cold for another 15 minutes, followed by addition of 1.0 mL (6.59 mmol) of 3-bromopropionaldehyde dimethyl acetal in one portion. The mixture is stirred cold for 40 minutes, then is slowly warmed to −10° C. The reaction is quenched with aqueous NH4Cl, extracted with diethyl ether. The combined extracts are washed with brine, dried (MgSO4), concentrated in vacuo and purified to give the biphenyl dimethyl acetal imidazole intermediate.

Step 3: Preparation of Biphenyl Bicyclic Imidazole

A solution of the crude biphenyl dimethyl acetal imidazole (3.18 mmol, obtained from Step 2) and 5.3 g (88 mmol) of NaOAc in 13 mL of water and 40 mL of glacial acetic acid is stirred at reflux until the reaction is complete. The solution is cooled and concentrated in vacuo. The residue is dissolved in methylene chloride and filtered. The filtrate is stirred with 2 g (7.2 mmol) of trityl chloride and 3 mL (21.5 mmol) of TEA at room temperature until the reaction is complete. The mixture is concentrated in vacuo. The residue is purified to give the biphenyl bicyclic imidazole.

Step 4: Detritylation of Trityl Tetrazole

A solution of the biphenyl bicyclic imidazole (0.144 mmol, obtained from Step 3) is stirred with 1 mL of water and 6 mL of acetic acid at room temperature until the reaction is complete. The solution is concentrated in vacuo, stirred in aqueous NaHCO3 and washed with ether. The aqueous residue is acidified with 3N HCl to pH 4 and extracted with methylene chloride. The combined extracts are dried (MgSO4), concentrated and purified to give the title compound of Example 1434.

EXAMPLE 1435

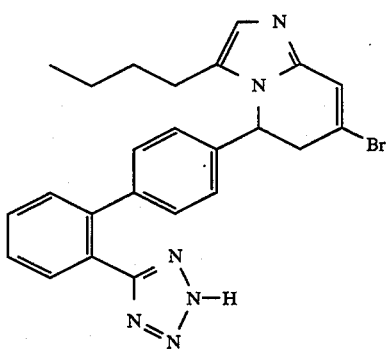

7-Bromo-3-butyl-5,6-dihydro-5-[2'-(1H-tetrazol-5-yl)[1,1'-biphenyl]-4-yl]imidazo[1,2-a]pyridine Step 1: Preparation of Bromo Olefin Imidazole A solution of trityl-protected bicyctic imidazole (0.101 mmol, obtained from Step 3 of Example 1434), 20 mg (0.112 mmol) of NBS and 7 mg (catalytic) of AIBN in 2.8 mL of CCl4 is stirred at reflux until the reaction is complete. The reaction mixture is diluted with CCl4 and washed with water. The organic layer is dried (MgSO4) and concentrated in vacuo. The residue is purified to give the biphenyl bromo olefin imidazole.

Step 2: Detritylation of the Trityl Tetrazole

A solution of bromo olefin imidazole (0.0427 mmol, obtained from Step 1) in 0.8 mL of water and 5 mL of acetic acid is stirred at room temperature until the reaction is complete. The mixture is concentrated in vacuo. The residue is worked up as described in Step 4 of Example 1434 and purified to give the title compound of Example 1435.

EXAMPLE 1436

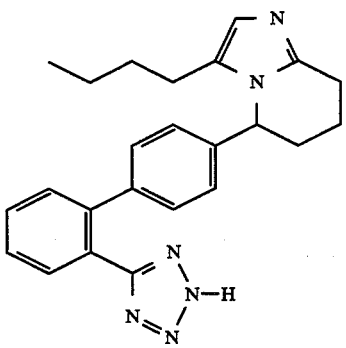

3-Butyl-5,6,7,8-tetrahydro-5-[2'-(1H-tetrazol-5-yl)[1,1'-biphenyl]-4-yl]imidazo[1,2-a]pyridine A suspension of bicyclic olefin imidazole (0.1 mmol, the title compound of Example 1434) and 20 mg (0,019 mmol) of 10% palladium on charcoal in 2 mL of absolute ethanol is agitated on a Parr apparatus under 50 psi of hydrogen gas at room temperature until the reaction is complete. The mixture is filtered through a pad of celite, concentrated in vacuo and purified to give the title compound of Example 1436.

EXAMPLE 1437

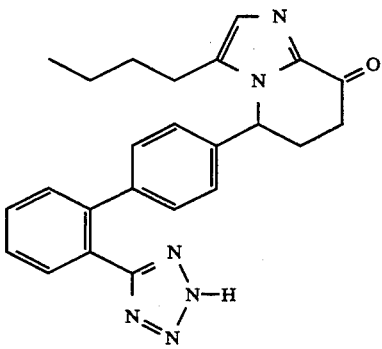

3-Butyl-5,6-dihydro-5 -[2'-(1H-tetrazol-5-yl )[1,1'-biphenyl]-4-yl]imidazo[1,2-a]pyridin-8(5H)-one Step 1: Preparation of the Bromohydrin Intermediate To a solution of biphenyl olefin imidazole (3.13 mmol, obtained from Step 4 of Example 1434) in 2.2 mL (0.122 mmol) of water and 22 mL of DMSO at room temperature is added 587 mg (3.30 mmol) of NBS in one portion. The resulting orange solution is stirred at room temperature for 40 min, quenched with aqueous Na$_2$SO$_3$, and extracted with chloroform. The combined extracts are washed with water, and the combined aqueous layers are extracted with chloroform. The combined extracts are washed with brine, dried (MgSO$_4$) and concentrated in vacuo to give a crude bromohydrin intermediate which can be used directly in the subsequent Step 2 without further purification.

Step 2: Preparation of the Biphenyl Hydroxy Imidazole

To the crude bromohydrin (3.13 mmol, obtained from Step 1) in 42 mL of degassed dry benzene is added 4.3 mL (14.7 mmol) of n-Bu$_3$SnH and 456 mg (2.7 mmol) of AIBN in one portion and the resulting solution is stirred at reflux until the reaction is complete. The mixture is concentrated in vacuo and partitioned between hexane and acetonitrile. The acetonitrile layer is washed with hexane, and the combined hexane layers are extracted with acetonitrile. The combined acetonitrile extracts are concentrated in vacuo to give an isomeric mixture of both cis- and trans-hydroxy imidazoles (relative to the biphenyl moiety). The crude mixture can be used directly in subsequent Step 3 without further purification. The mixture may also be used to prepare the trans-hydroxy title compound of Example 1439.

Step 3: Preparation of the Keto Imidazole

A suspension of the crude biphenyl hydroxy imidazole (2.72 mmol, obtained from Step 2) and 13 g of active MnO$_2$ in 15 mL of methylene chloride is stirred at room temperature until the reaction is complete. The mixture is filtered through a pad of celite, rinsed with IPA-methylene chloride, and concentrated in vacuo. The residue is purified to give the trityl-protected biphenyl keto imidazole.

Step 4: Detritylation of Trityl Tetrazole

A solution of trityl-protected keto imidazole (0.131 mmol, obtained from Step 3) in 1.0 mL of water and 5.0 mL of acetic acid is stirred at room temperature until the reaction is complete. The mixture is concentrated in vacuo. The residue is worked up as described in Step 4 of Example 1434 to give the title compound of Example 1437.

EXAMPLE 1438

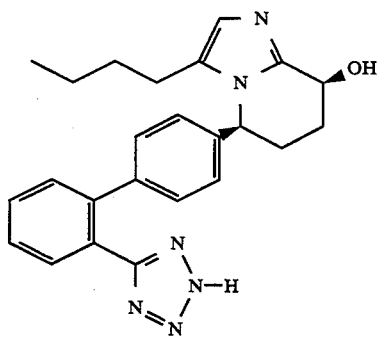

3-Butyl-5,6,7,8-tetrahydro-5-[2'-(1H-tetrazol-5-yl)[1,1'-biphenyl]-4-yl]imidazo[1,2-a]pyridin-cis-8-ol Step 1: Preparation of Cis-Hydroxy Imidazole To a solution of biphenyl keto imidazole (0.456 mmol, obtained from Step 3 of Example 1437) in 0.5 mL of methanol and 2.0 mL of THF at 0° C. is added in small portions 34 mg (0.899 mmol) of NaBH$_4$. The resulting solution is stirred at 0° C., and slowly warmed to room temperature. The reaction is quenched with aqueous NH$_4$Cl, extracted with methylene chloride, dried (MgSO$_4$) and concentrated in vacuo. The residue is purified to give the biphenyl hydroxy imidazole.

Step 2: Detritylation of Trityl Tetrazole

A solution of the biphenyl hydroxy imidazole (0.259 mmol, obtained from Step 1) in 0.4 mL of water and 2.0 mL of acetic acid is stirred at room temperature until the reaction is complete. The mixture is concentrated in vacuo. The residue is purified to give the title compound of Example 1438.

EXAMPLE 1439

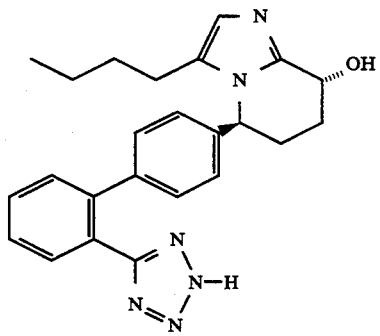

3-Butyl-5,6,7,8-tetrahydro-5-[2'-(1H-tetrazol-5-yl)[1,1'-biphenyl]-4-yl]imidazo[1,2-a]pyridin-trans-8-ol Step 1: Preparation of Biphenyl Trans-Hydroxy Imidazole A suspension of the crude biphenyl hydroxy imidazole (1,307 mmol, obtained from Step 2 of Example 1437) and 3.0 g of active MnO$_2$ in 5.0 mL of methylene chloride is stirred at room temperature. The reaction is worked up before its completion. The mixture is filtered through a pad of celite, rinsed with IPA-methylene chloride, and concentrated in vacuo. The residue is purified to give the trityl protected biphenyl trans-hydroxy imidazole.

Alternatively, the biphenyl trans-hydroxy imidazole can be prepared using the Mitsunobu reaction conditions, To a solution of diethyl azodicarboxylate (2.0 mmol) and 3-nitrobenzoic acid (2.0 mmol) in 2.0 mL of THF is added dropwise a solution of the biphenyl hydroxy imidazole (2.0 mmol, obtained from Step 1 of Example 1438), and triphenylphosphine (2.0 mmol) in 1.0 mL of THF at room temperature. The resulting solution is stirred at room temperature until the reaction is complete. The resulting mixture is diluted with ether or ethyl acetate, and washed with water. The extracts are dried MgSO4) and concentrated in vacuo to give the biphenyl imidazolyl nitrobenzoate. The crude benzoate is hydrolyzed with LiOH in aqueous THF at room temperature and purified to give the biphenyl trans-hydroxy imidazole.

Step 2: Detritylation of Trityl Tetrazole

A solution of the trityl protected biphenyl trans-hydroxy imidazole (0,079 mmol, obtained from Step i) in 0.4 mL of water and 2.0 mL of acetic acid is stirred at room temperature until the reaction is complete. The mixture is concentrated in vacuo. The residue is purified to give the title compound of Example 1439.

EXAMPLE 1440

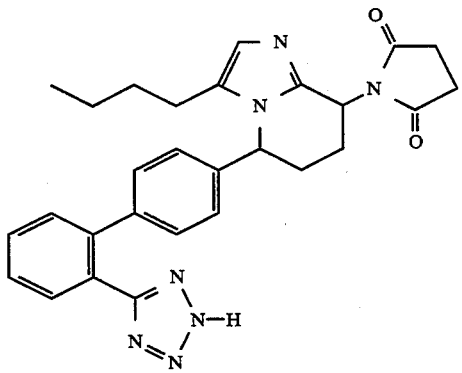

1-[3-Butyl-5,6,7,8-tetrahydro-5-[2'-(1H-tetrazol-5-yl)[1,1'-biphenyl]-4-yl]imidazo[1,2-a]pyridin-8-yl]-2,5-pyrrolidinedione Step 1: Preparation of Succinimidyl Imidazole To a solution of 2.00 g 3.13 mmol) of biphenyl bicyclic imidazole (Example 1434, Step 3) and 1.25 g (12.6 mmol) of succinimide in 20 mL of anhydrous acetonitrile is added 572 mg (3.21 mmol) of NBS in one portion. The resulting orange-red solution is stirred at room temperature for 30 min, then evaporated in vacuo. The residue is dissolved in ethyl acetate and washed with aqueous sodium bisulfite, water, and brine. The extracts are dried (MgSO4) and concentrated in vacuo The residue is purified to give the trityl protected succinimidyl imidazole.

Alternatively, the succinimide can be prepared from its corresponding hydroxy imidazole. To a solution of the biphenyl hydroxy imidazole (2.0 mmol, obtained from Step 1 of Example 1438 or 1439), succinimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (MgSO4) and concentrated in vacuo. The residue is purified to give the trityl protected succinimidyl imidazole.

Step 2: Detritylation of Trityl Tetrazole

A solution of trityl protected succinimidyl imidazole (0.16 mmol, obtained from Step 1) in 0.2 mL of water and 1 mL of acetic acid is stirred at room temperature until the reaction is complete. The mixture is concentrated in vacuo. The residue is worked up as described in Step 4 of Example 1434 and purified to give the title compound of Example 1440.

EXAMPLE 1441

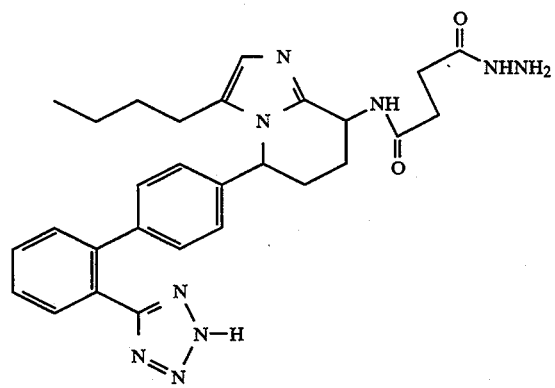

4-[3-Butyl-5,6,7,8-tetrahydro-5-[2'-(1H-tetrazol-5-yl)[1,1'-biphenyl]-4-yl]imidazo[1,2-a]pyridin-8-yl]amino]-4-oxobutanoic acid, hydrazide A solution of succinimidyl imidazole (0.06 mmol, obtained from Example 1440) and 11 μL (5.6 mmol) of hydrazine in 0.5 mL of ethanol is stirred at room temperature until the reaction is complete and concentrated in vacuo to give the title compound of Example 1441.

EXAMPLE 1442

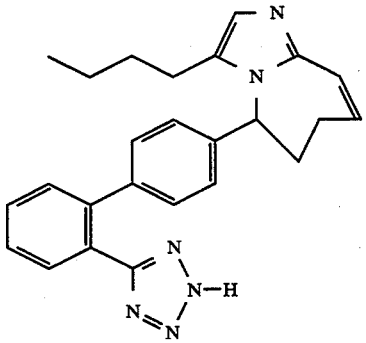

3-Butyl-6,7-dihydro-5-[2'-(1H-tetrazol-5-yl)[1,1'-biphenyl]-4-yl]-5H-imidazo[1,2-a]azepine Step 1: Alkylation of Biphenyl Imidazole To a solution of biphenyl imidazole (0.152 mmol, obtained from Step 2 of Example 1434) in 0.8 mL of DME cooled at −45° C. (acetonitrile-dry ice) is added 125 μL (0.2 mmol) of n-butyllithium (1.6M in hexane) over a 4-min period. The resulting dark red solution is stirred cold for another 15 min, followed by addition of 70 μL (0.37 mmol) of 2-(3-bromopropyl)-5,5-dimethyl-1,3-dioxane in one portion. The mixture is stirred cold for 40 min, then is slowly warmed to −10° C. The reaction is quenched with aqueous NH4Cl, extracted with diethyl ether. The combined extracts are washed with brine, dried (MgSO4) and concentrated in vacuo. The crude product can be used directly in the subsequent Step 2 without purification.

Step 2: Preparation of the Bicyclic Imidazole

A solution of the crude mixture (0.152 mmol, obtained from Step 1) and 255 mg (3 mmol) of NaOAc in 0.6 mL of water and 2 mL of glacial acetic acid is stirred at reflux until the reaction is complete. The mixture is cooled and concentrated in vacuo. The residue is dissolved in methylene chloride and filtered. The filtrate is stirred with 130 mg (0.46 mmol) of trityl chloride and 0.22 mL (1.6 mmol) of TEA at room temperature until the reaction is complete. The mixture is concentrated in vacuo. The residue is purified to give the biphenyl bicyclic imidazole.

Step 3: Detritylation of Trityl Tetrazole

A solution of the biphenyl bicyclic imidazole (0.035 mmol, obtained from Step 2) is stirred with 0.4 mL of water and 2 mL of acetic acid at room temperature until the reaction is complete. The solution is concentrated in vacuo. The residue is worked up as described in Step 4 of Example 1434 to give the title compound of Example 1442.

EXAMPLE 1443

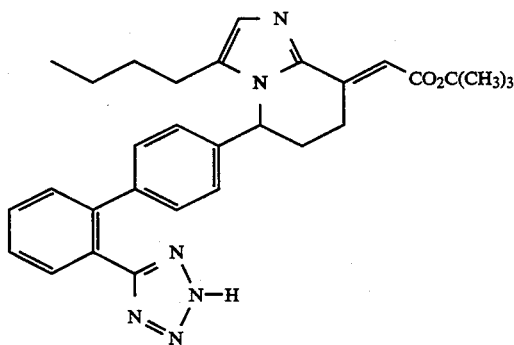

1,1-Dimethylethyl [3-butyl-6,7-dihydro-5-[2'-(1H-tetrazol-5-yl) [1,1'-biphenyl]-4-yl]imidazo[1,2-a]pyridin-8(5H)-ylidene]acetate

Step 1: Preparation of Tert-Butyl Ester

To a suspension of 64 mg (2.63 mmol) of magnesium in 3.0 mL of THF at 55° C. is added two 10μL portions of 1,2-dibromoethane, 5 min apart. The resulting mixture is stirred at 45° C. for 10 min, followed by dropwise addition of a solution of biphenyl keto imidazole (0.306 mmol, obtained from Step 3 of Example 1436) and 242 μL (1.50 mmol) of tert-butyl bromoacetate in 2.0 mL of THF at 55° C. over a 1 h period. The resulting solution is stirred until the reaction is complete. The mixture is cooled and quenched with aqueous NH₄Cl. The mixture is extracted with ether, dried (MgSO₄) and concentrated in vacuo. The crude mixture can be used directly in the subsequent Step 2 without further purification.

Step 2: Preparation of Unsaturated Butyl Ester

To a solution of the crude hydroxy butyl ester (0.306 mmol, obtained from Step 1) and 200 μL (2.47 mmol) of pyridine in 2 mL of methylene chloride at 0° C. is added dropwise 80 μL (1.1 mmol) of thionyl chloride. The resulting dark brown solution is stirred at 0° C. for 1 h, diluted with water and extracted with methylene chloride. The residue is purified to give the biphenyl imidazolyl unsaturated ester.

Step 3: Detritylation of Trityl Tetrazole

A solution of biphenyl imidazolyl unsaturated ester (0.133 mmol, obtained from Step 2) in 1.0 mL of water and 5.0 mL of acetic acid is stirred at room temperature until the reaction is complete. The mixture is concentrated in vacuo. The residue is worked up as described in Step 4 of Example 1434 to give the title compound of Example 1443.

EXAMPLE 1444

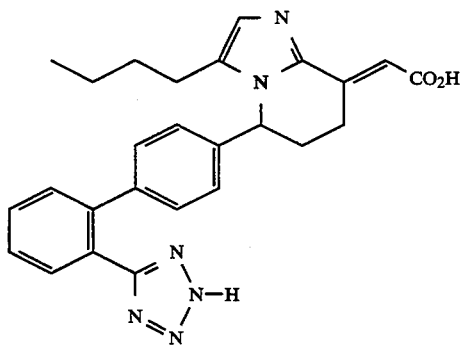

[3-Butyl -6,7-dihydro-5 -[2'-(1H-tetrazol -5-yl)[1,1'-biphenyl]-4-yl]imidazo[1,2-a]pyridin-8(5H) -ylidene]acetic acid To a solution of unsaturated tert-butyl ester (0.0627 mmol, the title compound of Example 1443) in 2 mL of CDCl₃ at room temperature is added 0.5 mL of TFA, and the progress of the reaction is monitored by ¹H NMR. The resulting yellow solution is stirred at room temperature until the reaction is complete. The mixture is concentrated in vacuo. The crude product is purified to give the title compound of Example 1444.

EXAMPLE 1445

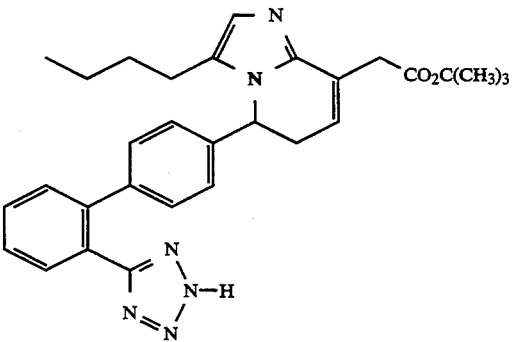

1,1-Dimethylethyl 3-butyl-5,6-dihydro-5-[2 '-(1H-tetrazol-5-yl) [1,1'-biphenyl]-4-yl]imidazo[1,2-a]pyridin-8-acetate

Step 1: Preparation of Deconjugated Ester

To a solution of ester (0.237 mmol, obtained from Step 2 of Example 1443) in 4 mL of THP at 0° C. is added 310 μL of 1.5M (0,467 mmol) LDA over a 2-min period, and the resulting solution is stirred at 0° C. for 10 min. The mixture is cooled to −78° C., stirred cold for 5 min, and quenched dropwise at −78° C. with 100 μL of acetic acid in 1 mL of hexane. The mixture is stirred cold, then warmed to room temperature and treated with aqueous NaHCO₃. The mixture is extracted with methylene chloride. The combined extracts are washed with water, dried (MgSO₄) and concentrated in vacuo to give a crude mixture. The crude product is purified to give the biphenyl imidazolyl deconjugated ester.

Step 2: Detritylation of Trityl Tetrazole

A solution of trityl-protected biphenyl imidazolyl deconjugated ester (0.165 mmol, obtained from Step 1) in 1 mL of water and 3 mL of acetic acid is stirred at room temperature until the reaction is complete. The mixture was concentrated in vacuo. The residue is worked up as described in Step 4 of Example 1448. The crude product is purified to give the title compound of Example 1445.

EXAMPLE 1446

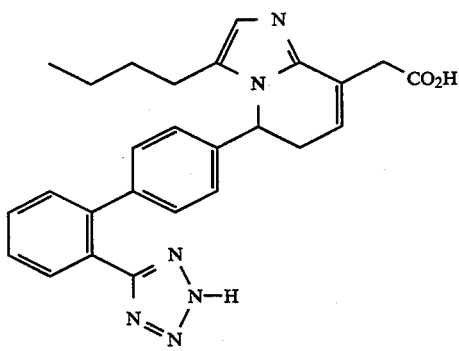

3-Butyl-5,6-dihydro-5-[2'-(1H-tetrazol-5-yl)[1,1'-biphenyl]-4-yl]imidazo[1,2-a]pyridin-8-acetic acid To a solution of biphenyl imidazolyl tert-butyl ester (0,039 mmol, the title compound of Example 1445) in 0.5 mL of chloroform is added 0.25 mL of TFA, and the progress of the reaction is monitored by $^1$H NMR. The resulting solution is stirred at room temperature until the reaction is complete. The mixture is quenched with methanol and concentrated in vacuo. The residue is purified to give the title compound of Example 1446.

EXAMPLE 1447

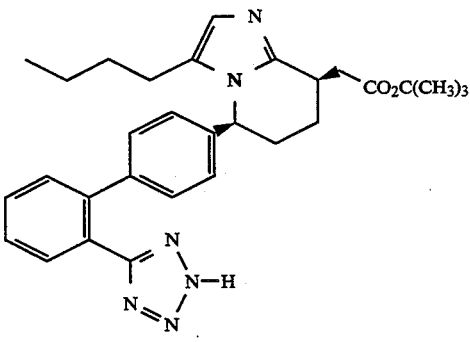

1,1-Dimethylethyl 3-butyl-5,6,7,8-tetrahydro-5-[2'-(1H-tetrazol-5-yl)[1,1'-biphenyl]-4-yl]imidazo[1,2-a]pyridin-cis-acetate A suspension of the biphenyl imidazolyl unsaturated ester (0.059 mmol, the title compound of Example 1445) and 20 mg (0.0188 mmol) of 10% palladium on charcoal in 1.5 mL of methanol is stirred at room temperature under an atmosphere of hydrogen gas until the reaction is complete. The mixture is filtered through a pad of celite and concentrated in vacuo. The residue is purified to give the title compound of Example 1447.

EXAMPLE 1448

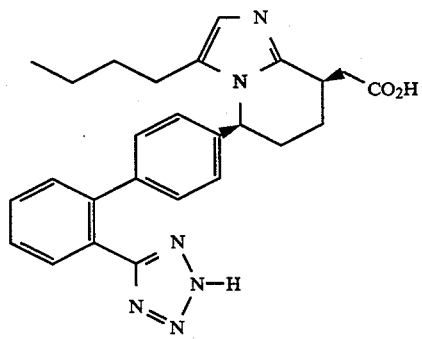

3-Butyl-5,6,7,8-tetrahydro-5-[2'-(1H-tetrazol-5-yl)[1,1'-biphenyl]-4-yl]imidazo[1,2-a]pyridin-cis-8-acetic acid To a solution of tert-butyl ester (0.0332 mmol, obtained from Example 1447) in 0.4 mL of CDCl$_3$ is added 0.2 mL of TFA, and the progress of the reaction is monitored by $^1$H NMR. The resulting solution is allowed to stand at room temperature until the reaction is complete. The reaction mixture is diluted with methanol and concentrated. The residue is purified to give the title compound of Example 1448.

EXAMPLE 1449

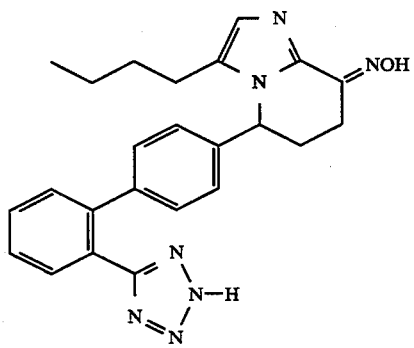

3-Butyl-5,6-dihydro-N-hydroxy-5-[2'-(1H-tetrazol-5-yl)[1.1'-biphenyl]-4-yl]imidazol[1,2-a]pyridin-8(7H)-imine A mixture of biphenyl keto imidazole (0.094 mmol, the title compound of Example 1437), 20 mg (0.29 mmol) of N-hydroxyamine (hydrochloride salt) and 30 mg of NaOAc in 2 mL of methanol is stirred at 60° C. until the reaction is complete. The mixture is diluted with chloroform and filtered. The solid is washed with methanol. The filtrate is concentrated in vacuo and purified to give the title compound of Example 1449.

EXAMPLE 1450

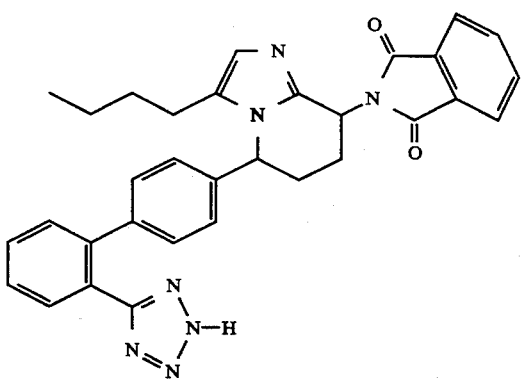

1-[3-Butyl-5,6,7,8-tetrahydro-5-[2'-(1H-tetrazol-5-yl)[1,1'-biphenyl]-4-yl]imidazo[1,2-a]pyridin-8-yl]phthalimide Step 1: Preparation of Biphenyl Phthalimidyl Imidazole To a solution of the hydroxy imidazole (2.0 mmol, obtained from Step 1 of Example 1438 or 1439), phthalimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (MgSO4) and concentrated in vacuo. The residue is purified to give the trityl protected phthalimidyl imidazole.

Step 2: Detritylation of Trityl Tetrazole

A solution of trityl-protected biphenyl phthalimidyl imidazole (2.0 mmol, obtained from Step 1) in 2 mL of water and 10 mL of acetic acid is stirred at room temperature until the reaction is complete. The mixture is concentrated in vacuo. The residue is worked up as described in Step 5 of Example 1 and purified give the title compound of Example 1450.

EXAMPLE 1451

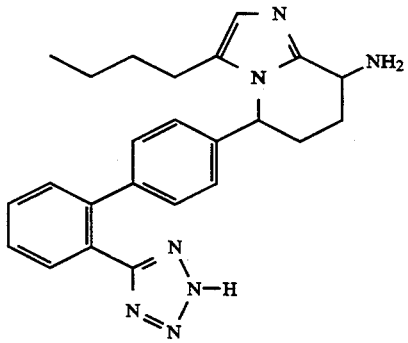

3-Butyl-5,6,7,8-tetrahydro-8-amino-5-[2'-(1H-tetrazol-5-yl) [1,1'-biphenyl]-4-yl]imidazo[1,2-a]pyridine A solution of phthalimidyl imidazole (0.6 mmol, the title compound of Example 1450) and 3 µL (1.5 mmol) of hydrazine in 1.0 mL of ethanol is stirred at room temperature until the reaction is complete. The mixture is concentrated in vacuo, and purified to give the title compound of Example 1451.

Alternatively, the title compound of Example 1451 can be prepared from the corresponding oxime. A suspension of the biphenyl imidazolyl oxime (0.059 mmol, the title compound of Example 1449) and 20 mg (0.0188 mmol) of 10% palladium on charcoal in 1.5 mL of methanol is stirred at room temperature under 50 psi of hydrogen gas until the reaction is complete. The mixture is filtered through a pad of celite, concentrated in vacuo and purified to give the title compound of Example 1451.

Examples 1452-1914, located in Tables XXV-XLVIII, are additional conformationally restricted angiotensin II antagonists embraced by Formula III above.

TABLE XXV

| EX.# | $R^{82}$ | $R^{83}$ |
|---|---|---|
| 1452 | $C_3H_7(n)$ | H |
| 1453 | $C_3H_7(n)$ | $C_2H_5$ |
| 1454 | $C_3H_7(n)$ | $C_3H_7(n)$ |
| 1455 | $C_3H_7(n)$ | (2-ethylphenyl) |
| 1456 | $C_3H_7(n)$ | (2,6-dimethylphenyl) |
| 1457 | $C_3H_7(n)$ | phenyl |
| 1458 | $C_3H_7(n)$ | benzyl |
| 1459 | $C_3H_7(n)$ | phenylethyl |
| 1460 | $C_3H_7(n)$ | $CH_2OH$ |
| 1461 | $C_3H_7(n)$ | $CO_2H$ |
| 1462 | $C_3H_7(n)$ | $CH_2CO_2H$ |
| 1463 | $C_4H_9(n)$ | $C_2H_5$ |
| 1464 | $C_4H_9(n)$ | $C_3H_7(n)$ |
| 1465 | $C_4H_9(n)$ | (2-ethylphenyl) |
| 1466 | $C_4H_9(n)$ | (2,6-dimethylphenyl) |
| 1467 | $C_4H_9(n)$ | phenyl |
| 1468 | $C_4H_9(n)$ | benzyl |
| 1469 | $C_4H_9(n)$ | phenylethyl |
| 1470 | $C_4H_9(n)$ | $CH_2OH$ |
| 1471 | $C_4H_9(n)$ | $CO_2H$ |

TABLE XXVI

| EX.# | $R^{84}$ | $R^{85}$ |
|---|---|---|
| 1472 | $C_3H_7(n)$ | O |
| 1473 | $C_3H_7(n)$ | S |
| 1474 | $C_3H_7(n)$ | NOH |
| 1475 | $C_3H_7(n)$ | $CHCO_2H$ |
| 1476 | $C_3H_7(n)$ | $C(C_2H_5)CO_2H$ |
| 1477 | $C_3H_7(n)$ | $C(CH_2C_6H_5)CO_2H$ |

TABLE XXVI-continued

| | | |
|---|---|---|
| 1478 | $C_3H_7(n)$ | $CHC_2H_5$ |
| 1479 | $C_4H_9(n)$ | S |
| 1480 | $C_4H_9(n)$ | $C(C_2H_5)CO_2H$ |
| 1481 | $C_4H_9(n)$ | $C(CH_2C_6H_5)CO_2H$ |
| 1482 | $C_4H_9(n)$ | $CHC_2H_5$ |

TABLE XXVII

| EX.# | $R^{86}$ | $R^{87}$ |
|---|---|---|
| 1483 | $C_3H_7(n)$ | $C_2H_5$ |
| 1484 | $C_3H_7(n)$ | $C_3H_7(n)$ |
| 1485 | $C_4H_9(n)$ | $C_2H_5$ |
| 1486 | $C_4H_9(n)$ | $C_3H_7(n)$ |

TABLE XXVIII

| EX.# | $R^{88}$ | $R^{89}$ |
|---|---|---|
| 1487 | $C_3H_7(n)$ | H |
| 1488 | $C_3H_7(n)$ | $C_2H_5$ |
| 1489 | $C_3H_7(n)$ | $C_3H_7(n)$ |
| 1490 | $C_3H_7(n)$ | (2-ethylphenyl) |
| 1491 | $C_3H_7(n)$ | (2,6-dimethylphenyl) |
| 1492 | $C_3H_7(n)$ | phenyl |
| 1493 | $C_3H_7(n)$ | benzyl |
| 1494 | $C_3H_7(n)$ | phenylethyl |
| 1495 | $C_3H_7(n)$ | $NH_2$ |
| 1496 | $C_3H_7(n)$ | OH |
| 1497 | $C_3H_7(n)$ | $CH_2OH$ |
| 1498 | $C_3H_7(n)$ | $CO_2H$ |
| 1499 | $C_4H_9(n)$ | $C_2H_5$ |
| 1500 | $C_4H_9(n)$ | $C_3H_7(n)$ |
| 1501 | $C_4H_9(n)$ | (2-ethylphenyl) |
| 1502 | $C_4H_9(n)$ | (2,6-dimethylphenyl) |
| 1503 | $C_4H_9(n)$ | phenyl |
| 1504 | $C_4H_9(n)$ | benzyl |
| 1505 | $C_4H_9(n)$ | phenylethyl |
| 1506 | $C_4H_9(n)$ | $CH_2OH$ |
| 1507 | $C_4H_9(n)$ | $CO_2H$ |

TABLE XXIX

| EX.# | $R^{90}$ | $R^{91}$ | $R^{92}$ |
|---|---|---|---|
| 1508 | $C_3H_7(n)$ | H | $CH_3$ |
| 1509 | $C_3H_7(n)$ | H | $C_2H_5$ |
| 1510 | $C_3H_7(n)$ | H | $C_6H_5$ |
| 1511 | $C_3H_7(n)$ | H | $C_6H_5CH_2$ |
| 1512 | $C_3H_7(n)$ | H | $CH_2CO_2H$ |
| 1513 | $C_3H_7(n)$ | H | $CH_2CH_2CO_2H$ |
| 1514 | $C_3H_7(n)$ | $CH_3$ | $CH_3$ |
| 1515 | $C_3H_7(n)$ | $CH_3$ | $C_2H_5$ |
| 1516 | $C_3H_7(n)$ | $CH_3$ | $C_6H_5$ |
| 1517 | $C_3H_7(n)$ | $CH_3$ | $C_6H_5CH_2$ |
| 1518 | $C_3H_7(n)$ | $CH_3$ | $CH_2CO_2H$ |
| 1519 | $C_3H_7(n)$ | $CH_3$ | $CH_2CH_2CO_2H$ |
| 1520 | $C_3H_7(n)$ | $C_2H_5$ | $CH_3$ |
| 1521 | $C_3H_7(n)$ | $C_2H_5$ | $C_2H_5$ |
| 1522 | $C_3H_7(n)$ | $C_2H_5$ | $C_6H_5$ |
| 1523 | $C_3H_7(n)$ | $C_2H_5$ | $C_6H_5CH_2$ |
| 1524 | $C_3H_7(n)$ | $C_2H_5$ | $CH_2CO_2H$ |
| 1525 | $C_3H_7(n)$ | $C_2H_5$ | $CH_2CH_2CO_2H$ |
| 1526 | $C_3H_7(n)$ | $C_3H_7(n)$ | $CH_3$ |
| 1527 | $C_3H_7(n)$ | $C_3H_7(n)$ | $C_2H_5$ |
| 1528 | $C_3H_7(n)$ | $C_3H_7(n)$ | $C_6H_5$ |
| 1529 | $C_3H_7(n)$ | $C_3H_7(n)$ | $C_6H_5CH_2$ |
| 1530 | $C_3H_7(n)$ | $C_3H_7(n)$ | $CH_2CO_2H$ |
| 1531 | $C_3H_7(n)$ | $C_3H_7(n)$ | $CH_2CH_2CO_2H$ |
| 1532 | $C_3H_7(n)$ | $CH_2C_6H_5$ | $CH_3$ |
| 1533 | $C_3H_7(n)$ | $CH_2C_6H_5$ | $C_2H_5$ |
| 1534 | $C_3H_7(n)$ | $CH_2C_6H_5$ | $C_6H_5$ |
| 1535 | $C_3H_7(n)$ | $CH_2C_6H_5$ | $CH_2CO_2H$ |
| 1536 | $C_3H_7(n)$ | $CH_2C_6H_5$ | $CH_2CH_2CO_2H$ |
| 1537 | $C_4H_9(n)$ | H | $CH_3$ |
| 1538 | $C_4H_9(n)$ | H | $C_2H_5$ |
| 1539 | $C_4H_9(n)$ | H | $C_6H_5$ |
| 1540 | $C_4H_9(n)$ | H | $C_6H_5CH_2$ |
| 1541 | $C_4H_9(n)$ | H | $CH_2CO_2H$ |
| 1542 | $C_4H_9(n)$ | H | $CH_2CH_2CO_2H$ |
| 1543 | $C_4H_9(n)$ | $CH_3$ | $CH_3$ |
| 1544 | $C_4H_9(n)$ | $CH_3$ | $C_2H_5$ |
| 1545 | $C_4H_9(n)$ | $CH_3$ | $C_6H_5$ |
| 1546 | $C_4H_9(n)$ | $CH_3$ | $C_6H_5CH_2$ |
| 1547 | $C_4H_9(n)$ | $CH_3$ | $CH_2CO_2H$ |
| 1548 | $C_4H_9(n)$ | $CH_3$ | $CH_2CH_2CO_2H$ |
| 1549 | $C_4H_9(n)$ | $C_2H_5$ | $CH_3$ |
| 1550 | $C_4H_9(n)$ | $C_2H_5$ | $C_2H_5$ |
| 1551 | $C_4H_9(n)$ | $C_2H_5$ | $C_6H_5$ |
| 1552 | $C_4H_9(n)$ | $C_2H_5$ | $C_6H_5CH_2$ |
| 1553 | $C_4H_9(n)$ | $C_2H_5$ | $CH_2CO_2H$ |
| 1554 | $C_4H_9(n)$ | $C_2H_5$ | $CH_2CH_2CO_2H$ |
| 1555 | $C_4H_9(n)$ | $C_3H_7(n)$ | $CH_3$ |
| 1556 | $C_4H_9(n)$ | $C_3H_7(n)$ | $C_2H_5$ |
| 1557 | $C_4H_9(n)$ | $C_3H_7(n)$ | $C_6H_5$ |
| 1558 | $C_4H_9(n)$ | $C_3H_7(n)$ | $C_6H_5CH_2$ |
| 1559 | $C_4H_9(n)$ | $C_3H_7(n)$ | $CH_2CO_2H$ |
| 1560 | $C_4H_9(n)$ | $C_3H_7(n)$ | $CH_2CH_2CO_2H$ |
| 1561 | $C_4H_9(n)$ | $CH_2C_6H_5$ | $CH_3$ |
| 1562 | $C_4H_9(n)$ | $CH_2C_6H_5$ | $C_2H_5$ |
| 1563 | $C_4H_9(n)$ | $CH_2C_6H_5$ | $C_6H_5$ |
| 1564 | $C_4H_9(n)$ | $CH_2C_6H_5$ | $CH_2CO_2H$ |
| 1565 | $C_4H_9(n)$ | $CH_2C_6H_5$ | $CH_2CH_2CO_2H$ |

TABLE XXX

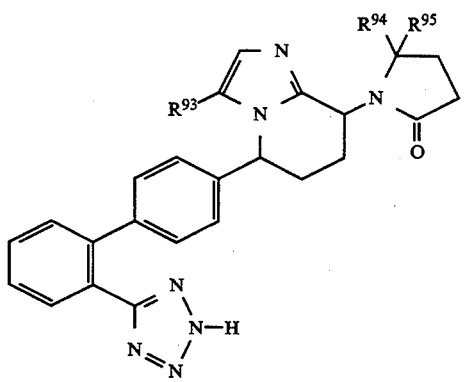

| EX.# | $R^{93}$ | $R^{94}, R^{95}$ |
|---|---|---|
| 1566 | $C_3H_7(n)$ | O |
| 1567 | $C_3H_7(n)$ | H,H |
| 1568 | $C_3H_7(n)$ | H,$CH_3$ |
| 1569 | $C_3H_7(n)$ | H,$C_2H_5$ |
| 1570 | $C_3H_7(n)$ | H,$CH_2OH$ |
| 1571 | $C_3H_7(n)$ | H,$CO_2H$ |
| 1572 | $C_4H_9(n)$ | H,H |
| 1573 | $C_4H_9(n)$ | H,$CH_3$ |
| 1574 | $C_4H_9(n)$ | H,$C_2H_5$ |
| 1575 | $C_4H_9(n)$ | H,$CH_2OH$ |
| 1576 | $C_4H_9(n)$ | H,$CO_2H$ |

TABLE XXXI

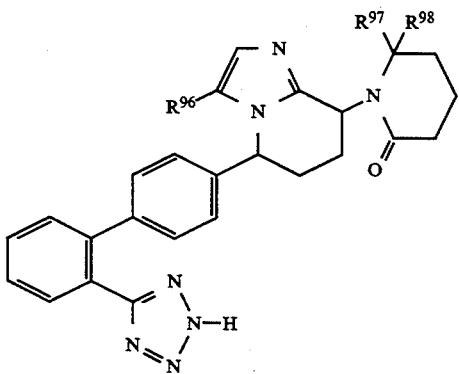

| EX.# | $R^{96}$ | $R^{97}, R^{98}$ |
|---|---|---|
| 1577 | $C_3H_7(n)$ | O |
| 1578 | $C_3H_7(n)$ | H,H |
| 1579 | $C_3H_7(n)$ | H,$CH_3$ |
| 1580 | $C_3H_7(n)$ | H,$C_2H_5$ |
| 1581 | $C_3H_7(n)$ | H,$CH_2OH$ |
| 1582 | $C_3H_7(n)$ | H,$CO_2H$ |
| 1583 | $C_4H_9(n)$ | O |
| 1584 | $C_4H_9(n)$ | H,H |
| 1585 | $C_4H_9(n)$ | H,$CH_3$ |
| 1586 | $C_4H_9(n)$ | H,$C_2H_5$ |
| 1587 | $C_4H_9(n)$ | H,$CH_2OH$ |
| 1588 | $C_4H_9(n)$ | H,$CO_2H$ |

TABLE XXXII

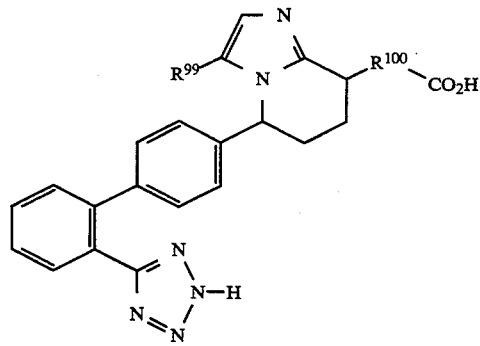

| EX.# | $R^{99}$ | $R^{100}$ |
|---|---|---|
| 1589 | $C_3H_7(n)$ | $CH_2$ |
| 1590 | $C_3H_7(n)$ | $CH(C_2H_5)$ |
| 1591 | $C_3H_7(n)$ | $CH(CH_2C_6H_5)$ |
| 1592 | $C_3H_7(n)$ | $CH_2CH_2$ |
| 1593 | $C_3H_7(n)$ | $CH(C_2H_5)CH_2$ |
| 1594 | $C_3H_7(n)$ | $CH(CH_2C_6H_5)CH_2$ |
| 1595 | $C_4H_9(n)$ | $CH(C_2H_5)$ |
| 1596 | $C_4H_9(n)$ | $CH(CH_2C_6H_5)$ |
| 1597 | $C_4H_9(n)$ | $CH_2CH_2$ |
| 1598 | $C_4H_9(n)$ | $CH(C_2H_5)CH_2$ |
| 1599 | $C_4H_9(n)$ | $CH(CH_2C_6H_5)CH_2$ |

TABLE XXXIII

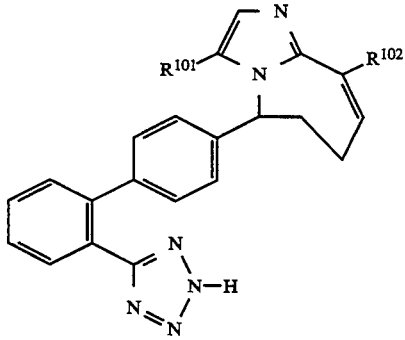

| EX.# | $R^{101}$ | $R^{102}$ |
|---|---|---|
| 1600 | $C_3H_7(n)$ | H |
| 1601 | $C_3H_7(n)$ | $C_2H_5$ |
| 1602 | $C_3H_7(n)$ | $C_3H_7(n)$ |
| 1603 | $C_3H_7(n)$ | (2-ethylphenyl) |
| 1604 | $C_3H_7(n)$ | (2,6-dimethylphenyl) |
| 1605 | $C_3H_7(n)$ | phenyl |
| 1606 | $C_3H_7(n)$ | benzyl |
| 1607 | $C_3H_7(n)$ | phenylethyl |
| 1608 | $C_3H_7(n)$ | $CH_2OH$ |
| 1609 | $C_3H_7(n)$ | $CO_2H$ |
| 1610 | $C_3H_7(n)$ | $CH_2CO_2H$ |
| 1611 | $C_4H_9(n)$ | $C_2H_5$ |
| 1612 | $C_4H_9(n)$ | $C_3H_7(n)$ |
| 1613 | $C_4H_9(n)$ | (2-ethylphenyl) |
| 1614 | $C_4H_9(n)$ | (2,6-dimethylphenyl) |
| 1615 | $C_4H_9(n)$ | phenyl |
| 1616 | $C_4H_9(n)$ | benzyl |
| 1617 | $C_4H_9(n)$ | phenylethyl |
| 1618 | $C_4H_9(n)$ | $CH_2OH$ |
| 1619 | $C_4H_9(n)$ | $CO_2H$ |
| 1620 | $C_4H_9(n)$ | $CH_2CO_2H$ |

TABLE XXXIV

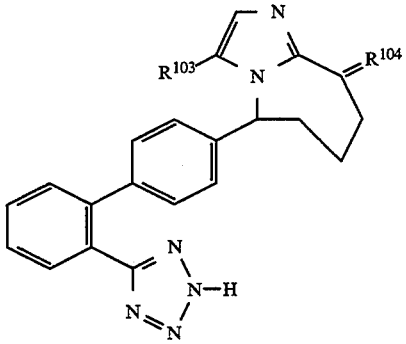

| EX.# | $R^{103}$ | $R^{104}$ |
|---|---|---|
| 1621 | $C_3H_7(n)$ | O |
| 1622 | $C_3H_7(n)$ | S |
| 1623 | $C_3H_7(n)$ | NOH |
| 1624 | $C_3H_7(n)$ | $CHCO_2H$ |
| 1625 | $C_3H_7(n)$ | $C(C_2H_5)CO_2H$ |
| 1626 | $C_3H_7(n)$ | $C(CH_2C_6H_5)CO_2H$ |
| 1627 | $C_3H_7(n)$ | $CHC_2H_5$ |
| 1628 | $C_4H_9(n)$ | O |
| 1629 | $C_4H_9(n)$ | S |
| 1630 | $C_4H_9(n)$ | NOH |
| 1631 | $C_4H_9(n)$ | $CHCO_2H$ |
| 1632 | $C_4H_9(n)$ | $C(C_2H_5)CO_2H$ |
| 1633 | $C_4H_9(n)$ | $C(CH_2C_6H_5)CO_2H$ |
| 1634 | $C_4H_9(n)$ | $CHC_2H_5$ |

TABLE XXXV

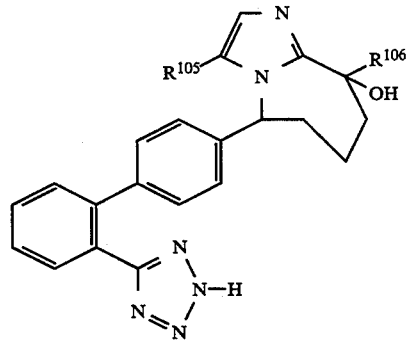

| EX.# | $R^{105}$ | $R^{106}$ |
|---|---|---|
| 1635 | $C_3H_7(n)$ | $C_2H_5$ |
| 1636 | $C_3H_7(n)$ | $C_3H_7(n)$ |
| 1637 | $C_4H_9(n)$ | $C_2H_5$ |
| 1638 | $C_4H_9(n)$ | $C_3H_7(n)$ |

TABLE XXXVI

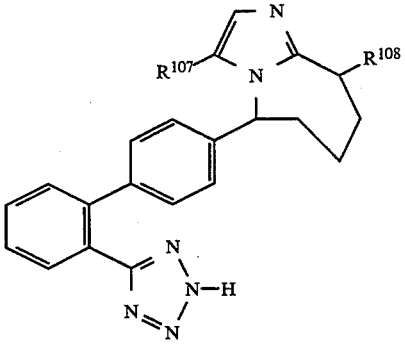

| EX.# | $R^{107}$ | $R^{108}$ |
|---|---|---|
| 1639 | $C_3H_7(n)$ | H |
| 1640 | $C_3H_7(n)$ | $C_2H_5$ |
| 1641 | $C_3H_7(n)$ | $C_3H_7(n)$ |
| 1642 | $C_3H_7(n)$ | (2-ethylphenyl) |
| 1643 | $C_3H_7(n)$ | (2,6-dimethylphenyl) |
| 1644 | $C_3H_7(n)$ | phenyl |
| 1645 | $C_3H_7(n)$ | benzyl |
| 1646 | $C_3H_7(n)$ | phenylethyl |
| 1647 | $C_3H_7(n)$ | $NH_2$ |
| 1648 | $C_3H_7(n)$ | OH |
| 1649 | $C_3H_7(n)$ | $CH_2OH$ |
| 1650 | $C_3H_7(n)$ | $CO_2H$ |
| 1651 | $C_4H_9(n)$ | H |
| 1652 | $C_4H_9(n)$ | $C_2H_5$ |
| 1653 | $C_4H_9(n)$ | $C_3H_7(n)$ |
| 1654 | $C_4H_9(n)$ | (2-ethylphenyl) |
| 1655 | $C_4H_9(n)$ | (2,6-dimethylphenyl) |
| 1656 | $C_4H_9(n)$ | phenyl |
| 1657 | $C_4H_9(n)$ | benzyl |
| 1658 | $C_4H_9(n)$ | phenylethyl |
| 1659 | $C_4H_9(n)$ | $NH_2$ |
| 1660 | $C_4H_9(n)$ | OH |
| 1661 | $C_4H_9(n)$ | $CH_2OH$ |
| 1662 | $C_4H_9(n)$ | $CO_2H$ |

TABLE XXXVII

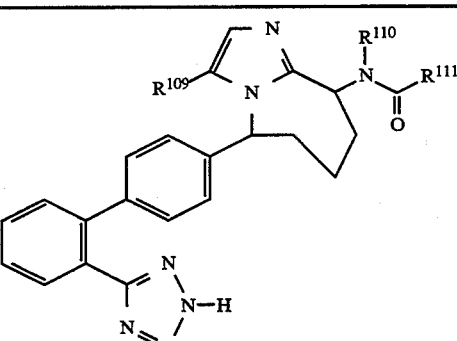

| EX.# | $R^{109}$ | $R^{110}$ | $R^{111}$ |
|---|---|---|---|
| 1663 | $C_3H_7(n)$ | H | $CH_3$ |
| 1664 | $C_3H_7(n)$ | H | $C_2H_5$ |
| 1665 | $C_3H_7(n)$ | H | $C_6H_5$ |
| 1666 | $C_3H_7(n)$ | H | $C_6H_5CH_2$ |
| 1667 | $C_3H_7(n)$ | H | $CH_2CO_2H$ |
| 1668 | $C_3H_7(n)$ | H | $CH_2CH_2CO_2H$ |
| 1669 | $C_3H_7(n)$ | $CH_3$ | $CH_3$ |
| 1670 | $C_3H_7(n)$ | $CH_3$ | $C_2H_5$ |
| 1671 | $C_3H_7(n)$ | $CH_3$ | $C_6H_5$ |
| 1672 | $C_3H_7(n)$ | $CH_3$ | $C_6H_5CH_2$ |
| 1673 | $C_3H_7(n)$ | $CH_3$ | $CH_2CO_2H$ |
| 1674 | $C_3H_7(n)$ | $CH_3$ | $CH_2CH_2CO_2H$ |
| 1675 | $C_3H_7(n)$ | $C_2H_5$ | $CH_3$ |
| 1676 | $C_3H_7(n)$ | $C_2H_5$ | $C_2H_5$ |
| 1677 | $C_3H_7(n)$ | $C_2H_5$ | $C_6H_5$ |
| 1678 | $C_3H_7(n)$ | $C_2H_5$ | $C_6H_5CH_2$ |
| 1679 | $C_3H_7(n)$ | $C_2H_5$ | $CH_2CO_2H$ |

TABLE XXXVII-continued

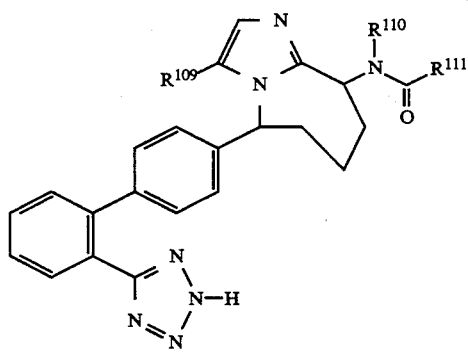

| EX.# | R109 | R110 | R111 |
|---|---|---|---|
| 1680 | C3H7(n) | C2H5 | CH2CH2CO2H |
| 1681 | C3H7(n) | C3H7(n) | CH3 |
| 1682 | C3H7(n) | C3H7(n) | C2H5 |
| 1683 | C3H7(n) | C3H7(n) | C6H5 |
| 1684 | C3H7(n) | C3H7(n) | C6H5CH2 |
| 1685 | C3H7(n) | C3H7(n) | CH2CO2H |
| 1686 | C3H7(n) | C3H7(n) | CH2CH2CO2H |
| 1687 | C3H7(n) | CH2C6H5 | CH3 |
| 1688 | C3H7(n) | CH2C6H5 | C2H5 |
| 1689 | C3H7(n) | CH2C6H5 | C6H5 |
| 1690 | C3H7(n) | CH2C6H5 | CH2CO2H |
| 1691 | C3H7(n) | CH2C6H5 | CH2CH2CO2H |
| 1692 | C4H9(n) | H | CH3 |
| 1693 | C4H9(n) | H | C2H5 |
| 1694 | C4H9(n) | H | C6H5 |
| 1695 | C4H9(n) | H | C6H5CH2 |
| 1696 | C4H9(n) | H | CH2CO2H |
| 1697 | C4H9(n) | H | CH2CH2CO2H |
| 1698 | C4H9(n) | CH3 | CH3 |
| 1699 | C4H9(n) | CH3 | C2H5 |
| 1700 | C4H9(n) | CH3 | C6H5 |
| 1701 | C4H9(n) | CH3 | C6H5CH2 |
| 1702 | C4H9(n) | CH3 | CH2CO2H |
| 1703 | C4H9(n) | CH3 | CH2CH2CO2H |
| 1704 | C4H9(n) | C2H5 | CH3 |
| 1705 | C4H9(n) | C2H5 | C2H5 |
| 1706 | C4H9(n) | C2H5 | C6H5 |
| 1707 | C4H9(n) | C2H5 | C6H5CH2 |
| 1708 | C4H9(n) | C2H5 | CH2CO2H |
| 1709 | C4H9(n) | C2H5 | CH2CH2CO2H |
| 1710 | C4H9(n) | C3H7(n) | CH3 |
| 1711 | C4H9(n) | C3H7(n) | C2H5 |
| 1712 | C4H9(n) | C3H7(n) | C6H5 |
| 1713 | C4H9(n) | C3H7(n) | C6H5CH2 |
| 1714 | C4H9(n) | C3H7(n) | CH2CO2H |
| 1715 | C4H9(n) | C3H7(n) | CH2CH2CO2H |
| 1716 | C4H9(n) | CH2C6H5 | CH3 |
| 1717 | C4H9(n) | CH2C6H5 | C2H5 |
| 1718 | C4H9(n) | CH2C6H5 | C6H5 |
| 1719 | C4H9(n) | CH2C6H5 | CH2CO2H |
| 1720 | C4H9(n) | CH2C6H5 | CH2CH2CO2H |

TABLE XXXVIII

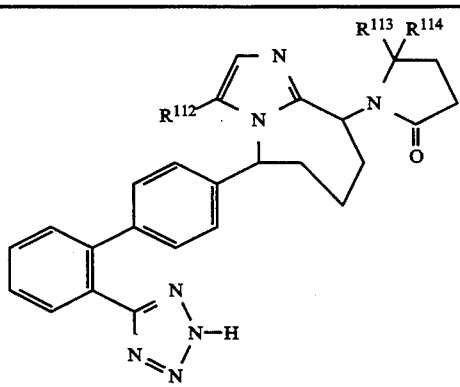

TABLE XXXVIII-continued

| EX.# | R112 | R113, R114 |
|---|---|---|
| 1721 | C3H7(n) | O |
| 1722 | C3H7(n) | H,H |
| 1723 | C3H7(n) | H,CH3 |
| 1724 | C3H7(n) | H,C2H5 |
| 1725 | C3H7(n) | H,CH2OH |
| 1726 | C3H7(n) | H,CO2H |
| 1727 | C4H9(n) | O |
| 1728 | C4H9(n) | H,H |
| 1729 | C4H9(n) | H,CH3 |
| 1730 | C4H9(n) | H,C2H5 |
| 1731 | C4H9(n) | H,CH2OH |
| 1732 | C4H9(n) | H,CO2H |

TABLE XXXIX

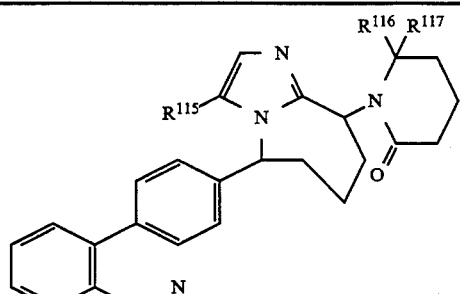

| EX.# | R115 | R116, R117 |
|---|---|---|
| 1733 | C3H7(n) | O |
| 1734 | C3H7(n) | H,H |
| 1735 | C3H7(n) | H,CH3 |
| 1736 | C3H7(n) | H,C2H5 |
| 1737 | C3H7(n) | H,CH2OH |
| 1738 | C3H7(n) | H,CO2H |
| 1739 | C4H9(n) | O |
| 1740 | C4H9(n) | H,H |
| 1741 | C4H9(n) | H,CH3 |
| 1742 | C4H9(n) | H,C2H5 |
| 1743 | C4H9(n) | H,CH2OH |
| 1744 | C4H9(n) | H,CO2H |

TABLE XL

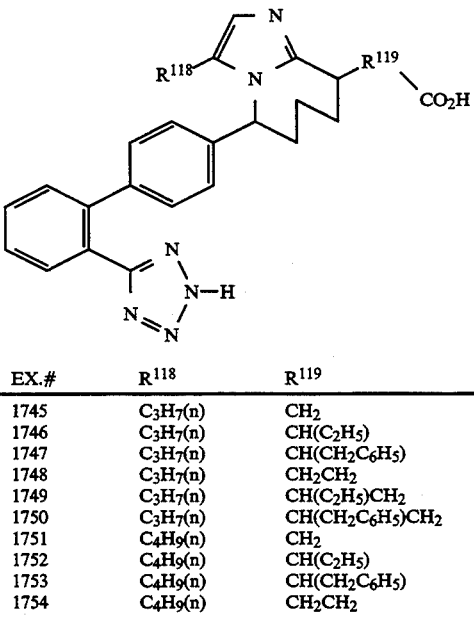

| EX.# | R118 | R119 |
|---|---|---|
| 1745 | C3H7(n) | CH2 |
| 1746 | C3H7(n) | CH(C2H5) |
| 1747 | C3H7(n) | CH(CH2C6H5) |
| 1748 | C3H7(n) | CH2CH2 |
| 1749 | C3H7(n) | CH(C2H5)CH2 |
| 1750 | C3H7(n) | CH(CH2C6H5)CH2 |
| 1751 | C4H9(n) | CH2 |
| 1752 | C4H9(n) | CH(C2H5) |
| 1753 | C4H9(n) | CH(CH2C6H5) |
| 1754 | C4H9(n) | CH2CH2 |

TABLE XL-continued

Structure: imidazole-N substituted with biphenyl-tetrazole, with R¹¹⁸ on imidazole and R¹¹⁹-CO₂H side chain.

| EX.# | R¹¹⁸ | R¹¹⁹ |
|---|---|---|
| 1755 | $C_4H_9(n)$ | $CH(C_2H_5)CH_2$ |
| 1756 | $C_4H_9(n)$ | $CH(CH_2C_6H_5)CH_2$ |

TABLE XLI

| EX.# | R¹²⁰ | R¹²¹ |
|---|---|---|
| 1757 | $C_3H_7(n)$ | H |
| 1758 | $C_3H_7(n)$ | $C_2H_5$ |
| 1759 | $C_3H_7(n)$ | $C_3H_7(n)$ |
| 1760 | $C_3H_7(n)$ | (2-ethylphenyl) |
| 1761 | $C_3H_7(n)$ | (2,6-dimethylphenyl) |
| 1762 | $C_3H_7(n)$ | phenyl |
| 1763 | $C_3H_7(n)$ | benzyl |
| 1764 | $C_3H_7(n)$ | phenylethyl |
| 1765 | $C_3H_7(n)$ | $CH_2OH$ |
| 1766 | $C_3H_7(n)$ | $CO_2H$ |
| 1767 | $C_3H_7(n)$ | $CH_2CO_2H$ |
| 1768 | $C_4H_9(n)$ | H |
| 1769 | $C_4H_9(n)$ | $C_2H_5$ |
| 1770 | $C_4H_9(n)$ | $C_3H_7(n)$ |
| 1771 | $C_4H_9(n)$ | (2-ethylphenyl) |
| 1772 | $C_4H_9(n)$ | (2,6-dimethylphenyl) |
| 1773 | $C_4H_9(n)$ | phenyl |
| 1774 | $C_4H_9(n)$ | benzyl |
| 1775 | $C_4H_9(n)$ | phenylethyl |
| 1776 | $C_4H_9(n)$ | $CH_2OH$ |
| 1777 | $C_4H_9(n)$ | $CO_2H$ |
| 1778 | $C_4H_9(n)$ | $CH_2CO_2H$ |

TABLE XLII

| EX.# | R¹²² | R¹²³ |
|---|---|---|
| 1779 | $C_3H_7(n)$ | O |
| 1780 | $C_3H_7(n)$ | S |
| 1781 | $C_3H_7(n)$ | NOH |
| 1782 | $C_3H_7(n)$ | $CHCO_2H$ |
| 1783 | $C_3H_7(n)$ | $C(C_2H_5)CO_2H$ |
| 1784 | $C_3H_7(n)$ | $C(CH_2C_6H_5)CO_2H$ |
| 1785 | $C_3H_7(n)$ | $CHC_2H_5$ |
| 1786 | $C_4H_9(n)$ | O |
| 1787 | $C_4H_9(n)$ | S |
| 1788 | $C_4H_9(n)$ | NOH |
| 1789 | $C_4H_9(n)$ | $CHCO_2H$ |
| 1790 | $C_4H_9(n)$ | $C(C_2H_5)CO_2H$ |
| 1791 | $C_4H_9(n)$ | $C(CH_2C_6H_5)CO_2H$ |
| 1792 | $C_4H_9(n)$ | $CHC_2H_5$ |

TABLE XLIII

| EX.# | R¹²⁴ | R¹²⁵ |
|---|---|---|
| 1793 | $C_3H_7(n)$ | $C_2H_5$ |
| 1794 | $C_3H_7(n)$ | $C_3H_7(n)$ |
| 1795 | $C_4H_9(n)$ | $C_2H_5$ |
| 1796 | $C_4H_9(n)$ | $C_3H_7(n)$ |

TABLE XLIV

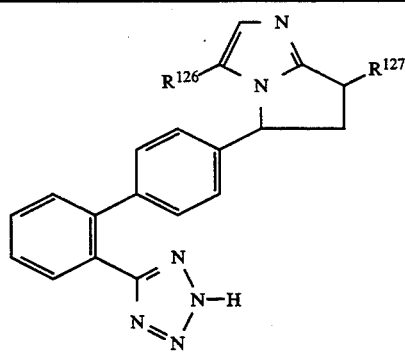

| EX.# | $R^{126}$ | $R^{127}$ |
|---|---|---|
| 1797 | $C_3H_7(n)$ | H |
| 1798 | $C_3H_7(n)$ | $C_2H_5$ |
| 1799 | $C_3H_7(n)$ | $C_3H_7(n)$ |
| 1800 | $C_3H_7(n)$ | (2-ethylphenyl) |
| 1801 | $C_3H_7(n)$ | (2,6-dimethylphenyl) |
| 1802 | $C_3H_7(n)$ | phenyl |
| 1803 | $C_3H_7(n)$ | benzyl |
| 1804 | $C_3H_7(n)$ | phenylethyl |
| 1805 | $C_3H_7(n)$ | $NH_2$ |
| 1806 | $C_3H_7(n)$ | OH |
| 1807 | $C_3H_7(n)$ | $CH_2OH$ |
| 1808 | $C_3H_7(n)$ | $CO_2H$ |
| 1809 | $C_4H_9(n)$ | H |
| 1810 | $C_4H_9(n)$ | $C_2H_5$ |
| 1811 | $C_4H_9(n)$ | $C_3H_7(n)$ |
| 1812 | $C_4H_9(n)$ | (2-ethylphenyl) |
| 1813 | $C_4H_9(n)$ | (2,6-dimethylphenyl) |
| 1814 | $C_4H_9(n)$ | phenyl |
| 1815 | $C_4H_9(n)$ | benzyl |
| 1816 | $C_4H_9(n)$ | phenylethyl |
| 1817 | $C_4H_9(n)$ | $NH_2$ |
| 1818 | $C_4H_9(n)$ | OH |
| 1819 | $C_4H_9(n)$ | $CH_2OH$ |
| 1820 | $C_4H_9(n)$ | $CO_2H$ |

TABLE XLV

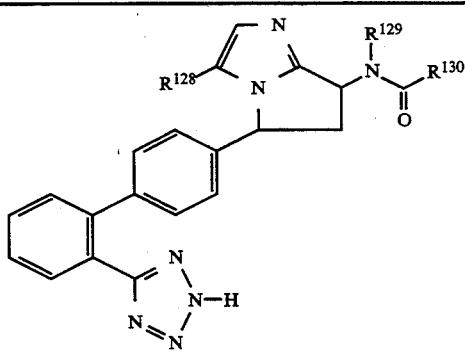

| EX.# | $R^{128}$ | $R^{129}$ | $R^{130}$ |
|---|---|---|---|
| 1821 | $C_3H_7(n)$ | H | $CH_3$ |
| 1822 | $C_3H_7(n)$ | H | $C_2H_5$ |
| 1823 | $C_3H_7(n)$ | H | $C_6H_5$ |
| 1824 | $C_3H_7(n)$ | H | $C_6H_5CH_2$ |
| 1825 | $C_3H_7(n)$ | H | $CH_2CO_2H$ |
| 1826 | $C_3H_7(n)$ | H | $CH_2CH_2CO_2H$ |
| 1827 | $C_3H_7(n)$ | $CH_3$ | $CH_3$ |
| 1828 | $C_3H_7(n)$ | $CH_3$ | $C_2H_5$ |
| 1829 | $C_3H_7(n)$ | $CH_3$ | $C_6H_5$ |
| 1830 | $C_3H_7(n)$ | $CH_3$ | $C_6H_5CH_2$ |
| 1831 | $C_3H_7(n)$ | $CH_3$ | $CH_2CO_2H$ |
| 1832 | $C_3H_7(n)$ | $CH_3$ | $CH_2CH_2CO_2H$ |
| 1833 | $C_3H_7(n)$ | $C_2H_5$ | $CH_3$ |
| 1834 | $C_3H_7(n)$ | $C_2H_5$ | $C_2H_5$ |
| 1835 | $C_3H_7(n)$ | $C_2H_5$ | $C_6H_5$ |
| 1836 | $C_3H_7(n)$ | $C_2H_5$ | $C_6H_5CH_2$ |
| 1837 | $C_3H_7(n)$ | $C_2H_5$ | $CH_2CO_2H$ |

TABLE XLV-continued

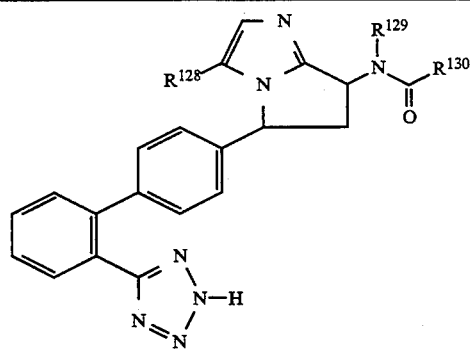

| EX.# | $R^{128}$ | $R^{129}$ | $R^{130}$ |
|---|---|---|---|
| 1838 | $C_3H_7(n)$ | $C_2H_5$ | $CH_2CH_2CO_2H$ |
| 1839 | $C_3H_7(n)$ | $C_3H_7(n)$ | $CH_3$ |
| 1840 | $C_3H_7(n)$ | $C_3H_7(n)$ | $C_2H_5$ |
| 1841 | $C_3H_7(n)$ | $C_3H_7(n)$ | $C_6H_5$ |
| 1842 | $C_3H_7(n)$ | $C_3H_7(n)$ | $C_6H_5CH_2$ |
| 1843 | $C_3H_7(n)$ | $C_3H_7(n)$ | $CH_2CO_2H$ |
| 1844 | $C_3H_7(n)$ | $C_3H_7(n)$ | $CH_2CH_2CO_2H$ |
| 1845 | $C_3H_7(n)$ | $CH_2C_6H_5$ | $CH_3$ |
| 1846 | $C_3H_7(n)$ | $CH_2C_6H_5$ | $C_2H_5$ |
| 1847 | $C_3H_7(n)$ | $CH_2C_6H_5$ | $C_6H_5$ |
| 1848 | $C_3H_7(n)$ | $CH_2C_6H_5$ | $CH_2CO_2H$ |
| 1849 | $C_3H_7(n)$ | $CH_2C_6H_5$ | $CH_2CH_2CO_2H$ |
| 1850 | $C_4H_9(n)$ | H | $CH_3$ |
| 1851 | $C_4H_9(n)$ | H | $C_2H_5$ |
| 1852 | $C_4H_9(n)$ | H | $C_6H_5$ |
| 1853 | $C_4H_9(n)$ | H | $C_6H_5CH_2$ |
| 1854 | $C_4H_9(n)$ | H | $CH_2CO_2H$ |
| 1855 | $C_4H_9(n)$ | H | $CH_2CH_2CO_2H$ |
| 1856 | $C_4H_9(n)$ | $CH_3$ | $CH_3$ |
| 1857 | $C_4H_9(n)$ | $CH_3$ | $C_2H_5$ |
| 1858 | $C_4H_9(n)$ | $CH_3$ | $C_6H_5$ |
| 1859 | $C_4H_9(n)$ | $CH_3$ | $C_6H_5CH_2$ |
| 1860 | $C_4H_9(n)$ | $CH_3$ | $CH_2CO_2H$ |
| 1861 | $C_4H_9(n)$ | $CH_3$ | $CH_2CH_2CO_2H$ |
| 1862 | $C_4H_9(n)$ | $C_2H_5$ | $CH_3$ |
| 1863 | $C_4H_9(n)$ | $C_2H_5$ | $C_2H_5$ |
| 1864 | $C_4H_9(n)$ | $C_2H_5$ | $C_6H_5$ |
| 1865 | $C_4H_9(n)$ | $C_2H_5$ | $C_6H_5CH_2$ |
| 1866 | $C_4H_9(n)$ | $C_2H_5$ | $CH_2CO_2H$ |
| 1867 | $C_4H_9(n)$ | $C_2H_5$ | $CH_2CH_2CO_2H$ |
| 1868 | $C_4H_9(n)$ | $C_3H_7(n)$ | $CH_3$ |
| 1869 | $C_4H_9(n)$ | $C_3H_7(n)$ | $C_2H_5$ |
| 1870 | $C_4H_9(n)$ | $C_3H_7(n)$ | $C_6H_5$ |
| 1871 | $C_4H_9(n)$ | $C_3H_7(n)$ | $C_6H_5CH_2$ |
| 1872 | $C_4H_9(n)$ | $C_3H_7(n)$ | $CH_2CO_2H$ |
| 1873 | $C_4H_9(n)$ | $C_3H_7(n)$ | $CH_2CH_2CO_2H$ |
| 1874 | $C_4H_9(n)$ | $CH_2C_6H_5$ | $CH_3$ |
| 1875 | $C_4H_9(n)$ | $CH_2C_6H_5$ | $C_2H_5$ |
| 1876 | $C_4H_9(n)$ | $CH_2C_6H_5$ | $C_6H_5$ |
| 1877 | $C_4H_9(n)$ | $CH_2C_6H_5$ | $CH_2CO_2H$ |
| 1878 | $C_4H_9(n)$ | $CH_2C_6H_5$ | $CH_2CH_2CO_2H$ |

TABLE XLVI

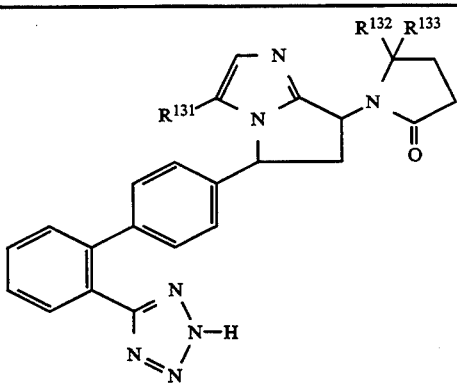

TABLE XLVI-continued

| EX.# | $R^{131}$ | $R^{132},R^{133}$ |
|---|---|---|
| 1879 | $C_3H_7(n)$ | O |
| 1880 | $C_3H_7(n)$ | H,H |
| 1881 | $C_3H_7(n)$ | H,$CH_3$ |
| 1882 | $C_3H_7(n)$ | H,$C_2H_5$ |
| 1883 | $C_3H_7(n)$ | H,$CH_2OH$ |
| 1884 | $C_3H_7(n)$ | H,$CO_2H$ |
| 1885 | $C_4H_9(n)$ | O |
| 1886 | $C_4H_9(n)$ | H,H |
| 1887 | $C_4H_9(n)$ | H,$CH_3$ |
| 1888 | $C_4H_9(n)$ | H,$C_2H_5$ |
| 1889 | $C_4H_9(n)$ | H,$CH_2OH$ |
| 1890 | $C_4H_9(n)$ | H,$CO_2H$ |

TABLE XLVII

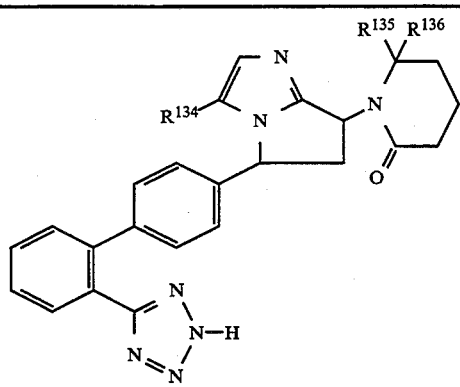

| EX.# | $R^{134}$ | $R^{135},R^{136}$ |
|---|---|---|
| 1891 | $C_3H_7(n)$ | O |
| 1892 | $C_3H_7(n)$ | H,H |
| 1893 | $C_3H_7(n)$ | H,$CH_3$ |
| 1894 | $C_3H_7(n)$ | H,$C_2H_5$ |
| 1895 | $C_3H_7(n)$ | H,$CH_2OH$ |
| 1896 | $C_3H_7(n)$ | H,$CO_2H$ |
| 1897 | $C_4H_9(n)$ | O |
| 1898 | $C_4H_9(n)$ | H,H |
| 1899 | $C_4H_9(n)$ | H,$CH_3$ |
| 1900 | $C_4H_9(n)$ | H,$C_2H_5$ |
| 1901 | $C_4H_9(n)$ | H,$CH_2OH$ |
| 1902 | $C_4H_9(n)$ | H,$CO_2H$ |

TABLE XLVIII

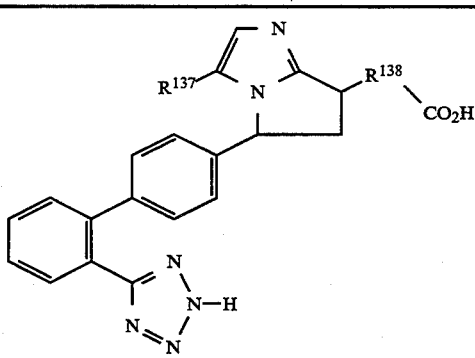

| EX.# | $R^{137}$ | $R^{138}$ |
|---|---|---|
| 1903 | $C_3H_7(n)$ | $CH_2$ |
| 1904 | $C_3H_7(n)$ | $CH(C_2H_5)$ |
| 1905 | $C_3H_7(n)$ | $CH(CH_2C_6H_5)$ |
| 1906 | $C_3H_7(n)$ | $CH_2CH_2$ |
| 1907 | $C_3H_7(n)$ | $CH(C_2H_5)CH_2$ |
| 1908 | $C_3H_7(n)$ | $CH(CH_2C_6H_5)CH_2$ |
| 1909 | $C_4H_9(n)$ | $CH_2$ |
| 1910 | $C_4H_9(n)$ | $CH(C_2H_5)$ |
| 1911 | $C_4H_9(n)$ | $CH(CH_2C_6H_5)$ |
| 1912 | $C_4H_9(n)$ | $CH_2CH_2$ |

TABLE XLVIII-continued

| 1913 | $C_4H_9(n)$ | $CH(C_2H_5)CH_2$ |
|---|---|---|
| 1914 | $C_4H_9(n)$ | $CH(CH_2C_6H_5)CH_2$ |

An appropriately substituted pyrrole 61, the heterocyclic starting material, may be prepared as described in the literature [G. P. Bean and A. H. Jackson; M. Artico; H. J. Anderson; C. E. Loader, A. Gossauer, P. Nesvadba; and N. Dennis in "Pyrroles", Vol 48 of *The Chemistry of Heterocyclic Compounds*, E. C. Taylor, A. Weissberger Eds., Wiley-Interscience, New York, 1990, pp 105–497]. The pyrrole 1 in N,N-dimethylformamide (DMF) is treated with base, such as potassium tert-butoxide, followed by addition of appropriate alkylating agent 62 to give the coupled product 63 (Scheme IX). For compounds where X is a substituted phenyl group, several procedures have been published for the preparations of the alkylating agent 62 [see references for compound 2].

SCHEME IX

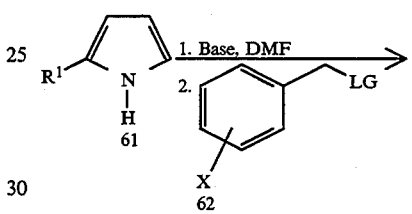

LG: as defined in Scheme I

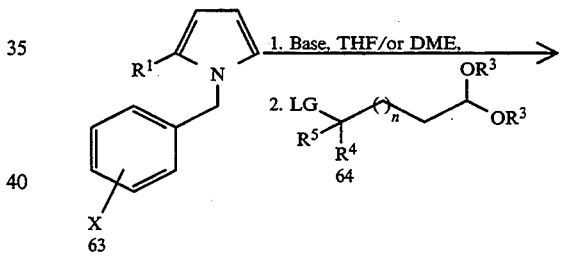

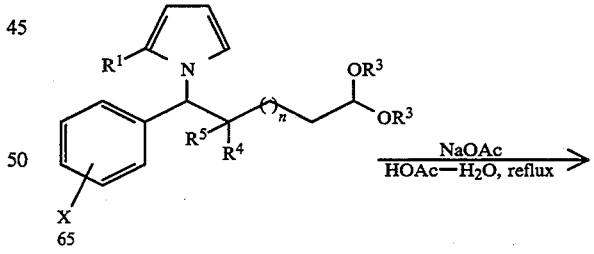

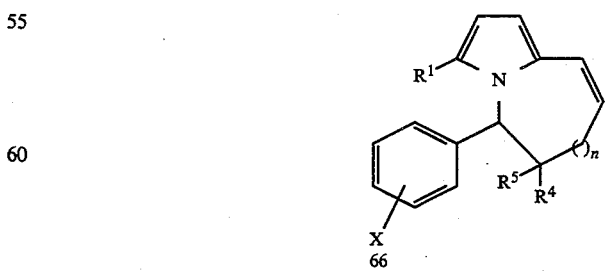

The coupled pyrrole 63 itself may be an angiotensin II receptor antagonist, but it may also be used as a key intermediate in the preparation of the compounds of the invention. Pyrrole 63 in THF (or DME) is treated with base (such as n-BuLi or LDA) at −78° C. (or −65° C.), followed by addition of an appropriate alkylating agent or other electrophiles 64 (the acetal shown in Scheme I may be other aldehyde masking group or equivalent, and LG is a leaving group such as halide, mesylate, triflate or tosylate). The resulting masked aldehyde 65 was stirred with NaOAc in aqueous acetic acid at reflux for a few days (1 to 5 days) to give one of the compounds of the invention, a cyclized pyrrole 66.

The pyrrole 66 may be used as an intermediate to prepare other substituted compounds with appropriate functional group transformations and preparations of some of those compounds are illustrated in Scheme X and XI (all of the intermediates shown in the sequences are also angiotensin II receptor antagonists). For example, The unsaturated pyrrole 66 and NBS in CCl₄ is stirred at reflux to give a bromide 67. The bromide 67 may be treated with organolithium, such as n-BuLi or tert-BuLi, followed by addition of an appropriate electrophile, (such as alkyl halides, carbon dioxide, aldehyde, ketone and others) to give the addition product 68. The olefin 68 may be hydrogenated to give its saturated product 69.

SCHEME X

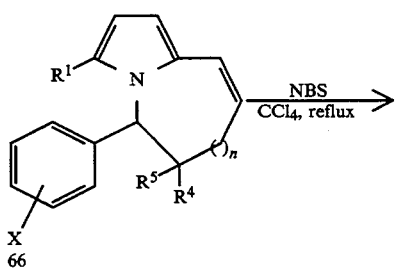

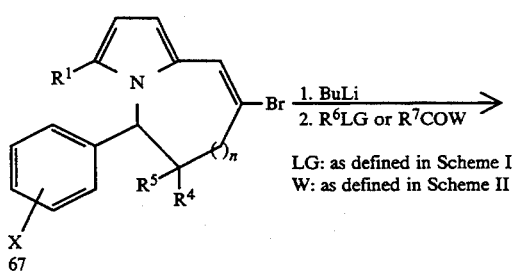

-continued
SCHEME X

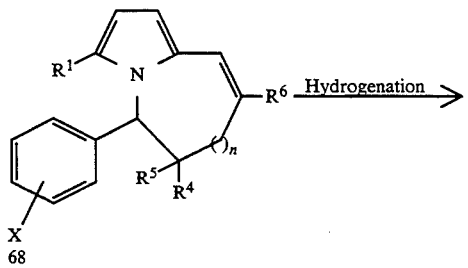

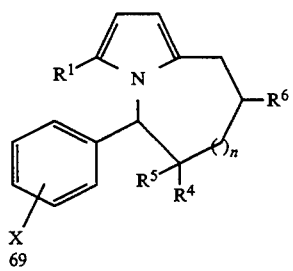

Alternatively, as illustrated in Scheme XI, the unsaturated pyrrole 66 may be treated with NBS in wet DMSO to give a bromohydrin which may be reduced with nBu₃SnH to an alcohol 70 and the oxidation of the alcolol with MnO₂ will afford a ketone 71. The ketone 71 may be condensed with appropriately substituted amine, then reduced to an amine 72 with an appropriate reducing agent (e.g. NaBH₄, or hydrogen over catalyst). The amine 72 may also be prepared directly from olefin 66 under bromination condition (NBS, CH₃CN) in the presence of large excess of succinimide. The amine 72 may be used to prepare other derivatives. Alternatively, the alcohol 70 may be treated with triphenylphosphine, diethoxyazo dicarboxylate and an imide (e.g. phthalimide) to give an imide analogue which may be converted to an amine 72.

The ketone 71 may be treated with appropriate organometallic reagents (such as Grignard, organolithium, organocerium, organozinc reagents or related reagents) to give the addition product, a tertiary alcohol. The alcohol may be dehydrated to give an olefin 73 or an isomeric mixture of olefins 73. The olefin 73 may be treated with base, such as LDA and kinetically quenched at low temperature with either organic acid or appropriate electrophile at low temperature to give the isomerized olefin 74. The olefins 73 or 74 may be hydrogenated to its saturated analogue 75.

SCHEME XI

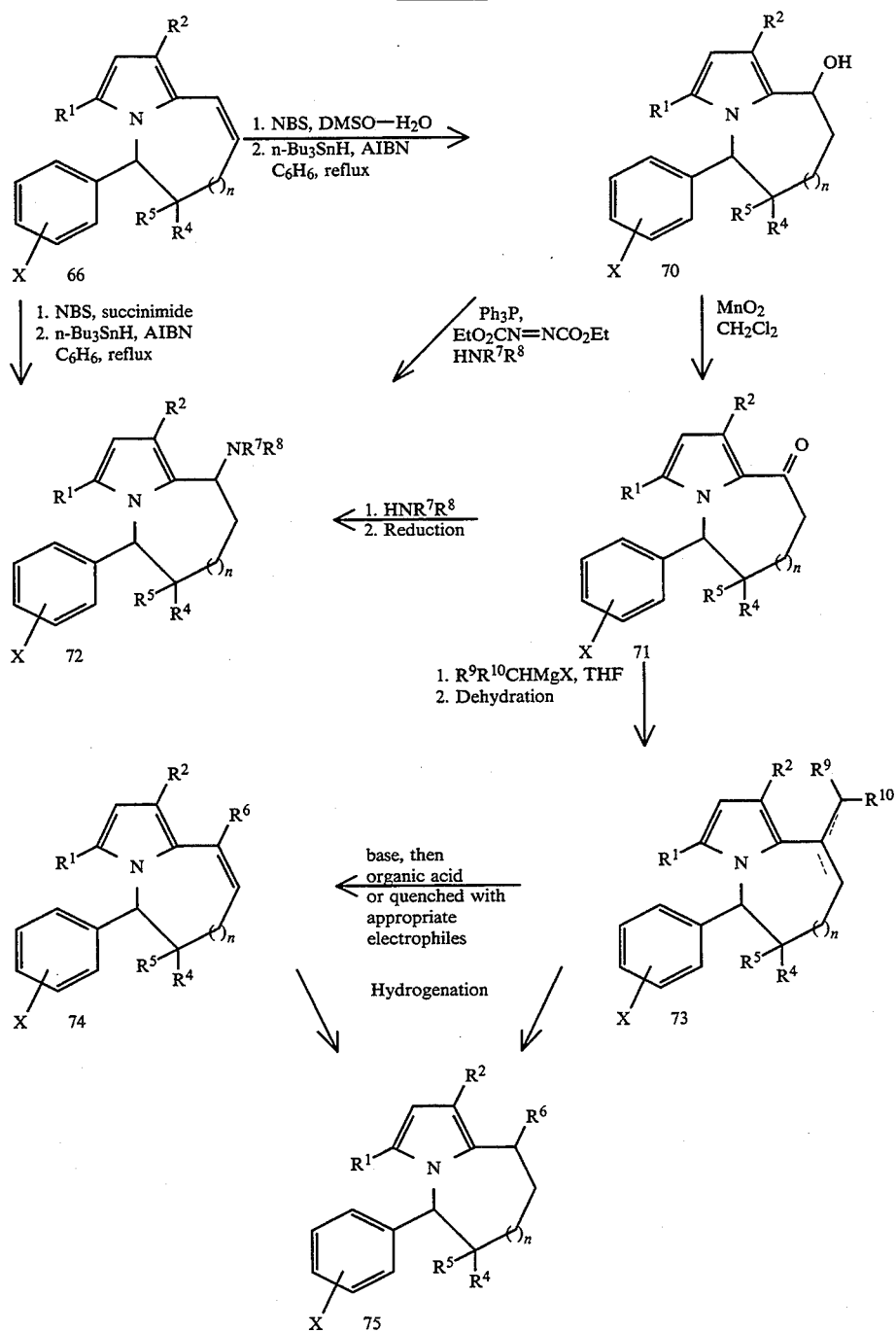

In Scheme XII, an alternative preparation for the compounds of the invention is described. An appropriately substituted pyrrole 61. may be treated with one equivalent of base, then protected as SEM or BOC derivative. The protected pyrrole then is treated with another equivalent of base followed by addition of electrophile 76 or 77. If necessary, the resulting lithium anion obtained from the two procedures described above may be converted to other organometallic reagents according to well-established procedures. Electrophiles 77 and 78 can be prepared from $HC(=O)(CR^4R^5)(CH_2)_nC(=O)LG$ and an appropriate organometallic reagent such as $XC_6H_4MgBr$.

If PLG is a hydroxyl group and Z is a proton, the resulting addition product 79, may be cyclized with triphenylphosphine and diethyl azodicarboxylate (Mitsunobu reaction or other modified conditions). If PLG is or is converted to a leaving group, such as halides, tosylate, and Z is a proton, the cyclization may be achieved with a weak base in DMF (e.g. $K_2CO_3$, $CsCO_3$) to give a ketone 71. The ketone 71 may be reduced to an alcohol 70 with $NaBH_4$ in methanol. The alcohol 70 may be dehydrated to olefin 66 with acid (e.g. HOAc and heat) or thionyl chloride and pyridine. Other compounds may be prepared from compounds 66, 70, or 71 as described in Scheme X and XI.

SCHEME XII

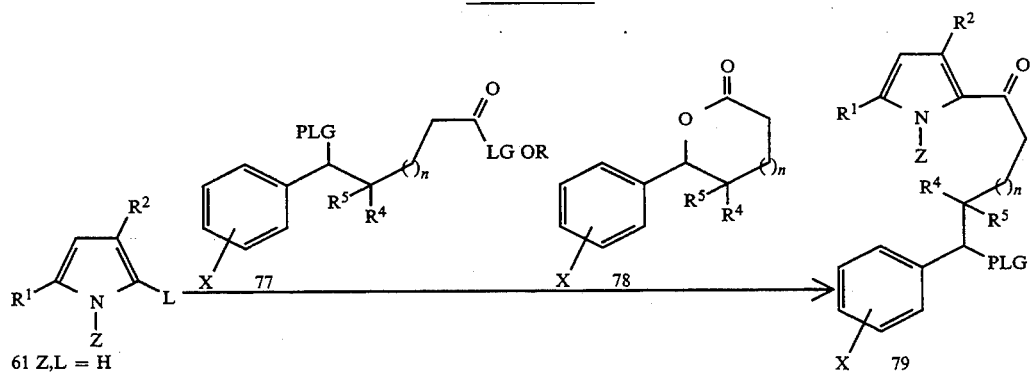

61 Z,L = H
76 Z = protecting group,
 e.g. SEM, or BOC
L = Mg, Ce, Cd, Zn halide
 or Li PLG = a leaving group or
a group that can be easily
converted to a leaving group

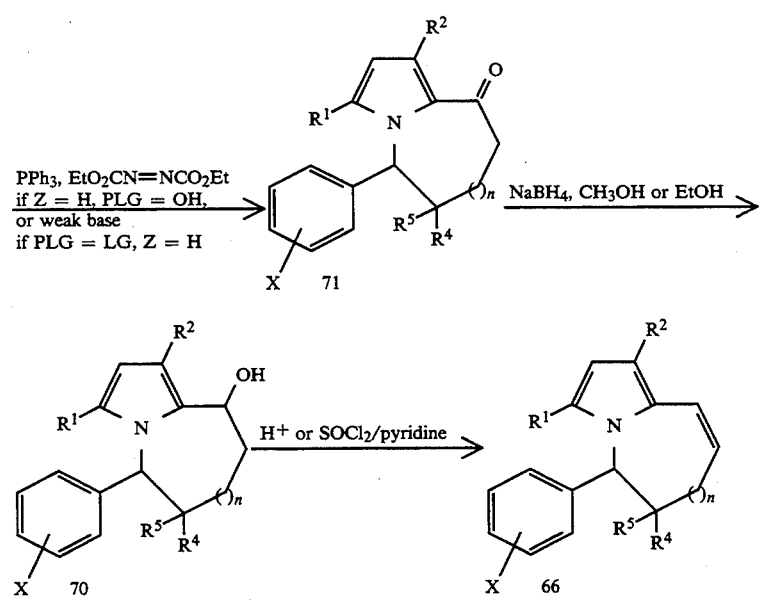

EXAMPLE 1915

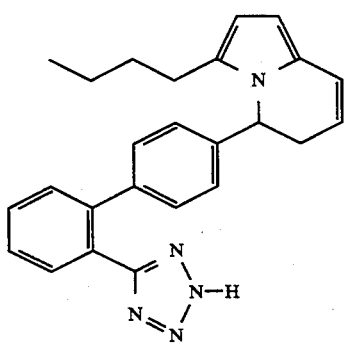

3-Butyl-5,6-dihydro-5-[2'-(1H-tetrazol-5-yl)[1,1'-biphenyl]-4-yl]indolizine

Step 1: Preparation of Biphenyl Pyrrole

To a solution of 2-butylpyrrole (2.65 mmol) in 5.3 mL of DMF is added 3.45 mL (3.45 mmol) of potassium tert-butoxide (1M in THF), and the resulting solution is stirred at room temperature for 30 min. To the dark brown mixture is added 2.75 g (3.45 mmol) of the bromomethyl biphenyl. The reaction mixture is stirred at room temperature until the reaction is complete. The mixture is concentrated in vacuo. The residue is purified to give the trityl-protected biphenyl pyrrole.

Step 2: Preparation of Biphenyl Dimethyl Acetal Pyrrole

To a solution of biphenyl pyrrole (3.18 mmol, obtained from Step 1) in 16 mL of THF cooled at −45° C. (acetonitrile-dry ice) is added 2.8 mL (4.06 mmol) of n-butyllithium (1.45M in hexane) over a 4-min period. The resulting dark purple solution is stirred cold for another 15 min, followed by addition of 1.0 mL (6.59 mmol) of 3-bromopropionaldehyde dimethyl acetal in one portion. The mixture is stirred cold for 40 min, then is slowly warmed to −10° C. The reaction is quenched with aqueous NH$_4$Cl, extracted with diethyl ether. The combined extracts are washed with brine, dried (MgSO$_4$), concentrated in vacuo and purified to give the biphenyl dimethyl acetal pyrrole intermediate.

Step 3: Preparation of Biphenyl Indolizine

A solution of the crude biphenyl dimethyl acetal pyrrole (3.18 mmol, obtained from Step 2) and 5.3 g (88 mmol) of NaOAc in 13 mL of water and 40 mL of glacial acetic acid is stirred at reflux until the reaction is complete. The solution is cooled and concentrated in vacuo. The residue is dissolved in methylene chloride and filtered. The filtrate is stirred with 2 g (7.2 mmol) of trityl chloride and 3 mL (21.5 mmol) of TEA at room temperature until the reaction is complete. The mixture is concentrated in vacuo. The residue is purified to give the biphenyl indolizine.

Step 4: Detritylation of Trityl Tetrazole

A solution of the biphenyl indolizine (0.144 mmol, obtained from Step 3) is stirred with 1 mL of water and 6 mL of acetic acid at room temperature until the reaction is complete. The solution is concentrated in vacuo, stirred in aqueous NaHCO₃ and washed with ether. The aqueous residue is acidified with 3N HCl to pH 4 and extracted with methylene chloride. The combined extracts are dried (MgSO₄), concentrated and purified to give the title compound of Example 1915.

EXAMPLE 1916

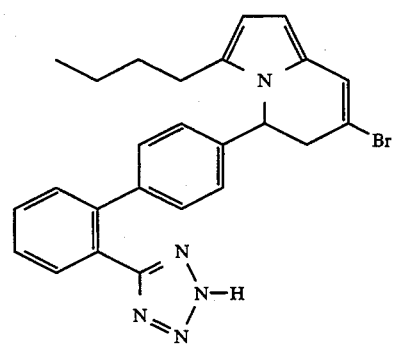

7-Bromo-3-butyl-5,6-dihydro-5-[2'-(1H-tetrazol-5-yl)[1,1'-biphenyl]-4-yl]indolizine Step 1: Preparation of Bromo Olefin Indolizine A solution of biphenyl indolizine (0.101 mmol, obtained from Step 3 of Example 1915), 20 mg (0.112 mmol) of NBS and 7 mg (catalytic) of AIBN in 2.8 mL of CCl₄ is stirred at reflux until the reaction is complete. The reaction mixture is diluted with CCl₄ and washed with water. The organic layer is dried (MgSO₄) and concentrated in vacuo. The residue is purified to give the biphenyl bromo olefin indolizine.

Step 2: Detritylation of the Trityl Tetrazole

A solution of bromo olefin indolizine (0.0427 mmol, obtained from Step 1) in 0.8 mL of water and 5 mL of acetic acid is stirred at room temperature until the reaction is complete. The mixture is concentrated in vacuo. The residue is worked up as described in Step 4 of Example 1915 and purified to give the title compound of Example 1916.

EXAMPLE 1917

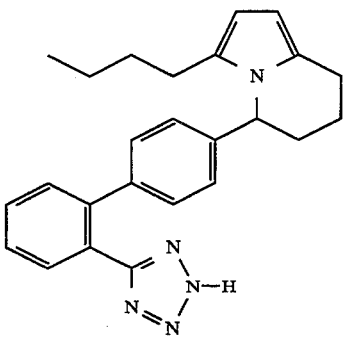

3-Butyl-5,6,7,8-tetrahydro-5-[2'-(1H-tetrazol-5-yl)[1,1'-biphenyl]-4-yl]indolizine A suspension of olefin indolizine (0.1 mmol, the title compound of Example 1915) and 20 mg (0.019 mmol) of 10% palladium on charcoal in 2 mL of absolute ethanol is agitated on a Parr apparatus under 50 psi of hydrogen gas at room temperature until the reaction is complete. The mixture is filtered through a pad of celite, concentrated in vacuo and purified to give the title compound of Example 1917.

EXAMPLE 1918

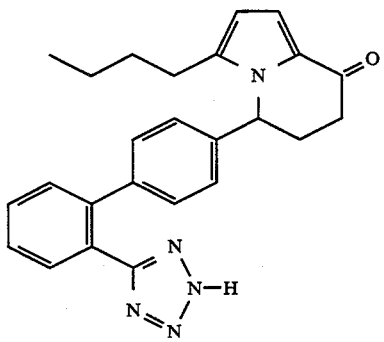

3-Butyl-5,6-dihydro-5-[2'-(1H-tetrazol-5-yl)[1,1'-biphenyl]-4-yl]indolizin-8(5H)-one Step 1: Preparation of the Bromohydrin Intermediate To a solution of biphenyl indolizine (3.13 mmol, obtained from Step 4 of Example 1915) in 2.2 mL (0.122 mmol) of water and 22 mL of DMSO at room temperature is added 587 mg (3.30 mmol) of NBS in one portion. The resulting orange solution is stirred at room temperature for 40 min, quenched with aqueous Na₂SO₃, and extracted with chloroform. The combined extracts are washed with water, and the combined aqueous layers are extracted with chloroform. The combined extracts are washed with brine, dried (MgSO₄) and concentrated in vacuo to give a crude bromohydrin intermediate which can be used directly in the subsequent Step 2 without further purification.

Step 2: Preparation of the Trityl-Protected Biphenyl Hydroxy Indolizine

To the crude bromohydrin (3.13 mmol, obtained from Step 1) in 42 mL of degassed dry benzene is added 4.3 mL (14.7 mmol) of n-Bu₃SnH and 456 mg (2.7 mmol) of AIBN in one portion and the resulting solution is stirred at reflux until the reaction is complete. The mixture is concentrated in vacuo and partitioned between hexane and acetonitrile. The acetonitrile layer is washed with hexane, and the combined hexane layers are extracted with acetonitrile. The combined acetonitrile extracts are concentrated in vacuo to give an isomeric mixture of both cis- and trans-hydroxy indolizines (relative to the biphenyl moiety). The crude mixture can be used directly in subsequent Step 3 without further purification. The mixture may also be used to prepare the biphenyl trans-hydroxy indolizine (the title compound of Example 1920).

Step 3: Preparation of the Keto Indolizine

A suspension of the crude biphenyl hydroxy indolizine (2.72 mmol, obtained from Step 2) and 13 g of active MnO2 in 15 mL of methylene chloride is stirred at room temperature until the reaction is complete. The mixture is filtered through a pad of celite, rinsed with IPA-methylene chloride, and concentrated in vacuo. The residue is purified to give the trityl-protected biphenyl keto indolizine.

Step 4: Detritylation of Trityl Tetrazole

A solution of trityl tetrazolyl keto indolizine (0.131 mmol, obtained from Step 3) in 1.0 mL of water and 5.0 mL of acetic acid is stirred at room temperature until the reaction is complete. The mixture is concentrated in vacuo. The residue is worked up as described in Step 4 of Example 1915 and purified to give the title compound of Example 1918.

EXAMPLE 1919

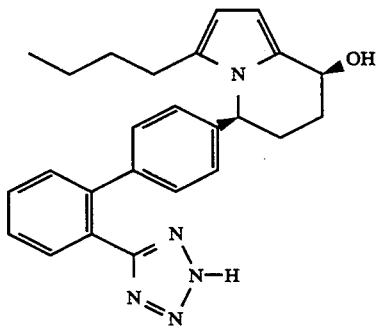

3-Butyl-5,6,7,8-tetrahydro-5-[2'-(1H-tetrazol-5-yl)[1,1'-biphenyl]-4-yl]indolizin-cis-8-ol Step 1: Preparation of Biphenyl Cis-Hydroxy Indolizine To a solution of biphenyl keto indolizine (0.456 mmol, obtained from Step 3 of Example 1918) in 0.5 mL of methanol and 2.0 mL of THF at 0° C. is added in small portions 34 mg (0.899 mmol) of NaBH4. The resulting solution is stirred at 0° C., and slowly warmed to room temperature. The reaction is quenched with aqueous NH4Cl, extracted with methylene chloride, dried (MgSO4) and concentrated in vacuo. The residue is purified to give the biphenyl hydroxy indolizine.

Step 2: Detritylation of Trityl Tetrazole

A solution of the biphenyl hydroxy indolizine (0.259 mmol, obtained from Step 1) in 0.4 mL of water and 2.0 mL of acetic acid is stirred at room temperature until the reaction is complete. The mixture is concentrated in vacuo. The residue is purified to give the title compound of Example 1919.

EXAMPLE 1920

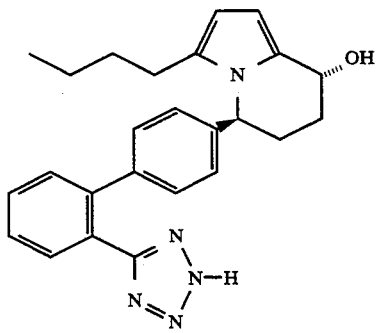

3-Butyl-5,6,7,8-tetrahydro-5-[2'-(1H-tetrazol-5-yl)[1,1'-biphenyl]-4-yl]indolizin-trans-8-ol Step 1: Preparation of Biphenyl Trans-Hydroxy Indolizine A suspension of the crude biphenyl hydroxy indolizine (1.307 mmol, obtained from Step 2 of Example 1918) and 3.0 g of active MnO2 in 5.0 mL of methylene chloride is stirred at room temperature. The reaction is worked up before its completion. The mixture is filtered through a pad of celite, rinsed with IPA-methylene chloride, and concentrated in vacuo. The residue is purified to give the trityl protected biphenyl trans-hydroxy indolizine.

Alternatively, the biphenyl trans-hydroxy indolizine can be prepared using the Mitsunobu reaction conditions. To a solution of diethyl azodicarboxylate (2.0 mmol) and 3-nitrobenzoic acid (2.0 mmol) in 2.0 mL of THF is added dropwise a solution of the biphenyl hydroxy indolizine (2.0 mmol, obtained from Step 1 of Example 1919), and triphenylphosphine (2.0 mmol) in 1.0 mL of THF at room temperature. The resulting solution is stirred at room temperature until the reaction is complete. The resulting mixture is diluted with ether or ethyl acetate, and washed with water. The extracts are dried (MgSO4) and concentrated in vacuo to give the biphenyl indolizinyl nitrobenzoate. The crude benzoate is hydrolyzed with LiOH in aqueous THF at room temperature and purified to give the biphenyl trans-hydroxy indolizine.

Step 2: Detritylation of Trityl Tetrazole

A solution of the trityl protected biphenyl trans-hydroxy indolizine (0.079 mmol, obtained from Step 1) in 0.4 mL of water and 2.0 mL of acetic acid is stirred at room temperature until the reaction is complete. The mixture is concentrated in vacuo. The residue is purified to give the title compound of Example 1920.

EXAMPLE 1921

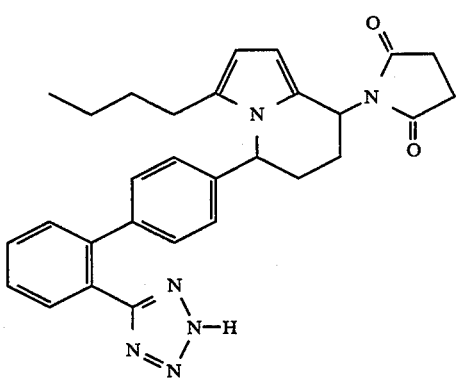

1-[3-Butyl-5,6,7,8-tetrahydro-5-[2'-(1H-tetrazol-5-yl)[1,1'-biphenyl]-4-yl]indolizin-8-yl]-2,5-pyrrolidinedione Step 1: Preparation of Succinimidyl Indolizine To a solution of biphenyl indolizine (3.13 mmol, Example 1915, Step 3) and 1.25 g (12.6 mmol) of succinimide in 20 mL of anhydrous acetonitrile is added 572 mg (3.21 mmol) of NBS in one portion. The resulting orange-red solution is stirred at room temperature for 30 min, then evaporated in vacuo. The residue is dissolved in ethyl acetate and washed with aqueous sodium bisulfite, water, and brine. The extracts are dried (MgSO₄) and concentrated in vacuo. The residue is purified to give the trityl protected succinimidyl indolizine.

Alternatively, the succinimide can be prepared from its corresponding hydroxy indolizine. To a solution of the biphenyl hydroxy indolizine (2.0 mmol, obtained from Step 1 of Example 1919 or 1920), succinimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (HgSO₄) and concentrated in vacuo. The residue is purified to give the trityl protected succinimidyl indolizine.

Step 2: Detritylation of Trityl Tetrazole

A solution of trityl protected succinimidyl indolizine (0.16 mmol, obtained from Step 1) in 0.2 mL of water and 1 mL of acetic acid is stirred at room temperature until the reaction is complete. The mixture is concentrated in vacuo. The residue is worked up as described in Step 4 of Example 1915 and purified to give the title compound of Example 1921.

EXAMPLE 1922

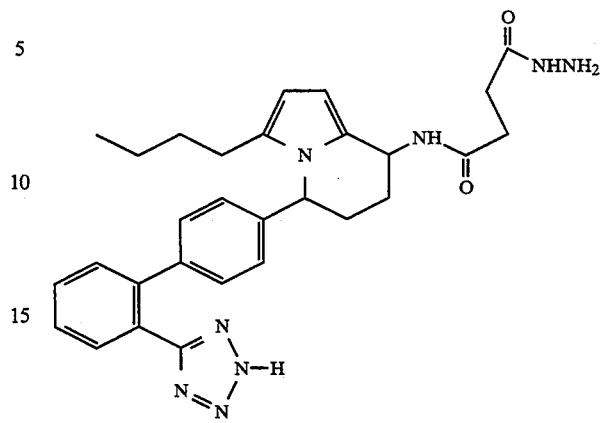

4-[3-Butyl-5,6,7,8-tetrahydro-5-[2'-(1H-tetrazol-5-yl)[1,1'-biphenyl]-4-yl]indolizin-8-yl]amino]-4-oxobutanoic acid, hydrazide A solution of succinimidyl indolizine (0.06 mmol, obtained from Example 1921) and 11 µL (5.6 mmol) of hydrazine in 0.5 mL of ethanol is stirred at room temperature until the reaction is complete and concentrated in vacuo to give the title compound of Example 1922.

EXAMPLE 1923

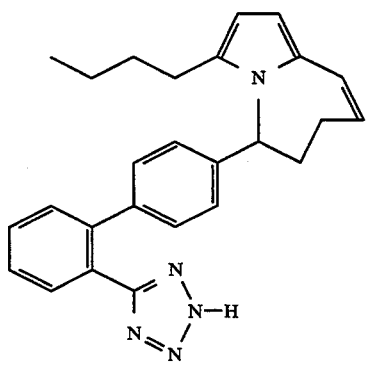

3-Butyl-6,7-dihydro-5-[2'-(1H-tetrazol-5-yl)[1,1'-biphenyl]-4-yl]-5H-pyrrolo[1,5-a]azepine Step 1: Alkylation of Biphenyl Pyrrole To a solution of biphenyl pyrrole (0.152 mmol, obtained from Step 2 of Example 1915) in 0.8 mL of DME cooled at −45° C. (acetonitrile-dry ice) is added 125 µL (0.2 mmol) of n-butyllithium (1.6 M in hexane) over a 4-min period. The resulting dark red solution is stirred cold for another 15 min, followed by addition of 70 µL (0.37 mmol) of 2-(3-bromopropyl)-5,5-dimethyl-1,3-dioxane in one portion. The mixture is stirred cold for 40 min, then is slowly warmed to −10° C. The reaction is quenched with aqueous NH₄Cl, extracted with diethyl ether. The combined extracts are washed with brine, dried (MgSO₄) and concentrated in vacuo. The crude product can be used directly in the subsequent Step 2 without purification.

Step 2: Preparation of the Indolizine

A solution of the crude mixture (0.152 mmol, obtained from Step 1) and 255 mg (3 mmol) of NaOAc in 0.6 mL of water and 2 mL of glacial acetic acid is stirred at reflux until the reaction is complete. The mixture is cooled and concentrated in vacuo. The residue is dissolved in methylene chloride and filtered. The filtrate is stirred with 130 mg (0.46 mmol) of trityl chloride and 0.22 mL (1.6 mmol) of TEA at room temperature until the reaction is complete. The mixture is concentrated in vacuo. The residue is purified to give the biphenyl indolizine.

Step 3: Detritylation of Trityl Tetrazole

A solution of the biphenyl indolizine (0.035 mmol, obtained from Step 2) is stirred with 0.4 mL of water and 2 mL of acetic acid at room temperature until the reaction is complete. The solution is concentrated in vacuo. The residue is worked up as described in Step 4 of Example 1915 and purified to give the title compound of Example 1923.

EXAMPLE 1924

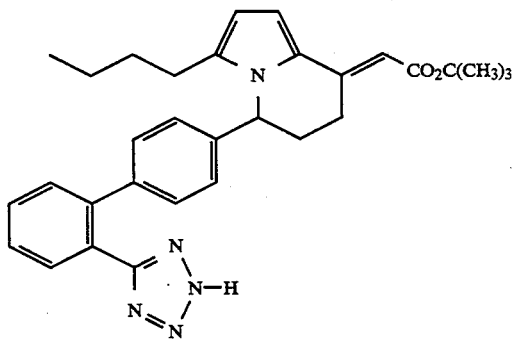

1,1-Dimethylethyl [3-Butyl-6,7-dihydro-5-[2'-(1H-tetrazol-5-yl) [1,1'-biphenyl]-4-yl]-8(5H)-indolizinylidene]acetate Step 1: Preparation of Tert-Butyl Ester To a suspension of 64 mg (2.63 mmol) of magnesium in 3.0 mL of THF at 55° C. is added two 10-μL portions of 1,2-dibromoethane, 5 min apart. The resulting mixture is stirred at 45° C. for 10 min, followed by dropwise addition of a solution of biphenyl keto indolizine (0.306 mmol, obtained from Step 3 of Example 1918) and 242 μL (1.50 mmol) of tert-butyl bromoacetate in 2.0 mL of THF at 55° C. over a 1 h period. The resulting solution is stirred until the reaction is complete. The mixture is cooled and quenched with aqueous NH4Cl. The mixture is extracted with ether, dried (MgSO4) and concentrated in vacuo. The crude mixture can be used directly in the subsequent Step 2 without further purification.

Step 2: Preparation of Unsaturated Butyl Ester

To a solution of the crude biphenyl tert-butyl ester intermediate (0.306 mmol, obtained from Step 1) and 200 μL (2.47 mmol) of pyridine in 2 mL of methylene chloride at 0° C. is added dropwise 80 μL (1.1 mmol) of thionyl chloride. The resulting dark brown solution is stirred at 0° C. for 1 h, diluted with water and extracted with methylene chloride. The residue is purified to give the biphenyl indolizinyl unsaturated ester.

Step 3: Detritylation of Trityl Tetrazole

A solution of biphenyl indolizinyl unsaturated ester (0.133 mmol, obtained from Step 2) in 1.0 mL of water and 5.0 mL of acetic acid is stirred at room temperature until the reaction is complete. The mixture is concentrated in vacuo. The residue is worked up as described in Step 4 of Example 1915 and purified to give the title compound of Example 1924.

EXAMPLE 1925

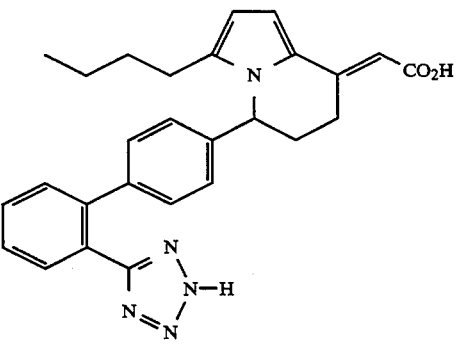

[3-Butyl-6,7-dihydro-5-[2'-(1H-tetrazol-5-yl)[1,1'-biphenyl]-4-yl]-8(5H) -indolizinylidene]acetic acid To a solution of unsaturated tert-butyl ester (0.0627 mmol, the title compound of Example 1924) in 2 mL of CDCl3 at room temperature is added 0.5 mL of TFA, and the progress of the reaction is monitored by 1H NMR. The resulting yellow solution is stirred at room temperature until the reaction is complete. The mixture is concentrated in vacuo. The crude product is purified to give the title compound of Example 1925.

EXAMPLE 1926

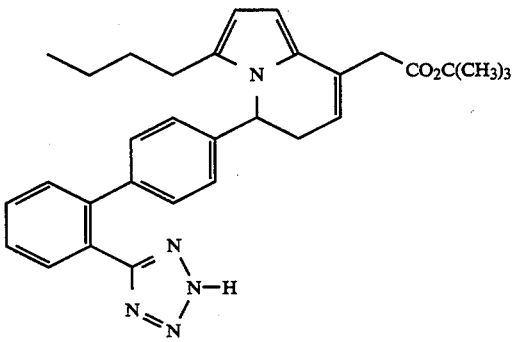

1,1-Dimethylethyl 3-butyl-5,6-dihydro-5-[2'-(1H-tetrazol-5-yl) [1,1'-biphenyl]-4-yl]indolizin-8-acetate Step 1: Preparation of Deconjugated Ester To a solution of ester (0.237 mmol, obtained from Step 2 of Example 1924) in 4 mL of THF at 0° C. is added 10 μL of 1.5M (0.467 mmol) LDA over a 2-min period, and the resulting solution is stirred at 0° C. for 10 min. The mixture is cooled to −78° C., stirred cold for 5 min, and quenched dropwise at −78° C. with 100 μL of acetic acid in 1 mL of hexane. The mixture is stirred cold, then warmed to room temperature and treated with aqueous NaHCO3. The mixture is extracted with methylene chloride. The combined extracts are washed with water, dried (MgSO4) and concentrated in vacuo to give a crude mixture. The crude product is purified to give the biphenyl indolizinyl deconjugated ester.

Step 2: Detritylation of Trityl Tetrazole

A solution of trityl-protected biphenyl indolizinyl deconjugated ester (0.165 mmol, obtained from Step 1) in 1 mL of water and 3 mL of acetic acid is stirred at room temperature until the reaction is complete. The mixture is concentrated in vacuo. The residue is worked up as described in Step 4 of Example 1915. The crude product is purified to give the title compound of Example 1926.

EXAMPLE 1927

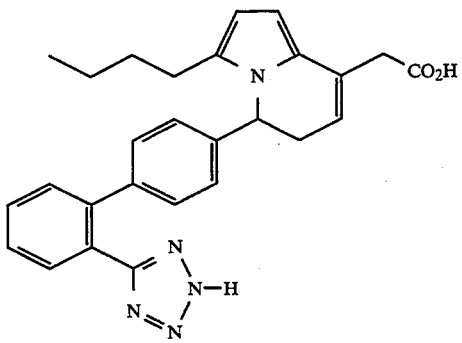

3-Butyl -5,6-dihydro-5-[2'-(1H-tetrazol -5-yl)[1,1'-biphenyl]-4-yl]indolizin-8-acetic acid To a solution of biphenyl indolizinyl tert-butyl ester (0.039 mmol, the title compound of Example 1926) in 0.5 mL of chloroform is added 0.25 mL of TFA, and the progress of the reaction is monitored by $^1$H NMR. The resulting solution is stirred at room temperature until the reaction is complete. The mixture is quenched with methanol and concentrated in vacuo. The residue is purified to give the title compound of Example 1927.

EXAMPLE 1928

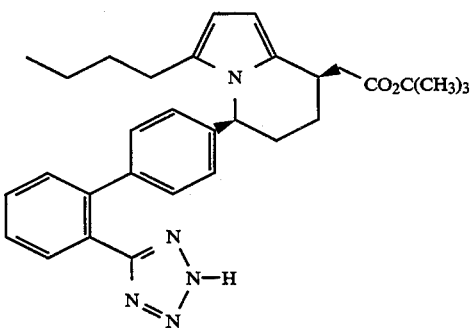

1,1-Dimethylethyl 3-butyl-5,6,7,8-tetrahydro-5-[2'-(1H-tetrazol-5-yl)[1,1'-biphenyl]-4-yl]indolizin-cis-8-acetate A suspension of the biphenyl indolizinyl unsaturated ester (0.059 mmol, the title compound of Example 1926) and 20 mg (0.0188 mmol) of 10% palladium on charcoal in 1.5 mL of methanol is stirred at room temperature under an atmosphere of hydrogen gas until the reaction is complete. The mixture is filtered through a pad of celite and concentrated in vacuo. The residue is purified to give the title compound of Example 1928.

EXAMPLE 1929

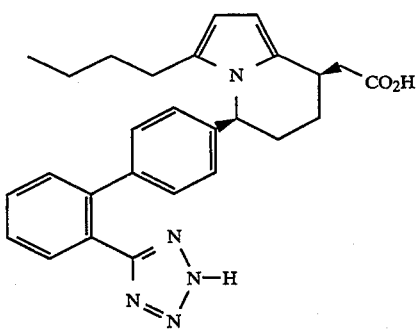

3-Butyl-5,6,7,8-tetrahydro-5-[2'-(1H-tetrazol-5-yl)[1,1'-biphenyl]-4-yl]indolizin-cis-8-acetic acid To a solution of tert-butyl ester (0.0332 mmol, obtained from Example 1928) in 0.4 mL of CDCl$_3$ is added 0.2 mL of TFA, and the progress of the reaction is monitored by $^1$H NMR. The resulting solution is allowed to stand at room temperature until the reaction is complete. The reaction mixture is diluted with methanol and concentrated. The residue is purified to give the title compound of Example 1929.

EXAMPLE 1930

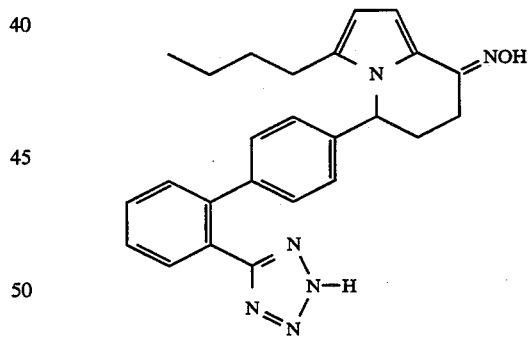

3-Butyl-5,6-dihydro-N-hydroxy-5-[2'-1H-tetrazol-5-yl)[1.1'-biphenyl]-4-yl]indolizin-8 (7H)-imine A mixture of biphenyl keto indolizine (0.094 mmol, the title compound of Example 1918), 20 mg (0.29 mmol) of N-hydroxyamine (hydrochloride salt) and 30 mg of NaOAc in 2 mL of methanol is stirred at 60° C. until the reaction is complete. The mixture is diluted with chloroform and filtered. The solid is washed with methanol. The filtrate is concentrated in vacuo and purified to give the title compound of Example 1930.

EXAMPLE 1931

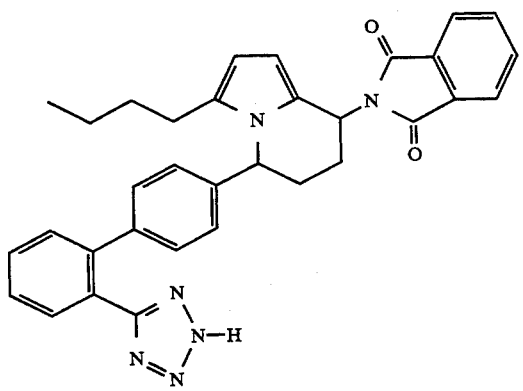

1-[3-Butyl-5,6,7,8-tetrahydro-5-[2'-(1H-tetrazol-5-yl)[1,1'-biphenyl]-4-yl]indolizin-8-yl]phthalimide Step 1: Preparation of Biphenyl Phthalimidyl Indolizine To a solution of the biphenyl hydroxy indolizine (2.0 mmol, obtained from Step 1 of Example 1919 or 1920), phthalimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (MgSO4) and concentrated in vacuo. The residue is purified to give the trityl protected phthalimidyl indolizine.

Step 2: Detritylation of Trityl Tetrazole

A solution of trityl-protected biphenyl phthalimidyl indolizine (2.0 mmol, obtained from Step 1) in 2 mL of water and 10 mL of acetic acid is stirred at room temperature until the reaction is complete. The mixture is concentrated in vacuo. The residue is worked up as described in Step 5 of Example 1915 and purified give the title compound of Example 1931.

EXAMPLE 1932

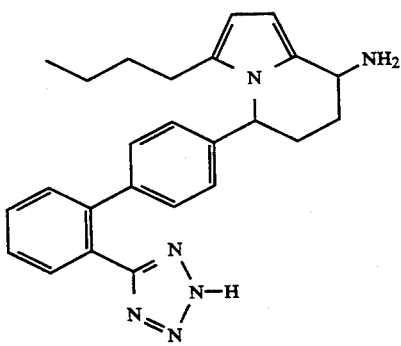

3-Butyl-5,6,7,8-tetrahydro-8-amino-5-[2'-(1H-tetrazol-5-yl) [1,1'-biphenyl]-4-yl]indolizine A solution of phthalimidyl indolizine (0.6 mmol, the title compound of Example 1931) and 3 µL (1.5 mmol) of hydrazine in 1.0 mL of ethanol is stirred at room temperature until the reaction is complete. The mixture is concentrated in vacuo, and purified to give the title compound of Example 1932.

Alternatively, the title compound of Example 1932 can be prepared from the corresponding oxime. A suspension of the biphenyl imidazolyl oxime (0.059 mmol, the title compound of Example 1930) and 20 mg (0.0188 mmol) of 10% palladium on charcoal in 1.5 mL of methanol is stirred at room temperature under 50 psi of hydrogen gas until the reaction is complete. The mixture is filtered through a pad of celite, concentrated in vacuo and purified to give the title compound of Example 1932.

Examples 1933–3219 located in Tables XLIV–LXXII, are further examples of conformationally restricted angiotensin II antagonists embraced by Formula IV.

TABLE XLIX

| EX.# | $R^{139}$ | $R^{140}$ | $R^{141}$ |
|---|---|---|---|
| 1933 | H | $C_3H_7(n)$ | H |
| 1934 | H | $C_3H_7(n)$ | $C_2H_5$ |
| 1935 | H | $C_3H_7(n)$ | $CH_2OH$ |
| 1936 | H | $C_3H_7(n)$ | $CO_2H$ |
| 1937 | H | $C_3H_7(n)$ | $CH_2CO_2H$ |
| 1938 | H | $C_3H_7(n)$ | $CH_2CO_2C(CH_3)_3$ |
| 1939 | H | $C_3H_7(n)$ | $CH(C_2H_5)CO_2H$ |
| 1940 | H | $C_3H_7(n)$ | $CH(C_2H_5)CO_2C(CH_3)_3$ |
| 1941 | H | $C_3H_7(n)$ | phenyl |
| 1942 | H | $C_3H_7(n)$ | benzyl |
| 1943 | H | $C_4H_9(n)$ | $C_2H_5$ |
| 1944 | H | $C_4H_9(n)$ | $CH_2OH$ |
| 1945 | H | $C_4H_9(n)$ | $CO_2H$ |
| 1946 | H | $C_4H_9(n)$ | $CH(C_2H_5)CO_2H$ |
| 1947 | H | $C_4H_9(n)$ | $CH(C_2H_5)CO_2C(CH_3)_3$ |
| 1948 | H | $C_4H_9(n)$ | phenyl |
| 1949 | H | $C_4H_9(n)$ | benzyl |
| 1950 | Cl | $C_3H_7(n)$ | H |
| 1951 | Cl | $C_3H_7(n)$ | $C_2H_5$ |
| 1952 | Cl | $C_3H_7(n)$ | $CH_2OH$ |
| 1953 | Cl | $C_3H_7(n)$ | $CO_2H$ |
| 1954 | Cl | $C_3H_7(n)$ | $CH_2CO_2H$ |
| 1955 | Cl | $C_3H_7(n)$ | $CH_2CO_2C(CH_3)_3$ |
| 1956 | Cl | $C_3H_7(n)$ | $CH(C_2H_5)CO_2H$ |
| 1957 | Cl | $C_3H_7(n)$ | $CH(C_2H_5)CO_2C(CH_3)_3$ |
| 1958 | Cl | $C_4H_9(n)$ | H |
| 1959 | Cl | $C_4H_9(n)$ | $C_2H_5$ |
| 1960 | Cl | $C_4H_9(n)$ | $CH_2OH$ |
| 1961 | Cl | $C_4H_9(n)$ | $CO_2H$ |
| 1962 | Cl | $C_4H_9(n)$ | $CH_2CO_2H$ |
| 1963 | Cl | $C_4H_9(n)$ | $CH_2CO_2C(CH_3)_3$ |
| 1964 | Cl | $C_4H_9(n)$ | $CH(C_2H_5)CO_2H$ |
| 1965 | Cl | $C_4H_9(n)$ | $CH(C_2H_5)CO_2C(CH_3)_3$ |
| 1966 | ethyl | $C_3H_7(n)$ | H |
| 1967 | ethyl | $C_3H_7(n)$ | $C_2H_5$ |
| 1968 | ethyl | $C_3H_7(n)$ | $CH_2OH$ |
| 1969 | ethyl | $C_3H_7(n)$ | $CO_2H$ |
| 1970 | ethyl | $C_3H_7(n)$ | $CH_2CO_2H$ |
| 1971 | ethyl | $C_3H_7(n)$ | $CH_2CO_2C(CH_3)_3$ |
| 1972 | ethyl | $C_4H_9(n)$ | H |
| 1973 | ethyl | $C_4H_9(n)$ | $C_2H_5$ |
| 1974 | ethyl | $C_4H_9(n)$ | $CH_2OH$ |
| 1975 | ethyl | $C_4H_9(n)$ | $CO_2H$ |
| 1976 | ethyl | $C_4H_9(n)$ | $CH_2CO_2H$ |
| 1977 | ethyl | $C_4H_9(n)$ | $CH_2CO_2C(CH_3)_3$ |
| 1978 | n-butyl | $C_3H_7(n)$ | H |

TABLE XLIX-continued

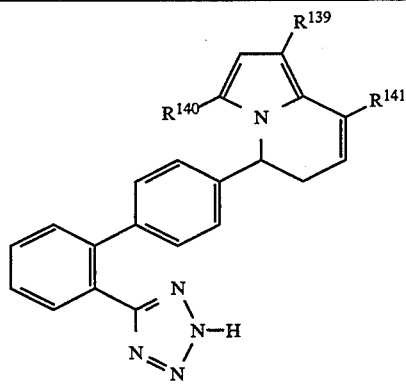

| EX.# | R139 | R140 | R141 |
|---|---|---|---|
| 1979 | n-butyl | C$_3$H$_7$(n) | C$_2$H$_5$ |
| 1980 | n-butyl | C$_3$H$_7$(n) | CH$_2$OH |
| 1981 | n-butyl | C$_3$H$_7$(n) | CO$_2$H |
| 1982 | n-butyl | C$_3$H$_7$(n) | CH$_2$CO$_2$H |
| 1983 | n-butyl | C$_3$H$_7$(n) | CH$_2$CO$_2$C(CH$_3$)$_3$ |
| 1984 | n-butyl | C$_4$H$_9$(n) | C$_2$H$_5$ |
| 1985 | n-butyl | C$_4$H$_9$(n) | H |
| 1986 | n-butyl | C$_4$H$_9$(n) | CH$_2$OH |
| 1987 | n-butyl | C$_4$H$_9$(n) | CO$_2$H |
| 1988 | n-butyl | C$_4$H$_9$(n) | CH$_2$CO$_2$H |
| 1989 | n-butyl | C$_4$H$_9$(n) | CH$_2$CO$_2$C(CH$_3$)$_3$ |
| 1990 | (2-ethylphenyl) | C$_3$H$_7$(n) | H |
| 1991 | (2-ethylphenyl) | C$_3$H$_7$(n) | C$_2$H$_5$ |
| 1992 | (2-ethylphenyl) | C$_3$H$_7$(n) | CH$_2$OH |
| 1993 | (2-ethylphenyl) | C$_3$H$_7$(n) | CO$_2$H |
| 1994 | (2-ethylphenyl) | C$_3$H$_7$(n) | CH$_2$CO$_2$H |
| 1995 | (2-ethylphenyl) | C$_3$H$_7$(n) | CH$_2$CO$_2$C(CH$_3$)$_3$ |
| 1996 | (2-ethylphenyl) | C$_4$H$_9$(n) | H |
| 1997 | (2-ethylphenyl) | C$_4$H$_9$(n) | C$_2$H$_5$ |
| 1998 | (2-ethylphenyl) | C$_4$H$_9$(n) | CH$_2$OH |
| 1999 | (2-ethylphenyl) | C$_4$H$_9$(n) | CO$_2$H |
| 2000 | (2-ethylphenyl) | C$_4$H$_9$(n) | CH$_2$CO$_2$H |
| 2001 | (2-ethylphenyl) | C$_4$H$_9$(n) | CH$_2$CO$_2$C(CH$_3$)$_3$ |

TABLE L

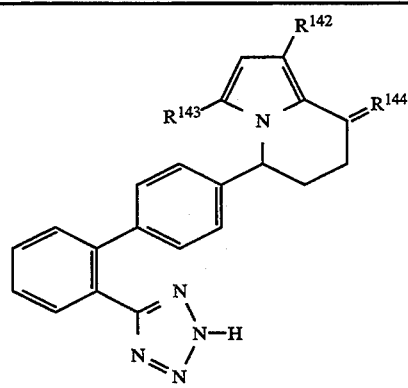

| EX.# | R142 | R143 | R144 |
|---|---|---|---|
| 2002 | H | C$_3$H$_7$(n) | O |
| 2003 | H | C$_3$H$_7$(n) | S |
| 2004 | H | C$_3$H$_7$(n) | CHCO$_2$H |
| 2005 | H | C$_3$H$_7$(n) | CHCO$_2$C(CH$_3$)$_3$ |
| 2006 | H | C$_3$H$_7$(n) | NOH |
| 2007 | H | C$_4$H$_9$(n) | S |
| 2008 | Cl | C$_3$H$_7$(n) | O |
| 2009 | Cl | C$_3$H$_7$(n) | S |
| 2010 | Cl | C$_3$H$_7$(n) | CHCO$_2$H |
| 2011 | Cl | C$_3$H$_7$(n) | CHCO$_2$C(CH$_3$)$_3$ |
| 2012 | Cl | C$_3$H$_7$(n) | NOH |
| 2013 | Cl | C$_4$H$_9$(n) | O |
| 2014 | Cl | C$_4$H$_9$(n) | S |
| 2015 | Cl | C$_4$H$_9$(n) | CHCO$_2$H |
| 2016 | Cl | C$_4$H$_9$(n) | CHCO$_2$C(CH$_3$)$_3$ |

TABLE L-continued

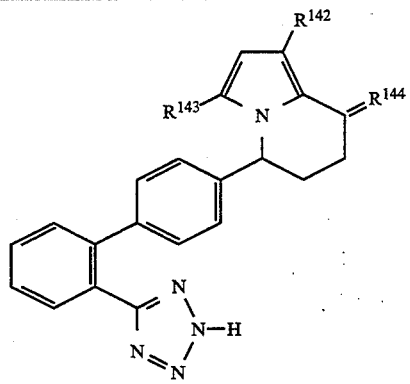

| EX.# | R142 | R143 | R144 |
|---|---|---|---|
| 2017 | Cl | C$_4$H$_9$(n) | NOH |
| 2018 | C$_2$H$_5$ | C$_3$H$_7$(n) | O |
| 2019 | C$_2$H$_5$ | C$_3$H$_7$(n) | S |
| 2020 | C$_2$H$_5$ | C$_3$H$_7$(n) | CHCO$_2$H |
| 2021 | C$_2$H$_5$ | C$_3$H$_7$(n) | CHCO$_2$C(CH$_3$)$_3$ |
| 2022 | C$_2$H$_5$ | C$_3$H$_7$(n) | NOH |
| 2023 | C$_2$H$_5$ | C$_4$H$_9$(n) | O |
| 2024 | C$_2$H$_5$ | C$_4$H$_9$(n) | S |
| 2025 | C$_2$H$_5$ | C$_4$H$_9$(n) | CHCO$_2$H |
| 2026 | C$_2$H$_5$ | C$_4$H$_9$(n) | CHCO$_2$C(CH$_3$)$_3$ |
| 2027 | C$_2$H$_5$ | C$_4$H$_9$(n) | NOH |
| 2028 | C$_4$H$_9$(n) | C$_3$H$_7$(n) | O |
| 2029 | C$_4$H$_9$(n) | C$_3$H$_7$(n) | S |
| 2030 | C$_4$H$_9$(n) | C$_3$H$_7$(n) | CHCO$_2$H |
| 2031 | C$_4$H$_9$(n) | C$_3$H$_7$(n) | CHCO$_2$C(CH$_3$)$_3$ |
| 2032 | C$_4$H$_9$(n) | C$_3$H$_7$(n) | NOH |
| 2033 | C$_4$H$_9$(n) | C$_4$H$_9$(n) | O |
| 2034 | C$_4$H$_9$(n) | C$_4$H$_9$(n) | S |
| 2035 | C$_4$H$_9$(n) | C$_4$H$_9$(n) | CHCO$_2$H |
| 2036 | C$_4$H$_9$(n) | C$_4$H$_9$(n) | CHCO$_2$C(CH$_3$)$_3$ |
| 2037 | C$_4$H$_9$(n) | C$_4$H$_9$(n) | NOH |
| 2038 | (2-ethylphenyl) | C$_3$H$_7$(n) | O |
| 2039 | (2-ethylphenyl) | C$_3$H$_7$(n) | S |
| 2040 | (2-ethylphenyl) | C$_3$H$_7$(n) | CHCO$_2$H |
| 2041 | (2-ethylphenyl) | C$_3$H$_7$(n) | NOH |
| 2042 | (2-ethylphenyl) | C$_4$H$_9$(n) | O |
| 2043 | (2-ethylphenyl) | C$_4$H$_9$(n) | S |
| 2044 | (2-ethylphenyl) | C$_4$H$_9$(n) | CHCO$_2$H |
| 2045 | (2-ethylphenyl) | C$_4$H$_9$(n) | NOH |

TABLE LI

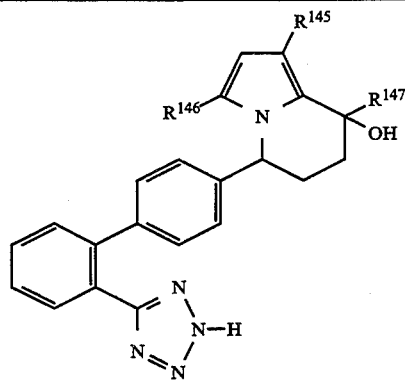

| EX.# | R145 | R146 | R147 |
|---|---|---|---|
| 2046 | H | C$_3$H$_7$(n) | C$_2$H$_5$ |
| 2047 | H | C$_3$H$_7$(n) | C$_3$H$_7$(n) |
| 2048 | H | C$_4$H$_9$(n) | C$_2$H$_5$ |
| 2049 | H | C$_4$H$_9$(n) | C$_3$H$_7$(n) |
| 2050 | Cl | C$_3$H$_7$(n) | C$_2$H$_5$ |
| 2051 | Cl | C$_3$H$_7$(n) | C$_3$H$_7$(n) |
| 2052 | Cl | C$_4$H$_9$(n) | C$_2$H$_5$ |
| 2053 | Cl | C$_4$H$_9$(n) | C$_3$H$_7$(n) |
| 2054 | C$_2$H$_5$ | C$_3$H$_7$(n) | C$_2$H$_5$ |

TABLE LI-continued

| | | | |
|---|---|---|---|
| 2055 | $C_2H_5$ | $C_3H_7(n)$ | $C_3H_7(n)$ |
| 2056 | $C_2H_5$ | $C_4H_9(n)$ | $C_2H_5$ |
| 2057 | $C_2H_5$ | $C_4H_9(n)$ | $C_3H_7(n)$ |
| 2058 | $C_4H_9(n)$ | $C_3H_7(n)$ | $C_2H_5$ |
| 2059 | $C_4H_9(n)$ | $C_4H_9(n)$ | $C_2H_5$ |
| 2060 | (2-ethylphenyl) | $C_3H_7(n)$ | $C_2H_5$ |
| 2061 | (2-ethylphenyl) | $C_4H_9(n)$ | $C_2H_5$ |

TABLE LII

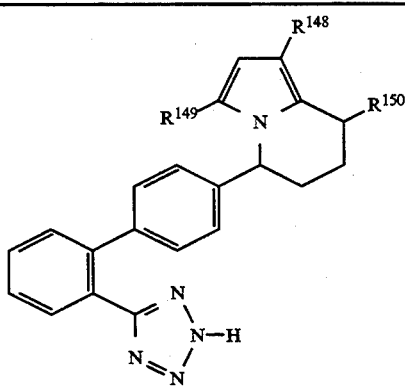

| EX.# | $R^{148}$ | $R^{149}$ | $R^{150}$ |
|---|---|---|---|
| 2062 | H | $C_3H_7(n)$ | H |
| 2063 | H | $C_3H_7(n)$ | $NH_2$ |
| 2064 | H | $C_3H_7(n)$ | OH |
| 2065 | H | $C_3H_7(n)$ | $CH_2OH$ |
| 2066 | H | $C_3H_7(n)$ | $CO_2H$ |
| 2067 | H | $C_3H_7(n)$ | $CO_2C(CH_3)_3$ |
| 2068 | H | $C_3H_7(n)$ | $C_2H_5$ |
| 2069 | H | $C_3H_7(n)$ | $C_3H_7(n)$ |
| 2070 | H | $C_3H_7(n)$ | $C_6H_5$ |
| 2071 | H | $C_3H_7(n)$ | $C_6H_5CH_2$ |
| 2072 | H | $C_3H_7(n)$ | (2-ethylphenyl) |
| 2073 | H | $C_4H_9(n)$ | $CH_2OH$ |
| 2074 | H | $C_4H_9(n)$ | $CO_2H$ |
| 2075 | H | $C_4H_9(n)$ | $CO_2C(CH_3)_3$ |
| 2076 | H | $C_4H_9(n)$ | $C_2H_5$ |
| 2077 | H | $C_4H_9(n)$ | $C_3H_7(n)$ |
| 2078 | H | $C_4H_9(n)$ | $C_6H_5$ |
| 2079 | H | $C_4H_9(n)$ | $C_6H_5CH_2$ |
| 2080 | H | $C_4H_9(n)$ | (2-ethylphenyl) |
| 2081 | Cl | $C_3H_7(n)$ | H |
| 2082 | Cl | $C_3H_7(n)$ | $NH_2$ |
| 2083 | Cl | $C_3H_7(n)$ | OH |
| 2084 | Cl | $C_3H_7(n)$ | $CH_2OH$ |
| 2085 | Cl | $C_3H_7(n)$ | $CO_2H$ |
| 2086 | Cl | $C_3H_7(n)$ | $CO_2C(CH_3)_3$ |
| 2087 | Cl | $C_3H_7(n)$ | $C_2H_5$ |
| 2088 | Cl | $C_3H_7(n)$ | $C_3H_7(n)$ |
| 2089 | Cl | $C_3H_7(n)$ | $C_6H_5$ |
| 2090 | Cl | $C_3H_7(n)$ | $C_6H_5CH_2$ |
| 2091 | Cl | $C_3H_7(n)$ | (2-ethylphenyl) |
| 2092 | Cl | $C_4H_9(n)$ | H |
| 2093 | Cl | $C_4H_9(n)$ | $NH_2$ |
| 2094 | Cl | $C_4H_9(n)$ | OH |
| 2095 | Cl | $C_4H_9(n)$ | $CH_2OH$ |
| 2096 | Cl | $C_4H_9(n)$ | $CO_2H$ |
| 2097 | Cl | $C_4H_9(n)$ | $CO_2C(CH_3)_3$ |
| 2098 | Cl | $C_4H_9(n)$ | $C_2H_5$ |
| 2099 | Cl | $C_4H_9(n)$ | $C_3H_7(n)$ |
| 2100 | Cl | $C_4H_9(n)$ | $C_6H_5$ |
| 2101 | Cl | $C_4H_9(n)$ | $C_6H_5CH_2$ |
| 2102 | Cl | $C_4H_9(n)$ | (2-ethylphenyl) |
| 2103 | $C_2H_5$ | $C_3H_7(n)$ | H |
| 2104 | $C_2H_5$ | $C_3H_7(n)$ | $NH_2$ |
| 2105 | $C_2H_5$ | $C_3H_7(n)$ | OH |
| 2106 | $C_2H_5$ | $C_3H_7(n)$ | $CH_2OH$ |
| 2107 | $C_2H_5$ | $C_3H_7(n)$ | $CO_2H$ |
| 2108 | $C_2H_5$ | $C_3H_7(n)$ | $CO_2C(CH_3)_3$ |
| 2109 | $C_2H_5$ | $C_3H_7(n)$ | $C_2H_5$ |
| 2110 | $C_2H_5$ | $C_4H_9(n)$ | H |
| 2111 | $C_2H_5$ | $C_4H_9(n)$ | $NH_2$ |
| 2112 | $C_2H_5$ | $C_4H_9(n)$ | OH |

TABLE LII-continued

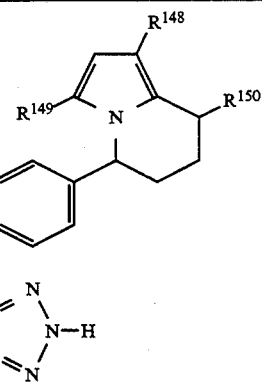

| EX.# | $R^{148}$ | $R^{149}$ | $R^{150}$ |
|---|---|---|---|
| 2113 | $C_2H_5$ | $C_4H_9(n)$ | $CH_2OH$ |
| 2114 | $C_2H_5$ | $C_4H_9(n)$ | $CO_2H$ |
| 2115 | $C_2H_5$ | $C_4H_9(n)$ | $CO_2C(CH_3)_3$ |
| 2116 | $C_2H_5$ | $C_4H_9(n)$ | $C_2H_5$ |
| 2117 | $C_4H_9(n)$ | $C_3H_7(n)$ | H |
| 2118 | $C_4H_9(n)$ | $C_3H_7(n)$ | $NH_2$ |
| 2119 | $C_4H_9(n)$ | $C_3H_7(n)$ | OH |
| 2120 | $C_4H_9(n)$ | $C_3H_7(n)$ | $CH_2OH$ |
| 2121 | $C_4H_9$ | $C_3H_7(n)$ | $CO_2H$ |
| 2122 | $C_4H_9$ | $C_3H_7(n)$ | $CO_2C(CH_3)_3$ |
| 2123 | $C_4H_9(n)$ | $C_3H_7(n)$ | $C_2H_5$ |
| 2124 | $C_4H_9(n)$ | $C_3H_7(n)$ | $C_6H_5CH_2$ |
| 2125 | $C_4H_9(n)$ | $C_4H_9(n)$ | H |
| 2126 | $C_4H_9(n)$ | $C_4H_9(n)$ | $NH_2$ |
| 2127 | $C_4H_9(n)$ | $C_4H_9(n)$ | OH |
| 2128 | $C_4H_9(n)$ | $C_4H_9(n)$ | $CH_2OH$ |
| 2129 | $C_4H_9$ | $C_4H_9(n)$ | $CO_2H$ |
| 2130 | $C_4H_9$ | $C_4H_9(n)$ | $CO_2C(CH_3)_3$ |
| 2131 | $C_4H_9(n)$ | $C_4H_9(n)$ | $C_2H_5$ |
| 2132 | (2-ethylphenyl) | $C_3H_7(n)$ | H |
| 2133 | (2-ethylphenyl) | $C_3H_7(n)$ | $NH_2$ |
| 2134 | (2-ethylphenyl) | $C_3H_7(n)$ | OH |
| 2135 | (2-ethylphenyl) | $C_3H_7(n)$ | $CH_2OH$ |
| 2136 | (2-ethylphenyl) | $C_3H_7(n)$ | $CO_2H$ |
| 2137 | (2-ethylphenyl) | $C_3H_7(n)$ | $CO_2C(CH_3)_3$ |
| 2138 | (2-ethylphenyl) | $C_3H_7(n)$ | $C_2H_5$ |
| 2139 | (2-ethylphenyl) | $C_4H_9(n)$ | H |
| 2140 | (2-ethylphenyl) | $C_4H_9(n)$ | $NH_2$ |
| 2141 | (2-ethylphenyl) | $C_4H_9(n)$ | OH |
| 2142 | (2-ethylphenyl) | $C_4H_9(n)$ | $CH_2OH$ |
| 2143 | (2-ethylphenyl) | $C_4H_9(n)$ | $CO_2H$ |
| 2144 | (2-ethylphenyl) | $C_4H_9(n)$ | $CO_2C(CH_3)_3$ |
| 2145 | (2-ethylphenyl) | $C_4H_9(n)$ | $C_2H_5$ |

TABLE LIII

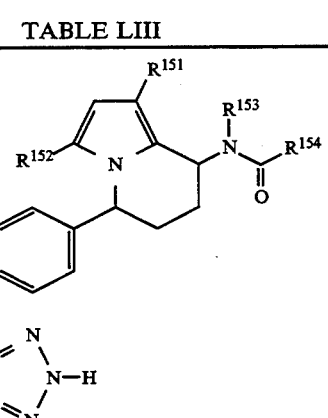

| EX. # | $R^{151}$ | $R^{152}$ | $R^{153}$ | $R^{154}$ |
|---|---|---|---|---|
| 2146 | H | $C_3H_7(n)$ | H | $CH_3$ |
| 2147 | H | $C_3H_7(n)$ | $CH_3$ | $CH_3$ |
| 2148 | H | $C_3H_7(n)$ | $C_6H_5CH_2$ | $CH_3$ |
| 2149 | H | $C_4H_9(n)$ | H | $CH_3$ |
| 2150 | H | $C_4H_9(n)$ | $CH_3$ | $CH_3$ |

TABLE LIII-continued

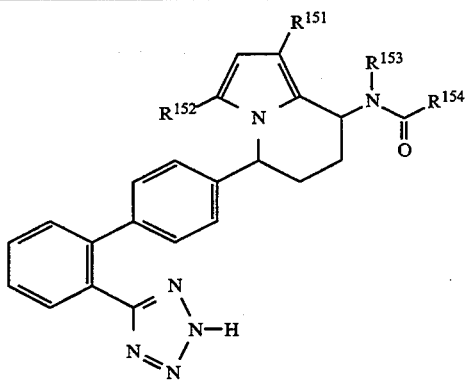

| EX. # | R¹⁵¹ | R¹⁵² | R¹⁵³ | R¹⁵⁴ |
|---|---|---|---|---|
| 2151 | H | C₄H₉(n) | C₆H₅CH₂ | CH₃ |
| 2152 | Cl | C₃H₇(n) | H | CH₃ |
| 2153 | Cl | C₃H₇(n) | CH₃ | CH₃ |
| 2154 | Cl | C₃H₇(n) | C₆H₅CH₂ | CH₃ |
| 2155 | Cl | C₄H₉(n) | H | CH₃ |
| 2156 | Cl | C₄H₉(n) | CH₃ | CH₃ |
| 2157 | Cl | C₄H₉(n) | C₆H₅CH₂ | CH₃ |
| 2158 | C₂H₅ | C₃H₇(n) | H | CH₃ |
| 2159 | C₂H₅ | C₃H₇(n) | CH₃ | CH₃ |
| 2160 | C₂H₅ | C₄H₉(n) | H | CH₃ |
| 2161 | C₂H₅ | C₄H₉(n) | CH₃ | CH₃ |
| 2162 | C₄H₉(n) | C₃H₇(n) | H | CH₃ |
| 2163 | C₄H₉(n) | C₃H₇(n) | CH₃ | CH₃ |
| 2164 | C₄H₉(n) | C₄H₉(n) | H | CH₃ |
| 2165 | C₄H₉(n) | C₄H₉(n) | CH₃ | CH₃ |
| 2166 | (2-ethylphenyl) | C₃H₇(n) | H | CH₃ |
| 2167 | (2-ethylphenyl) | C₃H₇(n) | CH₃ | CH₃ |
| 2168 | (2-ethylphenyl) | C₄H₉(n) | H | CH₃ |
| 2169 | (2-ethylphenyl) | C₄H₉(n) | CH₃ | CH₃ |
| 2170 | H | C₃H₇(n) | H | C₂H₅ |
| 2171 | H | C₃H₇(n) | CH₃ | C₂H₅ |
| 2172 | H | C₄H₉(n) | H | C₂H₅ |
| 2173 | H | C₄H₉(n) | CH₃ | C₂H₅ |
| 2174 | Cl | C₃H₇(n) | H | C₂H₅ |
| 2175 | Cl | C₃H₇(n) | CH₃ | C₂H₅ |
| 2176 | Cl | C₄H₉(n) | H | C₂H₅ |
| 2177 | Cl | C₄H₉(n) | CH₃ | C₂H₅ |
| 2178 | C₂H₅ | C₃H₇(n) | H | C₂H₅ |
| 2179 | C₂H₅ | C₃H₇(n) | CH₃ | C₂H₅ |
| 2180 | C₂H₅ | C₄H₉(n) | H | C₂H₅ |
| 2181 | C₂H₅ | C₄H₉(n) | CH₃ | C₂H₅ |
| 2182 | (2-ethylphenyl) | C₃H₇(n) | H | C₂H₅ |
| 2183 | (2-ethylphenyl) | C₄H₉(n) | H | C₂H₅ |
| 2184 | H | C₃H₇(n) | H | C₆H₅ |
| 2185 | H | C₃H₇(n) | CH₃ | C₆H₅ |
| 2186 | H | C₄H₉(n) | H | C₆H₅ |
| 2187 | H | C₄H₉(n) | CH₃ | C₆H₅ |
| 2188 | Cl | C₃H₇(n) | H | C₆H₅ |
| 2189 | Cl | C₃H₇(n) | CH₃ | C₆H₅ |
| 2190 | Cl | C₄H₉(n) | H | C₆H₅ |
| 2191 | Cl | C₄H₉(n) | CH₃ | C₆H₅ |
| 2192 | C₂H₅ | C₃H₇(n) | H | C₆H₅ |
| 2193 | C₂H₅ | C₃H₇(n) | CH₃ | C₆H₅ |
| 2194 | C₂H₅ | C₄H₉(n) | H | C₆H₅ |
| 2195 | C₂H₅ | C₄H₉(n) | CH₃ | C₆H₅ |
| 2196 | C₄H₉(n) | C₃H₇(n) | H | C₆H₅ |
| 2197 | C₄H₉(n) | C₃H₇(n) | CH₃ | C₆H₅ |
| 2198 | C₄H₉(n) | C₄H₉(n) | H | C₆H₅ |
| 2199 | C₄H₉(n) | C₄H₉(n) | CH₃ | C₆H₅ |
| 2200 | C₄H₉(n) | C₄H₉(n) | H | CH₂CH₂CO₂H |
| 2201 | C₄H₉(n) | C₄H₉(n) | CH₃ | CH₂CH₂CO₂H |
| 2202 | (2-ethylphenyl) | C₃H₇(n) | H | CH₂CH₂CO₂H |
| 2203 | (2-ethylphenyl) | C₃H₇(n) | CH₃ | CH₂CH₂CO₂H |
| 2204 | (2-ethylphenyl) | C₄H₉(n) | H | CH₂CH₂CO₂H |
| 2205 | (2-ethylphenyl) | C₄H₉(n) | CH₃ | CH₂CH₂CO₂H |

TABLE LIV

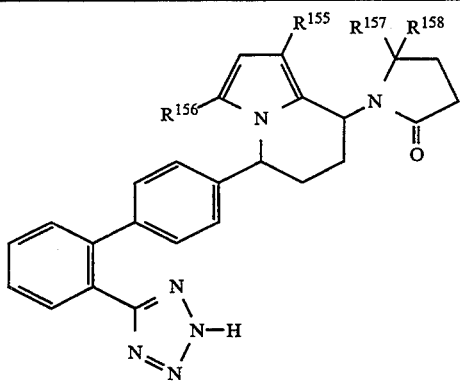

| EX. # | R¹⁵⁵ | R¹⁵⁶ | R¹⁵⁷, R¹⁵⁸ |
|---|---|---|---|
| 2206 | H | C₃H₇(n) | O |
| 2207 | H | C₃H₇(n) | H, H |
| 2208 | H | C₃H₇(n) | H, CH₃ |
| 2209 | H | C₃H₇(n) | H, C₂H₅ |
| 2210 | H | C₃H₇(n) | H, CH₂OH |
| 2211 | H | C₃H₇(n) | H, CO₂H |
| 2212 | H | C₄H₉(n) | H, H |
| 2213 | H | C₄H₉(n) | H, CH₃ |
| 2214 | H | C₄H₉(n) | H, C₂H₅ |
| 2215 | H | C₄H₉(n) | H, CH₂OH |
| 2216 | H | C₄H₉(n) | H, CO₂H |
| 2217 | Cl | C₃H₇(n) | O |
| 2218 | Cl | C₃H₇(n) | H, H |
| 2219 | Cl | C₃H₇(n) | H, CH₃ |
| 2220 | Cl | C₃H₇(n) | H, C₂H₅ |
| 2221 | Cl | C₃H₇(n) | H, CH₂OH |
| 2222 | Cl | C₃H₇(n) | H, CO₂H |
| 2223 | Cl | C₄H₉(n) | O |
| 2224 | Cl | C₄H₉(n) | H, H |
| 2225 | Cl | C₄H₉(n) | H, CH₃ |
| 2226 | Cl | C₄H₉(n) | H, C₂H₅ |
| 2227 | Cl | C₄H₉(n) | H, CH₂OH |
| 2228 | Cl | C₄H₉(n) | H, CO₂H |
| 2229 | C₂H₅ | C₃H₇(n) | O |
| 2230 | C₂H₅ | C₃H₇(n) | H, H |
| 2231 | C₂H₅ | C₃H₇(n) | H, CH₃ |
| 2232 | C₂H₅ | C₃H₇(n) | H, C₂H₅ |
| 2233 | C₂H₅ | C₃H₇(n) | H, CH₂OH |
| 2234 | C₂H₅ | C₃H₇(n) | H, CO₂H |
| 2235 | C₂H₅ | C₄H₉(n) | O |
| 2236 | C₂H₅ | C₄H₉(n) | H, H |
| 2237 | C₂H₅ | C₄H₉(n) | H, CH₃ |
| 2238 | C₂H₅ | C₄H₉(n) | H, C₂H₅ |
| 2239 | C₂H₅ | C₄H₉(n) | H, CH₂OH |
| 2240 | C₂H₅ | C₄H₉(n) | H, CO₂H |
| 2241 | C₄H₉(n) | C₃H₇(n) | O |
| 2242 | C₄H₉(n) | C₃H₇(n) | H, H |
| 2243 | C₄H₉(n) | C₃H₇(n) | H, CH₃ |
| 2244 | C₄H₉(n) | C₃H₇(n) | H, CH₂OH |
| 2245 | C₄H₉(n) | C₃H₇(n) | H, CO₂H |
| 2246 | C₄H₉(n) | C₄H₉(n) | O |
| 2247 | C₄H₉(n) | C₄H₉(n) | H, H |
| 2248 | C₄H₉(n) | C₄H₉(n) | H, CH₃ |
| 2249 | C₄H₉(n) | C₄H₉(n) | H, CH₂OH |
| 2250 | C₄H₉(n) | C₄H₉(n) | H, CO₂H |
| 2251 | (2-ethylphenyl) | C₃H₇(n) | O |
| 2252 | (2-ethylphenyl) | C₃H₇(n) | H, H |
| 2253 | (2-ethylphenyl) | C₃H₇(n) | H, CH₃ |
| 2254 | (2-ethylphenyl) | C₃H₇(n) | CH₃, CH₃ |
| 2255 | (2-ethylphenyl) | C₃H₇(n) | H, CH₂OH |
| 2256 | (2-ethylphenyl) | C₃H₇(n) | H, CO₂H |
| 2257 | (2-ethylphenyl) | C₄H₉(n) | O |
| 2258 | (2-ethylphenyl) | C₄H₉(n) | H, H |
| 2259 | (2-ethylphenyl) | C₄H₉(n) | H, CH₃ |
| 2260 | (2-ethylphenyl) | C₄H₉(n) | CH₃, CH₃ |
| 2261 | (2-ethylphenyl) | C₄H₉(n) | H, CH₂OH |
| 2262 | (2-ethylphenyl) | C₄H₉(n) | H, CO₂H |

TABLE LV

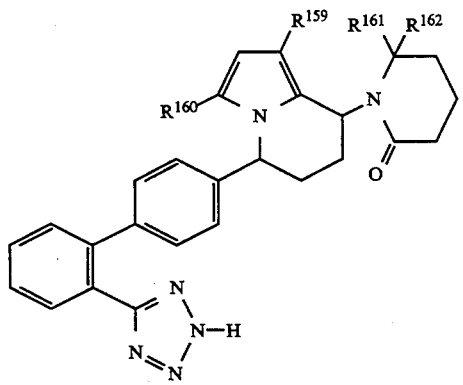

| EX. # | $R^{159}$ | $R^{160}$ | $R^{161}, R^{162}$ |
|---|---|---|---|
| 2263 | H | $C_3H_7(n)$ | O |
| 2264 | H | $C_3H_7(n)$ | H, H |
| 2265 | H | $C_3H_7(n)$ | H, $CH_3$ |
| 2266 | H | $C_3H_7(n)$ | H, $C_2H_5$ |
| 2267 | H | $C_3H_7(n)$ | H, $CH_2OH$ |
| 2268 | H | $C_3H_7(n)$ | H, $CO_2H$ |
| 2269 | H | $C_4H_9(n)$ | O |
| 2270 | H | $C_4H_9(n)$ | H, H |
| 2271 | H | $C_4H_9(n)$ | H, $CH_3$ |
| 2272 | H | $C_4H_9(n)$ | H, $C_2H_5$ |
| 2273 | H | $C_4H_9(n)$ | H, $CH_2OH$ |
| 2274 | H | $C_4H_9(n)$ | H, $CO_2H$ |
| 2275 | Cl | $C_3H_7(n)$ | O |
| 2276 | Cl | $C_3H_7(n)$ | H, H |
| 2277 | Cl | $C_3H_7(n)$ | H, $CH_3$ |
| 2278 | Cl | $C_3H_7(n)$ | $CH_3$, $CH_3$ |
| 2279 | Cl | $C_3H_7(n)$ | H, $CH_2OH$ |
| 2280 | Cl | $C_3H_7(n)$ | H, $CO_2H$ |
| 2281 | Cl | $C_4H_9(n)$ | O |
| 2282 | Cl | $C_4H_9(n)$ | H, H |
| 2283 | Cl | $C_4H_9(n)$ | H, $CH_3$ |
| 2284 | Cl | $C_4H_9(n)$ | H, $C_2H_5$ |
| 2285 | Cl | $C_4H_9(n)$ | H, $CH_2OH$ |
| 2286 | Cl | $C_4H_9(n)$ | H, $CO_2H$ |
| 2287 | $C_2H_5$ | $C_3H_7(n)$ | O |
| 2288 | $C_2H_5$ | $C_3H_7(n)$ | H, H |
| 2289 | $C_2H_5$ | $C_3H_7(n)$ | H, $CH_3$ |
| 2290 | $C_2H_5$ | $C_3H_7(n)$ | H, $C_2H_5$ |
| 2291 | $C_2H_5$ | $C_3H_7(n)$ | H, $CH_2OH$ |
| 2292 | $C_2H_5$ | $C_3H_7(n)$ | H, $CO_2H$ |
| 2293 | $C_2H_5$ | $C_4H_9(n)$ | O |
| 2294 | $C_2H_5$ | $C_4H_9(n)$ | H, H |
| 2295 | $C_2H_5$ | $C_4H_9(n)$ | H, $CH_3$ |
| 2296 | $C_2H_5$ | $C_4H_9(n)$ | H, $C_2H_5$ |
| 2297 | $C_2H_5$ | $C_4H_9(n)$ | H, $CH_2OH$ |
| 2298 | $C_2H_5$ | $C_4H_9(n)$ | H, $CO_2H$ |
| 2299 | $C_4H_9(n)$ | $C_3H_7(n)$ | O |
| 2300 | $C_4H_9(n)$ | $C_3H_7(n)$ | H, H |
| 2301 | $C_4H_9(n)$ | $C_3H_7(n)$ | H, $CH_3$ |
| 2302 | $C_4H_9(n)$ | $C_3H_7(n)$ | H, $CH_2OH$ |
| 2303 | $C_4H_9(n)$ | $C_3H_7(n)$ | H, $CO_2H$ |
| 2304 | $C_4H_9(n)$ | $C_4H_9(n)$ | O |
| 2305 | $C_4H_9(n)$ | $C_4H_9(n)$ | H, H |
| 2306 | $C_4H_9(n)$ | $C_4H_9(n)$ | H, $CH_3$ |
| 2307 | $C_4H_9(n)$ | $C_4H_9(n)$ | H, $CH_2OH$ |
| 2308 | $C_4H_9(n)$ | $C_4H_9(n)$ | H, $CO_2H$ |
| 2309 | (2-ethylphenyl) | $C_3H_7(n)$ | O |
| 2310 | (2-ethylphenyl) | $C_3H_7(n)$ | H, H |
| 2311 | (2-ethylphenyl) | $C_3H_7(n)$ | H, $CH_3$ |
| 2312 | (2-ethylphenyl) | $C_3H_7(n)$ | $CH_3$, $CH_3$ |
| 2313 | (2-ethylphenyl) | $C_3H_7(n)$ | H, $CH_2OH$ |
| 2314 | (2-ethylphenyl) | $C_3H_7(n)$ | H, $CO_2H$ |
| 2315 | (2-ethylphenyl) | $C_4H_9(n)$ | O |
| 2316 | (2-ethylphenyl) | $C_4H_9(n)$ | H, H |
| 2317 | (2-ethylphenyl) | $C_4H_9(n)$ | H, $CH_3$ |
| 2318 | (2-ethylphenyl) | $C_4H_9(n)$ | $CH_3$, $CH_3$ |
| 2319 | (2-ethylphenyl) | $C_4H_9(n)$ | H, $CH_2OH$ |
| 2320 | (2-ethylphenyl) | $C_4H_9(n)$ | H, $CO_2H$ |

TABLE LVI

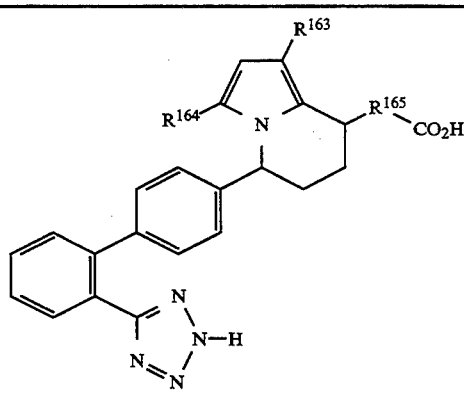

| EX. # | $R^{163}$ | $R^{164}$ | $R^{165}$ |
|---|---|---|---|
| 2321 | H | $C_3H_7(n)$ | $CH_2$ |
| 2322 | H | $C_3H_7(n)$ | $CH(C_2H_5)$ |
| 2323 | H | $C_3H_7(n)$ | $CH(CH_2C_6H_5)$ |
| 2324 | H | $C_3H_7(n)$ | $CH_2CH_2$ |
| 2325 | H | $C_3H_7(n)$ | $CH(C_2H_5)CH_2$ |
| 2326 | H | $C_3H_7(n)$ | $CH(CH_2C_6H_5)CH_2$ |
| 2327 | H | $C_4H_9(n)$ | $CH(C_2H_5)$ |
| 2328 | H | $C_4H_9(n)$ | $CH_2CH_2$ |
| 2329 | H | $C_4H_9(n)$ | $CH(C_2H_5)CH_2$ |
| 2330 | H | $C_4H_9(n)$ | $CH(CH_2C_6H_5)CH_2$ |
| 2331 | Cl | $C_3H_7(n)$ | $CH_2$ |
| 2332 | Cl | $C_3H_7(n)$ | $CH(C_2H_5)$ |
| 2333 | Cl | $C_3H_7(n)$ | $CH(CH_2C_6H_5)$ |
| 2334 | Cl | $C_3H_7(n)$ | $CH_2CH_2$ |
| 2335 | Cl | $C_3H_7(n)$ | $CH(C_2H_5)CH_2$ |
| 2336 | Cl | $C_3H_7(n)$ | $CH(CH_2C_6H_5)CH_2$ |
| 2337 | Cl | $C_4H_9(n)$ | $CH_2$ |
| 2338 | Cl | $C_4H_9(n)$ | $CH(C_2H_5)$ |
| 2339 | Cl | $C_4H_9(n)$ | $CH(CH_2C_6H_5)$ |
| 2340 | Cl | $C_4H_9(n)$ | $CH_2CH_2$ |
| 2341 | Cl | $C_4H_9(n)$ | $CH(C_2H_5)CH_2$ |
| 2342 | Cl | $C_4H_9(n)$ | $CH(CH_2C_6H_5)CH_2$ |
| 2343 | $C_2H_5$ | $C_3H_7(n)$ | $CH_2$ |
| 2344 | $C_2H_5$ | $C_3H_7(n)$ | $CH_2CH_2$ |
| 2345 | $C_2H_5$ | $C_4H_9(n)$ | $CH_2$ |
| 2346 | $C_2H_5$ | $C_4H_9(n)$ | $CH_2CH_2$ |
| 2347 | $C_4H_9(n)$ | $C_3H_7(n)$ | $CH_2$ |
| 2348 | $C_4H_9(n)$ | $C_3H_7(n)$ | $CH_2CH_2$ |
| 2349 | $C_4H_9(n)$ | $C_4H_9(n)$ | $CH_2$ |
| 2350 | $C_4H_9(n)$ | $C_4H_9(n)$ | $CH_2CH_2$ |
| 2351 | (2-ethylphenyl) | $C_3H_7(n)$ | $CH_2$ |
| 2352 | (2-ethylphenyl) | $C_3H_7(n)$ | $CH_2CH_2$ |
| 2353 | (2-ethylphenyl) | $C_4H_9(n)$ | $CH_2$ |
| 2354 | (2-ethylphenyl) | $C_4H_9(n)$ | $CH_2CH_2$ |

TABLE LVII

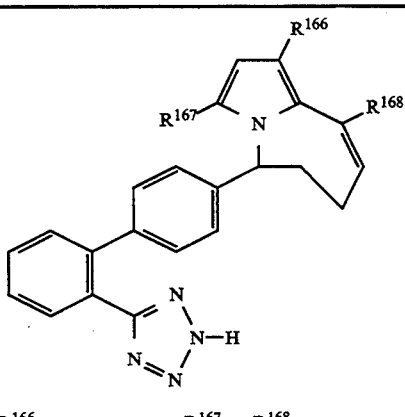

| EX. # | $R^{166}$ | $R^{167}$ | $R^{168}$ |
|---|---|---|---|
| 2355 | H | $C_3H_7(n)$ | H |
| 2356 | H | $C_3H_7(n)$ | $C_2H_5$ |
| 2357 | H | $C_3H_7(n)$ | $CH_2OH$ |
| 2358 | H | $C_3H_7(n)$ | $CO_2H$ |

TABLE LVII-continued

[Structure with $R^{166}$, $R^{167}$, $R^{168}$ substituents on pyrrole with biphenyl-tetrazole]

| EX. # | $R^{166}$ | $R^{167}$ | $R^{168}$ |
|---|---|---|---|
| 2359 | H | $C_3H_7(n)$ | $CH_2CO_2H$ |
| 2360 | H | $C_3H_7(n)$ | $CH_2CO_2C(CH_3)_3$ |
| 2361 | H | $C_3H_7(n)$ | $CH(C_2H_5)CO_2H$ |
| 2362 | H | $C_3H_7(n)$ | $CH(C_2H_5)CO_2C(CH_3)_3$ |
| 2363 | H | $C_3H_7(n)$ | phenyl |
| 2364 | H | $C_3H_7(n)$ | benzyl |
| 2365 | H | $C_4H_9(n)$ | $C_2H_5$ |
| 2366 | H | $C_4H_9(n)$ | $CH_2OH$ |
| 2367 | H | $C_4H_9(n)$ | $CO_2H$ |
| 2368 | H | $C_4H_9(n)$ | $CH_2CO_2H$ |
| 2369 | H | $C_4H_9(n)$ | $CH_2CO_2C(CH_3)_3$ |
| 2370 | H | $C_4H_9(n)$ | $CH(C_2H_5)CO_2H$ |
| 2371 | H | $C_4H_9(n)$ | $CH(C_2H_5)CO_2C(CH_3)_3$ |
| 2372 | H | $C_4H_9(n)$ | phenyl |
| 2373 | H | $C_4H_9(n)$ | benzyl |
| 2374 | Cl | $C_3H_7(n)$ | H |
| 2375 | Cl | $C_3H_7(n)$ | $C_2H_5$ |
| 2376 | Cl | $C_3H_7(n)$ | $CH_2OH$ |
| 2377 | Cl | $C_3H_7(n)$ | $CO_2H$ |
| 2378 | Cl | $C_3H_7(n)$ | $CH_2CO_2H$ |
| 2379 | Cl | $C_3H_7(n)$ | $CH_2CO_2C(CH_3)_3$ |
| 2380 | Cl | $C_3H_7(n)$ | $CH(C_2H_5)CO_2H$ |
| 2381 | Cl | $C_3H_7(n)$ | $CH(C_2H_5)CO_2C(CH_3)_3$ |
| 2382 | Cl | $C_4H_9(n)$ | H |
| 2383 | Cl | $C_4H_9(n)$ | $C_2H_5$ |
| 2384 | Cl | $C_4H_9(n)$ | $CH_2OH$ |
| 2385 | Cl | $C_4H_9(n)$ | $CO_2H$ |
| 2386 | Cl | $C_4H_9(n)$ | $CH_2CO_2H$ |
| 2387 | Cl | $C_4H_9(n)$ | $CH_2CO_2C(CH_3)_3$ |
| 2388 | Cl | $C_4H_9(n)$ | $CH(C_2H_5)CO_2H$ |
| 2389 | Cl | $C_4H_9(n)$ | $CH(C_2H_5)CO_2C(CH_3)_3$ |
| 2390 | ethyl | $C_3H_7(n)$ | H |
| 2391 | ethyl | $C_3H_7(n)$ | $C_2H_5$ |
| 2392 | ethyl | $C_3H_7(n)$ | $CH_2OH$ |
| 2393 | ethyl | $C_3H_7(n)$ | $CO_2H$ |
| 2394 | ethyl | $C_3H_7(n)$ | $CH_2CO_2H$ |
| 2395 | ethyl | $C_3H_7(n)$ | $CH_2CO_2C(CH_3)_3$ |
| 2396 | ethyl | $C_4H_9(n)$ | H |
| 2397 | ethyl | $C_4H_9(n)$ | $C_2H_5$ |
| 2398 | ethyl | $C_4H_9(n)$ | $CH_2OH$ |
| 2399 | ethyl | $C_4H_9(n)$ | $CO_2H$ |
| 2400 | ethyl | $C_4H_9(n)$ | $CH_2CO_2H$ |
| 2401 | ethyl | $C_4H_9(n)$ | $CH_2CO_2C(CH_3)_3$ |
| 2402 | n-butyl | $C_3H_7(n)$ | H |
| 2403 | n-butyl | $C_3H_7(n)$ | $C_2H_5$ |
| 2404 | n-butyl | $C_3H_7(n)$ | $CH_2OH$ |
| 2405 | n-butyl | $C_3H_7(n)$ | $CO_2H$ |
| 2406 | n-butyl | $C_3H_7(n)$ | $CH_2CO_2H$ |
| 2407 | n-butyl | $C_3H_7(n)$ | $CH_2CO_2C(CH_3)_3$ |
| 2408 | n-butyl | $C_4H_9(n)$ | $C_2H_5$ |
| 2409 | n-butyl | $C_4H_9(n)$ | H |
| 2410 | n-butyl | $C_4H_9(n)$ | $CH_2OH$ |
| 2411 | n-butyl | $C_4H_9(n)$ | $CO_2H$ |
| 2412 | n-butyl | $C_4H_9(n)$ | $CH_2CO_2H$ |
| 2413 | n-butyl | $C_4H_9(n)$ | $CH_2CO_2C(CH_3)_3$ |
| 2414 | (2-ethylphenyl) | $C_3H_7(n)$ | H |
| 2415 | (2-ethylphenyl) | $C_3H_7(n)$ | $C_2H_5$ |
| 2416 | (2-ethylphenyl) | $C_3H_7(n)$ | $CH_2OH$ |
| 2417 | (2-ethylphenyl) | $C_3H_7(n)$ | $CO_2H$ |
| 2418 | (2-ethylphenyl) | $C_3H_7(n)$ | $CH_2CO_2H$ |
| 2419 | (2-ethylphenyl) | $C_3H_7(n)$ | $CH_2CO_2C(CH_3)_3$ |
| 2420 | (2-ethylphenyl) | $C_4H_9(n)$ | H |
| 2421 | (2-ethylphenyl) | $C_4H_9(n)$ | $C_2H_5$ |
| 2422 | (2-ethylphenyl) | $C_4H_9(n)$ | $CH_2OH$ |
| 2423 | (2-ethylphenyl) | $C_4H_9(n)$ | $CO_2H$ |
| 2424 | (2-ethylphenyl) | $C_4H_9(n)$ | $CH_2CO_2H$ |
| 2425 | (2-ethylphenyl) | $C_4H_9(n)$ | $CH_2CO_2C(CH_3)_3$ |

TABLE LVIII

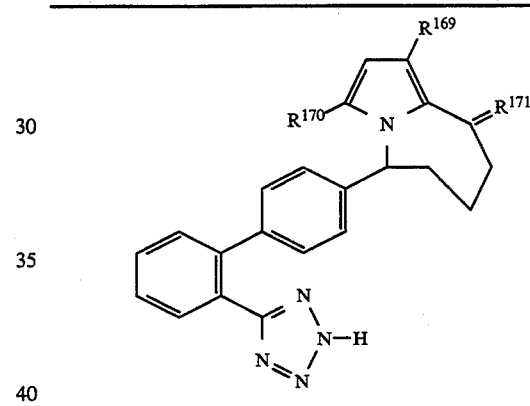

| EX. # | $R^{169}$ | $R^{170}$ | $R^{171}$ |
|---|---|---|---|
| 2426 | H | $C_3H_7(n)$ | O |
| 2427 | H | $C_3H_7(n)$ | S |
| 2428 | H | $C_3H_7(n)$ | $CHCO_2H$ |
| 2429 | H | $C_3H_7(n)$ | $CHCO_2C(CH_3)_3$ |
| 2430 | H | $C_3H_7(n)$ | NOH |
| 2431 | H | $C_4H_9(n)$ | O |
| 2432 | H | $C_4H_9(n)$ | S |
| 2433 | H | $C_4H_9(n)$ | $CHCO_2H$ |
| 2434 | H | $C_4H_9(n)$ | $CHCO_2C(CH_3)_3$ |
| 2435 | Cl | $C_3H_7(n)$ | O |
| 2436 | Cl | $C_3H_7(n)$ | S |
| 2437 | Cl | $C_3H_7(n)$ | $CHCO_2H$ |
| 2438 | Cl | $C_3H_7(n)$ | $CHCO_2C(CH_3)_3$ |
| 2439 | Cl | $C_3H_7(n)$ | NOH |
| 2440 | Cl | $C_4H_9(n)$ | O |
| 2441 | Cl | $C_4H_9(n)$ | S |
| 2442 | Cl | $C_4H_9(n)$ | $CHCO_2H$ |
| 2443 | Cl | $C_4H_9(n)$ | $CHCO_2C(CH_3)_3$ |
| 2444 | Cl | $C_4H_9(n)$ | NOH |
| 2445 | $C_2H_5$ | $C_3H_7(n)$ | O |
| 2446 | $C_2H_5$ | $C_3H_7(n)$ | S |
| 2447 | $C_2H_5$ | $C_3H_7(n)$ | $CHCO_2H$ |
| 2448 | $C_2H_5$ | $C_3H_7(n)$ | $CHCO_2C(CH_3)_3$ |
| 2449 | $C_2H_5$ | $C_3H_7(n)$ | NOH |
| 2450 | $C_2H_5$ | $C_4H_9(n)$ | O |
| 2451 | $C_2H_5$ | $C_4H_9(n)$ | S |
| 2452 | $C_2H_5$ | $C_4H_9(n)$ | $CHCO_2H$ |
| 2453 | $C_2H_5$ | $C_4H_9(n)$ | $CHCO_2C(CH_3)_3$ |
| 2454 | $C_2H_5$ | $C_4H_9(n)$ | NOH |
| 2455 | $C_4H_9(n)$ | $C_3H_7(n)$ | O |
| 2456 | $C_4H_9(n)$ | $C_3H_7(n)$ | S |
| 2457 | $C_4H_9(n)$ | $C_3H_7(n)$ | $CHCO_2H$ |
| 2458 | $C_4H_9(n)$ | $C_3H_7(n)$ | $CHCO_2C(CH_3)_3$ |

TABLE LVIII-continued

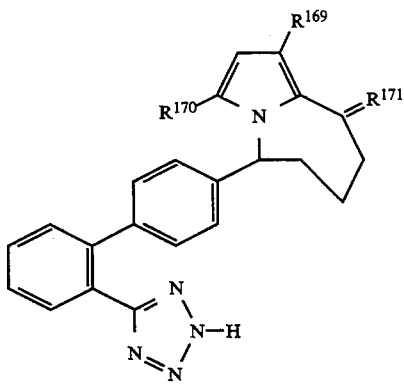

| EX. # | R169 | R170 | R171 |
|---|---|---|---|
| 2459 | C4H9(n) | C3H7(n) | NOH |
| 2460 | C4H9(n) | C4H9(n) | O |
| 2461 | C4H9(n) | C4H9(n) | S |
| 2462 | C4H9(n) | C4H9(n) | CHCO2H |
| 2463 | C4H9(n) | C4H9(n) | CHCO2C(CH3)3 |
| 2464 | C4H9(n) | C4H9(n) | NOH |
| 2465 | (2-ethylphenyl) | C3H7(n) | O |
| 2466 | (2-ethylphenyl) | C3H7(n) | S |
| 2467 | (2-ethylphenyl) | C3H7(n) | CHCO2H |
| 2468 | (2-ethylphenyl) | C3H7(n) | NOH |
| 2469 | (2-ethylphenyl) | C4H9(n) | O |
| 2470 | (2-ethylphenyl) | C4H9(n) | S |
| 2471 | (2-ethylphenyl) | C4H9(n) | CHCO2H |
| 2472 | (2-ethylphenyl) | C4H9(n) | NOH |

TABLE LIX

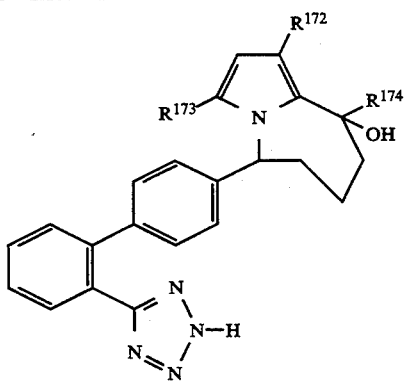

| EX. # | R172 | R173 | R174 |
|---|---|---|---|
| 2473 | H | C3H7(n) | C2H5 |
| 2474 | H | C3H7(n) | C3H7(n) |
| 2475 | H | C4H9(n) | C2H5 |
| 2476 | H | C4H9(n) | C3H7(n) |
| 2477 | Cl | C3H7(n) | C2H5 |
| 2478 | Cl | C3H7(n) | C3H7(n) |
| 2479 | Cl | C4H9(n) | C2H5 |
| 2480 | Cl | C4H9(n) | C3H7(n) |
| 2481 | C2H5 | C3H7(n) | C2H5 |
| 2482 | C2H5 | C3H7(n) | C3H7(n) |
| 2483 | C2H5 | C4H9(n) | C2H5 |
| 2484 | C2H5 | C4H9(n) | C3H7(n) |
| 2485 | C4H9(n) | C3H7(n) | C2H5 |
| 2486 | C4H9(n) | C4H9(n) | C2H5 |
| 2487 | (2-ethylphenyl) | C3H7(n) | C2H5 |
| 2488 | (2-ethylphenyl) | C4H9(n) | C2H5 |

TABLE LX

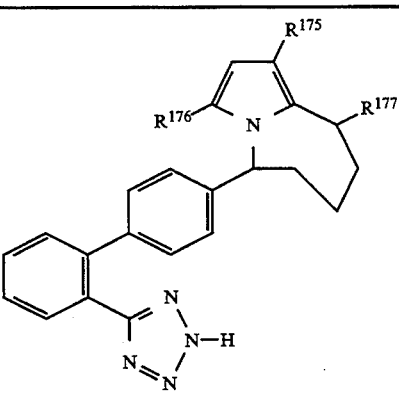

| EX. # | R175 | R176 | R177 |
|---|---|---|---|
| 2489 | H | C3H7(n) | H |
| 2490 | H | C3H7(n) | NH2 |
| 2491 | H | C3H7(n) | OH |
| 2492 | H | C3H7(n) | CH2OH |
| 2493 | H | C3H7(n) | CO2H |
| 2494 | H | C3H7(n) | CO2C(CH3)3 |
| 2495 | H | C3H7(n) | C2H5 |
| 2496 | H | C3H7(n) | C3H7(n) |
| 2497 | H | C3H7(n) | C6H5 |
| 2498 | H | C3H7(n) | C6H5CH2 |
| 2499 | H | C3H7(n) | (2-ethylphenyl) |
| 2500 | H | C3H7(n) | H |
| 2501 | H | C3H7(n) | NH2 |
| 2502 | H | C3H7(n) | OH |
| 2503 | H | C4H9(n) | CH2OH |
| 2504 | H | C4H9(n) | CO2H |
| 2505 | H | C4H9(n) | CO2C(CH3)3 |
| 2506 | H | C4H9(n) | C2H5 |
| 2507 | H | C4H9(n) | C3H7(n) |
| 2508 | H | C4H9(n) | C6H5 |
| 2509 | H | C4H9(n) | C6H5CH2 |
| 2510 | H | C4H9(n) | (2-ethylphenyl) |
| 2511 | Cl | C4H9(n) | H |
| 2512 | Cl | C4H9(n) | NH2 |
| 2513 | Cl | C3H7(n) | OH |
| 2514 | Cl | C3H7(n) | CH2OH |
| 2515 | Cl | C3H7(n) | CO2H |
| 2516 | Cl | C3H7(n) | CO2C(CH3)3 |
| 2517 | Cl | C3H7(n) | C2H5 |
| 2518 | Cl | C3H7(n) | C3H7(n) |
| 2519 | Cl | C3H7(n) | C6H5 |
| 2520 | Cl | C3H7(n) | C6H5CH2 |
| 2521 | Cl | C3H7(n) | (2-ethylphenyl) |
| 2522 | Cl | C4H9(n) | H |
| 2523 | Cl | C4H9(n) | NH2 |
| 2524 | Cl | C4H9(n) | OH |
| 2525 | Cl | C4H9(n) | CH2OH |
| 2526 | Cl | C4H9(n) | CO2H |
| 2527 | Cl | C4H9(n) | CO2C(CH3)3 |
| 2528 | Cl | C4H9(n) | C2H5 |
| 2529 | Cl | C4H9(n) | C3H7(n) |
| 2530 | Cl | C4H9(n) | C6H5 |
| 2531 | Cl | C4H9(n) | C6H5CH2 |
| 2532 | Cl | C4H9(n) | (2-ethylphenyl) |
| 2533 | C2H5 | C3H7(n) | H |
| 2534 | C2H5 | C3H7(n) | NH2 |
| 2535 | C2H5 | C3H7(n) | OH |
| 2536 | C2H5 | C3H7(n) | CH2OH |
| 2537 | C2H5 | C3H7(n) | CO2H |
| 2538 | C2H5 | C3H7(n) | CO2C(CH3)3 |
| 2539 | C2H5 | C3H7(n) | C2H5 |
| 2540 | C2H5 | C4H9(n) | H |
| 2541 | C2H5 | C4H9(n) | NH2 |
| 2542 | C2H5 | C4H9(n) | OH |
| 2543 | C2H5 | C4H9(n) | CH2OH |
| 2544 | C2H5 | C4H9(n) | CO2H |
| 2545 | C2H5 | C4H9(n) | CO2C(CH3)3 |
| 2546 | C2H5 | C4H9(n) | C2H5 |
| 2547 | C4H9(n) | C3H7(n) | H |
| 2548 | C4H9(n) | C3H7(n) | NH2 |
| 2549 | C4H9(n) | C3H7(n) | OH |
| 2550 | C4H9(n) | C3H7(n) | CH2OH |

TABLE LX-continued

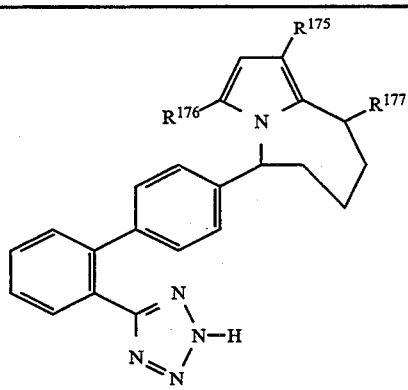

| EX. # | R175 | R176 | R177 |
|---|---|---|---|
| 2551 | C4H9 | C3H7(n) | CO2H |
| 2552 | C4H9 | C3H7(n) | CO2C(CH3)3 |
| 2553 | C4H9(n) | C3H7(n) | C2H5 |
| 2554 | C4H9(n) | C3H7(n) | C6H5CH2 |
| 2555 | C4H9(n) | C4H9(n) | H |
| 2556 | C4H9(n) | C4H9(n) | NH2 |
| 2557 | C4H9(n) | C4H9(n) | OH |
| 2558 | C4H9(n) | C4H9(n) | CH2OH |
| 2559 | C4H9 | C4H9(n) | CO2H |
| 2560 | C4H9 | C4H9(n) | CO2C(CH3)3 |
| 2561 | C4H9(n) | C4H9(n) | C2H5 |
| 2562 | (2-ethylphenyl) | C3H7(n) | H |
| 2563 | (2-ethylphenyl) | C3H7(n) | NH2 |
| 2564 | (2-ethylphenyl) | C3H7(n) | OH |
| 2565 | (2-ethylphenyl) | C3H7(n) | CH2OH |
| 2566 | (2-ethylphenyl) | C3H7(n) | CO2H |
| 2567 | (2-ethylphenyl) | C3H7(n) | CO2C(CH3)3 |
| 2568 | (2-ethylphenyl) | C3H7(n) | C2H5 |
| 2569 | (2-ethylphenyl) | C4H9(n) | H |
| 2570 | (2-ethylphenyl) | C4H9(n) | NH2 |
| 2571 | (2-ethylphenyl) | C4H9(n) | OH |
| 2572 | (2-ethylphenyl) | C4H9(n) | CH2OH |
| 2573 | (2-ethylphenyl) | C4H9(n) | CO2H |
| 2574 | (2-ethylphenyl) | C4H9(n) | CO2C(CH3)3 |
| 2575 | (2-ethylphenyl) | C4H9(n) | C2H5 |

TABLE LXI

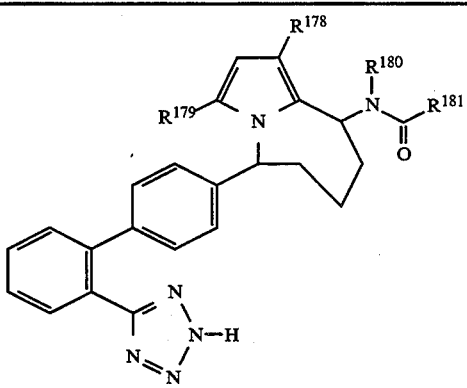

| EX. # | R178 | R179 | R180 | R181 |
|---|---|---|---|---|
| 2576 | H | C3H7(n) | H | CH3 |
| 2577 | H | C3H7(n) | CH3 | CH3 |
| 2578 | H | C3H7(n) | C6H5CH2 | CH3 |
| 2579 | H | C4H9(n) | H | CH3 |
| 2580 | H | C4H9(n) | CH3 | CH3 |
| 2581 | H | C4H9(n) | C6H5CH2 | CH3 |
| 2582 | Cl | C3H7(n) | H | CH3 |
| 2583 | Cl | C3H7(n) | CH3 | CH3 |
| 2584 | Cl | C3H7(n) | C6H5CH2 | CH3 |
| 2585 | Cl | C4H9(n) | H | CH3 |
| 2586 | Cl | C4H9(n) | CH3 | CH3 |
| 2587 | Cl | C4H9(n) | C6H5CH2 | CH3 |
| 2588 | C2H5 | C3H7(n) | H | CH3 |

TABLE LXI-continued

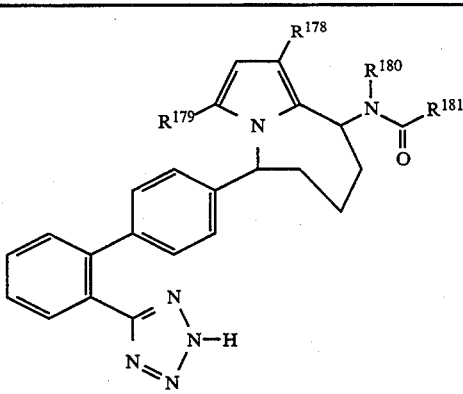

| EX. # | R178 | R179 | R180 | R181 |
|---|---|---|---|---|
| 2589 | C2H5 | C3H7(n) | CH3 | CH3 |
| 2590 | C2H5 | C4H9(n) | H | CH3 |
| 2591 | C2H5 | C4H9(n) | CH3 | CH3 |
| 2592 | C4H9(n) | C3H7(n) | H | CH3 |
| 2593 | C4H9(n) | C3H7(n) | CH3 | CH3 |
| 2594 | C4H9(n) | C4H9(n) | H | CH3 |
| 2595 | C4H9(n) | C4H9(n) | CH3 | CH3 |
| 2596 | (2-ethylphenyl) | C3H7(n) | H | CH3 |
| 2597 | (2-ethylphenyl) | C3H7(n) | CH3 | CH3 |
| 2598 | (2-ethylphenyl) | C4H9(n) | H | CH3 |
| 2599 | (2-ethylphenyl) | C4H9(n) | CH3 | CH3 |
| 2600 | H | C3H7(n) | H | C2H5 |
| 2601 | H | C3H7(n) | CH3 | C2H5 |
| 2602 | H | C4H9(n) | H | C2H5 |
| 2603 | H | C4H9(n) | CH3 | C2H5 |
| 2604 | Cl | C3H7(n) | H | C2H5 |
| 2605 | Cl | C3H7(n) | CH3 | C2H5 |
| 2606 | Cl | C4H9(n) | H | C2H5 |
| 2607 | Cl | C4H9(n) | CH3 | C2H5 |
| 2608 | C2H5 | C3H7(n) | H | C2H5 |
| 2609 | C2H5 | C3H7(n) | CH3 | C2H5 |
| 2610 | C2H5 | C4H9(n) | H | C2H5 |
| 2611 | C2H5 | C4H9(n) | CH3 | C2H5 |
| 2612 | (2-ethylphenyl) | C3H7(n) | H | C2H5 |
| 2613 | (2-ethylphenyl) | C4H9(n) | H | C2H5 |
| 2614 | H | C3H7(n) | H | C6H5 |
| 2615 | H | C3H7(n) | CH3 | C6H5 |
| 2616 | H | C4H9(n) | H | C6H5 |
| 2617 | H | C4H9(n) | CH3 | C6H5 |
| 2618 | Cl | C3H7(n) | H | C6H5 |
| 2619 | Cl | C3H7(n) | CH3 | C6H5 |
| 2620 | Cl | C4H9(n) | H | C6H5 |
| 2621 | Cl | C4H9(n) | CH3 | C6H5 |
| 2622 | C2H5 | C3H7(n) | H | C6H5 |
| 2623 | C2H5 | C3H7(n) | CH3 | C6H5 |
| 2624 | C2H5 | C4H9(n) | H | C6H5 |
| 2625 | C2H5 | C4H9(n) | CH3 | C6H5 |
| 2626 | C4H9(n) | C3H7(n) | H | C6H5 |
| 2627 | C4H9(n) | C3H7(n) | CH3 | C6H5 |
| 2628 | C4H9(n) | C4H9(n) | H | C6H5 |
| 2629 | C4H9(n) | C4H9(n) | CH3 | C6H5 |
| 2630 | C4H9(n) | C4H9(n) | H | CH2CH2CO2H |
| 2631 | C4H9(n) | C4H9(n) | CH3 | CH2CH2CO2H |
| 2632 | (2-ethylphenyl) | C3H7(n) | H | CH2CH2CO2H |
| 2633 | (2-ethylphenyl) | C3H7(n) | CH3 | CH2CH2CO2H |
| 2634 | (2-ethylphenyl) | C4H9(n) | H | CH2CH2CO2H |
| 2635 | (2-ethylphenyl) | C4H9(n) | CH3 | CH2CH2CO2H |

TABLE LXII

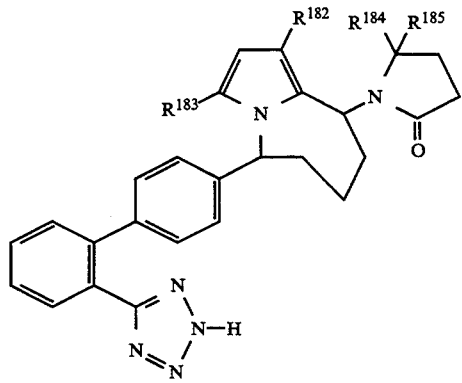

| EX. # | R¹⁸² | R¹⁸³ | R¹⁸⁴, R¹⁸⁵ |
|---|---|---|---|
| 2636 | H | $C_3H_7(n)$ | O |
| 2637 | H | $C_3H_7(n)$ | H, H |
| 2638 | H | $C_3H_7(n)$ | H, $CH_3$ |
| 2639 | H | $C_3H_7(n)$ | H, $C_2H_5$ |
| 2640 | H | $C_3H_7(n)$ | H, $CH_2OH$ |
| 2641 | H | $C_3H_7(n)$ | H, $CO_2H$ |
| 2642 | H | $C_4H_9(n)$ | O |
| 2643 | H | $C_4H_9(n)$ | H, H |
| 2644 | H | $C_4H_9(n)$ | H, $CH_3$ |
| 2645 | H | $C_4H_9(n)$ | H, $C_2H_5$ |
| 2646 | H | $C_4H_9(n)$ | H, $CH_2OH$ |
| 2647 | H | $C_4H_9(n)$ | H, $CO_2H$ |
| 2648 | Cl | $C_3H_7(n)$ | O |
| 2649 | Cl | $C_3H_7(n)$ | H, H |
| 2650 | Cl | $C_3H_7(n)$ | H, $CH_3$ |
| 2651 | Cl | $C_3H_7(n)$ | H, $C_2H_5$ |
| 2652 | Cl | $C_3H_7(n)$ | H, $CH_2OH$ |
| 2653 | Cl | $C_3H_7(n)$ | H, $CO_2H$ |
| 2654 | Cl | $C_4H_9(n)$ | O |
| 2655 | Cl | $C_4H_9(n)$ | H, H |
| 2656 | Cl | $C_4H_9(n)$ | H, $CH_3$ |
| 2657 | Cl | $C_4H_9(n)$ | H, $C_2H_5$ |
| 2658 | Cl | $C_4H_9(n)$ | H, $CH_2OH$ |
| 2659 | Cl | $C_4H_9(n)$ | H, $CO_2H$ |
| 2660 | $C_2H_5$ | $C_3H_7(n)$ | O |
| 2661 | $C_2H_5$ | $C_3H_7(n)$ | H, H |
| 2662 | $C_2H_5$ | $C_3H_7(n)$ | H, $CH_3$ |
| 2663 | $C_2H_5$ | $C_3H_7(n)$ | H, $C_2H_5$ |
| 2664 | $C_2H_5$ | $C_3H_7(n)$ | H, $CH_2OH$ |
| 2665 | $C_2H_5$ | $C_3H_7(n)$ | H, $CO_2H$ |
| 2666 | $C_2H_5$ | $C_4H_9(n)$ | O |
| 2667 | $C_2H_5$ | $C_4H_9(n)$ | H, H |
| 2668 | $C_2H_5$ | $C_4H_9(n)$ | H, $CH_3$ |
| 2669 | $C_2H_5$ | $C_4H_9(n)$ | H, $C_2H_5$ |
| 2670 | $C_2H_5$ | $C_4H_9(n)$ | H, $CH_2OH$ |
| 2671 | $C_2H_5$ | $C_4H_9(n)$ | H, $CO_2H$ |
| 2672 | $C_4H_9(n)$ | $C_3H_7(n)$ | O |
| 2673 | $C_4H_9(n)$ | $C_3H_7(n)$ | H, H |
| 2674 | $C_4H_9(n)$ | $C_3H_7(n)$ | H, $CH_3$ |
| 2675 | $C_4H_9(n)$ | $C_3H_7(n)$ | H, $CH_2OH$ |
| 2676 | $C_4H_9(n)$ | $C_3H_7(n)$ | H, $CO_2H$ |
| 2677 | $C_4H_9(n)$ | $C_4H_9(n)$ | O |
| 2678 | $C_4H_9(n)$ | $C_4H_9(n)$ | H, H |
| 2679 | $C_4H_9(n)$ | $C_4H_9(n)$ | H, $CH_3$ |
| 2680 | $C_4H_9(n)$ | $C_4H_9(n)$ | H, $CH_2OH$ |
| 2681 | $C_4H_9(n)$ | $C_4H_9(n)$ | H, $CO_2H$ |
| 2682 | (2-ethylphenyl) | $C_3H_7(n)$ | O |
| 2683 | (2-ethylphenyl) | $C_3H_7(n)$ | H, H |
| 2684 | (2-ethylphenyl) | $C_3H_7(n)$ | H, $CH_3$ |
| 2685 | (2-ethylphenyl) | $C_3H_7(n)$ | $CH_3$, $CH_3$ |
| 2686 | (2-ethylphenyl) | $C_3H_7(n)$ | H, $CH_2OH$ |
| 2687 | (2-ethylphenyl) | $C_3H_7(n)$ | H, $CO_2H$ |
| 2688 | (2-ethylphenyl) | $C_4H_9(n)$ | O |
| 2689 | (2-ethylphenyl) | $C_4H_9(n)$ | H, H |
| 2690 | (2-ethylphenyl) | $C_4H_9(n)$ | H, $CH_3$ |
| 2691 | (2-ethylphenyl) | $C_4H_9(n)$ | $CH_3$, $CH_3$ |
| 2692 | (2-ethylphenyl) | $C_4H_9(n)$ | H, $CH_2OH$ |
| 2693 | (2-ethylphenyl) | $C_4H_9(n)$ | H, $CO_2H$ |

TABLE LXIII

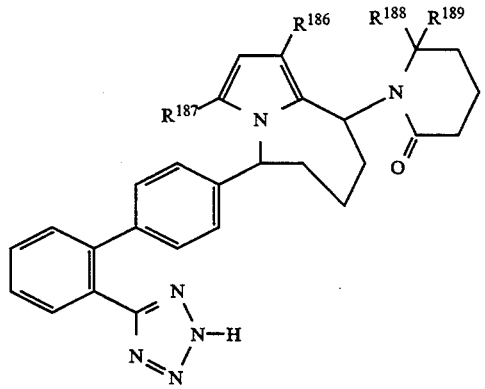

| EX. # | R¹⁸⁶ | R¹⁸⁷ | R¹⁸⁸, R¹⁸⁹ |
|---|---|---|---|
| 2694 | H | $C_3H_7(n)$ | O |
| 2695 | H | $C_3H_7(n)$ | H, H |
| 2696 | H | $C_3H_7(n)$ | H, $CH_3$ |
| 2697 | H | $C_3H_7(n)$ | H, $C_2H_5$ |
| 2698 | H | $C_3H_7(n)$ | H, $CH_2OH$ |
| 2699 | H | $C_3H_7(n)$ | H, $CO_2H$ |
| 2700 | H | $C_4H_9(n)$ | O |
| 2701 | H | $C_4H_9(n)$ | H, H |
| 2702 | H | $C_4H_9(n)$ | H, $CH_3$ |
| 2703 | H | $C_4H_9(n)$ | H, $C_2H_5$ |
| 2704 | H | $C_4H_9(n)$ | H, $CH_2OH$ |
| 2705 | H | $C_4H_9(n)$ | H, $CO_2H$ |
| 2706 | Cl | $C_3H_7(n)$ | O |
| 2707 | Cl | $C_3H_7(n)$ | H, H |
| 2708 | Cl | $C_3H_7(n)$ | H, $CH_3$ |
| 2709 | Cl | $C_3H_7(n)$ | $CH_3$, $CH_3$ |
| 2710 | Cl | $C_3H_7(n)$ | H, $CH_2OH$ |
| 2711 | Cl | $C_3H_7(n)$ | H, $CO_2H$ |
| 2712 | Cl | $C_4H_9(n)$ | O |
| 2713 | Cl | $C_4H_9(n)$ | H, H |
| 2714 | Cl | $C_4H_9(n)$ | H, $CH_3$ |
| 2715 | Cl | $C_4H_9(n)$ | H, $C_2H_5$ |
| 2716 | Cl | $C_4H_9(n)$ | H, $CH_2OH$ |
| 2717 | Cl | $C_4H_9(n)$ | H, $CO_2H$ |
| 2718 | $C_2H_5$ | $C_3H_7(n)$ | O |
| 2719 | $C_2H_5$ | $C_3H_7(n)$ | H, H |
| 2720 | $C_2H_5$ | $C_3H_7(n)$ | H, $CH_3$ |
| 2721 | $C_2H_5$ | $C_3H_7(n)$ | H, $C_2H_5$ |
| 2722 | $C_2H_5$ | $C_3H_7(n)$ | H, $CH_2OH$ |
| 2723 | $C_2H_5$ | $C_3H_7(n)$ | H, $CO_2H$ |
| 2724 | $C_2H_5$ | $C_4H_9(n)$ | O |
| 2725 | $C_2H_5$ | $C_4H_9(n)$ | H, H |
| 2726 | $C_2H_5$ | $C_4H_9(n)$ | H, $CH_3$ |
| 2727 | $C_2H_5$ | $C_4H_9(n)$ | H, $C_2H_5$ |
| 2728 | $C_2H_5$ | $C_4H_9(n)$ | H, $CH_2OH$ |
| 2729 | $C_2H_5$ | $C_4H_9(n)$ | H, $CO_2H$ |
| 2730 | $C_4H_9(n)$ | $C_3H_7(n)$ | O |
| 2731 | $C_4H_9(n)$ | $C_3H_7(n)$ | H, H |
| 2732 | $C_4H_9(n)$ | $C_3H_7(n)$ | H, $CH_3$ |
| 2733 | $C_4H_9(n)$ | $C_3H_7(n)$ | H, $CH_2OH$ |
| 2734 | $C_4H_9(n)$ | $C_3H_7(n)$ | H, $CO_2H$ |
| 2735 | $C_4H_9(n)$ | $C_4H_9(n)$ | O |
| 2736 | $C_4H_9(n)$ | $C_4H_9(n)$ | H, H |
| 2737 | $C_4H_9(n)$ | $C_4H_9(n)$ | H, $CH_3$ |
| 2738 | $C_4H_9(n)$ | $C_4H_9(n)$ | H, $CH_2OH$ |
| 2739 | $C_4H_9(n)$ | $C_4H_9(n)$ | H, $CO_2H$ |
| 2740 | (2-ethylphenyl) | $C_3H_7(n)$ | O |
| 2741 | (2-ethylphenyl) | $C_3H_7(n)$ | H, H |
| 2742 | (2-ethylphenyl) | $C_3H_7(n)$ | H, $CH_3$ |
| 2743 | (2-ethylphenyl) | $C_3H_7(n)$ | $CH_3$, $CH_3$ |
| 2744 | (2-ethylphenyl) | $C_3H_7(n)$ | H, $CH_2OH$ |
| 2745 | (2-ethylphenyl) | $C_3H_7(n)$ | H, $CO_2H$ |
| 2746 | (2-ethylphenyl) | $C_4H_9(n)$ | O |
| 2747 | (2-ethylphenyl) | $C_4H_9(n)$ | H, H |
| 2748 | (2-ethylphenyl) | $C_4H_9(n)$ | H, $CH_3$ |
| 2749 | (2-ethylphenyl) | $C_4H_9(n)$ | $CH_3$, $CH_3$ |
| 2750 | (2-ethylphenyl) | $C_4H_9(n)$ | H, $CH_2OH$ |
| 2751 | (2-ethylphenyl) | $C_4H_9(n)$ | H, $CO_2H$ |

TABLE LXIV

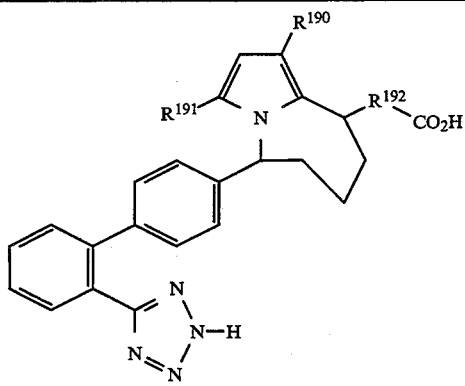

| EX. # | R¹⁹⁰ | R¹⁹¹ | R¹⁹² |
|---|---|---|---|
| 2752 | H | $C_3H_7(n)$ | $CH_2$ |
| 2753 | H | $C_3H_7(n)$ | $CH(C_2H_5)$ |
| 2754 | H | $C_3H_7(n)$ | $CH(CH_2C_6H_5)$ |
| 2755 | H | $C_3H_7(n)$ | $CH_2CH_2$ |
| 2756 | H | $C_3H_7(n)$ | $CH(C_2H_5)CH_2$ |
| 2757 | H | $C_3H_7(n)$ | $CH(CH_2C_6H_5)CH_2$ |
| 2758 | H | $C_4H_9(n)$ | $CH_2$ |
| 2759 | H | $C_4H_9(n)$ | $CH(C_2H_5)$ |
| 2760 | H | $C_4H_9(n)$ | $CH_2CH_2$ |
| 2761 | H | $C_4H_9(n)$ | $CH(C_2H_5)CH_2$ |
| 2762 | H | $C_4H_9(n)$ | $CH(CH_2C_6H_5)CH_2$ |
| 2763 | Cl | $C_3H_7(n)$ | $CH_2$ |
| 2764 | Cl | $C_3H_7(n)$ | $CH(C_2H_5)$ |
| 2765 | Cl | $C_3H_7(n)$ | $CH(CH_2C_6H_5)$ |
| 2766 | Cl | $C_3H_7(n)$ | $CH_2CH_2$ |
| 2767 | Cl | $C_3H_7(n)$ | $CH(C_2H_5)CH_2$ |
| 2768 | Cl | $C_3H_7(n)$ | $CH(CH_2C_6H_5)CH_2$ |
| 2769 | Cl | $C_4H_9(n)$ | $CH_2$ |
| 2770 | Cl | $C_4H_9(n)$ | $CH(C_2H_5)$ |
| 2771 | Cl | $C_4H_9(n)$ | $CH(CH_2C_6H_5)$ |
| 2772 | Cl | $C_4H_9(n)$ | $CH_2CH_2$ |
| 2773 | Cl | $C_4H_9(n)$ | $CH(C_2H_5)CH_2$ |
| 2774 | Cl | $C_4H_9(n)$ | $CH(CH_2C_6H_5)CH_2$ |
| 2775 | $C_2H_5$ | $C_3H_7(n)$ | $CH_2$ |
| 2776 | $C_2H_5$ | $C_3H_7(n)$ | $CH_2CH_2$ |
| 2777 | $C_2H_5$ | $C_4H_9(n)$ | $CH_2$ |
| 2778 | $C_2H_5$ | $C_4H_9(n)$ | $CH_2CH_2$ |
| 2779 | $C_4H_9(n)$ | $C_3H_7(n)$ | $CH_2$ |
| 2780 | $C_4H_9(n)$ | $C_3H_7(n)$ | $CH_2CH_2$ |
| 2781 | $C_4H_9(n)$ | $C_4H_9(n)$ | $CH_2$ |
| 2782 | $C_4H_9(n)$ | $C_4H_9(n)$ | $CH_2CH_2$ |
| 2783 | (2-ethylphenyl) | $C_3H_7(n)$ | $CH_2$ |
| 2784 | (2-ethylphenyl) | $C_3H_7(n)$ | $CH_2CH_2$ |
| 2785 | (2-ethylphenyl) | $C_4H_9(n)$ | $CH_2$ |
| 2786 | (2-ethylphenyl) | $C_4H_9(n)$ | $CH_2CH_2$ |

TABLE LXV

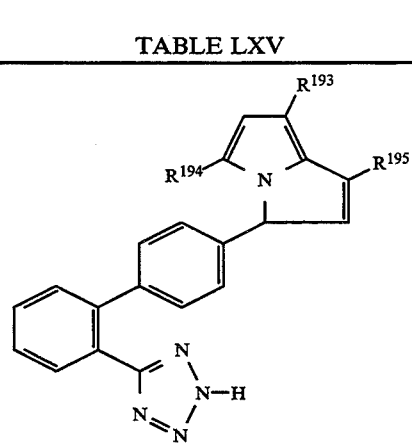

| EX. # | R¹⁹³ | R¹⁹⁴ | R¹⁹⁵ |
|---|---|---|---|
| 2787 | H | $C_3H_7(n)$ | H |
| 2788 | H | $C_3H_7(n)$ | $C_2H_5$ |
| 2789 | H | $C_3H_7(n)$ | $CH_2OH$ |

TABLE LXV-continued

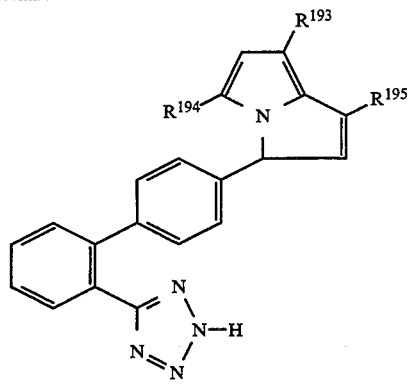

| EX. # | R¹⁹³ | R¹⁹⁴ | R¹⁹⁵ |
|---|---|---|---|
| 2790 | H | $C_3H_7(n)$ | $CO_2H$ |
| 2791 | H | $C_3H_7(n)$ | $CH_2CO_2H$ |
| 2792 | H | $C_3H_7(n)$ | $CH_2CO_2C(CH_3)_3$ |
| 2793 | H | $C_3H_7(n)$ | $CH(C_2H_5)CO_2H$ |
| 2794 | H | $C_3H_7(n)$ | $CH(C_2H_5)CO_2C(CH_3)_3$ |
| 2795 | H | $C_3H_7(n)$ | phenyl |
| 2796 | H | $C_3H_7(n)$ | benzyl |
| 2797 | H | $C_4H_9(n)$ | H |
| 2798 | H | $C_4H_9(n)$ | $C_2H_5$ |
| 2799 | H | $C_4H_9(n)$ | $CH_2OH$ |
| 2800 | H | $C_4H_9(n)$ | $CO_2H$ |
| 2801 | H | $C_4H_9(n)$ | $CH_2CO_2H$ |
| 2802 | H | $C_4H_9(n)$ | $CH_2CO_2C(CH_3)_3$ |
| 2803 | H | $C_4H_9(n)$ | $CH(C_2H_5)CO_2H$ |
| 2804 | H | $C_4H_9(n)$ | $CH(C_2H_5)CO_2C(CH_3)_3$ |
| 2805 | H | $C_4H_9(n)$ | phenyl |
| 2806 | H | $C_4H_9(n)$ | benzyl |
| 2807 | Cl | $C_3H_7(n)$ | H |
| 2808 | Cl | $C_3H_7(n)$ | $C_2H_5$ |
| 2809 | Cl | $C_3H_7(n)$ | $CH_2OH$ |
| 2810 | Cl | $C_3H_7(n)$ | $CO_2H$ |
| 2811 | Cl | $C_3H_7(n)$ | $CH_2CO_2H$ |
| 2812 | Cl | $C_3H_7(n)$ | $CH_2CO_2C(CH_3)_3$ |
| 2813 | Cl | $C_3H_7(n)$ | $CH(C_2H_5)CO_2H$ |
| 2814 | Cl | $C_3H_7(n)$ | $CH(C_2H_5)CO_2C(CH_3)_3$ |
| 2815 | Cl | $C_4H_9(n)$ | H |
| 2816 | Cl | $C_4H_9(n)$ | $C_2H_5$ |
| 2817 | Cl | $C_4H_9(n)$ | $CH_2OH$ |
| 2818 | Cl | $C_4H_9(n)$ | $CO_2H$ |
| 2819 | Cl | $C_4H_9(n)$ | $CH_2CO_2H$ |
| 2820 | Cl | $C_4H_9(n)$ | $CH_2CO_2C(CH_3)_3$ |
| 2821 | Cl | $C_4H_9(n)$ | $CH(C_2H_5)CO_2H$ |
| 2822 | Cl | $C_4H_9(n)$ | $CH(C_2H_5)CO_2C(CH_3)_3$ |
| 2823 | ethyl | $C_3H_7(n)$ | H |
| 2824 | ethyl | $C_3H_7(n)$ | $C_2H_5$ |
| 2825 | ethyl | $C_3H_7(n)$ | $CH_2OH$ |
| 2826 | ethyl | $C_3H_7(n)$ | $CO_2H$ |
| 2827 | ethyl | $C_3H_7(n)$ | $CH_2CO_2H$ |
| 2828 | ethyl | $C_3H_7(n)$ | $CH_2CO_2C(CH_3)_3$ |
| 2829 | ethyl | $C_4H_9(n)$ | H |
| 2830 | ethyl | $C_4H_9(n)$ | $C_2H_5$ |
| 2831 | ethyl | $C_4H_9(n)$ | $CH_2OH$ |
| 2832 | ethyl | $C_4H_9(n)$ | $CO_2H$ |
| 2833 | ethyl | $C_4H_9(n)$ | $CH_2CO_2H$ |
| 2834 | ethyl | $C_4H_9(n)$ | $CH_2CO_2C(CH_3)_3$ |
| 2835 | n-butyl | $C_3H_7(n)$ | H |
| 2836 | n-butyl | $C_3H_7(n)$ | $C_2H_5$ |
| 2837 | n-butyl | $C_3H_7(n)$ | $CH_2OH$ |
| 2838 | n-butyl | $C_3H_7(n)$ | $CO_2H$ |
| 2839 | n-butyl | $C_3H_7(n)$ | $CH_2CO_2H$ |
| 2840 | n-butyl | $C_3H_7(n)$ | $CH_2CO_2C(CH_3)_3$ |
| 2841 | n-butyl | $C_4H_9(n)$ | $C_2H_5$ |
| 2842 | n-butyl | $C_4H_9(n)$ | H |
| 2843 | n-butyl | $C_4H_9(n)$ | $CH_2OH$ |
| 2844 | n-butyl | $C_4H_9(n)$ | $CO_2H$ |
| 2845 | n-butyl | $C_4H_9(n)$ | $CH_2CO_2H$ |
| 2846 | n-butyl | $C_4H_9(n)$ | $CH_2CO_2C(CH_3)_3$ |
| 2847 | (2-ethylphenyl) | $C_3H_7(n)$ | H |
| 2848 | (2-ethylphenyl) | $C_3H_7(n)$ | $C_2H_5$ |
| 2849 | (2-ethylphenyl) | $C_3H_7(n)$ | $CH_2OH$ |
| 2850 | (2-ethylphenyl) | $C_3H_7(n)$ | $CO_2H$ |
| 2851 | (2-ethylphenyl) | $C_3H_7(n)$ | $CH_2CO_2H$ |

TABLE LXV-continued

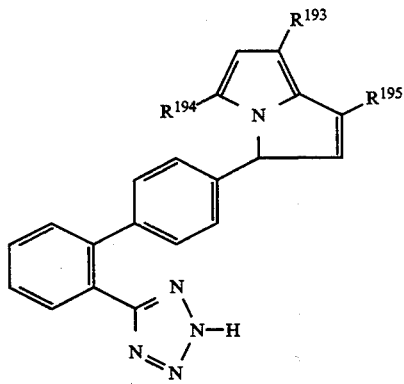

| EX. # | R193 | R194 | R195 |
|---|---|---|---|
| 2852 | (2-ethylphenyl) | $C_3H_7(n)$ | $CH_2CO_2C(CH_3)_3$ |
| 2853 | (2-ethylphenyl) | $C_4H_9(n)$ | H |
| 2854 | (2-ethylphenyl) | $C_4H_9(n)$ | $C_2H_5$ |
| 2855 | (2-ethylphenyl) | $C_4H_9(n)$ | $CH_2OH$ |
| 2856 | (2-ethylphenyl) | $C_4H_9(n)$ | $CO_2H$ |
| 2857 | (2-ethylphenyl) | $C_4H_9(n)$ | $CH_2CO_2H$ |
| 2858 | (2-ethylphenyl) | $C_4H_9(n)$ | $CH_2CO_2C(CH_3)_3$ |

TABLE LXVI

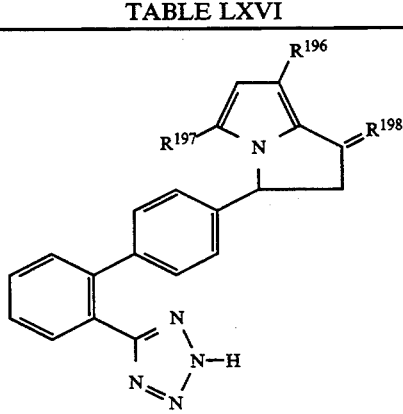

| EX. # | R196 | R197 | R198 |
|---|---|---|---|
| 2859 | H | $C_3H_7(n)$ | O |
| 2860 | H | $C_3H_7(n)$ | S |
| 2861 | H | $C_3H_7(n)$ | $CHCO_2H$ |
| 2862 | H | $C_3H_7(n)$ | $CHCO_2C(CH_3)_3$ |
| 2863 | H | $C_3H_7(n)$ | NOH |
| 2864 | H | $C_4H_9(n)$ | O |
| 2865 | H | $C_4H_9(n)$ | S |
| 2866 | H | $C_4H_9(n)$ | $CHCO_2H$ |
| 2867 | H | $C_4H_9(n)$ | $CHCO_2C(CH_3)_3$ |
| 2868 | Cl | $C_3H_7(n)$ | O |
| 2869 | Cl | $C_3H_7(n)$ | S |
| 2870 | Cl | $C_3H_7(n)$ | $CHCO_2H$ |
| 2871 | Cl | $C_3H_7(n)$ | $CHCO_2C(CH_3)_3$ |
| 2872 | Cl | $C_3H_7(n)$ | NOH |
| 2873 | Cl | $C_4H_9(n)$ | O |
| 2874 | Cl | $C_4H_9(n)$ | S |
| 2875 | Cl | $C_4H_9(n)$ | $CHCO_2H$ |
| 2876 | Cl | $C_4H_9(n)$ | $CHCO_2C(CH_3)_3$ |
| 2877 | Cl | $C_4H_9(n)$ | NOH |
| 2878 | $C_2H_5$ | $C_3H_7(n)$ | O |
| 2879 | $C_2H_5$ | $C_3H_7(n)$ | S |
| 2880 | $C_2H_5$ | $C_3H_7(n)$ | $CHCO_2H$ |
| 2881 | $C_2H_5$ | $C_3H_7(n)$ | $CHCO_2C(CH_3)_3$ |
| 2992 | $C_2H_5$ | $C_3H_7(n)$ | NOH |
| 2883 | $C_2H_5$ | $C_4H_9(n)$ | O |
| 2884 | $C_2H_5$ | $C_4H_9(n)$ | S |
| 2885 | $C_2H_5$ | $C_4H_9(n)$ | $CHCO_2H$ |
| 2886 | $C_2H_5$ | $C_4H_9(n)$ | $CHCO_2C(CH_3)_3$ |
| 2887 | $C_2H_5$ | $C_4H_9(n)$ | NOH |
| 2888 | $C_4H_9(n)$ | $C_3H_7(n)$ | O |
| 2889 | $C_4H_9(n)$ | $C_3H_7(n)$ | S |

TABLE LXVI-continued

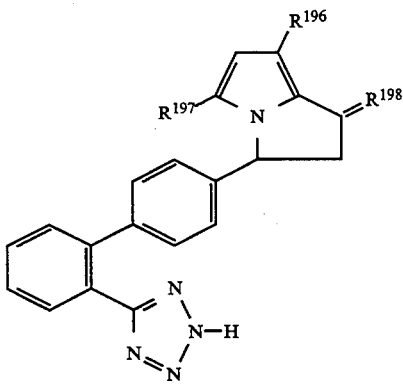

| EX. # | R196 | R197 | R198 |
|---|---|---|---|
| 2890 | $C_4H_9(n)$ | $C_3H_7(n)$ | $CHCO_2H$ |
| 2891 | $C_4H_9(n)$ | $C_3H_7(n)$ | $CHCO_2C(CH_3)_3$ |
| 2892 | $C_4H_9(n)$ | $C_3H_7(n)$ | NOH |
| 2893 | $C_4H_9(n)$ | $C_4H_9(n)$ | O |
| 2894 | $C_4H_9(n)$ | $C_4H_9(n)$ | S |
| 2895 | $C_4H_9(n)$ | $C_4H_9(n)$ | $CHCO_2H$ |
| 2896 | $C_4H_9(n)$ | $C_4H_9(n)$ | $CHCO_2C(CH_3)_3$ |
| 2897 | $C_4H_9(n)$ | $C_4H_9(n)$ | NOH |
| 2898 | (2-ethylphenyl) | $C_3H_7(n)$ | O |
| 2899 | (2-ethylphenyl) | $C_3H_7(n)$ | S |
| 2900 | (2-ethylphenyl) | $C_3H_7(n)$ | $CHCO_2S$ |
| 2901 | (2-ethylphenyl) | $C_3H_7(n)$ | NOH |
| 2902 | (2-ethylphenyl) | $C_4H_9(n)$ | O |
| 2903 | (2-ethylphenyl) | $C_4H_9(n)$ | S |
| 2904 | (2-ethylphenyl) | $C_4H_9(n)$ | $CHCO_2H$ |
| 2905 | (2-ethylphenyl) | $C_4H_9(n)$ | NOH |

TABLE LXVII

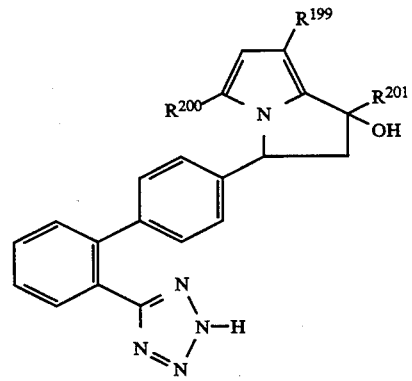

| EX. # | R199 | R200 | R201 |
|---|---|---|---|
| 2906 | H | $C_3H_7(n)$ | $C_2H_5$ |
| 2907 | H | $C_3H_7(n)$ | $C_3H_7(n)$ |
| 2908 | H | $C_4H_9(n)$ | $C_2H_5$ |
| 2909 | H | $C_4H_9(n)$ | $C_3H_7(n)$ |
| 2910 | Cl | $C_3H_7(n)$ | $C_2H_5$ |
| 2911 | Cl | $C_3H_7(n)$ | $C_3H_7(n)$ |
| 2912 | Cl | $C_4H_9(n)$ | $C_2H_5$ |
| 2913 | Cl | $C_4H_9(n)$ | $C_3H_7(n)$ |
| 2914 | $C_2H_5$ | $C_3H_7(n)$ | $C_2H_5$ |
| 2915 | $C_2H_5$ | $C_3H_7(n)$ | $C_3H_7(n)$ |
| 2916 | $C_2H_5$ | $C_4H_9(n)$ | $C_2H_5$ |
| 2917 | $C_2H_5$ | $C_4H_9(n)$ | $C_3H_7(n)$ |
| 2918 | $C_4H_9(n)$ | $C_3H_7(n)$ | $C_2H_5$ |
| 2919 | $C_4H_9(n)$ | $C_4H_9(n)$ | $C_2H_5$ |
| 2920 | (2-ethylphenyl) | $C_3H_7(n)$ | $C_2H_5$ |
| 2921 | (2-ethylphenyl) | $C_4H_9(n)$ | $C_2H_5$ |

TABLE LXVIII

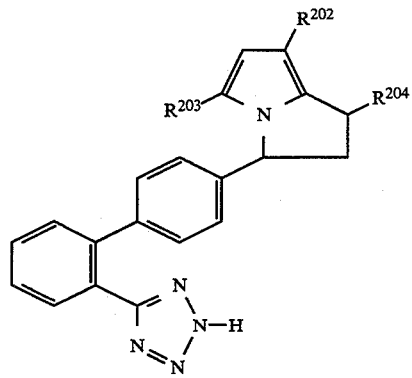

| EX. # | $R^{202}$ | $R^{203}$ | $R^{204}$ |
|---|---|---|---|
| 2922 | H | $C_3H_7(n)$ | H |
| 2923 | H | $C_3H_7(n)$ | $NH_2$ |
| 2924 | H | $C_3H_7(n)$ | OH |
| 2925 | H | $C_3H_7(n)$ | $CH_2OH$ |
| 2926 | H | $C_3H_7(n)$ | $CO_2H$ |
| 2927 | H | $C_3H_7(n)$ | $CO_2C(CH_3)_3$ |
| 2928 | H | $C_3H_7(n)$ | $C_2H_5$ |
| 2929 | H | $C_3H_7(n)$ | $C_3H_7(n)$ |
| 2930 | H | $C_3H_7(n)$ | $C_6H_5$ |
| 2931 | H | $C_3H_7(n)$ | $C_6H_5CH_2$ |
| 2932 | H | $C_3H_7(n)$ | (2-ethylphenyl) |
| 2933 | H | $C_3H_7(n)$ | H |
| 2934 | H | $C_3H_7(n)$ | $NH_2$ |
| 2935 | H | $C_3H_7(n)$ | OH |
| 2936 | H | $C_4H_9(n)$ | $CH_2OH$ |
| 2937 | H | $C_4H_9(n)$ | $CO_2H$ |
| 2938 | H | $C_4H_9(n)$ | $CO_2C(CH_3)_3$ |
| 2939 | H | $C_4H_9(n)$ | $C_2H_5$ |
| 2940 | H | $C_4H_9(n)$ | $C_3H_7(n)$ |
| 2941 | H | $C_4H_9(n)$ | $C_6H_5$ |
| 2942 | H | $C_4H_9(n)$ | $C_6H_5CH_2$ |
| 2943 | H | $C_4H_9(n)$ | (2-ethylphenyl) |
| 2944 | Cl | $C_4H_9(n)$ | H |
| 2945 | Cl | $C_4H_9(n)$ | $NH_2$ |
| 2946 | Cl | $C_3H_7(n)$ | OH |
| 2947 | Cl | $C_3H_7(n)$ | $CH_2OH$ |
| 2948 | Cl | $C_3H_7(n)$ | $CO_2H$ |
| 2949 | Cl | $C_3H_7(n)$ | $CO_2C(CH_3)_3$ |
| 2950 | Cl | $C_3H_7(n)$ | $C_2H_5$ |
| 2951 | Cl | $C_3H_7(n)$ | $C_3H_7(n)$ |
| 2952 | Cl | $C_3H_7(n)$ | $C_6H_5$ |
| 2953 | Cl | $C_3H_7(n)$ | $C_6H_5CH_2$ |
| 2954 | Cl | $C_3H_7(n)$ | (2-ethylphenyl) |
| 2955 | Cl | $C_4H_9(n)$ | H |
| 2956 | Cl | $C_4H_9(n)$ | $NH_2$ |
| 2957 | Cl | $C_4H_9(n)$ | OH |
| 2958 | Cl | $C_4H_9(n)$ | $CH_2OH$ |
| 2959 | Cl | $C_4H_9(n)$ | $CO_2H$ |
| 2960 | Cl | $C_4H_9(n)$ | $CO_2C(CH_3)_3$ |
| 2961 | Cl | $C_4H_9(n)$ | $C_2H_5$ |
| 2962 | Cl | $C_4H_9(n)$ | $C_3H_7(n)$ |
| 2963 | Cl | $C_4H_9(n)$ | $C_6H_5$ |
| 2964 | Cl | $C_4H_9(n)$ | $C_6H_5CH_2$ |
| 2965 | Cl | $C_4H_9(n)$ | (2-ethylphenyl) |
| 2966 | $C_2H_5$ | $C_3H_7(n)$ | H |
| 2967 | $C_2H_5$ | $C_3H_7(n)$ | $NH_2$ |
| 2968 | $C_2H_5$ | $C_3H_7(n)$ | OH |
| 2969 | $C_2H_5$ | $C_3H_7(n)$ | $CH_2OH$ |
| 2970 | $C_2H_5$ | $C_3H_7(n)$ | $CO_2H$ |
| 2971 | $C_2H_5$ | $C_3H_7(n)$ | $CO_2C(CH_3)_3$ |
| 2972 | $C_2H_5$ | $C_3H_7(n)$ | $C_2H_5$ |
| 2973 | $C_2H_5$ | $C_4H_9(n)$ | H |
| 2974 | $C_2H_5$ | $C_4H_9(n)$ | $NH_2$ |
| 2975 | $C_2H_5$ | $C_4H_9(n)$ | OH |
| 2976 | $C_2H_5$ | $C_4H_9(n)$ | $CH_2OH$ |
| 2977 | $C_2H_5$ | $C_4H_9(n)$ | $CO_2H$ |
| 2978 | $C_2H_5$ | $C_4H_9(n)$ | $CO_2C(CH_3)_3$ |
| 2979 | $C_2H_5$ | $C_4H_9(n)$ | $C_2H_5$ |
| 2980 | $C_4H_9(n)$ | $C_3H_7(n)$ | H |
| 2981 | $C_4H_9(n)$ | $C_3H_7(n)$ | $NH_2$ |
| 2982 | $C_4H_9(n)$ | $C_3H_7(n)$ | OH |
| 2983 | $C_4H_9(n)$ | $C_3H_7(n)$ | $CH_2OH$ |
| 2984 | $C_4H_9$ | $C_3H_7(n)$ | $CO_2H$ |
| 2985 | $C_4H_9$ | $C_3H_7(n)$ | $CO_2C(CH_3)_3$ |
| 2986 | $C_4H_9(n)$ | $C_3H_7(n)$ | $C_2H_5$ |
| 2987 | $C_4H_9(n)$ | $C_3H_7(n)$ | $C_6H_5CH_2$ |
| 2988 | $C_4H_9(n)$ | $C_4H_9(n)$ | H |
| 2989 | $C_4H_9(n)$ | $C_4H_9(n)$ | $NH_2$ |
| 2990 | $C_4H_9(n)$ | $C_4H_9(n)$ | OH |
| 2991 | $C_4H_9(n)$ | $C_4H_9(n)$ | $CH_2OH$ |
| 2992 | $C_4H_9$ | $C_4H_9(n)$ | $CO_2H$ |
| 2993 | $C_4H_9$ | $C_4H_9(n)$ | $CO_2C(CH_3)_3$ |
| 2994 | $C_4H_9(n)$ | $C_4H_9(n)$ | $C_2H_5$ |
| 2995 | (2-ethylphenyl) | $C_3H_7(n)$ | H |
| 2996 | (2-ethylphenyl) | $C_3H_7(n)$ | $NH_2$ |
| 2997 | (2-ethylphenyl) | $C_3H_7(n)$ | OH |
| 2998 | (2-ethylphenyl) | $C_3H_7(n)$ | $CH_2OH$ |
| 2999 | (2-ethylphenyl) | $C_3H_7(n)$ | $CO_2H$ |
| 3000 | (2-ethylphenyl) | $C_3H_7(n)$ | $CO_2C(CH_3)_3$ |
| 3001 | (2-ethylphenyl) | $C_3H_7(n)$ | $C_2H_5$ |
| 3002 | (2-ethylphenyl) | $C_4H_9(n)$ | H |
| 3003 | (2-ethylphenyl) | $C_4H_9(n)$ | $NH_2$ |
| 3004 | (2-ethylphenyl) | $C_4H_9(n)$ | OH |
| 3005 | (2-ethylphenyl) | $C_4H_9(n)$ | $CH_2OH$ |
| 3006 | (2-ethylphenyl) | $C_4H_9(n)$ | $CO_2H$ |
| 3007 | (2-ethylphenyl) | $C_4H_9(n)$ | $CO_2C(CH_3)_3$ |
| 3008 | (2-ethylphenyl) | $C_4H_9(n)$ | $C_2H_5$ |

TABLE LXIX

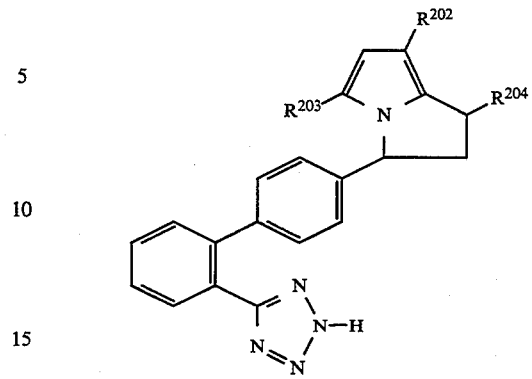

| EX. # | $R^{205}$ | $R^{206}$ | $R^{207}$ | $R^{208}$ |
|---|---|---|---|---|
| 3009 | H | $C_3H_7(n)$ | H | $CH_3$ |
| 3010 | H | $C_3H_7(n)$ | $CH_3$ | $CH_3$ |
| 3011 | H | $C_3H_7(n)$ | $C_6H_5CH_2$ | $CH_3$ |
| 3012 | H | $C_4H_9(n)$ | H | $CH_3$ |
| 3013 | H | $C_4H_9(n)$ | $CH_3$ | $CH_3$ |
| 3014 | H | $C_4H_9(n)$ | $C_6H_5CH_2$ | $CH_3$ |
| 3015 | Cl | $C_3H_7(n)$ | H | $CH_3$ |
| 3016 | Cl | $C_3H_7(n)$ | $CH_3$ | $CH_3$ |
| 3017 | Cl | $C_3H_7(n)$ | $C_6H_5CH_2$ | $CH_3$ |
| 3018 | Cl | $C_4H_9(n)$ | H | $CH_3$ |
| 3019 | Cl | $C_4H_9(n)$ | $CH_3$ | $CH_3$ |
| 3020 | Cl | $C_4H_9(n)$ | $C_6H_5CH_2$ | $CH_3$ |
| 3021 | $C_2H_5$ | $C_3H_7(n)$ | H | $CH_3$ |

TABLE LXIX-continued

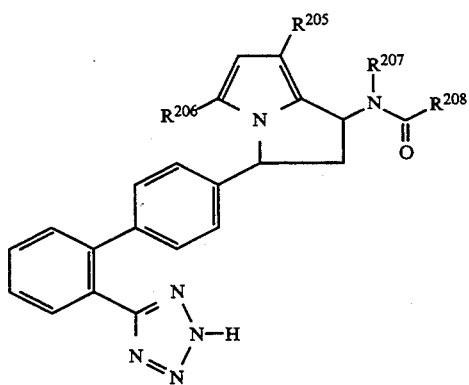

| EX. # | $R^{205}$ | $R^{206}$ | $R^{207}$ | $R^{208}$ |
|---|---|---|---|---|
| 3022 | $C_2H_5$ | $C_3H_7(n)$ | $CH_3$ | $CH_3$ |
| 3023 | $C_2H_5$ | $C_4H_9(n)$ | H | $CH_3$ |
| 3024 | $C_2H_5$ | $C_4H_9(n)$ | $CH_3$ | $CH_3$ |
| 3025 | $C_4H_9(n)$ | $C_3H_7(n)$ | H | $CH_3$ |
| 3026 | $C_4H_9(n)$ | $C_3H_7(n)$ | $CH_3$ | $CH_3$ |
| 3027 | $C_4H_9(n)$ | $C_4H_9(n)$ | H | $CH_3$ |
| 3028 | $C_4H_9(n)$ | $C_4H_9(n)$ | $CH_3$ | $CH_3$ |
| 3029 | (2-ethylphenyl) | $C_3H_7(n)$ | H | $CH_3$ |
| 3030 | (2-ethylphenyl) | $C_3H_7(n)$ | $CH_3$ | $CH_3$ |
| 3031 | (2-ethylphenyl) | $C_4H_9(n)$ | H | $CH_3$ |
| 3032 | (2-ethylphenyl) | $C_4H_9(n)$ | $CH_3$ | $CH_3$ |
| 3033 | H | $C_3H_7(n)$ | H | $C_2H_5$ |
| 3034 | H | $C_3H_7(n)$ | $CH_3$ | $C_2H_5$ |
| 3035 | H | $C_4H_9(n)$ | H | $C_2H_5$ |
| 3036 | H | $C_4H_9(n)$ | $CH_3$ | $C_2H_5$ |
| 3037 | Cl | $C_3H_7(n)$ | H | $C_2H_5$ |
| 3038 | Cl | $C_3H_7(n)$ | $CH_3$ | $C_2H_5$ |
| 3039 | Cl | $C_4H_9(n)$ | H | $C_2H_5$ |
| 3040 | Cl | $C_4H_9(n)$ | $CH_3$ | $C_2H_5$ |
| 3041 | $C_2H_5$ | $C_3H_7(n)$ | H | $C_2H_5$ |
| 3042 | $C_2H_5$ | $C_3H_7(n)$ | $CH_3$ | $C_2H_5$ |
| 3043 | $C_2H_5$ | $C_4H_9(n)$ | H | $C_2H_5$ |
| 3044 | $C_2H_5$ | $C_4H_9(n)$ | $CH_3$ | $C_2H_5$ |
| 3045 | (2-ethylphenyl) | $C_3H_7(n)$ | H | $C_2H_5$ |
| 3046 | (2-ethylphenyl) | $C_4H_9(n)$ | H | $C_2H_5$ |
| 3047 | H | $C_3H_7(n)$ | H | $C_6H_5$ |
| 3048 | H | $C_3H_7(n)$ | $CH_3$ | $C_6H_5$ |
| 3049 | H | $C_4H_9(n)$ | H | $C_6H_5$ |
| 3050 | H | $C_4H_9(n)$ | $CH_3$ | $C_6H_5$ |
| 3051 | Cl | $C_3H_7(n)$ | H | $C_6H_5$ |
| 3052 | Cl | $C_3H_7(n)$ | $CH_3$ | $C_6H_5$ |
| 3053 | Cl | $C_4H_9(n)$ | H | $C_6H_5$ |
| 3054 | Cl | $C_4H_9(n)$ | $CH_3$ | $C_6H_5$ |
| 3055 | $C_2H_5$ | $C_3H_7(n)$ | H | $C_6H_5$ |
| 3056 | $C_2H_5$ | $C_3H_7(n)$ | $CH_3$ | $C_6H_5$ |
| 3057 | $C_2H_5$ | $C_4H_9(n)$ | H | $C_6H_5$ |
| 3058 | $C_2H_5$ | $C_4H_9(n)$ | $CH_3$ | $C_6H_5$ |
| 3059 | $C_4H_9(n)$ | $C_3H_7(n)$ | H | $C_6H_5$ |
| 3060 | $C_4H_9(n)$ | $C_3H_7(n)$ | $CH_3$ | $C_6H_5$ |
| 3061 | $C_4H_9(n)$ | $C_4H_9(n)$ | H | $C_6H_5$ |
| 3062 | $C_4H_9(n)$ | $C_4H_9(n)$ | $CH_3$ | $C_6H_5$ |
| 3063 | $C_4H_9(n)$ | $C_4H_9(n)$ | H | $CH_2CH_2CO_2H$ |
| 3064 | $C_4H_9(n)$ | $C_4H_9(n)$ | $CH_3$ | $CH_2CH_2CO_2H$ |
| 3065 | (2-ethylphenyl) | $C_3H_7(n)$ | H | $CH_2CH_2CO_2H$ |
| 3066 | (2-ethylphenyl) | $C_3H_7(n)$ | $CH_3$ | $CH_2CH_2CO_2H$ |
| 3067 | (2-ethylphenyl) | $C_4H_9(n)$ | H | $CH_2CH_2CO_2H$ |
| 3068 | (2-ethylphenyl) | $C_4H_9(n)$ | $CH_3$ | $CH_2CH_2CO_2H$ |

TABLE LXX

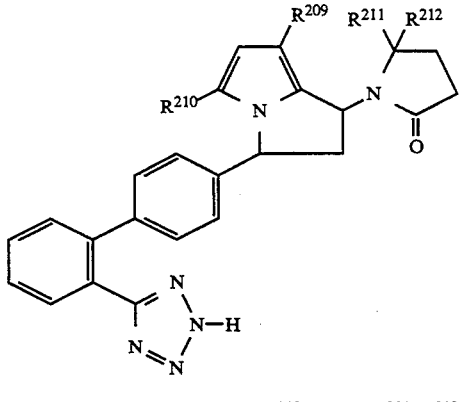

| EX. # | $R^{209}$ | $R^{210}$ | $R^{211}, R^{212}$ |
|---|---|---|---|
| 3069 | H | $C_3H_7(n)$ | O |
| 3070 | H | $C_3H_7(n)$ | H,H |
| 3071 | H | $C_3H_7(n)$ | H,$CH_3$ |
| 3072 | H | $C_3H_7(n)$ | H,$C_2H_5$ |
| 3073 | H | $C_3H_7(n)$ | H,$CH_2OH$ |
| 3074 | H | $C_3H_7(n)$ | H,$CO_2H$ |
| 3075 | H | $C_4H_9(n)$ | O |
| 3076 | H | $C_4H_9(n)$ | H,H |
| 3077 | H | $C_4H_9(n)$ | H,$CH_3$ |
| 3078 | H | $C_4H_9(n)$ | H,$C_2H_5$ |
| 3079 | H | $C_4H_9(n)$ | H,$CH_2OH$ |
| 3080 | H | $C_4H_9(n)$ | H,$CO_2H$ |
| 3081 | Cl | $C_3H_7(n)$ | O |
| 3082 | Cl | $C_3H_7(n)$ | H,H |
| 3083 | Cl | $C_3H_7(n)$ | H,$CH_3$ |
| 3084 | Cl | $C_3H_7(n)$ | H,$C_2H_5$ |
| 3085 | Cl | $C_3H_7(n)$ | H,$CH_2OH$ |
| 3086 | Cl | $C_3H_7(n)$ | H,$CO_2H$ |
| 3087 | Cl | $C_4H_9(n)$ | O |
| 3088 | Cl | $C_4H_9(n)$ | H,H |
| 3089 | Cl | $C_4H_9(n)$ | H,$CH_3$ |
| 3090 | Cl | $C_4H_9(n)$ | H,$C_2H_5$ |
| 3091 | Cl | $C_4H_9(n)$ | H,$CH_2OH$ |
| 3092 | Cl | $C_4H_9(n)$ | H,$CO_2H$ |
| 3093 | $C_2H_5$ | $C_3H_7(n)$ | O |
| 3094 | $C_2H_5$ | $C_3H_7(n)$ | H,H |
| 3095 | $C_2H_5$ | $C_3H_7(n)$ | H,$CH_3$ |
| 3096 | $C_2H_5$ | $C_3H_7(n)$ | H,$C_2H_5$ |
| 3097 | $C_2H_5$ | $C_3H_7(n)$ | H,$CH_2OH$ |
| 3098 | $C_2H_5$ | $C_3H_7(n)$ | H,$CO_2H$ |
| 3099 | $C_2H_5$ | $C_4H_9(n)$ | O |
| 3100 | $C_2H_5$ | $C_4H_9(n)$ | H,H |
| 3101 | $C_2H_5$ | $C_4H_9(n)$ | H,$CH_3$ |
| 3102 | $C_2H_5$ | $C_4H_9(n)$ | H,$C_2H_5$ |
| 3103 | $C_2H_5$ | $C_4H_9(n)$ | H,$CH_2OH$ |
| 3104 | $C_2H_5$ | $C_4H_9(n)$ | H,$CO_2H$ |
| 3105 | $C_4H_9(n)$ | $C_3H_7(n)$ | O |
| 3106 | $C_4H_9(n)$ | $C_3H_7(n)$ | H,H |
| 3107 | $C_4H_9(n)$ | $C_3H_7(n)$ | H,$CH_3$ |
| 3108 | $C_4H_9(n)$ | $C_3H_7(n)$ | H,$CH_2OH$ |
| 3109 | $C_4H_9(n)$ | $C_3H_7(n)$ | H,$CO_2H$ |
| 3110 | $C_4H_9(n)$ | $C_4H_9(n)$ | O |
| 3111 | $C_4H_9(n)$ | $C_4H_9(n)$ | H,H |
| 3112 | $C_4H_9(n)$ | $C_4H_9(n)$ | H,$CH_3$ |
| 3113 | $C_4H_9(n)$ | $C_4H_9(n)$ | H,$CH_2OH$ |
| 3114 | $C_4H_9(n)$ | $C_4H_9(n)$ | H,$CO_2H$ |
| 3115 | (2-ethylphenyl) | $C_3H_7(n)$ | O |
| 3116 | (2-ethylphenyl) | $C_3H_7(n)$ | H,H |
| 3117 | (2-ethylphenyl) | $C_3H_7(n)$ | H,$CH_3$ |
| 3118 | (2-ethylphenyl) | $C_3H_7(n)$ | $CH_3$,$CH_3$ |
| 3119 | (2-ethylphenyl) | $C_3H_7(n)$ | H,$CH_2OH$ |
| 3120 | (2-ethylphenyl) | $C_3H_7(n)$ | H,$CO_2H$ |
| 3121 | (2-ethylphenyl) | $C_4H_9(n)$ | O |
| 3122 | (2-ethylphenyl) | $C_4H_9(n)$ | H,H |
| 3123 | (2-ethylphenyl) | $C_4H_9(n)$ | H,$CH_3$ |
| 3124 | (2-ethylphenyl) | $C_4H_9(n)$ | $CH_3$,$CH_3$ |
| 3125 | (2-ethylphenyl) | $C_4H_9(n)$ | H,$CH_2OH$ |
| 3126 | (2-ethylphenyl) | $C_4H_9(n)$ | H,$CO_2H$ |

TABLE LXXI

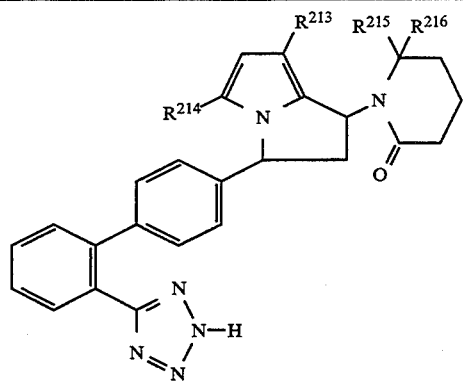

| EX. # | R²¹³ | R²¹⁴ | R²¹⁵, R²¹⁶ |
|---|---|---|---|
| 3127 | H | $C_3H_7(n)$ | O |
| 3128 | H | $C_3H_7(n)$ | H,H |
| 3129 | H | $C_3H_7(n)$ | H,$CH_3$ |
| 3130 | H | $C_3H_7(n)$ | H,$C_2H_5$ |
| 3131 | H | $C_3H_7(n)$ | H,$CH_2OH$ |
| 3132 | H | $C_3H_7(n)$ | H,$CO_2H$ |
| 3133 | H | $C_4H_9(n)$ | O |
| 3134 | H | $C_4H_9(n)$ | H,H |
| 3135 | H | $C_4H_9(n)$ | H,$CH_3$ |
| 3136 | H | $C_4H_9(n)$ | H,$C_2H_5$ |
| 3137 | H | $C_4H_9(n)$ | H,$CH_2OH$ |
| 3138 | H | $C_4H_9(n)$ | H,$CO_2H$ |
| 3139 | Cl | $C_3H_7(n)$ | O |
| 3140 | Cl | $C_3H_7(n)$ | H,H |
| 3141 | Cl | $C_3H_7(n)$ | H,$CH_3$ |
| 3142 | Cl | $C_3H_7(n)$ | $CH_3$,$CH_3$ |
| 3143 | Cl | $C_3H_7(n)$ | H,$CH_2OH$ |
| 3144 | Cl | $C_3H_7(n)$ | H,$CO_2H$ |
| 3145 | Cl | $C_4H_9(n)$ | O |
| 3146 | Cl | $C_4H_9(n)$ | H,H |
| 3147 | Cl | $C_4H_9(n)$ | H,$CH_3$ |
| 3148 | Cl | $C_4H_9(n)$ | H,$C_2H_5$ |
| 3149 | Cl | $C_4H_9(n)$ | H,$CH_2OH$ |
| 3150 | Cl | $C_4H_9(n)$ | H,$CO_2H$ |
| 3151 | $C_2H_5$ | $C_3H_7(n)$ | O |
| 3152 | $C_2H_5$ | $C_3H_7(n)$ | H,H |
| 3153 | $C_2H_5$ | $C_3H_7(n)$ | H,$CH_3$ |
| 3154 | $C_2H_5$ | $C_3H_7(n)$ | H,$C_2H_5$ |
| 3155 | $C_2H_5$ | $C_3H_7(n)$ | H,$CH_2OH$ |
| 3156 | $C_2H_5$ | $C_3H_7(n)$ | H,$CO_2H$ |
| 3157 | $C_2H_5$ | $C_4H_9(n)$ | O |
| 3158 | $C_2H_5$ | $C_4H_9(n)$ | H,H |
| 3159 | $C_2H_5$ | $C_4H_9(n)$ | H,$CH_3$ |
| 3160 | $C_2H_5$ | $C_4H_9(n)$ | H,$C_2H_5$ |
| 3161 | $C_2H_5$ | $C_4H_9(n)$ | H,$CH_2OH$ |
| 3162 | $C_2H_5$ | $C_4H_9(n)$ | H,$CO_2H$ |
| 3163 | $C_4H_9(n)$ | $C_3H_7(n)$ | O |
| 3164 | $C_4H_9(n)$ | $C_3H_7(n)$ | H,H |
| 3165 | $C_4H_9(n)$ | $C_3H_7(n)$ | H,$CH_3$ |
| 3166 | $C_4H_9(n)$ | $C_3H_7(n)$ | H,$CH_2OH$ |
| 3167 | $C_4H_9(n)$ | $C_3H_7(n)$ | H,$CO_2H$ |
| 3168 | $C_4H_9(n)$ | $C_4H_9(n)$ | O |
| 3169 | $C_4H_9(n)$ | $C_4H_9(n)$ | H,H |
| 3170 | $C_4H_9(n)$ | $C_4H_9(n)$ | H,$CH_3$ |
| 3171 | $C_4H_9(n)$ | $C_4H_9(n)$ | H,$CH_2OH$ |
| 3172 | $C_4H_9(n)$ | $C_4H_9(n)$ | H,$CO_2H$ |
| 3173 | (2-ethylphenyl) | $C_3H_7(n)$ | O |
| 3174 | (2-ethylphenyl) | $C_3H_7(n)$ | H,H |
| 3175 | (2-ethylphenyl) | $C_3H_7(n)$ | H,$CH_3$ |
| 3176 | (2-ethylphenyl) | $C_3H_7(n)$ | $CH_3$,$CH_3$ |
| 3177 | (2-ethylphenyl) | $C_3H_7(n)$ | H,$CH_2OH$ |
| 3178 | (2-ethylphenyl) | $C_3H_7(n)$ | H,$CO_2H$ |
| 3179 | (2-ethylphenyl) | $C_4H_9(n)$ | O |
| 3180 | (2-ethylphenyl) | $C_4H_9(n)$ | H,H |
| 3181 | (2-ethylphenyl) | $C_4H_9(n)$ | H,$CH_3$ |
| 3182 | (2-ethylphenyl) | $C_4H_9(n)$ | $CH_3$,$CH_3$ |
| 3183 | (2-ethylphenyl) | $C_4H_9(n)$ | H,$CH_2OH$ |
| 3184 | (2-ethylphenyl) | $C_4H_9(n)$ | H,$CO_2H$ |

TABLE LXXII

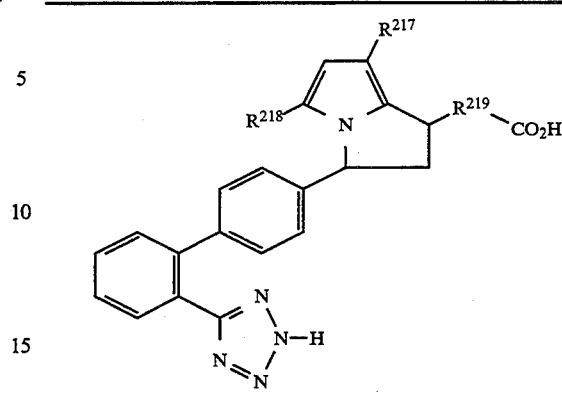

| EX. # | R²¹⁷ | R²¹⁸ | R²¹⁹ |
|---|---|---|---|
| 3185 | H | $C_3H_7(n)$ | $CH_2$ |
| 3186 | H | $C_3H_7(n)$ | $CH(C_2H_5)$ |
| 3187 | H | $C_3H_7(n)$ | $CH(CH_2C_6H_5)$ |
| 3188 | H | $C_3H_7(n)$ | $CH_2CH_2$ |
| 3189 | H | $C_3H_7(n)$ | $CH(C_2H_5)CH_2$ |
| 3190 | H | $C_3H_7(n)$ | $CH(CH_2C_6H_5)CH_2$ |
| 3191 | H | $C_4H_9(n)$ | $CH_2$ |
| 3192 | H | $C_4H_9(n)$ | $CH(C_2H_5)$ |
| 3193 | H | $C_4H_9(n)$ | $CH_2CH_2$ |
| 3194 | H | $C_4H_9(n)$ | $CH(C_2H_5)CH_2$ |
| 3195 | H | $C_4H_9(n)$ | $CH(CH_2C_6H_5)CH_2$ |
| 3196 | Cl | $C_3H_7(n)$ | $CH_2$ |
| 3197 | Cl | $C_3H_7(n)$ | $CH(C_2H_5)$ |
| 3198 | Cl | $C_3H_7(n)$ | $CH(CH_2C_6H_5)$ |
| 3199 | Cl | $C_3H_7(n)$ | $CH_2CH_2$ |
| 3200 | Cl | $C_3H_7(n)$ | $CH(C_2H_5)CH_2$ |
| 3201 | Cl | $C_3H_7(n)$ | $CH(CH_2C_6H_5)CH_2$ |
| 3202 | Cl | $C_4H_9(n)$ | $CH_2$ |
| 3203 | Cl | $C_4H_9(n)$ | $CH(C_2H_5)$ |
| 3204 | Cl | $C_4H_9(n)$ | $CH(CH_2C_6H_5)$ |
| 3205 | Cl | $C_4H_9(n)$ | $CH_2CH_2$ |
| 3206 | Cl | $C_4H_9(n)$ | $CH(C_2H_5)CH_2$ |
| 3207 | Cl | $C_4H_9(n)$ | $CH(CH_2C_6H_5)CH_2$ |
| 3208 | $C_2H_5$ | $C_3H_7(n)$ | $CH_2$ |
| 3209 | $C_2H_5$ | $C_3H_7(n)$ | $CH_2CH_2$ |
| 3210 | $C_2H_5$ | $C_4H_9(n)$ | $CH_2$ |
| 3211 | $C_2H_5$ | $C_4H_9(n)$ | $CH_2CH_2$ |
| 3212 | $C_4H_9(n)$ | $C_3H_7(n)$ | $CH_2$ |
| 3213 | $C_4H_9(n)$ | $C_3H_7(n)$ | $CH_2CH_2$ |
| 3214 | $C_4H_9(n)$ | $C_4H_9(n)$ | $CH_2$ |
| 3215 | $C_4H_9(n)$ | $C_4H_9(n)$ | $CH_2CH_2$ |
| 3216 | (2-ethylphenyl) | $C_3H_7(n)$ | $CH_2$ |
| 3217 | (2-ethylphenyl) | $C_3H_7(n)$ | $CH_2CH_2$ |
| 3218 | (2-ethylphenyl) | $C_4H_9(n)$ | $CH_2$ |
| 3219 | (2-ethylphenyl) | $C_4H_9(n)$ | $CH_2CH_2$ |

An appropriately substituted triazole 91, the heterocyclic starting material, may be prepared as described in the literature [E. C. Taylor in "Triazoles: 1,2,4" Vol. 37 of *The Chemistry of Heterocyclic Compounds*. A. Weissberger Eds., Wiley-Interscience, New York, 1981]. The triazole 1 in N,N-dimethylformamide (DMF) is treated with base, such as potassium tert-butoxide, followed by addition of appropriate alkylating agent 92 to give the coupled product 93 (Scheme XIII). For compounds where X is a substituted phenyl group, several procedures have been published for the preparations of the alkylating agent 92 [see references for compound 2].

SCHEME XIII

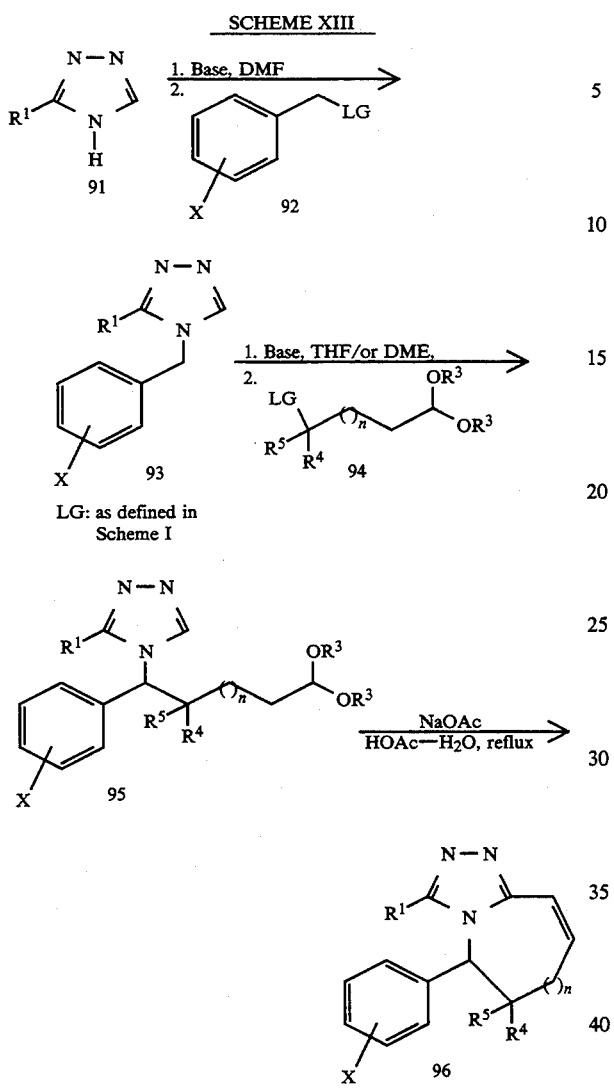

LG: as defined in Scheme I

The coupled triazole 93 itself may be an angiotensin II receptor antagonist, but it may also be used as a key intermediate in the preparation of the compounds of the invention. Triazole 93 in THF (or DME) is treated with base (such as n-BuLi or LDA) at −78° C. (or −65° C.), followed by addition of an appropriate alkylating agent or other electrophiles 94 (the acetal shown in Scheme I may be other aldehyde masking group or equivalent, and LG is a leaving group such as halide, mesylate, triflate or tosylate). The resulting masked aldehyde 95 was stirred with NaOAc in aqueous acetic acid at reflux for a few days (1 to 5 days) to give one of the compounds of the invention, a cyclized triazole 96.

The triazole 96 may be used as an intermediate to prepare other substituted compounds with appropriate functional group transformations and preparations of some of those compounds are illustrated in Scheme XIV and XV (all of the intermediates shown in the sequences are also angiotensin II receptor antagonists). For example, The unsaturated triazole 96, NaHCO₃ and NBS in CCl₄ is stirred at reflux to give a bromide 97. The bromide 97 may be treated with organolithium, such as n-BuLi or tert-BuLi, followed by addition of an appropriate electrophile, (such as alkyl halides, carbon dioxide, aldehyde, ketone and others) to give the addition product 98. The olefin 98 may be hydrogenated to give its saturated product 99.

SCHEME XIV

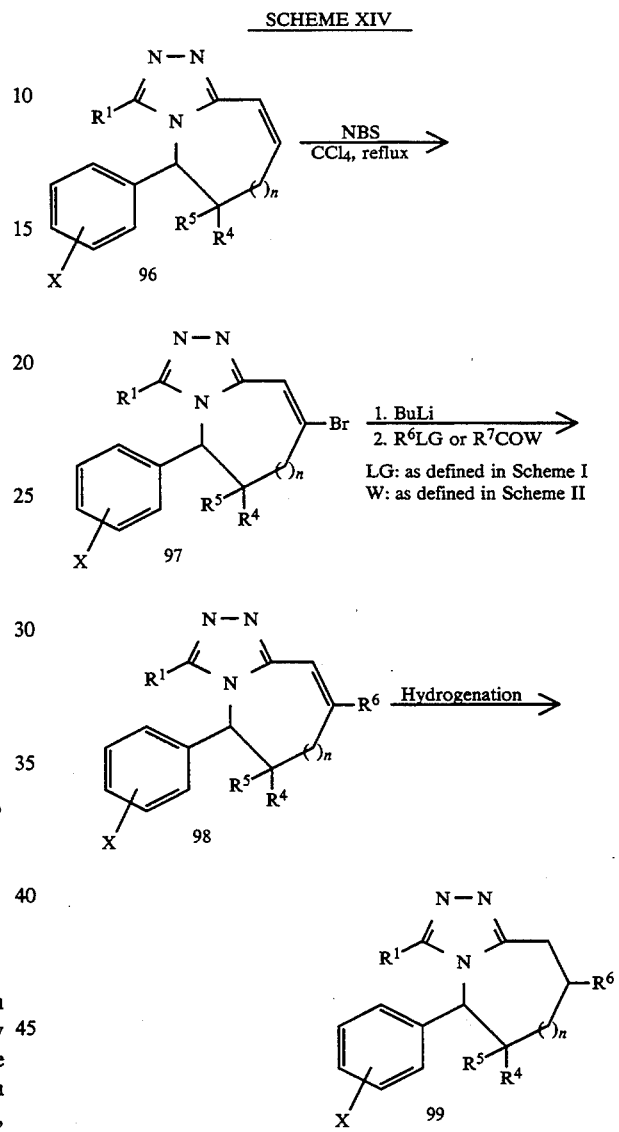

LG: as defined in Scheme I
W: as defined in Scheme II

Alternatively, as illustrated in Scheme XV, the unsaturated triazole 96 may be treated with NBS in wet DMSO to give a bromohydrin which may be reduced with nBu₃SnH to an alcohol 100 and the oxidation of the alcolol with MnO₂ will afford a ketone 101. The ketone 101 may be condensed with appropriately substituted amine, then reduced to an amine 102 with an appropriate reducing agent (e.g. NaBH₄, or hydrogen over catalyst). The amine 102 may also be prepared directly from olefin 96 under bromination condition (NBS, CH₃CN) with a large excess of succinimide. The amine 102 may be used to prepare other derivatives. Alternatively, the alcohol 100 may be treated with triphenylphosphine, diethoxyazo dicarboxylate and an imide (e.g. phthalimide) to give an imide analogue which may be converted to an amine 102.

SCHEME XV

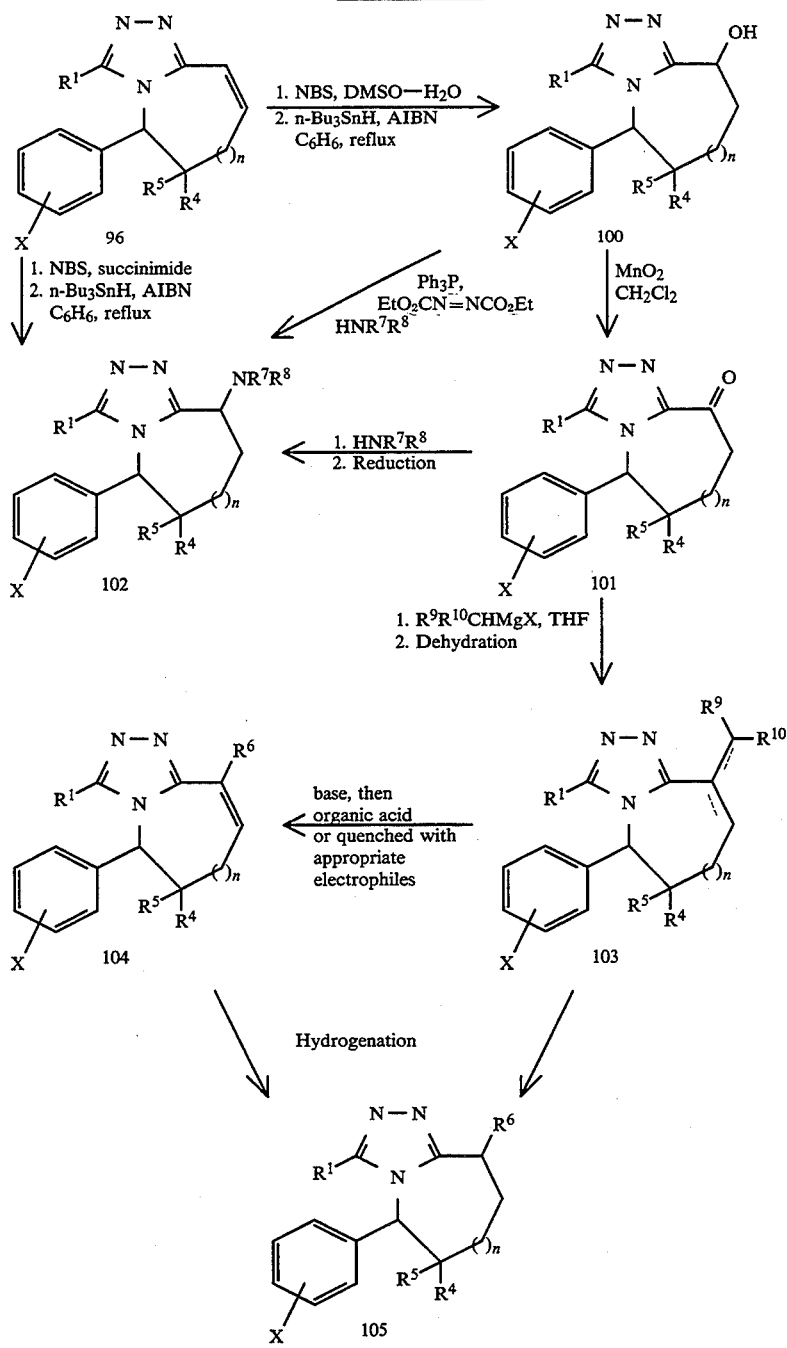

In Scheme XVI, an alternative preparation for the compounds of the invention is described. An appropriately substituted triazole 91 may be treated with one equivalent of base, then protected as SEM or BOC derivative. The protected triazole then is treated with another equivalent of base followed by addition of electrophile 107 or 108. Electrophiles 107 and 108 can be prepared from $HC(=O)(CR^4R^5)(CH_2)_nC(=O)LG$ and an appropriate organometallic reagent such as $XC_6H_4MgBr$. If necessary, the resulting lithium anion obtained from the procedure described above may be converted to other organometallic reagents according to well-established procedures.

If PLG is a hydroxyl group and Z is a proton, the resulting addition product 109, may be cyclized with triphenylphosphine and diethyl azodicarboxylate [Hitsunobu, O. *Synthesis*, 1981, 1-27; or other modified conditions]. If PLG is or is converted to a leaving group, such as halides, tosylate, and Z is a proton, the cyclization may be achieved with a weak base in DHF (e.g. $K_2CO_3$, $Cs_2CO_3$) to give a ketone 101. The ketone 101 may be reduced to an alcohol 100 with $NaBH_4$ in methanol. The alcohol 100 may be dehydrated to olefin 96 with acid (e.g. HOAc and heat) or thionyl chloride and pyridine. Other compounds may be prepared from compounds 96, 100, or 101 as described in Scheme XIV and XV.

SCHEME XVI

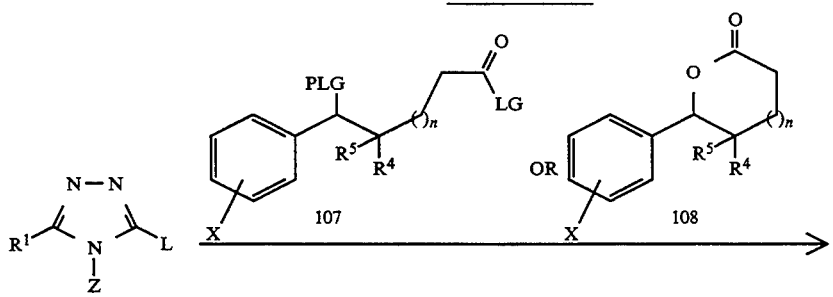

91 Z,L = H
106 Z = protecting group,
e.g. SEM, or BOC
L = Mg, Ce, Cd, Zn halide
or Li

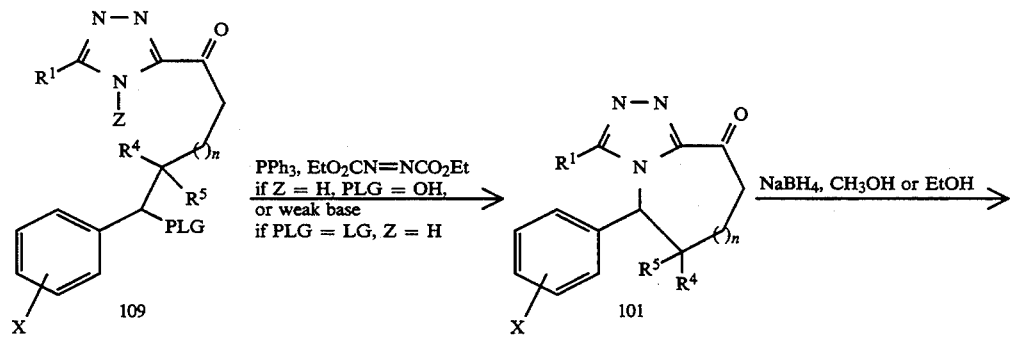

PLG = a leaving group or
a group that can be easily
converted to a leaving group

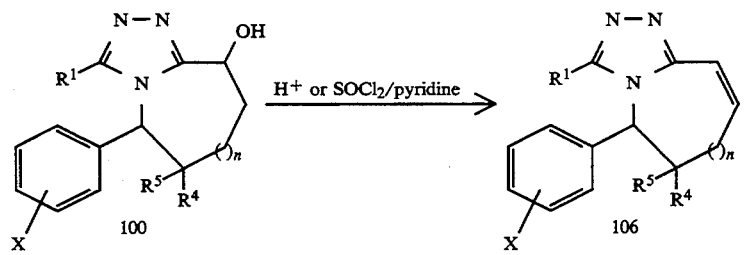

EXAMPLE 3220

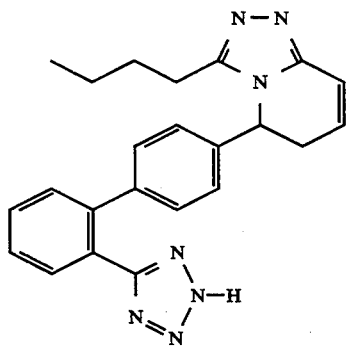

3-Butyl-5,6-dihydro-5-[2'-(1H-tetrazol-5-yl)[1,1'-biphenyl]-4-yl]-1,2,4-triazolo[4,3-a]pyridine Step 1: Preparation of Biphenyl Triazole To a solution of 2-butylpyrrole (2.65 mmol) in 5.3 mL of DHF is added 3.45 mL (3.45 mmol) of potassium tert-butoxide (1M in THF), and the resulting solution is stirred at room temperature for 30 min. To the dark brown mixture is added 2.75 g (3.45 mmol) of the bromomethyl biphenyl. The reaction mixture is stirred at room temperature until the reaction is complete. The mixture is concentrated in vacuo. The residue is purified to give the trityl-protected biphenyl triazole.

Step 2: Preparation of Dimethyl Acetal Triazole

To a solution of biphenyl triazole (3.18 mmol, obtained from Step 1) in 16 mL of THF cooled at −45° C. (acetonitrile-dry ice) is added 2.8 mL (4.06 mmol) of n-butyllithium (1.45 H in hexane) over a 4-min period. The resulting dark purple solution is stirred cold for another 15 min, followed by addition of 1.0 mL (6.59 mmol) of 3-bromopropionaldehyde dimethyl acetal in one portion. The mixture is stirred cold for 40 min, then is slowly warmed to −10° C. The reaction is quenched with aqueous NH$_4$Cl, extracted with diethyl ether. The combined extracts are washed with brine, dried (HgSO$_4$), concentrated in vacuo and purified to give the biphenyl dimethyl acetal triazole intermediate.

Step 3: Preparation of Biphenyl Bicyclic Triazole

A solution of the crude biphenyl dimethyl acetal triazole (3.18 mmol, obtained from Step 2) and 5.3 g (88 mmol) of NaOAc in 13 mL of water and 40 mL of glacial acetic acid is stirred at reflux until the reaction is complete. The solution is cooled and concentrated in vacuo. The residue is dissolved in methylene chloride and filtered. The filtrate is stirred with 2 g (7.2 mmol) of trityl chloride and 3 mL (21.5 mmol) of TEA at room temperature until the reaction is complete. The mixture is concentrated in vacuo. The residue is purified to give the biphenyl bicyclic triazole.

Step 4: Detritylation of Trityl Tetrazole

A solution of the biphenyl bicyclic triazole (0.144 mmol, obtained from Step 3) is stirred with 1 mL of water and 6 mL of acetic acid at room temperature until the reaction is complete. The solution is concentrated in vacuo, stirred in aqueous NaHCO3 and washed with ether. The aqueous residue is acidified with 3N HCl to pH 4 and extracted with methylene chloride. The combined extracts are dried (MgSO4), concentrated and purified to give the title compound of Example 3220.

EXAMPLE 3221

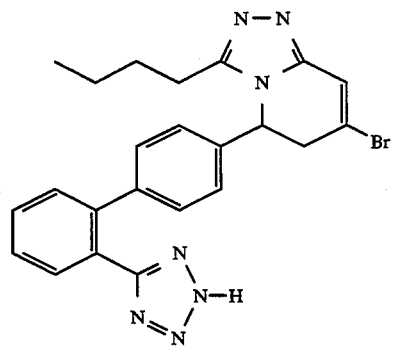

7-Bromo-3-butyl-5,6-dihydro-5-[2'-(1H-tetrazol-5-yl)[1,1'-biphenyl]-4-yl]-1,2,4-triazolo[4,3-a]pyridine Step 1: Preparation of Bromo Olefin Triazole A solution of trityl-protected bicyclic triazole (0.101 mmol, obtained from Step 3 of Example 3220), 20 mg (0.112 mmol) of NBS and 7 mg (catalytic) of AIBN in 2.8 mL of CCl4 is stirred at reflux until the reaction is complete. The reaction mixture is diluted with CCl4 and washed with water. The organic layer is dried (MgSO4) and concentrated in vacuo. The residue is purified to give the biphenyl bromo olefin triazole.

Step 2: Detritylation of the Trityl Tetrazole

A solution of bromo olefin triazole (0.0427 mmol, obtained from Step 1) in 0.8 mL of water and 5 mL of acetic acid is stirred at room temperature until the reaction is complete. The mixture is concentrated in vacuo. The residue is worked up as described in Step 4 of Example 3220 and purified to give the title compound of Example 3221.

EXAMPLE 3222

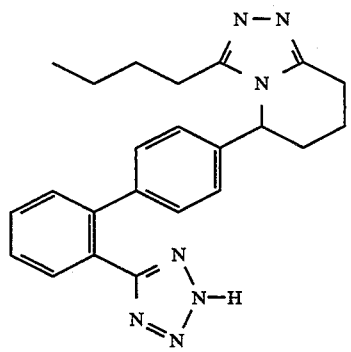

3-Butyl-5,6,7,8-tetrahydro-5-[2'-(1H-tetrazol-5-yl)[1,1'-biphenyl]-4-yl]-1,2,4-triazolo[4,3-a]pyridine A suspension of bicyclic olefin triazole (0.1 mmol, the title compound of Example 3220) and 20 mg (0.019 mmol) of 10% palladium on charcoal in 2 mL of absolute ethanol is agitated on a Parr apparatus under 50 psi of hydrogen gas at room temperature until the reaction is complete. The mixture is filtered through a pad of celite, concentrated in vacuo and purified to give the title compound of Example 3222.

EXAMPLE 3223

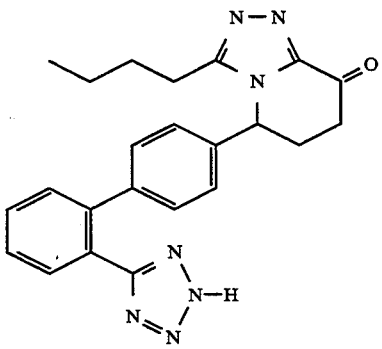

3-Butyl -5,6-dihydro-5-[2'-(1H-tetrazol -5-yl)[1,1'-biphenyl]-4-yl]-1,2,4-triazolo[4,3-a]pyridin-8(5H) -one Step 1: Preparation of the Bromohydrin Intermediate To a solution of biphenyl olefin triazole (3.13 mmol, obtained from Step 4 of Example 3220) in 22 mL (0,122 mmol) of water and 22 mL of DMSO at room temperature is added 587 mg (3.30 mmol) of NBS in one portion. The resulting orange solution is stirred at room temperature for 40 min, quenched with aqueous Na2SO3, and extracted with chloroform. The combined extracts are washed with water, and the combined aqueous layers are extracted with chloroform. The combined extracts are washed with brine, dried (MgSO4) and concentrated in vacuo to give a crude bromohydrin intermediate which can be used directly in the subsequent Step 2 without further purification.

Step 2: Preparation of the Trityl-Protected Biphenyl Hydroxy Triazole

To the crude bromohydrin (3.13 mmol, obtained from Step 1) in 42 mL of degassed dry benzene is added 4.3 mL (14.7 mmol) of n-Bu3SnH and 456 mg (2.7 mmol) of AIBN in one portion and the resulting solution is stirred at reflux until the reaction is complete.

The mixture is concentrated in vacuo and partitioned between hexane and acetonitrile. The acetonitrile layer is washed with hexane, and the combined hexane layers are extracted with acetonitrile. The combined acetonitrile extracts are concentrated in vacuo to give an isomeric mixture of both cis- and trans-hydroxy triazoles (relative to the biphenyl moiety). The crude mixture can be used directly in subsequent Step 3 without further purification. The mixture may also be used to prepare the biphenyl trans-hydroxy triazole (the title compound of Example 3225).

Step 3: Preparation of the Keto Triazole

A suspension of the crude biphenyl hydroxy triazole (2.72 mmol, obtained from Step 2) and 13 g of active $MnO_2$ in 15 mL of methylene chloride is stirred at room temperature until the reaction is complete. The mixture is filtered through a pad of celite, rinsed with IPA-methylene chloride, and concentrated in vacuo. The residue is purified to give the trityl-protected biphenyl keto triazole.

Step 4: Detritylation of Trityl Tetrazole

A solution of trityl-protected biphenyl keto triazole (0.131 mmol, obtained from Step 3) in 1.0 mL of water and 5.0 mL of acetic acid is stirred at room temperature until the reaction is complete. The mixture is concentrated in vacuo. The residue is worked up as described in Step 4 of Example 3220 and purified to give the title compound of Example 3223.

EXAMPLE 3224

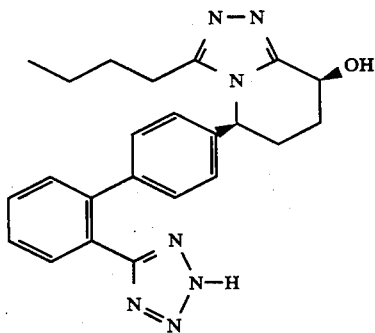

3-Butyl-5,6,7,8-tetrahydro-5-[2'-(1H-tetrazol-5-yl)[1,1'-biphenyl]-4-yl]-1,2,4-triazolo[4,3-a]pyridin-cis-8-ol Step 1: Preparation of Biphenyl Cis-Hydroxy Triazole To a solution of biphenyl keto triazole (0.456 mmol, obtained from Step 3 of Example 3223) in 0.5 mL of methanol and 2.0 mL of THF at 0° C. is added in small portions 34 mg (0.899 mmol) of $NaBH_4$. The resulting solution is stirred at 0° C., and slowly warmed to room temperature. The reaction is quenched with aqueous $NH_4Cl$, extracted with methylene chloride, dried ($MgSO_4$) and concentrated in vacuo. The residue is purified to give the biphenyl hydroxy triazole.

Step 2: Detritylation of Trityl Tetrazole

A solution of the biphenyl hydroxy triazole (0.259 mmol, obtained from Step 1) in 0.4 mL of water and 2.0 mL of acetic acid is stirred at room temperature until the reaction is complete. The mixture is concentrated in vacuo. The residue is purified to give the title compound of Example 3224.

EXAMPLE 3225

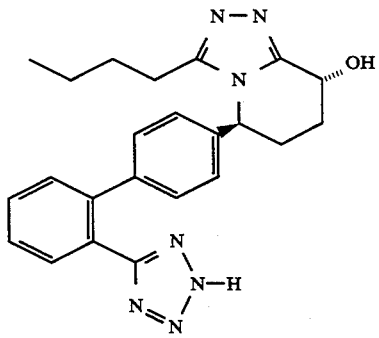

3-Butyl-5,6,7,8-tetrahydro-5-[2'-(1H-tetrazol-5-yl)[1,1'-biphenyl]-4-yl]-1,2,4-triazolo[4,3-a]pyridin-trans-8-ol Step 1: Preparation of Biphenyl Trans-Hydroxy Triazole A suspension of the crude biphenyl hydroxy triazole (1.307 mmol, obtained from Step 2 of Example 3223) and 3.0 g of active $MnO_2$ in 5.0 mL of methylene chloride is stirred at room temperature. The reaction is worked up before its completion. The mixture is filtered through a pad of celite, rinsed with IPA-methylene chloride, and concentrated in vacuo. The residue is purified to give the trityl protected biphenyl trans-hydroxy triazole.

Alternatively, the biphenyl trans-hydroxy triazole can be prepared using the Mitsunobu reaction conditions. To a solution of diethyl azodicarboxylate (2.0 mmol) and 3-nitrobenzoic acid (2.0 mmol) in 2.0 mL of THF is added dropwise a solution of the biphenyl hydroxy triazole (2.0 mmol, obtained from Step 1 of Example 3224), and triphenylphosphine (2.0 mmol) in 1.0 mL of THF at room temperature. The resulting solution is stirred at room temperature until the reaction is complete. The resulting mixture is diluted with ether or ethyl acetate, and washed with water. The extracts are dried ($MgSO_4$) and concentrated in vacuo to give the biphenyl indolizinyl nitrobenzoate. The crude benzoate is hydrolyzed with LiOH in aqueous THF at room temperature and purified to give the biphenyl trans-hydroxy triazole.

Step 2: Detritylation of Trityl Tetrazole

A solution of the trityl protected biphenyl trans-hydroxy triazole (0.079 mmol, obtained from Step 1) in 0.4 mL of water and 2.0 mL of acetic acid is stirred at room temperature until the reaction is complete. The mixture is concentrated in Vacuo. The residue is purified to give the title compound of Example 3225.

EXAMPLE 3226

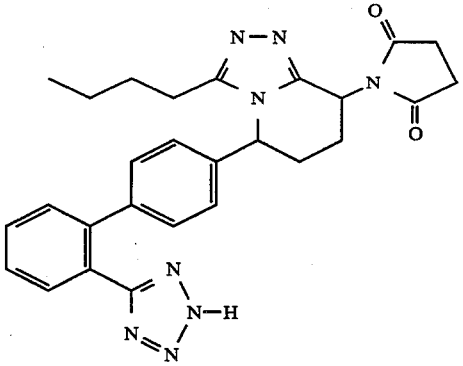

1-[3-Butyl-5,6,7,8-tetrahydro-5-[2'-(1H-tetrazol-5-yl)[1,1'-biphenyl]-4-yl]-1,2,4-triazolo[4,3-a]pyridin-8-yl]-2,5-pyrrolidinedione Step 1: Preparation of Succinimidyl Triazole To a solution of biphenyl triazole (3.13 mmol, Example 3220, Step 3) and 1.25 g (12.6 mmol) of succinimide in 20 mL of anhydrous acetonitrile is added 572 mg (3.21 mmol) of NBS in one portion. The resulting orange-red solution is stirred at room temperature for 30 min, then evaporated in vacuo. The residue is dissolved in ethyl acetate and washed with aqueous sodium bisulfite, water, and brine. The extracts are dried (MgSO4) and concentrated in vacuo. The residue is purified to give the trityl protected succinimidyl triazole.

Alternatively, the succinimide can be prepared from its corresponding hydroxy triazole. To a solution of the biphenyl hydroxy triazole (2.0 mmol, obtained from Step i of Example 3224 or 3225), succinimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (MgSO4) and concentrated in vacuo. The residue is purified to give the trityl protected succinimidyl triazole.

Step 2: Detritylation of Trityl Tetrazole

A solution of trityl protected succinimidyl triazole (0.16 mmol, obtained from Step 1) in 0.2 mL of water and 1 mL of acetic acid is stirred at room temperature until the reaction is complete. The mixture is concentrated in vacuo. The residue is worked up as described in Step 4 of Example 3220 and purified to give the title compound of Example 3226.

EXAMPLE 3227

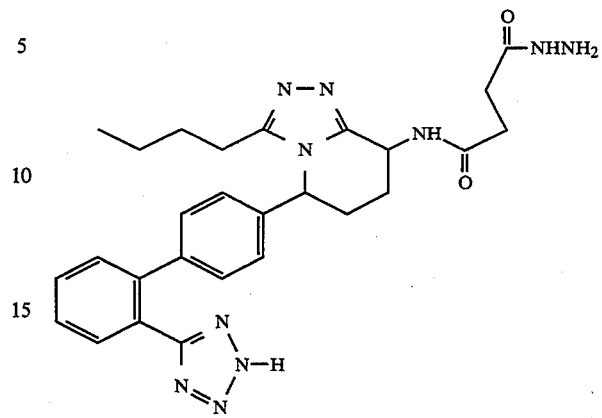

4-[3-Butyl-5,6,7,8-tetrahydro-5-[2'-(1H-tetrazol-5-yl)[1,1'-biphenyl]-4-yl]-1,2,4-triazolo[4,3- a]pyridin-8-yl]amino]-4-oxobutanoic acid, hydrazide A solution of succinimidyl triazole (0.06 mmol, obtained from Example 3226) and 11 µL (5.6 mmol) of hydrazine in 0.5 mL of ethanol is stirred at room temperature until the reaction is complete and concentrated in vacuo to give the title compound of Example 3227.

EXAMPLE 3228

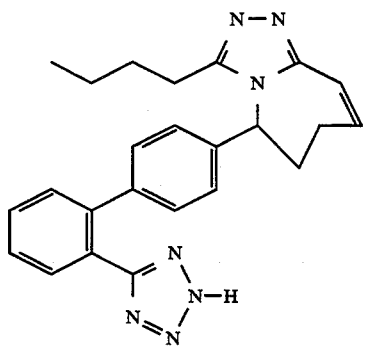

3-Butyl-6,7-dihydro-5-[2'-(1H-tetrazol-5-yl)[1,1'-biphenyl]-4-yl]-5H-1,2,4-triazolo[4,3-a]azepine Step 1: Alkylation of Biphenyl Triazole To a solution of biphenyl triazole (0.152 mmol, obtained from Step 2 of Example 3220) in 0.8 mL of DME cooled at −45° C. (acetonitrile-dry ice) is added 125 µL (0.2 mmol) of n-butyllithium (1.6M in hexane) over a 4-min period. The resulting dark red solution is stirred cold for another 15 min, followed by addition of 70 µL (0.37 mmol) of 2-(3-bromopropyl)-5,5-dimethyl-1,3-dioxane in one portion. The mixture is stirred cold for 40 min, then is slowly warmed to −10° C. The reaction is quenched with aqueous NH4Cl, extracted with diethyl ether. The combined extracts are washed with brine, dried (MgSO4) and concentrated in vacuo. The crude product can be used directly in the subsequent Step 2 without purification.

Step 2: Preparation of the Bicyclic Triazole

A solution of the crude mixture (0.152 mmol, obtained from Step 1) and 255 mg (3 mmol) of NaOAc in 0.6 mL of water and 2 mL of glacial acetic acid is stirred at reflux until the reaction is complete. The mixture is cooled and concentrated in vacuo. The residue is dissolved in methylene chloride and filtered. The filtrate is stirred with 130 mg (0.46 mmol) of trityl chloride and 0.22 mL (1.6 mmol) of TEA at room temperature until the reaction is complete. The mixture is concentrated in vacuo. The residue is purified to give the biphenyl bicyclic triazole.

Step 3: Detritylation of Trityl Tetrazole

A solution of the biphenyl bicyclic triazole (0.035 mmol, obtained from Step 2) is stirred with 0.4 mL of water and 2 mL of acetic acid at room temperature until the reaction is complete. The solution is concentrated in vacuo. The residue is worked up as described in Step 4 of Example 3220 and purified to give the title compound of Example 3228.

EXAMPLE 3229

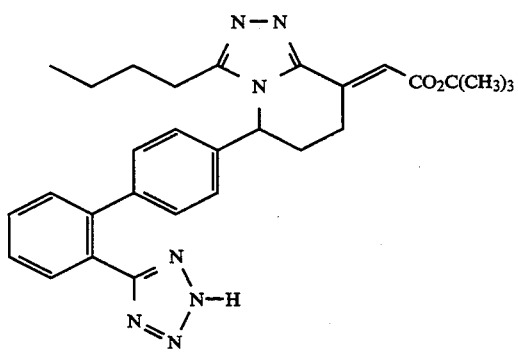

1,1-Dimethylethyl [3-butyl-6,7-dihydro-5-[2'-(1H-tetrazol-5 -yl) [1,1'-biphenyl]-4-yl]-1,2,4-triazolo[4,3-a]pyridin-8(5H)-ylidene]acetate Step 1: Preparation of Tert-Butyl Ester To a suspension of 64 mg (2.63 mmol) of magnesium in 3.0 mL of THF at 55° C. is added two 10-μL portions of 1,2-dibromoethane, 5 min apart. The resulting mixture is stirred at 45° C. for 10 min, followed by dropwise addition of a solution of biphenyl keto triazole (0.306 mmol, obtained from Step 3 of Example 3223) and 242 μL (1.50 mmol) of tert-butyl bromoacetate in 2.0 mL of THF at 55° C. over a 1-h period. The resulting solution is stirred until the reaction is complete. The mixture is cooled and quenched with aqueous NH4Cl. The mixture is extracted with ether, dried (MgSO4) and concentrated in vacuo. The crude mixture can be used directly in the subsequent Step 2 without further purification.

Step 2: Preparation of Unsaturated Butyl Ester

To a solution of the crude biphenyl tert-butyl ester intermediate (0.306 mmol, obtained from Step 1) and 200 μL (2.47 mmol) of pyridine in 2 mL of methylene chloride at 0° C. is added dropwise 80 μL (1.1 mmol) of thionyl chloride. The resulting dark brown solution is stirred at 0° C. for 1 h, diluted with water and extracted with methylene chloride. The residue is purified to give the biphenyl indolizinyl unsaturated ester.

Step 3: Detritylation of Trityl Tetrazole

A solution of biphenyl indolizinyl unsaturated ester (0.133 mmol, obtained from Step 2) in 1.0 mL of water and 5.0 mL of acetic acid is stirred at room temperature until the reaction is complete. The mixture is concentrated in vacuo. The residue is worked up as described in Step 4 of Example 3220 and purified to give the title compound of Example 3229.

EXAMPLE 3230

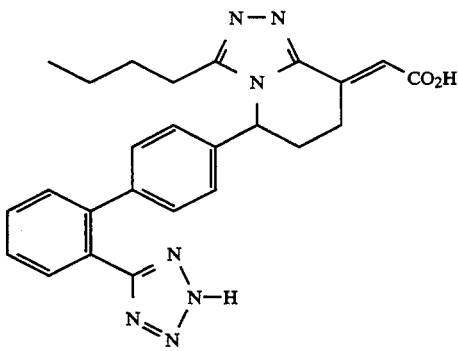

[3-Butyl-6,7-dihydro-5-[2'-(1H-tetrazol-5-yl)[1,1'-biphenyl]-4-yl]-1,2,4-triazolo[4,3-a]pyridin-8(5H)-ylidene]acetic acid To a solution of unsaturated tert-butyl ester (0.0627 mmol, the title compound of Example 3229) in 2 mL of CDCl3 at room temperature is added 0.5 mL of TFA, and the progress of the reaction is monitored by 1H NMR. The resulting yellow solution is stirred at room temperature until the reaction is complete. The mixture is concentrated in vacuo. The crude product is purified to give the title compound of Example 3230.

EXAMPLE 3231

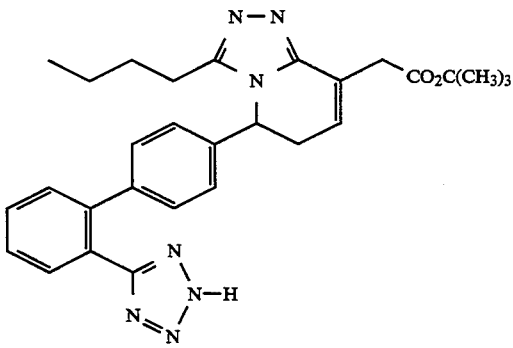

1,1-Dimethylethyl 3-butyl-5,6-dihydro-5-[2'-(1H-tetrazol-5-yl) [1,1'-biphenyl]-4-yl]-1,2,4-triazolo[4,3-a]pyridin-8-acetate Step 1: Preparation of Deconjugated Ester To a solution of ester (0.237 mmol, obtained from Step 2 of Example 3229) in 4 mL of THF at 0° C. is added 310 μL of 1.5M (0.467 mmol) LDA over a 2-min period, and the resulting solution is stirred at 0° C. for 10 min. The mixture is cooled to −78° C., stirred cold for 5 min, and quenched dropwise at −78° C. with 100 μL of acetic acid in 1 mL of hexane. The mixture is stirred cold, then warmed to room temperature and treated with aqueous NaHCO3. The mixture is extracted with methylene chloride. The combined extracts are washed with water, dried (MgSO4) and concentrated in vacuo to give a crude mixture. The crude product is purified to give the biphenyl indolizinyl deconjugated ester.

Step 2: Detritylation of Trityl Tetrazole

A solution of trityl-protected biphenyl indolizinyl deconjugated ester (0.165 mmol, obtained from Step 1) in 1 mL of water and 3 mL of acetic acid is stirred at room temperature until the reaction is complete. The mixture is concentrated in vacuo. The residue is worked up as described in Step 4 of Example 3220. The crude product is purified to give the title compound of Example 3231.

EXAMPLE 3232

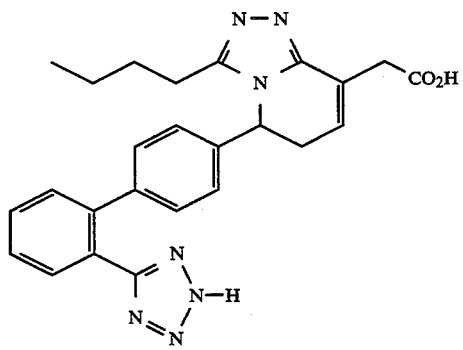

3-Butyl-5,6-dihydro-5-[2'-(1H-tetrazol-5-yl)[1,1'-biphenyl]-4-yl]-1,2,4-triazolo[4,3-a]pyridin-8-acetic acid To a solution of biphenyl indolizinyl tert-butyl ester (0.039 mmol, the title compound of Example 3231) in 0.5 mL of chloroform is added 0.25 mL of TFA, and the progress of the reaction is monitored by $^1$H NMR. The resulting solution is stirred at room temperature until the reaction is complete. The mixture is quenched with methanol and concentrated in vacuo. The residue is purified to give the title compound of Example 3232.

EXAMPLE 3233

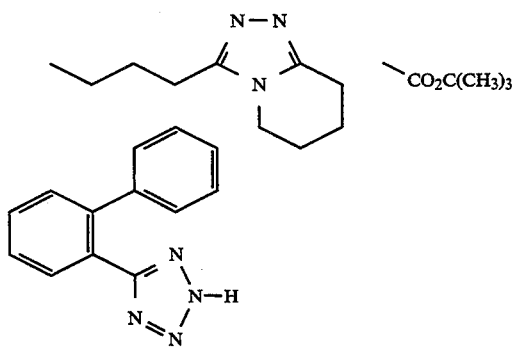

1,1-Dimethylethyl 3-butyl-5,6,7,8-tetrahydro-5-[2'-(1H-tetrazol-5-yl)[1,1'-biphenyl]-4-yl]-1,2,4-triazolo[4,3-a]pyridin-cis-8-acetate A suspension of the biphenyl indolizinyl unsaturated ester (0.059 mmol, the title compound of Example 3231) and 20 mg (0.0188 mmol) of 10% palladium on charcoal in 1.5 mL of methanol is stirred at room temperature under an atmosphere of hydrogen gas until the reaction is complete. The mixture is filtered through a pad of celite and concentrated in vacuo. The residue is purified to give the title compound of Example 3233.

EXAMPLE 3234

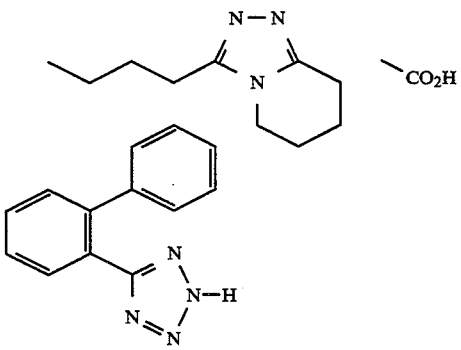

3-Butyl-5,6,7,8-tetrahydro-5-[2'-(1H-tetrazol-5-yl)[1,1'-biphenyl]-4-yl]-1,2,4-triazolo[4,3-a]pyridin-cis-8-acetic acid To a solution of tert-butyl ester (0.0332 mmol, obtained from Example 3233) in 0.4 mL of CDCl$_3$ is added 0.2 mL of TFA, and the progress of the reaction is monitored by $^1$H NMR. The resulting solution is allowed to stand at room temperature until the reaction is complete. The reaction mixture is diluted with methanol and concentrated. The residue is purified to give the title compound of Example 3234.

EXAMPLE 3235

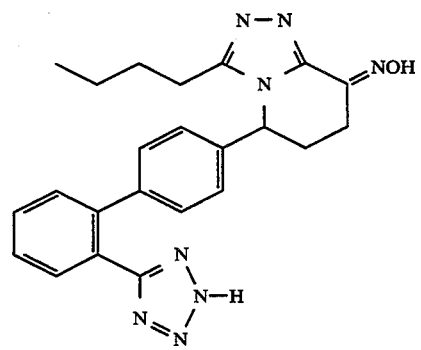

3-Butyl-5,6-dihydro-N-hydroxy-5-[2'-(1H-tetrazol-5-yl)[1.1'-biphenyl]-4-yl]triazolo[4,3-a]pyridin-8(7H)-imine A mixture of biphenyl keto imidazole (0.094 mmol, the title compound of Example 3223), 20 mg (0.29 mmol) of N-hydroxyamine (hydrochloride salt) and 30 mg of NaOAc in 2 mL of methanol is stirred at 60° C. until the reaction is complete. The mixture is diluted with chloroform and filtered. The solid is washed with methanol. The filtrate is concentrated in vacuo and purified to give the title compound of Example 3235.

EXAMPLE 3236

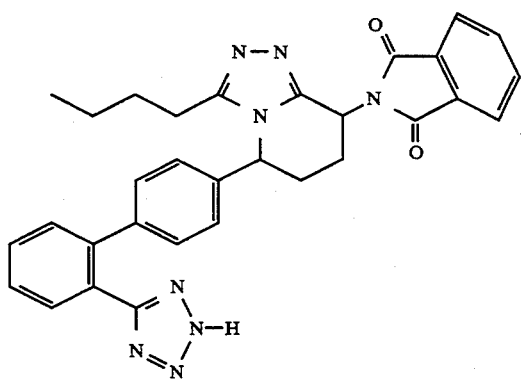

1-[3-Butyl-5,6,7,8-tetrahydro-5-[2'-(1H-tetrazol-5-yl)[1,1'-biphenyl]-4-yl]-1,2,4-triazolo[4,3-a]pyridin-8-yl]phthalimide Step 1: Preparation of Biphenyl Phthalimidyl Triazole To a solution of the biphenyl hydroxy triazole (2.0 mmol, obtained from Step 1 of Example 3224 or 3225), phthalimide (2.0 mmol), and triphenylphosphine (2.0 mmol) in 2.0 mL of THF is added dropwise a solution of diethyl azodicarboxylate (2.0 mmol) in 1 mL of THF at room temperature. The resulting solution is stirred at room temperature until the reaction is complete. The resulting mixture is diluted with ether or ethyl acetate and washed with water. The extracts are dried (MgSO4) and concentrated in vacuo. The residue is purified to give the trityl protected phthalimidyl triazole.

Step 2: Detritylation of Trityl Tetrazole

A solution of trityl-protected biphenyl phthalimidyl triazole (2.0 mmol, obtained from Step 1) in 2 mL of water and 10 mL of acetic acid is stirred at room temperature until the reaction is complete. The mixture is concentrated in vacuo. The residue is worked up as described in Step 5 of Example 3220 and purified give the title compound of Example 3236.

EXAMPLE 3237

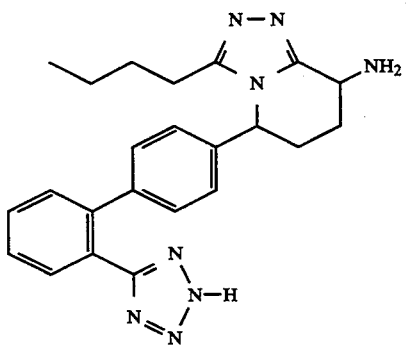

3-Butyl-5,6,7,8-tetrahydro-8-amino-5-[2'-(1H-tetrazol-5-yl) [1,1'-biphenyl]-4-yl]triazole A solution of phthalimidyl triazole (0.6 mmol, the title compound of Example 3236) and 3 µL (1.5 mmol) of hydrazine in 1.0 mL of ethanol is stirred at room temperature until the reaction is complete. The mixture is concentrated in vacuo, and purified to give the title compound of Example 3237.

Alternatively, the title compound of Example 3237 can be prepared from the corresponding oxime. A suspension of the biphenyl imidazolyl oxime (0.059 mmol, the title compound of Example 3235) and 20 mg (0.0188 mmol) of 10% palladium on charcoal in 1.5 mL of methanol is stirred at room temperature under 50 psi of hydrogen gas until the reaction is complete. The mixture is filtered through a pad of celite, concentrated in vacuo and purified to give the title compound of Example 3237.

Further examples of conformationally restricted angiotensin II antagonists (3238–3700) embraced by Formula V above are located in Tables LXXIII–XCVI.

TABLE LXXIII

| EX. # | $R^{220}$ | $R^{221}$ |
|---|---|---|
| 3238 | $C_3H_7(n)$ | H |
| 3239 | $C_3H_7(n)$ | $C_2H_5$ |
| 3240 | $C_3H_7(n)$ | $C_3H_7(n)$ |
| 3241 | $C_3H_7(n)$ | (2-ethylphenyl) |
| 3242 | $C_3H_7(n)$ | (2,6-dimethylphenyl) |
| 3243 | $C_3H_7(n)$ | phenyl |
| 3244 | $C_3H_7(n)$ | benzyl |
| 3245 | $C_3H_7(n)$ | phenylethyl |
| 3246 | $C_3H_7(n)$ | $CH_2OH$ |
| 3247 | $C_3H_7(n)$ | $CO_2H$ |
| 3248 | $C_3H_7(n)$ | $CH_2CO_2H$ |
| 3249 | $C_4H_9(n)$ | $C_2H_5$ |
| 3250 | $C_4H_9(n)$ | $C_3H_7(n)$ |
| 3251 | $C_4H_9(n)$ | (2-ethylphenyl) |
| 3252 | $C_4H_9(n)$ | (2,6-dimethylphenyl) |
| 3253 | $C_4H_9(n)$ | phenyl |
| 3254 | $C_4H_9(n)$ | benzyl |
| 3255 | $C_4H_9(n)$ | phenylethyl |
| 3256 | $C_4H_9(n)$ | $CH_2OH$ |
| 3257 | $C_4H_9(n)$ | $CO_2H$ |

TABLE LXXIV

| EX. # | $R^{222}$ | $R^{223}$ |
|---|---|---|
| 3258 | $C_3H_7(n)$ | O |
| 3259 | $C_3H_7(n)$ | S |
| 3260 | $C_3H_7(n)$ | NOH |
| 3261 | $C_3H_7(n)$ | $CHCO_2H$ |

TABLE LXXIV-continued

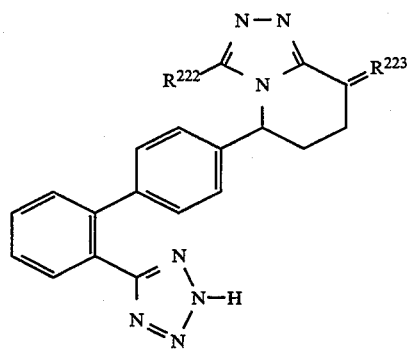

| EX. # | R²²² | R²²³ |
|---|---|---|
| 3262 | $C_3H_7(n)$ | $C(C_2H_5)CO_2H$ |
| 3263 | $C_3H_7(n)$ | $C(CH_2C_6H_5)CO_2H$ |
| 3264 | $C_3H_7(n)$ | $CHC_2H_5$ |
| 3265 | $C_4H_9(n)$ | S |
| 3266 | $C_4H_9(n)$ | $C(C_2H_5)CO_2H$ |
| 3267 | $C_4H_9(n)$ | $C(CH_2C_6H_5)CO_2H$ |
| 3268 | $C_4H_9(n)$ | $CHC_2H_5$ |

TABLE LXXV

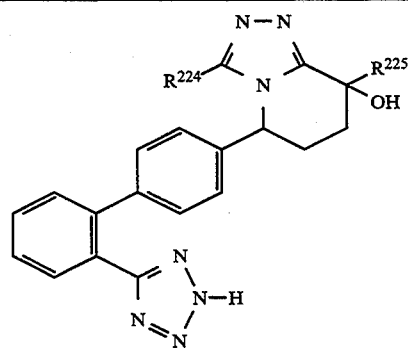

| EX. # | R²²⁴ | R²²⁵ |
|---|---|---|
| 3269 | $C_3H_7(n)$ | $C_2H_5$ |
| 3270 | $C_3H_7(n)$ | $C_3H_7(n)$ |
| 3271 | $C_4H_9(n)$ | $C_2H_5$ |
| 3272 | $C_4H_9(n)$ | $C_3H_7(n)$ |

TABLE LXXVI

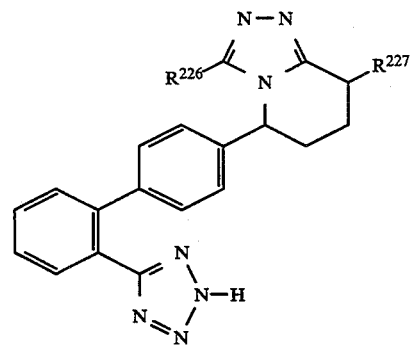

| EX. # | R²²⁶ | R²²⁷ |
|---|---|---|
| 3273 | $C_3H_7(n)$ | H |
| 3274 | $C_3H_7(n)$ | $C_2H_5$ |
| 3275 | $C_3H_7(n)$ | $C_3H_7(n)$ |
| 3276 | $C_3H_7(n)$ | (2-ethylphenyl) |
| 3277 | $C_3H_7(n)$ | (2,6-dimethylphenyl) |
| 3278 | $C_3H_7(n)$ | phenyl |
| 3279 | $C_3H_7(n)$ | benzyl |

TABLE LXXVI-continued

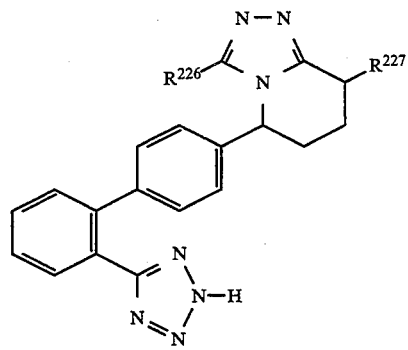

| EX. # | R²²⁶ | R²²⁷ |
|---|---|---|
| 3280 | $C_3H_7(n)$ | phenylethyl |
| 3281 | $C_3H_7(n)$ | $NH_2$ |
| 3282 | $C_3H_7(n)$ | OH |
| 3283 | $C_3H_7(n)$ | $CH_2OH$ |
| 3284 | $C_3H_7(n)$ | $CO_2H$ |
| 3285 | $C_4H_9(n)$ | $C_2H_5$ |
| 3286 | $C_4H_9(n)$ | $C_3H_7(n)$ |
| 3287 | $C_4H_9(n)$ | (2-ethylphenyl) |
| 3288 | $C_4H_9(n)$ | (2,6-dimethylphenyl) |
| 3289 | $C_4H_9(n)$ | phenyl |
| 3290 | $C_4H_9(n)$ | benzyl |
| 3291 | $C_4H_9(n)$ | phenylethyl |
| 3292 | $C_4H_9(n)$ | $CH_2OH$ |
| 3293 | $C_4H_9(n)$ | $CO_2H$ |

TABLE LXXVII

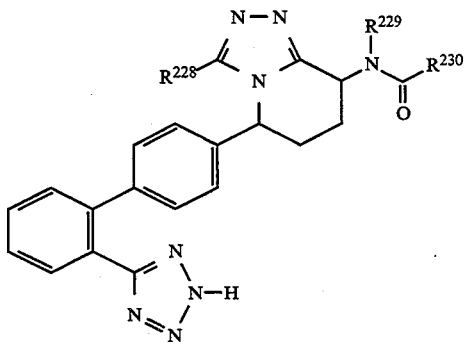

| EX. # | R²²⁸ | R²²⁹ | R²³⁰ |
|---|---|---|---|
| 3294 | $C_3H_7(n)$ | H | $CH_3$ |
| 3295 | $C_3H_7(n)$ | H | $C_2H_5$ |
| 3296 | $C_3H_7(n)$ | H | $C_6H_5$ |
| 3297 | $C_3H_7(n)$ | H | $C_6H_5CH_2$ |
| 3298 | $C_3H_7(n)$ | H | $CH_2CO_2H$ |
| 3299 | $C_3H_7(n)$ | H | $CH_2CH_2CO_2H$ |
| 3300 | $C_3H_7(n)$ | $CH_3$ | $CH_3$ |
| 3301 | $C_3H_7(n)$ | $CH_3$ | $C_2H_5$ |
| 3302 | $C_3H_7(n)$ | $CH_3$ | $C_6H_5$ |
| 3303 | $C_3H_7(n)$ | $CH_3$ | $C_6H_5CH_2$ |
| 3304 | $C_3H_7(n)$ | $CH_3$ | $CH_2CO_2H$ |
| 3305 | $C_3H_7(n)$ | $CH_3$ | $CH_2CH_2CO_2H$ |
| 3306 | $C_3H_7(n)$ | $C_2H_5$ | $CH_3$ |
| 3307 | $C_3H_7(n)$ | $C_2H_5$ | $C_2H_5$ |
| 3308 | $C_3H_7(n)$ | $C_2H_5$ | $C_6H_5$ |
| 3309 | $C_3H_7(n)$ | $C_2H_5$ | $C_6H_5CH_2$ |
| 3310 | $C_3H_7(n)$ | $C_2H_5$ | $CH_2CO_2H$ |
| 3311 | $C_3H_7(n)$ | $C_2H_5$ | $CH_2CH_2CO_2H$ |
| 3312 | $C_3H_7(n)$ | $C_3H_7(n)$ | $CH_3$ |
| 3313 | $C_3H_7(n)$ | $C_3H_7(n)$ | $C_2H_5$ |
| 3314 | $C_3H_7(n)$ | $C_3H_7(n)$ | $C_6H_5$ |
| 3315 | $C_3H_7(n)$ | $C_3H_7(n)$ | $C_6H_5CH_2$ |
| 3316 | $C_3H_7(n)$ | $C_3H_7(n)$ | $CH_2CO_2H$ |
| 3317 | $C_3H_7(n)$ | $C_3H_7(n)$ | $CH_2CH_2CO_2H$ |
| 3318 | $C_3H_7(n)$ | $CH_2C_6H_5$ | $CH_3$ |
| 3319 | $C_3H_7(n)$ | $CH_2C_6H_5$ | $C_2H_5$ |
| 3320 | $C_3H_7(n)$ | $CH_2C_6H_5$ | $C_6H_5$ |

TABLE LXXVII-continued

| EX. # | $R^{228}$ | $R^{229}$ | $R^{230}$ |
|---|---|---|---|
| 3321 | $C_3H_7(n)$ | $CH_2C_6H_5$ | $CH_2CO_2H$ |
| 3322 | $C_3H_7(n)$ | $CH_2C_6H_5$ | $CH_2CH_2CO_2H$ |
| 3323 | $C_4H_9(n)$ | H | $CH_3$ |
| 3324 | $C_4H_9(n)$ | H | $C_2H_5$ |
| 3325 | $C_4H_9(n)$ | H | $C_6H_5$ |
| 3326 | $C_4H_9(n)$ | H | $C_6H_5CH_2$ |
| 3327 | $C_4H_9(n)$ | H | $CH_2CO_2H$ |
| 3328 | $C_4H_9(n)$ | H | $CH_2CH_2CO_2H$ |
| 3329 | $C_4H_9(n)$ | $CH_3$ | $CH_3$ |
| 3330 | $C_4H_9(n)$ | $CH_3$ | $C_2H_5$ |
| 3331 | $C_4H_9(n)$ | $CH_3$ | $C_6H_5$ |
| 3332 | $C_4H_9(n)$ | $CH_3$ | $C_6H_5CH_2$ |
| 3333 | $C_4H_9(n)$ | $CH_3$ | $CH_2CO_2H$ |
| 3334 | $C_4H_9(n)$ | $CH_3$ | $CH_2CH_2CO_2H$ |
| 3335 | $C_4H_9(n)$ | $C_2H_5$ | $CH_3$ |
| 3336 | $C_4H_9(n)$ | $C_2H_5$ | $C_2H_5$ |
| 3337 | $C_4H_9(n)$ | $C_2H_5$ | $C_6H_5$ |
| 3338 | $C_4H_9(n)$ | $C_2H_5$ | $C_6H_5CH_2$ |
| 3339 | $C_4H_9(n)$ | $C_2H_5$ | $CH_2CO_2H$ |
| 3340 | $C_4H_9(n)$ | $C_2H_5$ | $CH_2CH_2CO_2H$ |
| 3341 | $C_4H_9(n)$ | $C_3H_7(n)$ | $CH_3$ |
| 3342 | $C_4H_9(n)$ | $C_3H_7(n)$ | $C_2H_5$ |
| 3343 | $C_4H_9(n)$ | $C_3H_7(n)$ | $C_6H_5$ |
| 3344 | $C_4H_9(n)$ | $C_3H_7(n)$ | $C_6H_5CH_2$ |
| 3345 | $C_4H_9(n)$ | $C_3H_7(n)$ | $CH_2CO_2H$ |
| 3346 | $C_4H_9(n)$ | $C_3H_7(n)$ | $CH_2CH_2CO_2H$ |
| 3347 | $C_4H_9(n)$ | $CH_2C_6H_5$ | $CH_3$ |
| 3348 | $C_4H_9(n)$ | $CH_2C_6H_5$ | $C_2H_5$ |
| 3349 | $C_4H_9(n)$ | $CH_2C_6H_5$ | $C_6H_5$ |
| 3350 | $C_4H_9(n)$ | $CH_2C_6H_5$ | $CH_2CO_2H$ |
| 3351 | $C_4H_9(n)$ | $CH_2C_6H_5$ | $CH_2CH_2CO_2H$ |

TABLE LXXVIII

| EX. # | $R^{231}$ | $R^{232}, R^{233}$ |
|---|---|---|
| 3352 | $C_3H_7(n)$ | O |
| 3353 | $C_3H_7(n)$ | H,H |
| 3354 | $C_3H_7(n)$ | $H,CH_3$ |
| 3355 | $C_3H_7(n)$ | $H,C_2H_5$ |
| 3356 | $C_3H_7(n)$ | $H,CH_2OH$ |
| 3357 | $C_3H_7(n)$ | $H,CO_2H$ |
| 3358 | $C_4H_9(n)$ | H,H |
| 3359 | $C_4H_9(n)$ | $H,CH_3$ |

TABLE LXXVIII-continued

| EX. # | $R^{231}$ | $R^{232}, R^{233}$ |
|---|---|---|
| 3360 | $C_4H_9(n)$ | $H,C_2H_5$ |
| 3361 | $C_4H_9(n)$ | $H,CH_2OH$ |
| 3362 | $C_4H_9(n)$ | $H,CO_2H$ |

TABLE LXXIX

| EX. # | $R^{234}$ | $R^{235}, R^{236}$ |
|---|---|---|
| 3363 | $C_3H_7(n)$ | O |
| 3364 | $C_3H_7(n)$ | H,H |
| 3365 | $C_3H_7(n)$ | $H,CH_3$ |
| 3366 | $C_3H_7(n)$ | $H,C_2H_5$ |
| 3367 | $C_3H_7(n)$ | $H,CH_2OH$ |
| 3368 | $C_3H_7(n)$ | $H,CO_2H$ |
| 3369 | $C_4H_9(n)$ | O |
| 3370 | $C_4H_9(n)$ | H,H |
| 3371 | $C_4H_9(n)$ | $H,CH_3$ |
| 3372 | $C_4H_9(n)$ | $H,C_2H_5$ |
| 3373 | $C_4H_9(n)$ | $H,CH_2OH$ |
| 3374 | $C_4H_9(n)$ | $H,CO_2H$ |

TABLE LXXX

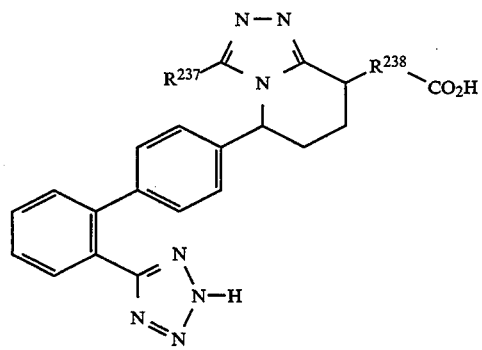

| EX. # | R²³⁷ | R²³⁸ |
|---|---|---|
| 3375 | $C_3H_7(n)$ | $CH_2$ |
| 3376 | $C_3H_7(n)$ | $CH(C_2H_5)$ |
| 3377 | $C_3H_7(n)$ | $CH(CH_2C_6H_5)$ |
| 3378 | $C_3H_7(n)$ | $CH_2CH_2$ |
| 3379 | $C_3H_7(n)$ | $CH(C_2H_5)CH_2$ |
| 3380 | $C_3H_7(n)$ | $CH(CH_2C_6H_5)CH_2$ |
| 3381 | $C_4H_9(n)$ | $CH(C_2H_5)$ |
| 3382 | $C_4H_9(n)$ | $CH(CH_2C_6H_5)$ |
| 3383 | $C_4H_9(n)$ | $CH_2CH_2$ |
| 3384 | $C_4H_9(n)$ | $CH(C_2H_5)CH_2$ |
| 3385 | $C_4H_9(n)$ | $CH(CH_2C_6H_5)CH_2$ |

TABLE LXXXI

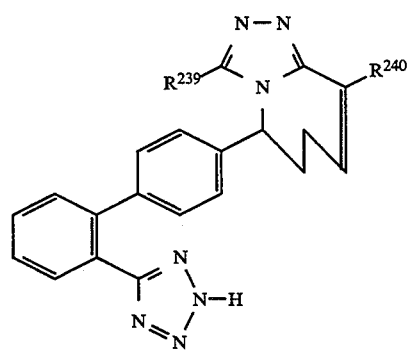

| EX. # | R²³⁹ | R²⁴⁰ |
|---|---|---|
| 3386 | $C_3H_7(n)$ | H |
| 3387 | $C_3H_7(n)$ | $C_2H_5$ |
| 3388 | $C_3H_7(n)$ | $C_3H_7(n)$ |
| 3389 | $C_3H_7(n)$ | (2-ethylphenyl) |
| 3390 | $C_3H_7(n)$ | (2,6-dimethylphenyl) |
| 3391 | $C_3H_7(n)$ | phenyl |
| 3392 | $C_3H_7(n)$ | benzyl |
| 3393 | $C_3H_7(n)$ | phenylethyl |
| 3394 | $C_3H_7(n)$ | $CH_2OH$ |
| 3395 | $C_3H_7(n)$ | $CO_2H$ |
| 3396 | $C_3H_7(n)$ | $CH_2CO_2H$ |
| 3397 | $C_4H_9(n)$ | $C_2H_5$ |
| 3398 | $C_4H_9(n)$ | $C_3H_7(n)$ |
| 3399 | $C_4H_9(n)$ | (2-ethylphenyl) |
| 3400 | $C_4H_9(n)$ | (2,6-dimethylphenyl) |
| 3401 | $C_4H_9(n)$ | phenyl |
| 3402 | $C_4H_9(n)$ | benzyl |
| 3403 | $C_4H_9(n)$ | phenylethyl |
| 3404 | $C_4H_9(n)$ | $CH_2OH$ |
| 3405 | $C_4H_9(n)$ | $CO_2H$ |
| 3406 | $C_4H_9(n)$ | $CH_2CO_2H$ |

TABLE LXXXII

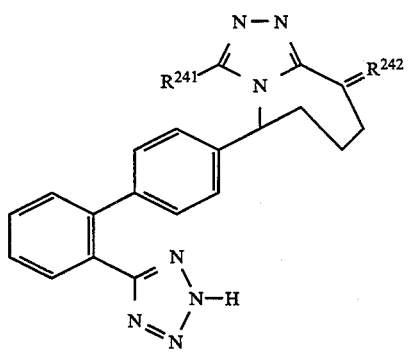

| EX. # | R²⁴¹ | R²⁴² |
|---|---|---|
| 3407 | $C_3H_7(n)$ | O |
| 3408 | $C_3H_7(n)$ | S |
| 3409 | $C_3H_7(n)$ | NOH |
| 3410 | $C_3H_7(n)$ | $CHCO_2H$ |
| 3411 | $C_3H_7(n)$ | $C(C_2H_5)CO_2H$ |
| 3412 | $C_3H_7(n)$ | $C(CH_2C_6H_5)CO_2H$ |
| 3413 | $C_3H_7(n)$ | $CHC_2H_5$ |
| 3414 | $C_4H_9(n)$ | O |
| 3415 | $C_4H_9(n)$ | S |
| 3416 | $C_4H_9(n)$ | NOH |
| 3417 | $C_4H_9(n)$ | $CHCO_2H$ |
| 3418 | $C_4H_9(n)$ | $C(C_2H_5)CO_2H$ |
| 3419 | $C_4H_9(n)$ | $C(CH_2C_6H_5)CO_2H$ |
| 3420 | $C_4H_9(n)$ | $CHC_2H_5$ |

TABLE LXXXIII

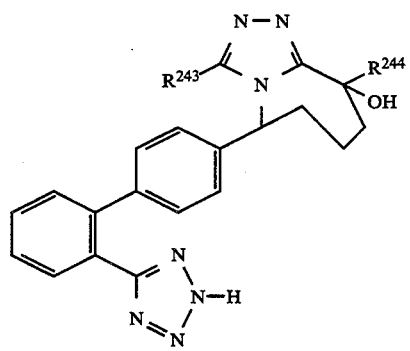

| EX. # | R²⁴³ | R²⁴⁴ |
|---|---|---|
| 3421 | $C_3H_7(n)$ | $C_2H_5$ |
| 3422 | $C_3H_7(n)$ | $C_3H_7(n)$ |
| 3423 | $C_4H_9(n)$ | $C_2H_5$ |
| 3424 | $C_4H_9(n)$ | $C_3H_7(n)$ |

TABLE LXXXIV

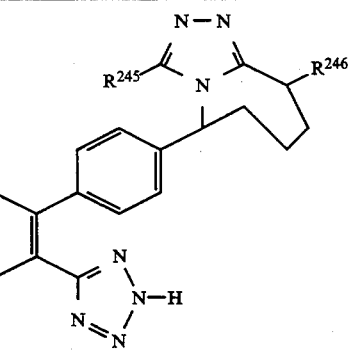

| EX. # | R245 | R246 |
|---|---|---|
| 3425 | C3H7(n) | H |
| 3426 | C3H7(n) | C2H5 |
| 3427 | C3H7(n) | C3H7(n) |
| 3428 | C3H7(n) | (2-ethylphenyl) |
| 3429 | C3H7(n) | (2,6-dimethylphenyl) |
| 3430 | C3H7(n) | phenyl |
| 3431 | C3H7(n) | benzyl |
| 3432 | C3H7(n) | phenylethyl |
| 3433 | C3H7(n) | NH2 |
| 3434 | C3H7(n) | OH |
| 3435 | C3H7(n) | CH2OH |
| 3436 | C3H7(n) | CO2H |
| 3437 | C4H9(n) | H |
| 3438 | C4H9(n) | C2H5 |
| 3439 | C4H9(n) | C3H7(n) |
| 3440 | C4H9(n) | (2-ethylphenyl) |
| 3441 | C4H9(n) | (2,6-dimethylphenyl) |
| 3442 | C4H9(n) | phenyl |
| 3443 | C4H9(n) | benzyl |
| 3444 | C4H9(n) | phenylethyl |
| 3445 | C4H9(n) | NH2 |
| 3446 | C4H9(n) | OH |
| 3447 | C4H9(n) | CH2OH |
| 3448 | C4H9(n) | CO2H |

TABLE LXXXV

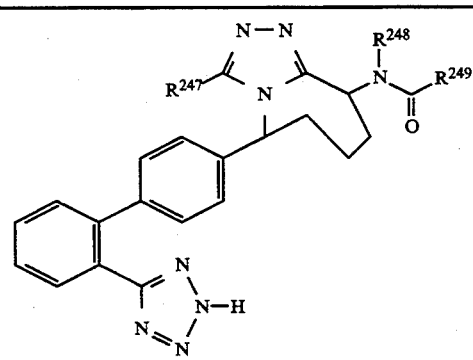

| EX. # | R247 | R248 | R249 |
|---|---|---|---|
| 3449 | C3H7(n) | H | CH3 |
| 3450 | C3H7(n) | H | C2H5 |
| 3451 | C3H7(n) | H | C6H5 |
| 3452 | C3H7(n) | H | C6H5CH2 |
| 3453 | C3H7(n) | H | CH2CO2H |
| 3454 | C3H7(n) | H | CH2CH2CO2H |
| 3455 | C3H7(n) | CH3 | CH3 |
| 3456 | C3H7(n) | CH3 | C2H5 |
| 3457 | C3H7(n) | CH3 | C6H5 |
| 3458 | C3H7(n) | CH3 | C6H5CH2 |
| 3459 | C3H7(n) | CH3 | CH2CO2H |
| 3460 | C3H7(n) | CH3 | CH2CH2CO2H |
| 3461 | C3H7(n) | C2H5 | CH3 |
| 3462 | C3H7(n) | C2H5 | C2H5 |
| 3463 | C3H7(n) | C2H5 | C6H5 |
| 3464 | C3H7(n) | C2H5 | C6H5CH2 |
| 3465 | C3H7(n) | C2H5 | CH2CO2H |

TABLE LXXXV-continued

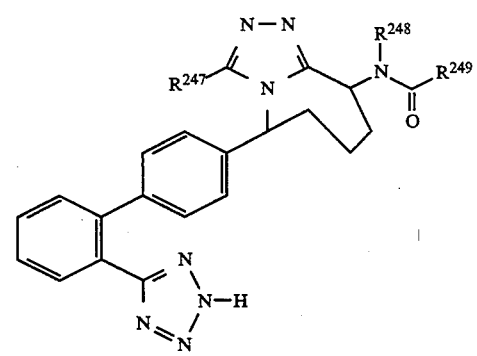

| EX. # | R247 | R248 | R249 |
|---|---|---|---|
| 3466 | C3H7(n) | C2H5 | CH2CH2CO2H |
| 3467 | C3H7(n) | C3H7(n) | CH3 |
| 3468 | C3H7(n) | C3H7(n) | C2H5 |
| 3469 | C3H7(n) | C3H7(n) | C6H5 |
| 3470 | C3H7(n) | C3H7(n) | C6H5CH2 |
| 3471 | C3H7(n) | C3H7(n) | CH2CO2H |
| 3472 | C3H7(n) | C3H7(n) | CH2CH2CO2H |
| 3473 | C3H7(n) | CH2C6H5 | CH3 |
| 3474 | C3H7(n) | CH2C6H5 | C2H5 |
| 3475 | C3H7(n) | CH2C6H5 | C6H5 |
| 3476 | C3H7(n) | CH2C6H5 | CH2CO2H |
| 3477 | C3H7(n) | CH2C6H5 | CH2CH2CO2H |
| 3478 | C4H9(n) | H | CH3 |
| 3479 | C4H9(n) | H | C2H5 |
| 3480 | C4H9(n) | H | C6H5 |
| 3481 | C4H9(n) | H | C6H5CH2 |
| 3482 | C4H9(n) | H | CH2CO2H |
| 3483 | C4H9(n) | H | CH2CH2CO2H |
| 3484 | C4H9(n) | CH3 | CH3 |
| 3485 | C4H9(n) | CH3 | C2H5 |
| 3486 | C4H9(n) | CH3 | C6H5 |
| 3487 | C4H9(n) | CH3 | C6H5CH2 |
| 3488 | C4H9(n) | CH3 | CH2CO2H |
| 3489 | C4H9(n) | CH3 | CH2CH2CO2H |
| 3490 | C4H9(n) | C2H5 | CH3 |
| 3491 | C4H9(n) | C2H5 | C2H5 |
| 3492 | C4H9(n) | C2H5 | C6H5 |
| 3493 | C4H9(n) | C2H5 | C6H5CH2 |
| 3494 | C4H9(n) | C2H5 | CH2CO2H |
| 3495 | C4H9(n) | C2H5 | CH2CH2CO2H |
| 3496 | C4H9(n) | C3H7(n) | CH3 |
| 3497 | C4H9(n) | C3H7(n) | C2H5 |
| 3498 | C4H9(n) | C3H7(n) | C6H5 |
| 3499 | C4H9(n) | C3H7(n) | C6H5CH2 |
| 3500 | C4H9(n) | C3H7(n) | CH2CO2H |
| 3501 | C4H9(n) | C3H7(n) | CH2CH2CO2H |
| 3502 | C4H9(n) | CH2C6H5 | CH3 |
| 3503 | C4H9(n) | CH2C6H5 | C2H5 |
| 3504 | C4H9(n) | CH2C6H5 | C6H5 |
| 3505 | C4H9(n) | CH2C6H5 | CH2CO2H |
| 3506 | C4H9(n) | CH2C6H5 | CH2CH2CO2H |

TABLE LXXXVI

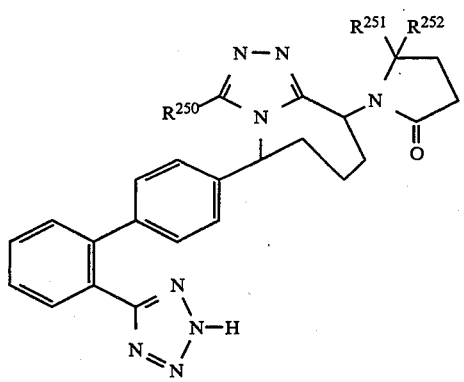

| EX. # | R²⁵⁰ | R²⁵¹, R²⁵² |
|---|---|---|
| 3507 | C₃H₇(n) | O |
| 3508 | C₃H₇(n) | H,H |
| 3509 | C₃H₇(n) | H,CH₃ |
| 3510 | C₃H₇(n) | H,C₂H₅ |
| 3511 | C₃H₇(n) | H,CH₂OH |
| 3512 | C₃H₇(n) | H,CO₂H |
| 3513 | C₄H₉(n) | O |
| 3514 | C₄H₉(n) | H,H |
| 3515 | C₄H₉(n) | H,CH₃ |
| 3516 | C₄H₉(n) | H,C₂H₅ |
| 3517 | C₄H₉(n) | H,CH₂OH |
| 3518 | C₄H₉(n) | H,CO₂H |

TABLE LXXXVII

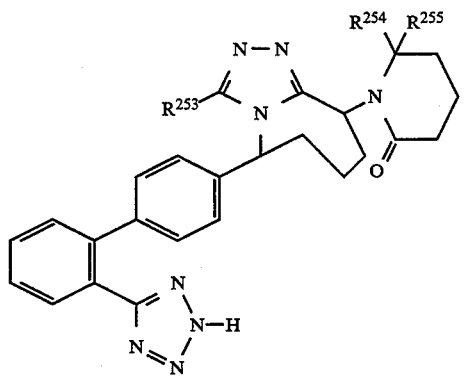

| EX. # | R²⁵³ | R²⁵⁴, R²⁵⁵ |
|---|---|---|
| 3519 | C₃H₇(n) | O |
| 3520 | C₃H₇(n) | H,H |
| 3521 | C₃H₇(n) | H,CH₃ |
| 3522 | C₃H₇(n) | H,C₂H₅ |
| 3523 | C₃H₇(n) | H,CH₂OH |
| 3524 | C₃H₇(n) | H,CO₂H |
| 3525 | C₄H₉(n) | O |
| 3526 | C₄H₉(n) | H,H |
| 3527 | C₄H₉(n) | H,CH₃ |
| 3528 | C₄H₉(n) | H,C₂H₅ |
| 3529 | C₄H₉(n) | H,CH₂OH |
| 3530 | C₄H₉(n) | H,CO₂H |

TABLE LXXXVIII

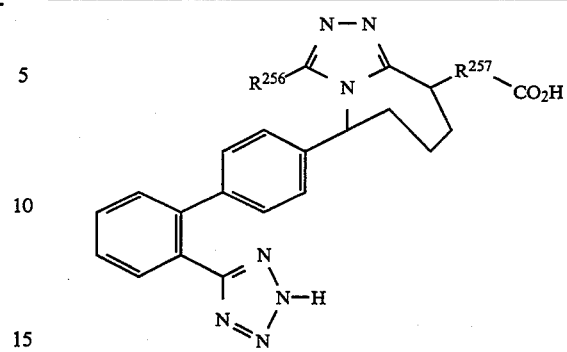

| EX. # | R²⁵⁶ | R²⁵⁷ |
|---|---|---|
| 3531 | C₃H₇(n) | CH₂ |
| 3532 | C₃H₇(n) | CH(C₂H₅) |
| 3533 | C₃H₇(n) | CH(CH₂C₆H₅) |
| 3534 | C₃H₇(n) | CH₂CH₂ |
| 3535 | C₃H₇(n) | CH(C₂H₅)CH₂ |
| 3536 | C₃H₇(n) | CH(CH₂C₆H₅)CH₂ |
| 3537 | C₄H₉(n) | CH₂ |
| 3538 | C₄H₉(n) | CH(C₂H₅) |
| 3539 | C₄H₉(n) | CH(CH₂C₆H₅) |
| 3540 | C₄H₉(n) | CH₂CH₂ |
| 3541 | C₄H₉(n) | CH(C₂H₅)CH₂ |
| 3542 | C₄H₉(n) | CH(CH₂C₆H₅)CH₂ |

TABLE LXXXIX

| EX. # | R²⁵⁸ | R²⁵⁹ |
|---|---|---|
| 3543 | C₃H₇(n) | H |
| 3544 | C₃H₇(n) | C₂H₅ |
| 3545 | C₃H₇(n) | C₃H₇(n) |
| 3546 | C₃H₇(n) | (2-ethylphenyl) |
| 3547 | C₃H₇(n) | (2,6-dimethylphenyl) |
| 3548 | C₃H₇(n) | phenyl |
| 3549 | C₃H₇(n) | benzyl |
| 3550 | C₃H₇(n) | phenylethyl |
| 3551 | C₃H₇(n) | CH₂OH |
| 3552 | C₃H₇(n) | CO₂H |
| 3553 | C₃H₇(n) | CH₂CO₂H |
| 3554 | C₄H₉(n) | H |
| 3555 | C₄H₉(n) | C₂H₅ |
| 3556 | C₄H₉(n) | C₃H₇(n) |
| 3557 | C₄H₉(n) | (2-ethylphenyl) |
| 3558 | C₄H₉(n) | (2,6-dimethylphenyl) |
| 3559 | C₄H₉(n) | phenyl |
| 3560 | C₄H₉(n) | benzyl |
| 3561 | C₄H₉(n) | phenylethyl |
| 3562 | C₄H₉(n) | CH₂OH |
| 3563 | C₄H₉(n) | CO₂H |
| 3564 | C₄H₉(n) | CH₂CO₂H |

TABLE XC

| EX. # | $R^{260}$ | $R^{261}$ |
|---|---|---|
| 3565 | $C_3H_7(n)$ | O |
| 3566 | $C_3H_7(n)$ | S |
| 3567 | $C_3H_7(n)$ | NOH |
| 3568 | $C_3H_7(n)$ | $CHCO_2H$ |
| 3569 | $C_3H_7(n)$ | $C(C_2H_5)CO_2H$ |
| 3570 | $C_3H_7(n)$ | $C(CH_2C_6H_5)CO_2H$ |
| 3571 | $C_3H_7(n)$ | $CHC_2H_5$ |
| 3572 | $C_4H_9(n)$ | O |
| 3573 | $C_4H_9(n)$ | S |
| 3574 | $C_4H_9(n)$ | NOH |
| 3575 | $C_4H_9(n)$ | $CHCO_2H$ |
| 3576 | $C_4H_9(n)$ | $C(C_2H_5)CO_2H$ |
| 3577 | $C_4H_9(n)$ | $C(CH_2C_6H_5)CO_2H$ |
| 3578 | $C_4H_9(n)$ | $CHC_2H_5$ |

TABLE XCI

| EX. # | $R^{262}$ | $R^{263}$ |
|---|---|---|
| 3579 | $C_3H_7(n)$ | $C_2H_5$ |
| 3580 | $C_3H_7(n)$ | $C_3H_7(n)$ |
| 3581 | $C_4H_9(n)$ | $C_2H_5$ |
| 3582 | $C_4H_9(n)$ | $C_3H_7(n)$ |

TABLE XCII

| EX. # | $R^{264}$ | $R^{265}$ |
|---|---|---|
| 3583 | $C_3H_7(n)$ | H |
| 3584 | $C_3H_7(n)$ | $C_2H_5$ |
| 3585 | $C_3H_7(n)$ | $C_3H_7(n)$ |
| 3586 | $C_3H_7(n)$ | (2-ethylphenyl) |
| 3587 | $C_3H_7(n)$ | (2,6-dimethylphenyl) |
| 3588 | $C_3H_7(n)$ | phenyl |
| 3589 | $C_3H_7(n)$ | benzyl |
| 3590 | $C_3H_7(n)$ | phenylethyl |
| 3591 | $C_3H_7(n)$ | $NH_2$ |
| 3592 | $C_3H_7(n)$ | OH |
| 3593 | $C_3H_7(n)$ | $CH_2OH$ |
| 3594 | $C_3H_7(n)$ | $CO_2H$ |
| 3595 | $C_4H_9(n)$ | H |
| 3596 | $C_4H_9(n)$ | $C_2H_5$ |
| 3597 | $C_4H_9(n)$ | $C_3H_7(n)$ |
| 3598 | $C_4H_9(n)$ | (2-ethylphenyl) |
| 3599 | $C_4H_9(n)$ | (2,6-dimethylphenyl) |
| 3600 | $C_4H_9(n)$ | phenyl |
| 3601 | $C_4H_9(n)$ | benzyl |
| 3602 | $C_4H_9(n)$ | phenylethyl |
| 3603 | $C_4H_9(n)$ | $NH_2$ |
| 3604 | $C_4H_9(n)$ | OH |
| 3605 | $C_4H_9(n)$ | $CH_2OH$ |
| 3606 | $C_4H_9(n)$ | $CO_2H$ |

TABLE XCIII

| EX. # | $R^{266}$ | $R^{267}$ | $R^{268}$ |
|---|---|---|---|
| 3607 | $C_3H_7(n)$ | H | $CH_3$ |
| 3608 | $C_3H_7(n)$ | H | $C_2H_5$ |
| 3609 | $C_3H_7(n)$ | H | $C_6H_5$ |
| 3610 | $C_3H_7(n)$ | H | $C_6H_5CH_2$ |
| 3611 | $C_3H_7(n)$ | H | $CH_2CO_2H$ |
| 3612 | $C_3H_7(n)$ | H | $CH_2CH_2CO_2H$ |
| 3613 | $C_3H_7(n)$ | $CH_3$ | $CH_3$ |
| 3614 | $C_3H_7(n)$ | $CH_3$ | $C_2H_5$ |
| 3615 | $C_3H_7(n)$ | $CH_3$ | $C_6H_5$ |
| 3616 | $C_3H_7(n)$ | $CH_3$ | $C_6H_5CH_2$ |
| 3617 | $C_3H_7(n)$ | $CH_3$ | $CH_2CO_2H$ |
| 3618 | $C_3H_7(n)$ | $CH_3$ | $CH_2CH_2CO_2H$ |
| 3619 | $C_3H_7(n)$ | $C_2H_5$ | $CH_3$ |
| 3620 | $C_3H_7(n)$ | $C_2H_5$ | $C_2H_5$ |
| 3621 | $C_3H_7(n)$ | $C_2H_5$ | $C_6H_5$ |
| 3622 | $C_3H_7(n)$ | $C_2H_5$ | $C_6H_5CH_2$ |
| 3623 | $C_3H_7(n)$ | $C_2H_5$ | $CH_2CO_2H$ |

TABLE XCIII-continued

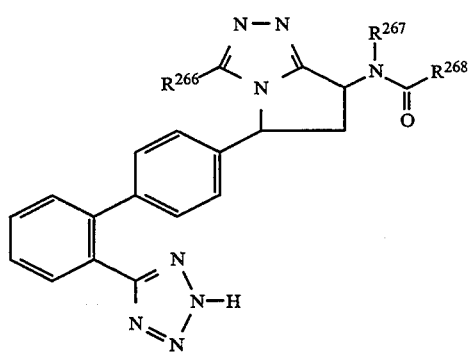

| EX. # | $R^{266}$ | $R^{267}$ | $R^{268}$ |
|---|---|---|---|
| 3624 | $C_3H_7(n)$ | $C_2H_5$ | $CH_2CH_2CO_2H$ |
| 3625 | $C_3H_7(n)$ | $C_3H_7(n)$ | $CH_3$ |
| 3626 | $C_3H_7(n)$ | $C_3H_7(n)$ | $C_2H_5$ |
| 3627 | $C_3H_7(n)$ | $C_3H_7(n)$ | $C_6H_5$ |
| 3628 | $C_3H_7(n)$ | $C_3H_7(n)$ | $C_6H_5CH_2$ |
| 3629 | $C_3H_7(n)$ | $C_3H_7(n)$ | $CH_2CO_2H$ |
| 3630 | $C_3H_7(n)$ | $C_3H_7(n)$ | $CH_2CH_2CO_2H$ |
| 3631 | $C_3H_7(n)$ | $CH_2C_6H_5$ | $CH_3$ |
| 3632 | $C_3H_7(n)$ | $CH_2C_6H_5$ | $C_2H_5$ |
| 3633 | $C_3H_7(n)$ | $CH_2C_6H_5$ | $C_6H_5$ |
| 3634 | $C_3H_7(n)$ | $CH_2C_6H_5$ | $CH_2CO_2H$ |
| 3635 | $C_3H_7(n)$ | $CH_2C_6H_5$ | $CH_2CH_2CO_2H$ |
| 3636 | $C_4H_9(n)$ | H | $CH_3$ |
| 3637 | $C_4H_9(n)$ | H | $C_2H_5$ |
| 3638 | $C_4H_9(n)$ | H | $C_6H_5$ |
| 3639 | $C_4H_9(n)$ | H | $C_6H_5CH_2$ |
| 3640 | $C_4H_9(n)$ | H | $CH_2CO_2H$ |
| 3641 | $C_4H_9(n)$ | H | $CH_2CH_2CO_2H$ |
| 3642 | $C_4H_9(n)$ | $CH_3$ | $CH_3$ |
| 3643 | $C_4H_9(n)$ | $CH_3$ | $C_2H_5$ |
| 3644 | $C_4H_9(n)$ | $CH_3$ | $C_6H_5$ |
| 3645 | $C_4H_9(n)$ | $CH_3$ | $C_6H_5CH_2$ |
| 3646 | $C_4H_9(n)$ | $CH_3$ | $CH_2CO_2H$ |
| 3647 | $C_4H_9(n)$ | $CH_3$ | $CH_2CH_2CO_2H$ |
| 3648 | $C_4H_9(n)$ | $C_2H_5$ | $CH_3$ |
| 3649 | $C_4H_9(n)$ | $C_2H_5$ | $C_2H_5$ |
| 3650 | $C_4H_9(n)$ | $C_2H_5$ | $C_6H_5$ |
| 3651 | $C_4H_9(n)$ | $C_2H_5$ | $C_6H_5CH_2$ |
| 3652 | $C_4H_9(n)$ | $C_2H_5$ | $CH_2CO_2H$ |
| 3653 | $C_4H_9(n)$ | $C_2H_5$ | $CH_2CH_2CO_2H$ |
| 3654 | $C_4H_9(n)$ | $C_3H_7(n)$ | $CH_3$ |
| 3655 | $C_4H_9(n)$ | $C_3H_7(n)$ | $C_2H_5$ |
| 3656 | $C_4H_9(n)$ | $C_3H_7(n)$ | $C_6H_5$ |
| 3657 | $C_4H_9(n)$ | $C_3H_7(n)$ | $C_6H_5CH_2$ |
| 3658 | $C_4H_9(n)$ | $C_3H_7(n)$ | $CH_2CO_2H$ |
| 3659 | $C_4H_9(n)$ | $C_3H_7(n)$ | $CH_2CH_2CO_2H$ |
| 3660 | $C_4H_9(n)$ | $CH_2C_6H_5$ | $CH_3$ |
| 3661 | $C_4H_9(n)$ | $CH_2C_6H_5$ | $C_2H_5$ |
| 3662 | $C_4H_9(n)$ | $CH_2C_6H_5$ | $C_6H_5$ |
| 3663 | $C_4H_9(n)$ | $CH_2C_6H_5$ | $CH_2CO_2H$ |
| 3664 | $C_4H_9(n)$ | $CH_2C_6H_5$ | $CH_2CH_2CO_2H$ |

TABLE XCIV

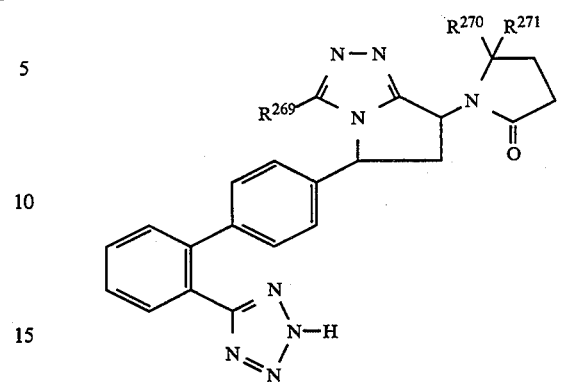

| EX. # | $R^{269}$ | $R^{270}, R^{271}$ |
|---|---|---|
| 3665 | $C_3H_7(n)$ | O |
| 3666 | $C_3H_7(n)$ | H,H |
| 3667 | $C_3H_7(n)$ | $H,CH_3$ |
| 3668 | $C_3H_7(n)$ | $H,C_2H_5$ |
| 3669 | $C_3H_7(n)$ | $H,CH_2OH$ |
| 3670 | $C_3H_7(n)$ | $H,CO_2H$ |
| 3671 | $C_4H_9(n)$ | O |
| 3672 | $C_4H_9(n)$ | H,H |
| 3673 | $C_4H_9(n)$ | $H,CH_3$ |
| 3674 | $C_4H_9(n)$ | $H,C_2H_5$ |
| 3675 | $C_4H_9(n)$ | $H,CH_2OH$ |
| 3676 | $C_4H_9(n)$ | $H,CO_2H$ |

TABLE XCV

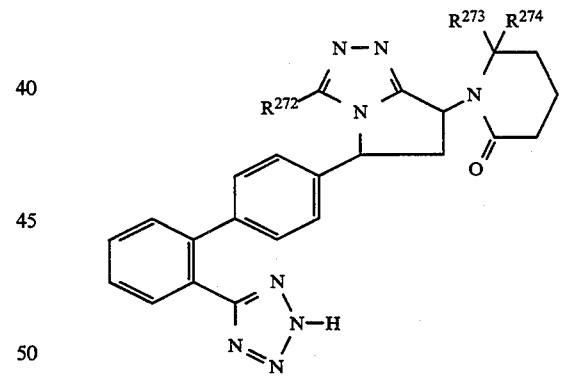

| EX. # | $R^{272}$ | $R^{273}, R^{274}$ |
|---|---|---|
| 3677 | $C_3H_7(n)$ | O |
| 3678 | $C_3H_7(n)$ | H,H |
| 3679 | $C_3H_7(n)$ | $H,CH_3$ |
| 3680 | $C_3H_7(n)$ | $H,C_2H_5$ |
| 3681 | $C_3H_7(n)$ | $H,CH_2OH$ |
| 3682 | $C_3H_7(n)$ | $H,CO_2H$ |
| 3683 | $C_4H_9(n)$ | O |
| 3684 | $C_4H_9(n)$ | H,H |
| 3685 | $C_4H_9(n)$ | $H,CH_3$ |
| 3686 | $C_4H_9(n)$ | $H,C_2H_5$ |
| 3687 | $C_4H_9(n)$ | $H,CH_2OH$ |
| 3688 | $C_4H_9(n)$ | $H,CO_2H$ |

TABLE XCVI

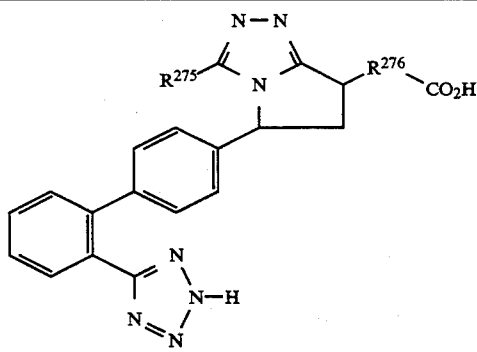

| EX. # | R²⁷⁵ | R²⁷⁶ |
|---|---|---|
| 3689 | C₃H₇(n) | CH₂ |
| 3690 | C₃H₇(n) | CH(C₂H₅) |
| 3691 | C₃H₇(n) | CH(CH₂C₆H₅) |
| 3692 | C₃H₇(n) | CH₂CH₂ |
| 3693 | C₃H₇(n) | CH(C₂H₅)CH₂ |
| 3694 | C₃H₇(n) | CH(CH₂C₆H₅)CH₂ |
| 3695 | C₄H₉(n) | CH₂ |
| 3696 | C₄H₉(n) | CH(C₂H₅) |
| 3697 | C₄H₉(n) | CH(CH₂C₆H₅) |
| 3698 | C₄H₉(n) | CH₂CH₂ |
| 3699 | C₄H₉(n) | CH(C₂H₅)CH₂ |
| 3700 | C₄H₉(n) | CH(CH₂C₆H₅)CH₂ |

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mgCl₂, 2 mM EDTA, 0.5% bovine serum albumin, 50 mM Tris-HCl, pH 7.5 and $^{125}$I-AII (approximately 10⁵ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labeled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC₅₀) of the tested AII antagonist which gives 50% displacement of the total specifically bound $^{125}$I-AII from the high affinity AII receptor. Binding data were analyzed by a nonlinear least-squares curve fitting program. Results are reported in Table XCVII.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between movable and fixed ends of a stainless steel wire with the movable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 NaHCO₃, 15 KCl, 1.2 NaH₂PO₄, 1.2 MgSO₄, 2.5 CaCl₂, and 11.4 glucose. The preparations were equilibrated for one hour before approximately one gram of passive tension was placed on the rings. Angiotensin II concentration-response curves were then recorded (3×10⁻¹⁰ to 1×10⁻⁵M). Each concentration of AII was allowed to elicit its maximal contraction, and then AII was washed out repeatedly for 30 minutes before rechallenging with a higher concentration of AII. Aorta rings were exposed to the test antagonist at 10⁻⁵M for 5 minutes before challenging with AII. Adjacent segments of the same aorta ring were used for all concentration-response curves in the presence or absence of the test antagonist. The effectiveness of the test compound was expressed in terms of pA₂ values and were calculated according to H. O. Schild [*Br. J. Pharmacol. Chemother.*, 2,189–206 (1947)]. The pA₂ value is the concentration of the antagonist which increases the IC50 value for AII by a factor of two. Each test antagonist was evaluated in aorta rings from two rabbits. Results are reported in Table XCVII.

TABLE XCVII

In Vitro Angiotensin II
Activity of Compounds of the Invention

| Test Compound Example # | [1]Assay A IC₅₀ (nM) | [2]Assay B pA₂ |
|---|---|---|
| 1 | 190 | 6.40/6.27 |
| 2 | 2100 | 5.84/6.58 |
| 3 | 270 | 7.27/6.65 |
| 4 | 51 | 7.65/7.84 |
| 5 | 60 | 7.86/8.15 |
| 6 | 2800 | NA |
| 7 | 15000 | NA |
| 8 | 27 | NA |
| 9 | 44 | 7.15/7.24 |
| 10 | 330 | NA |
| 11 | 120 | NA |
| 12 | 110 | 6.66/7.05 |
| 13 | 23 | 7.00/6.86 |
| 14 | 120 | 6.48/6.26 |
| 15 | 160 | 6.46/6.73 |
| 16 | 440 | 8.11/7.79 |
| 17 | 41 | 7.79/7.27 |
| 18 | 200 | NA |
| 19 | 67 | 7.15/6.85 |
| 20 | 240 | 6.89/6.85 |

TABLE XCVII-continued

In Vitro Angiotensin II
Activity of Compounds of the Invention

| Test Compound Example # | [1]Assay A IC$_{50}$ (nM) | [2]Assay B pA$_2$ |
|---|---|---|
| 21 | 66 | 6.98/6.13 |

[1]Assay A: Angiotensin II Binding Activity
[2]Assay B: In Vitro Vascular Smooth Muscle Response
* NA = Not Assayed Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

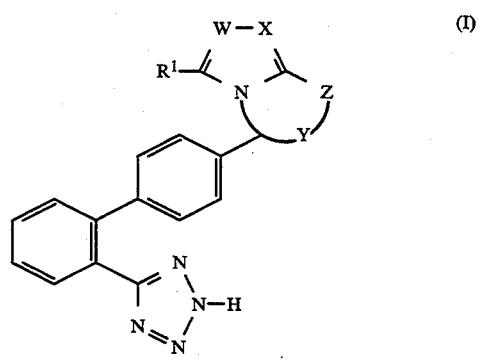

(I)

wherein W is N or CH$_2$;
wherein X is N or CR$^2$;
wherein Y is (CH$_2$)$_n$ and n is 1 to 3;
wherein Z is C=R$^3$ or CR$^4$R$^5$, or
wherein Y and Z together forms —CR$^7$=CR$^6$—, —CH$_2$—CR$^7$=CR$^6$— or —CH$_2$—CH$_2$—CR$^7$=CR$^6$—;
wherein R$^1$ is alkyl;
wherein R$^2$ is selected from hydrido, halo, alkyl and aryl;
wherein R$^3$ is selected from oxygen, sulfur, hydroxyamino, alkylidene, alkylcarboxyalkylidene and carboxyalkylidene;
wherein R$^4$ is selected from hydrido, alkyl, amino, hydroxyalkyl, carboxyl, carboxyalkyl, aryl, aralkyl, alkylcarboxyalkyl, hydroxyl, carboxyaralkyl, phthalimidyl, aralkoxy,

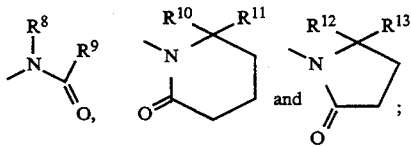

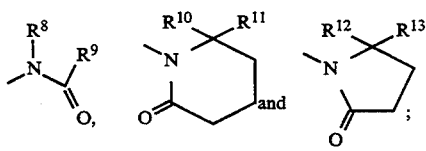

aralkoxy, wherein $R^5$ is hydrido or hydroxyl;

wherein $R^6$ is selected from hydrido, alkyl, hydroxyalkyl, carboxyalkyl, carboxyl, alkylcarboxyalkyl, aryl and aralkyl;

wherein $R^7$ is hydrido or halo;

wherein $R^8$ is selected from hydrido, alkyl and aralkyl;

wherein $R^9$ is selected from alkyl, aryl, aralkyl, carboxyl, hydrazidylcarboalkyl and carboxyalkyl;

wherein $R^{10}$ is hydrido or alkyl;

wherein $R^{11}$ is selected from hydrido, alkyl, hydroxyalkyl and carboxyl, or wherein $R^{10}$ and $R^{11}$ taken together is =O;

wherein $R^{12}$ is hydrido or alkyl; and wherein $R^{13}$ is selected from hydrido, alkyl, hydroxyalkyl and carboxyl, or wherein $R^{12}$ and $R^{13}$ taken together is =O;

or a pharmaceutically suitable salt or tautomer thereof.

2. The compound of claim 1 wherein $R^4$ is selected from aryl or aralkyl only when $R^2$, if present, is hydrido or halo;

wherein $R^4$ is alkyl when $R^5$ is hydroxyl;

wherein $R^8$ is aralkyl when $R^2$, if present is hydrido or halo;

wherein $R^8$ and $R^9$ are not both aralkyl; and wherein $R^{11}$ and $R^{13}$ is alkyl when $R^2$ is aryl or halo;

or a pharmaceutically suitable salt thereof.

3. The compound of claim 1 wherein $R^1$ is n-propyl or n-butyl;

wherein $R^2$ is selected from hydrido, chloro, methyl, ethyl, n-propyl, n-butyl, 2-ethylphenyl and 2,6-dimethylphenyl;

wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;

wherein $R^4$ is selected from hydrido, ethyl, n-propyl, hydroxymethyl, hydroxyl, t-butoxycarbonylmethyl, amino, t-butoxycarbonylpropyl, $-(CH_2)_3CO_2H$, $-CH_2CO_2H$, $-(CH_2)_2CO_2H$, $-CH(CH_2C_6H_5)CO_2H$, $-CH(C_2H_5)CH_2CO_2H$, $-CH(CH_2C_6H_5)CH_2CO_2H$, phenyl, 2-ethylphenyl, 2,6-dimethylphenyl, phenethyl, benzyl, phenylmethoxy,

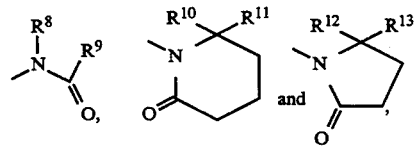

provided $R^4$ is selected from phenyl, benzyl and phenethyl only when $R^2$, if present, is hydrido or chloro;

wherein $R^5$ is hydrido or hydroxyl, provided that when $R^5$ is hydroxyl, $R^4$ is ethyl or n-propyl;

wherein $R^6$ is selected from hydrido, ethyl, n-propyl, hydroxymethyl, $-(CH_2)_3CO_2H$, $-CH_2CO_2H$, $-(CH_2)_2CO_2H$, benzyl, t-butoxycarbonylmethyl, t-butoxycarbonylpropyl, $-CH(CH_2C_6H_5)CO_2H$, $-CH(C_2H_5)CH_2CO_2H$, $-CH(CH_2C_6H_5)CH_2CO_2H$, phenyl, 2-ethylphenyl, 2,6-dimethylphenyl and phenethyl;

wherein $R^7$ is selected from hydrido, bromo, fluoro, chloro and iodo;

wherein $R^8$ is selected from hydrido, methyl, ethyl, propyl and benzyl, provided that $R^8$ is benzyl where $R^2$, if present, is hydrido or chloro;

wherein $R^9$ is selected from methyl, ethyl, phenyl, benzyl, $-(CH_2)_2CONHNH_2$, $-CH_2CO_2H$ and $-(CH_2)_2CO_2H$, provided that $R^9$ and $R^8$ are not both benzyl;

wherein $R^{10}$ is hydrido or methyl;

wherein $R^{11}$ is selected from hydrido, methyl, ethyl, hydroxymethyl and carboxy, or wherein $R^{10}$ and $R^{11}$ taken together is =O;

wherein $R^{12}$ is hydrido or methyl; and wherein $R^{13}$ is selected from hydrido, methyl, ethyl, hydroxymethyl and carboxy, or wherein $R^{12}$ and $R^{13}$ taken together is =O; or a pharmaceutically suitable salt thereof.

4. A compound of Formula II

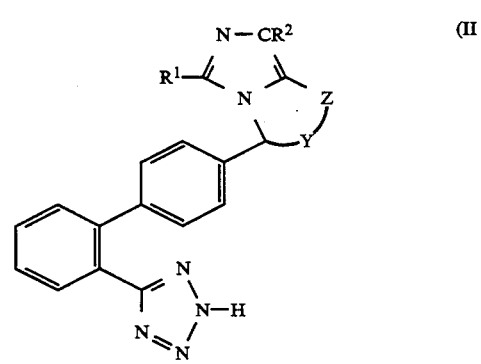

wherein Y is $(CH_2)_n$ and n is 1 to 3;

wherein Z is $C=R^3$ or $CR^4R^5$, or wherein Y and Z together forms $-CR^7=CR^6-$, $-CH_2-CR^7=CR^6-$ or $-CH_2-CH_2-CR^7=CR^6-$;

wherein $R^1$ is alkyl;

wherein $R^2$ is selected from hydrido, halo, alkyl and aryl;

wherein $R^3$ is selected from oxygen, sulfur, hydroxyamino, alkylidene alkylcarboxyalkylidene and carboxyalkylidene;

wherein $R^4$ is selected from hydrido, alkyl, hydroxyalkyl, carboxyl, carboxyalkyl, alkylcarboxyalkyl, aryl, aralkyl, hydroxyl, amino, carboxyaralkyl, phthalimidyl, aralkoxy,

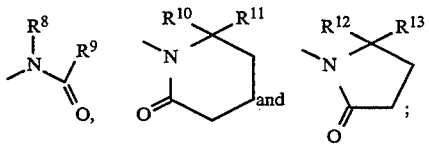

wherein $R^5$ is hydrido or hydroxyl;
wherein $R^6$ is selected from hydrido, alkyl, hydroxyalkyl, carboxyl, carboxyalkyl, alkylcarboxyalkyl, aryl, and aralkyl;
wherein $R^7$ is hydrido or halo;
wherein $R^8$ is selected from hydrido, alkyl and aralkyl;
wherein $R^9$ is selected from alkyl, aryl, aralkyl, carboxyl, carboxyalkyl and hydrazidylcarboalkyl;
wherein $R^{10}$ is hydrido or alkyl;
wherein $R^{11}$ is selected from hydrido, alkyl, hydroxyalkyl, carboxyl and carboxyalkyl, or
wherein $R^{10}$ and $R^{11}$ taken together is =O;
wherein $R^{12}$ is hydrido or alkyl;
wherein $R^{13}$ is selected from hydrido, alkyl, hydroxyalkyl, carboxyl and carboxyalkyl, or
wherein $R^{12}$ and $R^{13}$ taken together is =O; or a pharmaceutically suitable salt thereof.

5. The compound of claim 4 wherein $R^4$ is aryl or aralkyl only when $R^2$ is hydrido or halo;
wherein $R^4$ is alkyl when $R^5$ is hydroxyl;
wherein $R^8$ is aralkyl when $R^2$, if present, is hydrido or halo;
wherein $R^8$ and $R^9$ are not both aralkyl;
wherein $R^{11}$ is alkyl when $R^2$ is aryl or halo; and
wherein $R^{13}$ is alkyl when $R^2$ is aryl or halo; or a pharmaceutically suitable salt thereof.

6. The compound of claim 4 wherein $R^1$ is n-propyl or n-butyl;
wherein $R^2$ is selected from hydrido, chloro, methyl, ethyl, n-propyl, n-butyl, 2-ethylphenyl and 2,6-dimethylphenyl;
wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;
wherein $R^4$ is selected from hydrido, ethyl, n-propyl, hydroxymethyl, hydroxyl, t-butoxycarbonylmethyl, phenyl, t-butoxycarbonylpropyl, —$(CH_2)_3CO_2H$, —$CH_2CO_2H$, —$(CH_2)_2CO_2H$, —$CH(CH_2C_6H_5)CO_2H$, —$CH(C_2H_5)CH_2CO_2H$, —$CH(CH_2C_6H_5)CH_2CO_2H$, 2-ethylphenyl, 2,6-dimethylphenyl, phenethyl, benzyl, amino, phenylmethoxy,

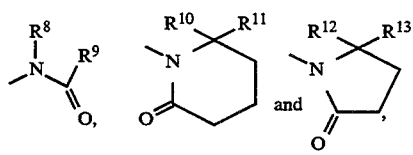

provided $R^4$ is selected from phenyl, benzyl and phenethyl only when $R^2$ is hydrido or chloro;
wherein $R^5$ is hydrido or hydroxyl, provided that when $R^5$ is hydroxyl, $R^4$ is ethyl or n-propyl;
wherein $R^6$ is selected from hydrido, ethyl, n-propyl, hydroxymethyl, —$(CH_2)_3CO_2H$, —$CH_2CO_2H$, —$(CH_2)_2CO_2H$, benzyl, t-butoxycarbonylmethyl, t-butoxycarbonylpropyl, —$CH(CH_2C_6H_5)CO_2H$, —$CH(C_2H_5)CH_2CO_2H$, —$CH(CH_2C_6H_5)CH_2CO_2H$, phenyl, 2-ethylphenyl, 2,6-dimethylphenyl and phenethyl;
wherein $R^7$ is selected from hydrido, fluoro, bromo, chloro and iodo;
wherein $R^8$ is selected from hydrido, methyl, ethyl, propyl and benzyl, provided that $R^8$ is benzyl where $R^2$, if present, is hydrido or chloro;
wherein $R^9$ is selected from methyl, ethyl, phenyl, benzyl, —$(CH_2)_2CONHNH_2$, —$CH_2CO_2H$ and —$(CH_2)_2CO_2H$, provided that $R^9$ and $R^8$ are not both benzyl;
wherein $R^{10}$ is hydrido or methyl;
wherein $R^{11}$ is selected from hydrido, methyl, ethyl, hydroxymethyl and carboxy, or
wherein $R^{10}$ and $R^{11}$ taken together is =O;
wherein $R^{12}$ is hydrido or methyl; and
wherein $R^{13}$ is selected from hydrido, methyl, ethyl, hydroxymethyl and carboxy, or
wherein $R^{12}$ and $R^{13}$ taken together is =O; or a pharmaceutically suitable salt thereof.

7. Compound of claim 6 selected from compounds of Formula II, and their pharmaceutically-acceptable salts, of the group of compounds consisting of
1,3-Dibutyl-5,6-dihydro-5-[2'-(1H-tetrazol-5-yl) [1,1'-biphenyl]-4-yl]imidazo[1,5-a]pyridine;
7-Bromo-1,3-dibutyl-5,6-dihydro-5-[2'-(1H-tetrazol-5-yl) [1,1'-biphenyl]-4-yl]imidazo[1,5-a]pyridine;
1,3-Dibutyl-5,6,7,8-tetrahydro-5-[2'-(1H-tetrazol-5-yl) [1,1'-biphenyl]-4-yl]imidazo[1,5-a]pyridine;
1,3-Dibutyl-5,6,7,8-tetrahydro-5-[2'-(1H-tetrazol-5-yl) [1,1'-biphenyl]-4-yl]imidazo[1,5-a]pyridin-8-ol;
1,3-Dibutyl-5,6-dihydro-5-[2'-(1H-tetrazol-5-yl)[1,1'-biphenyl]-4-yl]imidazo[1,5-a]pyridin-8(5H)-one;
1,3-Dibutyl-5,6-dihydro-8-phenyl-5-[2'-(1H-tetrazol-5-yl) [1,1'-biphenyl]-4-yl]imidazo[1,5-a]pyridine;
[1,3-Dibutyl-6,7-dihydro-5-[2'-(1H-tetrazol-5-yl)[1,1'-biphenyl]-4-yl]imidazo[1,5-a]pyridin-8(5H)-ylidene]acetic acid;
1-[1,3-Dibutyl-5,6,7,8-tetrahydro-5-[2'-(1H-tetrazol-5-yl) [1,1'-biphenyl]-4-yl]imidazo[1,5-a]pyridin-8-yl]-2,5-pyrrolidinedione;
4-[1,3-Dibutyl-5,6,7,8-tetrahydro-5-[2'-(1H-tetrazol-5-yl) [1,1'-biphenyl]-4-yl]imidazo[1,5-a]pyridin-8-yl]amino]-4-oxobutanoic acid, hydrazide;
1,3-Dibutyl-6,7-dihydro-5-[2'-(1H-tetrazol-5-yl)[1,1'-biphenyl]-4-yl]-5H-imidazo[1,5-a]azepine;
3-Butyl-5,6-dihydro-5-[2'-(1H-tetrazol-5-yl)[1,1'-biphenyl]-4-yl]imidazo[1,5-a]pyridine;
3-Butyl-5,6-dihydro-5-[2'-(1H-tetrazol-5-yl)[1,1'-biphenyl]-4-yl]imidazo[1,5-a]pyridin-8(5H)-one;
3-Butyl-5,6,7,8-tetrahydro-5-[2'-(1H-tetrazol-5-yl) [1,1'-biphenyl]-4-yl]imidazo[1,5-a]pyridin-cis-8-ol;
3-Butyl-5,6,7,8-tetrahydro-5-[2'-(1H-tetrazol-5-yl) [1,1'-biphenyl]-4-yl]imidazo[1,5-a]pyridin-trans-8-ol;
1,1-Dimethylethyl [3-butyl-6,7-dihydro-5-[2'-(1H-tetrazol-5-yl)[1,1'-biphenyl]-4-yl]imidazo[1,5a]pyridin-8(5H)-ylidene]acetate;
[3-Butyl-6,7-dihydro-5-[2'-(1H-tetrazol-5-yl[1,1'-biphenyl]-4-yl]imidazo[1,5-a]pyridin-8(5H)-ylidene]acetic acid;
1,1-Dimethylethyl 3-butyl-5,6-dihydro-5-[2'-1H-tetrazol-5-yl)[1,1'-biphenyl]-4-yl]imidazo[1,5-a]pyridin-8-acetate;
3-Butyl-5,6-dihydro-5-[2'-(1H-tetrazol-5-yl)[1,1'-phenyl]-4-yl]imidazo[1,5-a]pyridin-8-acetic acid;
1,1-Dimethylethyl 3-butyl-5,6,7,8-tetrahydro-5-[2'-(1H-tetrazol-5-yl)[1,1'-biphenyl]-4-yl]imidazo[1,5-a]pyridin-cis-8-acetate;

3-Butyl-5,6,7,8-tetrahydro-5-[2'-(1H-tetrazol-5-yl) [1,1'-biphenyl]-4-yl]imidazo[1,5-a]pyridin-cis-8-acetic acid;

1,3-Dibutyl-5,6-dihydro-N-hydroxy-5-[2'-(1H-tetrazol-5-yl) [1.1'-biphenyl]-4-yl]imidazol[1,5-a]pyridin-8(7H)-imine;

1-[3-Butyl-5,6,7,8-tetrahydro-5-[2'-(1H-tetrazol-5-yl) [1,1'-biphenyl]-4-yl]imidazo[1,5-a]pyridin-8-yl]phthalimide;

1,3-Dibutyl-8-phenyl-5,6-dihydro-5-{2'-(1H-tetrazol-5-yl){1,1'-biphenyl]-4-yl]imidazo[1,5-a]pyridine;

1-[3-Butyl-5,6,7,8-tetrahydro-5-[2'-(1H-tetrazol-5-yl) [1,1'-biphenyl]-4-yl]imidazo[1,5-a]pyridin-8-yl]-cis-2,5-pyrrolidinedione;

1-[3-Butyl-5,6,7,8-tetrahydro-5-[2'-(1H-tetrazol-5-yl) [1,1'-biphenyl]-4-yl]imidazo[1,5-a]pyridin-8-yl]-trans-2,5-pyrrolidinedione;

1-[3-Butyl-1-chloro-5,6,7,8-tetrahydro-5-[2'-(1H-tetrazol-5-yl)[1,1'-biphenyl]-4-yl]imidazo[1,5-a]pyridin-8-yl]-cis-2,5-pyrrolidinedione;

1-[3-Butyl-1-chloro-5,6,7,8-tetrahydro-5-[2'-(1H-tetrazol-5-yl)[1,1'-biphenyl]-4-yl]imidazo[1,5-a]pyridin-8-yl]-trans-2,5-pyrrolidinedione;

3-Butyl-8-phenylmethoxy-5,6,7,8-tetrahydro-5-[2'-(1H-tetrazol-5-yl)[1,1'-biphenyl]-4-yl]imidazo[1,5-a]pyridine; and 3-Butyl-5,6,7,8-tetrahydro-8-amino-5-[2'-(1H-tetrazol-5-yl)[1,1'-biphenyl]-4-yl]imidazo[1,5-a]pyridine.

8. Compound of claim 7 and pharmaceutically-acceptable salts, which is 1-[1,3-Dibutyl-5,6,7,8-tetrahydro-5-[2'-(1H-tetrazol-5-yl)[1,1'-biphenyl]-4-yl]imidazo[1,5-a]pyridin-8-yl]-2,5-pyrrolidinedione.

9. Compound of claim 7 and pharmaceutically-acceptable salts, which is 4-[1,3 Dibutyl-5,6,7,8-tetrahydro-5-[2'-(1H-tetrazol-5-yl)[1,1'-biphenyl]-4-yl]imidazo[1,5-a]pyridin-8-yl]amino]-4-oxobutanoic acid, hydrazide.

10. Compound of claim 7 and pharmaceutically-acceptable salts, which is 1,3-Dibutyl-5,6,7,8-tetrahydro-5-[2'-(1H-tetrazol-5-yl)[1,1'-biphenyl]-4-yl]imidazo[1,5-a]pyridin-8-ol.

11. A compound of Formula III

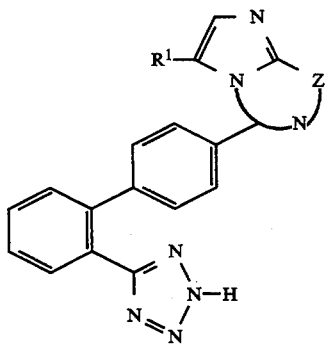

wherein Y is $(CH_2)_n$ and n is 1 to 3;
wherein Z is $C=R^3$ or $CR^4R^5$ or
wherein Y and Z together forms $—CR^7=CR^6—$, $—CH_2—CR^7=CR^6—$ or $—CH_2—CH_2—CR^7=CR^6—$;
wherein $R^1$ is alkyl;
wherein $R^3$ is selected from oxygen, sulfur, hydroxyamino, alkylidene, alkylcarboxyalkylidene and carboxyalkylidene;
wherein $R^4$ is selected from hydrido, alkyl, carboxyl, hydroxyalkyl, carboxyalkyl, carboxyaralkyl, aryl, aralkyl, alkylcarboxyalkyl, hydroxyl, amino, phthalimidyl, aralkoxy,

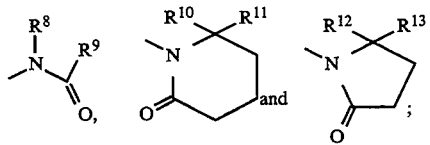

wherein $R^5$ is hydrido or hydroxyl;
wherein $R^6$ is selected from hydrido, alkyl, carboxyl, hydroxyalkyl, carboxyalkyl, alkylcarboxyalkyl, aryl and aralkyl;
wherein $R^7$ is hydrido or halo;
wherein $R^8$ is selected from hydrido, alkyl and aralkyl;
wherein $R^9$ is selected from alkyl, aryl, aralkyl, carboxyl and carboxyalkyl;
wherein $R^{10}$ is hydrido or alkyl;
wherein $R^{11}$ is selected from hydrido, alkyl, hydroxyalkyl, carboxyl and carboxyalkyl, or
wherein $R^{11}$ and $R^{10}$ taken together is $=O$;
wherein $R^{12}$ is hydrido or alkyl; and
wherein $R^{13}$ is selected from hydrido, alkyl, hydroxyalkyl, carboxyl and carboxyalkyl, or
wherein $R^{12}$ and $R^{13}$ taken together is $=O$;
or a pharmaceutically suitable salt thereof.

12. The compound of claim 11 wherein $R^1$ is n-propyl or n-butyl;
wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;
wherein $R^4$ is selected from hydrido, ethyl, n-propyl, hydroxymethyl, hydroxyl, t-butoxycarbonylmethyl, amino, t-butoxycarbonylpropyl, $—(CH_2)_3CO_2H$, $—CH_2CO_2H$, $—(CH_2)_2CO_2H$, $—CH(CH_2C_6H_5)CO_2H$, $—CH(C_2H_5)CH_2CO_2H$, $—CH(CH_2C_6H_5)CH_2CO_2H$, phenyl, 2-ethylphenyl, 2,6-dimethylphenyl, phenethyl, benzyl, phenylmethoxy,

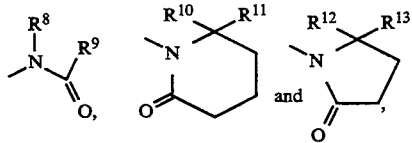

provided $R^4$ is selected from phenyl, benzyl and phenethyl only when $R^2$, if present, is hydrido or chloro;
wherein $R^5$ is hydrido or hydroxyl, provided that $R^4$ is ethyl or n-propyl when $R^5$ is hydroxyl;
wherein $R^6$ is selected from hydrido, ethyl, n-propyl, hydroxymethyl, $—(CH_2)_3CO_2H$, $—CH_2CO_2H$, $—(CH_2)_2CO_2H$, t-butoxycarbonylmethyl, t-butoxycarbonylpropyl, benzyl, $—CH(CH_2C_6H_5)CO_2H$, $—CH(C_2H_5)CH_2CO_2H$, $—CH(CH_2C_6H_5)CH_2CO_2H$, phenyl, 2-ethylphenyl, 2,6-dimethylphenyl and phenethyl;
wherein $R^7$ is selected from hydrido, bromo, chloro, fluoro and iodo;
wherein $R^8$ is selected from hydrido, methyl, ethyl, propyl and benzyl, provided that $R^8$ is benzyl where $R^2$, if present, is hydrido or chloro;

wherein R[9] is selected from methyl, ethyl, phenyl, benzyl, —(CH$_2$)$_2$CONHNH$_2$, —CH$_2$CO$_2$H and —(CH$_2$)$_2$CO$_2$H, provided that R[9] and R[8] are not both benzyl;

wherein R[10] is hydrido or methyl;

wherein R[11] is selected from hydrido, methyl, ethyl, hydroxymethyl and carboxy, or wherein R[11] and R[10] taken together is =O;

wherein R[12] is hydrido or methyl; and wherein R[13] is selected from hydrido, methyl, ethyl, hydroxymethyl and carboxy, or wherein R[13] and R[12] taken together is =O; or a pharmaceutically acceptable salt thereof.

13. A compound of Formula IV

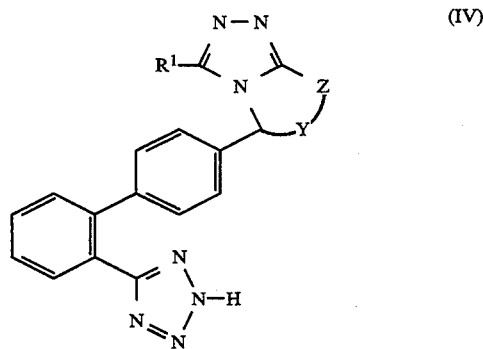

(IV)

wherein Y is (CH$_2$)$_n$ and n is 1 to 3;

wherein Z is C=R[3] or CR[4]R[5], or wherein Y and Z together forms —CR[7]=CR[6]—, —CH$_2$—CR[7]=CR[6]— or —CH$_2$—CH$_2$—CR[7]=CR[6]—;

wherein R[1] is alkyl;

wherein R[3] is selected from oxygen, sulfur, hydroxyamino, alkylidene, alkylcarboxyalkylidene and carboxyalkylidene;

wherein R[4] is selected from hydrido, alkyl, carboxyl, hydroxyalkyl, carboxyalkyl, carboxyaralkyl, phthalimidyl, alkylcarboxyalkyl, aryl, aralkyl, hydroxyl, amino, aralkoxy,

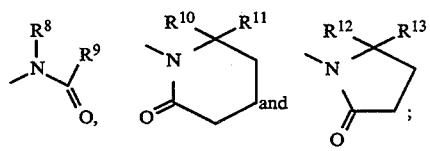

wherein R[5] is hydrido or hydroxyl;

wherein R[6] is selected from hydrido, alkyl, carboxyl, hydroxyalkyl, carboxyalkyl, alkylcarboxyalkyl, aryl, aralkyl, hydroxyl and amino;

wherein R[7] is hydrido or halo;

wherein R[8] is selected from hydrido, alkyl and aralkyl;

wherein R[9] is selected from alkyl, aryl, aralkyl, hydrazidylcarboalkyl, carboxyl and carboxyalkyl;

wherein R[10] is hydrido or alkyl;

wherein R[11] is selected from hydrido, alkyl, hydroxyalkyl, carboxyl and carboxyalkyl, or wherein R[11] and R[10] taken together is =O;

wherein R[12] is hydrido or alkyl; and wherein R[13] is selected from hydrido, alkyl, hydroxyalkyl, carboxyl and carboxyalkyl, or wherein R[12] and R[13] taken together is =O;

or a pharmaceutically suitable salt thereof.

14. The compound of claim 13 wherein R[1] is n-propyl or n-butyl;

wherein R[3] is selected from oxygen, sulfur, hydroxyamino, CHCO$_2$H, C(CH$_2$C$_6$H$_5$)CO$_2$H, C(C$_2$H$_5$)CO$_2$H and CHCO$_2$C(CH$_3$)$_3$;

wherein R[4] is selected from hydrido, ethyl, n-propyl, hydroxymethyl, t-butoxycarbonylmethyl, hydroxyl, amino, t-butoxycarbonylpropyl, —(CH$_2$)$_3$CO$_2$H, —CH$_2$CO$_2$H, —(CH$_2$)$_2$CO$_2$H, —CH(CH$_2$C$_6$H$_5$)CO$_2$H, —CH(C$_2$H$_5$)CH$_2$CO$_2$H, —CH(CH$_2$C$_6$H$_5$)CH$_2$CO$_2$H, phenyl, 2-ethylphenyl, 2,6-dimethylphenyl, phenethyl, benzyl, phenylmethoxy,

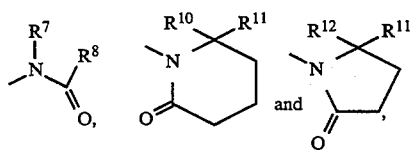

provided R[4] is selected from phenyl, benzyl and phenethyl only when R[2], if present, is hydrido or chloro;

wherein R[5] is hydrido or hydroxyl, provided that R[4] is ethyl or n-propyl when R[5] is hydroxyl;

wherein R[6] is selected from hydrido, ethyl, n-propyl, hydroxymethyl, —(CH$_2$)$_3$CO$_2$H, —CH$_2$CO$_2$H, —(CH$_2$)$_2$CO$_2$H, t-butoxycarbonylmethyl, t-butoxycarbonylpropyl, —CH (CH$_2$C$_6$H$_5$)CO$_2$H, —CH(C$_2$H$_5$)CH$_2$CO$_2$H, —CH(CH$_2$C$_6$H$_5$)CH$_2$CO$_2$H, phenyl, 2-ethylphenyl, 2,6-dimethylphenyl, phenethyl and benzyl;

wherein R[7] is selected from hydrido, bromo, chloro, iodo and fluoro;

wherein R[8] is selected from hydrido, methyl, ethyl, propyl and benzyl, provided that R[8] is benzyl where R[2], if present, is hydrido or chloro;

wherein R[9] is selected from methyl, ethyl, phenyl, benzyl, —(CH$_2$)$_2$CONHNH$_2$, —CH$_2$CO$_2$H and —(CH$_2$)$_2$CO$_2$H, provided that R[9] and R[8] are not both benzyl;

wherein R[10] is hydrido or methyl;

wherein R[10] is selected from hydrido, methyl, ethyl, hydroxymethyl and carboxy; or wherein R[11] and R[10] taken together is =O;

wherein R[12] is hydrido or methyl; and wherein R[13] is selected from hydrido, methyl, ethyl, hydroxymethyl and carboxy, or wherein R[13] and R[12] taken together is =O; or a pharmaceutically suitable salt thereof.

15. A compound of Formula V

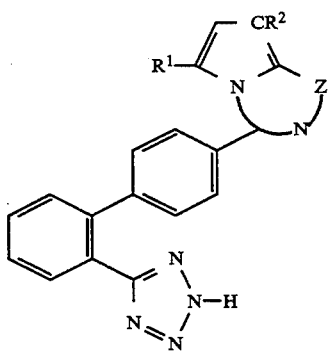

(V)

wherein Y is (CH$_2$)$_n$ and n is 1 to 3;
wherein Z is C=R$^3$ or CR$^4$R$^5$, or
wherein Y and Z together forms —CR$^7$=CR$^6$—, —CH$_2$—CR$^7$=CR$^6$— or —CH$_2$—CH$_2$—CR$^7$=CR$^6$—;
wherein R$^1$ is alkyl;
wherein R$^2$ is selected from hydrido, halo, alkyl and aryl;
wherein R$^3$ is selected from oxygen, sulfur, alkylidene, alkylcarboxyalkylidene, carboxyalkylidene and hydroxyamino;
wherein R$^4$ is selected from hydrido, alkyl, hydroxyalkyl, carboxyl, alkylcarboxyalkyl, carboxyalkyl, carboxyaralkyl, aryl, aralkyl, hydroxyl, amino, phthalimidyl, aralkoxy,

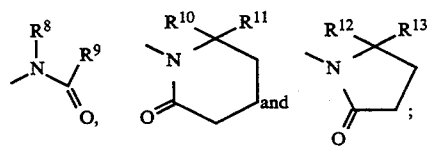

wherein R$^5$ is hydrido or hydroxyl;
wherein R$^6$ is selected from hydrido, alkyl, hydroxyalkyl, carboxyl, alkylcarboxyalkyl, carboxyalkyl, aryl, aralkyl and hydroxyl;
wherein R$^7$ is halo or hydrido;
wherein R$^8$ is selected from hydrido, alkyl and aralkyl;
wherein R$^9$ is selected from alkyl, aryl, aralkyl, hydrazidylcarboalkyl, carboxyl and carboxyalkyl;
wherein R$^{10}$ is hydrido or alkyl;
wherein R$^{11}$ is selected from hydrido, alkyl, hydroxyalkyl, carboxyl and carboxyalkyl, or
wherein R$^{10}$ and R$^{11}$ taken together is =O;
wherein R$^{12}$ is hydrido or alkyl; and
wherein R$^{13}$ is selected from hydrido, alkyl, hydroxyalkyl, carboxyl and carboxyalkyl, or
wherein R$^{13}$ and R$^{12}$ taken together is =O;
or a pharmaceutically suitable salt thereof.

16. The compound of claim 15 wherein R$^1$ is n-propyl or n-butyl;
wherein R$^2$ is selected from hydrido, chloro, methyl, ethyl, n-propyl, n-butyl, 2-ethylphenyl and 2,6-dimethylphenyl;
wherein R$^3$ is selected from oxygen, sulfur, hydroxyamino, CHCO$_2$H, C(CH$_2$C$_6$H$_5$)CO$_2$H, C(C$_2$H$_5$)CO$_2$H and CHCO$_2$C(CH$_3$)$_3$;
wherein R$^4$ is selected from hydrido, ethyl, n-propyl, hydroxymethyl, hydroxyl, t-butoxycarbonylmethyl, phenyl, t-butoxycarbonylpropyl, —(CH$_2$)$_3$CO$_2$H, —CH$_2$CO$_2$H, —(CH$_2$)$_2$CO$_2$H, —CH(CH$_2$C$_6$H$_5$)CO$_2$H, —CH(C$_2$H$_5$)CH$_2$CO$_2$H, —CH(CH$_2$C$_6$H$_5$)CH$_2$CO$_2$H, 2-ethylphenyl, 2,6-dimethylphenyl, phenethyl, benzyl, amino, phenylmethoxy,

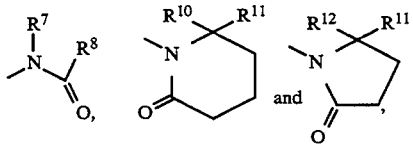

provided R$^4$ is selected from phenyl, benzyl and phenethyl only when R$^2$ is hydrido or chloro;
wherein R$^5$ is hydrido or hydroxyl, provided that R$^4$ is ethyl or n-propyl when R$^5$ is hydroxyl;
wherein R$^6$ is selected from hydrido, ethyl, n-propyl, hydroxymethyl, —CH$_2$)$_3$CO$_2$H, —CH$_2$CO$_2$H, —CH$_2$)$_2$CO$_2$H, t-butoxycarbonylmethyl, t-butoxycarbonylpropyl, —CH(CH$_2$C$_6$H$_5$)CO$_2$H, —CH(C$_2$H$_5$)CH$_2$CO$_2$H, —CH(CH$_2$C$_6$H$_5$)CH$_2$CO$_2$H, phenyl, 2-ethylphenyl, 2,6-dimethylphenyl, phenethyl and benzyl;
wherein R$^7$ is selected from hydrido, chloro, bromo, fluoro and iodo;
wherein R$^8$ is selected from hydrido, methyl, ethyl, propyl and benzyl, provided that R$^8$ is benzyl where R$^2$, if present, is hydrido or chloro;
wherein R$^9$ is selected from methyl, ethyl, phenyl, benzyl, —(CH$_2$)$_2$CONHNH$_2$, —CH$_2$CO$_2$H and —(CH$_2$)$_2$CO$_2$H, provided that R$^9$ and R$^8$ are not both benzyl;
wherein R$^{10}$ is hydrido or methyl;
wherein R$^{11}$ is selected from hydrido, methyl, ethyl, hydroxymethyl and carboxy, or
wherein R$^{11}$ and R$^{10}$ taken together is =O;
wherein R$^{12}$ is hydrido or methyl; and
wherein R$^{13}$ is selected from hydrido, methyl, ethyl, hydroxymethyl and carboxy, or
wherein R$^{13}$ and R$^{12}$ taken together is =O; or a pharmaceutically suitable salt thereof.

17. A pharmaceutical composition comprising a therapeutically-effective amount of an angiotensin II antagonist compound and a pharmaceutically-acceptable carrier or diluent, said antagonist compound selected from a family of compounds of Formula II:

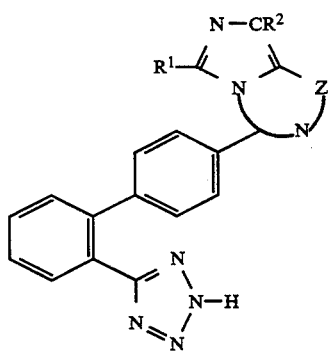

II wherein Y is (CH$_2$)$_n$ and n is 1 to 3;
wherein Z is C=R$^3$ or CR$^4$R$^5$, or
wherein Y and Z together forms —CR$^7$=CR$^6$—, —CH$_2$—CR$^7$=CR$^6$— or —CH$_2$—CH$_2$—CR$^7$=CR$^6$—;
wherein R$^1$ is alkyl;

wherein $R^2$ is selected from hydrido, halo, alkyl and aryl;

wherein $R^3$ is selected from oxygen, sulfur, hydroxyamino, alkylidene, alkylcarboxyalkylidene and carboxyalkylidene;

wherein $R^4$ is selected from hydrido, alkyl, hydroxyalkyl, carboxyl, carboxyalkyl, alkylcarboxyalkyl, aryl, aralkyl, hydroxyl, amino, carboxyaralkyl, phthalimidyl, aralkoxy,

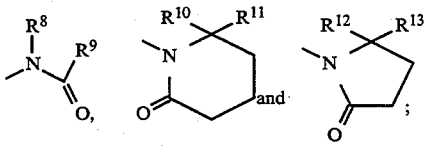

wherein $R^5$ is hydrido or hydroxyl;

wherein $R^6$ is selected from hydrido, alkyl, hydroxyalkyl, carboxyl, carboxyalkyl, alkylcarboxyalkyl, aryl, and aralkyl;

wherein $R^7$ is hydrido or halo;

wherein $R^8$ is selected from hydrido, alkyl and aralkyl;

wherein $R^9$ is selected from alkyl, aryl, aralkyl, carboxyl, carboxyalkyl and hydrazidylcarboalkyl;

wherein $R^{10}$ is hydrido or alkyl;

wherein $R^{11}$ is selected from hydrido, alkyl, hydroxyalkyl, carboxyl and carboxyalkyl, or wherein $R^{11}$ and $R^{10}$ taken together is $=O$;

wherein $R^{12}$ is hydrido or alkyl;

wherein $R^{13}$ is selected from hydrido, alkyl, hydroxyalkyl, carboxyl and carboxyalkyl, or wherein $R^{13}$ and $R^{12}$ taken together is $=O$; or a pharmaceutically suitable salt thereof.

18. The composition of claim 17 wherein $R^1$ is n-propyl or n-butyl;

wherein $R^2$ is selected from hydrido, chloro, methyl, ethyl, n-propyl, n-butyl, 2-ethylphenyl and 2,6-dimethylphenyl;

wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;

wherein $R^4$ is selected from hydrido, ethyl, n-propyl, hydroxymethyl, hydroxyl, t-butoxycarbonylmethyl, phenyl, t-butoxycarbonylpropyl, $—(CH_2)_3CO_2H$, $—CH_2CO_2H$, $—(CH_2)_2CO_2H$, $—CH(CH_2C_6H_5)CO_2H$, $—CH(C_2H_5)CH_2CO_2H$, $—CH(CH_2C_6H_5)CH_2CO_2H$, phenylmethoxy, 2-ethylphenyl, 2,6-dimethylphenyl, phenethyl, benzyl, amino,

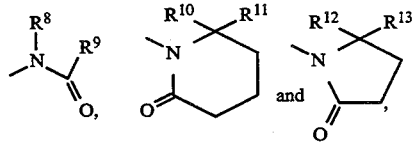

provided $R^4$ is selected from phenyl, benzyl and phenethyl only when $R^2$ is hydrido or chloro;

wherein $R^5$ is hydrido or hydroxyl, provided that when $R^5$ is hydroxyl, $R^4$ is ethyl or n-propyl;

wherein $R^6$ is selected from hydrido, ethyl, n-propyl, hydroxymethyl, $—(CH_2)_3CO_2H$, $—CH_2CO_2H$, $—(CH_2)_2CO_2H$, t-butoxycarbonylmethyl, t-butoxycarbonylpropyl, $—CH(CH_2C_6H_5)CO_2H$, $—CH(C_2H_5)CH_2CO_2H$, $—CH(CH_2C_6H_5)CH_2CO_2H$, phenyl, 2-ethylphenyl, 2,6-dimethylphenyl, phenethyl and benzyl;

wherein $R^7$ is selected from hydrido, fluoro, chloro, bromo and iodo;

wherein $R^8$ is selected from hydrido, methyl, ethyl, propyl and benzyl, provided that $R^8$ is benzyl where $R^2$, if present, is hydrido or chloro;

wherein $R^9$ is selected from methyl, ethyl, phenyl, benzyl, $—CH_2CO_2H$ and $—(CH_2)_2CO_2H$, provided that $R^9$ and $R^8$ are not both benzyl;

wherein $R^{10}$ is hydrido or methyl;

wherein $R^{11}$ is selected from hydrido, methyl, ethyl, hydroxymethyl and carboxy, or wherein $R^{11}$ and $R^{10}$ taken together is $=O$;

wherein $R^{12}$ is hydrido or methyl; and wherein $R^{13}$ is selected from hydrido, methyl, ethyl, hydroxymethyl and carboxy, or wherein $R^{13}$ and $R^{12}$ taken together is $=O$; or a pharmaceutically suitable salt thereof.

19. The composition of claim 18 wherein said antagonist compound is selected from compounds, and their pharmaceutically-acceptable salts, of the group of compounds consisting of 1,3-Dibutyl-5,6-dihydro-5-[2'-(1H-tetrazol-5-yl) [1,1'-biphenyl]-4-yl]imidazo[1,5-a]pyridine;

7-Bromo-1,3-dibutyl-5,6-dihydro-5-[2'-(1H-tetrazol-5-yl) [1,1'-biphenyl]-4-yl]imidazo[1,5-a]pyridine;

1,3-Dibutyl-5,6,7,8-tetrahydro-5-[2'-(1H-tetrazol-5-yl) [1,1'-biphenyl]-4-yl]imidazo[1,5-a]pyridine;

1,3-Dibutyl-5,6,7,8-tetrahydro-5-[2'-(1H-tetrazol-5-yl) [1,1'-biphenyl]-4-yl]imidazo[1,5-a]pyridin-8-ol;

1,3-Dibutyl-5,6-dihydro-5-[2'-(1H-tetrazol-5-yl)[1,1'-biphenyl]-4-yl]imidazo[1,5-a]pyridin-8(5H)-one;

1,3-Dibutyl-5,6-dihydro-8-phenyl-5-[2'-(1H-tetrazol-5-yl) [1,1'-biphenyl]-4-yl]imidazo[1,5-a]pyridine;

[1,3-Dibutyl-6,7-dihydro-5-[2'-(1H-tetrazol-5-yl)[1,1'-biphenyl]-4-yl]imidazo[1,5-a]pyridin-8(5H)-ylidene]acetic acid;

1-[1,3-Dibutyl-5,6,7,8-tetrahydro-5-[2'-(1H-tetrazol-5-yl) [1,1'-biphenyl]-4-yl]imidazo[1,5-a]pyridin-8-yl]-2,5-pyrrolidinedione;

4-[1,3-Dibutyl-5,6,7,8-tetrahydro-5-[2'-(1H-tetrazol-5-yl) [1,1'-biphenyl]-4-yl]imidazo[1,5-a]pyridin-8-yl]amino]-4-oxobutanoic acid, hydrazide;

1,3-Dibutyl-6,7-dihydro-5-[2'-(1H-tetrazol-5-yl)[1,1'biphenyl]-4-yl]-5H-imidazo[1,5-a]azepine;

3-Butyl-5,6-dihydro-5-[2'-(1H-tetrazol-5-yl)[1,1'-biphenyl]-4-yl]imidazo[1,5-a]pyridine;

3-Butyl-5,6-dihydro-5-[2'-(1H-tetrazol-5-yl)[1,1'-biphenyl]-4-yl]imidazo[1,5-a]pyridin-8(5H)-one;

3-Butyl-5,6,7,8-tetrahydro-5-[2'-(1H-tetrazol-5-yl) [1,1'-biphenyl]-4-yl]imidazo[1,5-a]pyridin-cis-8-ol;

3-Butyl-5,6,7,8-tetrahydro-5-[2'-(1H-tetrazol-5-yl) [1,1'-biphenyl]-4-yl]imidazo[1,5-a]pyridin-trans-8-ol;

1,1-Dimethylethyl [3-butyl-6,7-dihydro-5-[2'-(1H-tetrazol-5-yl)[1,1'-biphenyl]-4-yl]imidazo[1,5-a]pyridin-8(5H)-ylidene]acetate;

[3-Butyl-6,7-dihydro-5-[2'-(1H-tetrazol-5-yl)[1,1'-biphenyl]-4-yl]imidazo[1,5-a]pyridin-8(5H)-ylidene]acetic acid;

1,1-Dimethylethyl 3-butyl-5,6-dihydro-5-[2'-(1H-tetrazol-5-yl)[1,1'-biphenyl]-4-yl]imidazo[1,5-a]pyridin-8-acetate;

3-Butyl-5,6-dihydro-5-[2'-(1H-tetrazol-5-yl)[1,1'-biphenyl]-4-yl]imidazo[1,5-a]pyridin-8-acetic acid;

1,1-Dimethylethyl 3-butyl-5,6,7,8-tetrahydro-5-[2'-(1H-tetrazol-5-yl)[1,1'-biphenyl]-4-yl]imidazo[1,5-a]pyridin-cis-8-acetate;

3-Butyl-5,6,7,8-tetrahydro-5-[2'-(1H-tetrazol-5-yl) [1,1'-biphenyl]-4-yl]imidazo[1,5-a]pyridin-cis-8-acetic acid;

1,3-Dibutyl-5,6-dihydro-N-hydroxy-5-[2'-(1H-tetrazol-5-yl) [1.1'-biphenyl]-4-yl]imidazol[1,5-a]pyridin-8(7H)-imine;

1-[3-Butyl-5,6,7,8-tetrahydro-5-[2'-(1H-tetrazol-5-yl) [1,1'-biphenyl]-4-yl]imidazo[1,5-a]pyridin-8-yl]phthalimide;

1,3-Dibutyl-8-phenyl-5,6-dihydro-5-{2'-(1H-tetrazol-5-yl){1,1'-biphenyl]-4-yl]imidazo[1,5-a]pyridine;

1-[3-Butyl-5,6,7,8-tetrahydro-5-[2'-(1H-tetrazol-5-yl)[1,1'-biphenyl]-4-yl]imidazo[1,5-a]pyridin-8-yl]-cis-2,5-pyrrolidinedione;

1-[3-Butyl-5,6,7,8-tetrahydro-5-[2'-(1H-tetrazol-5-yl) [1,1'-biphenyl]-4-yl]imidazo[1,5-a]pyridin-8-yl]-trans-2,5-pyrrolidinedione;

1-[3-Butyl-1-chloro-5,6,7,8-tetrahydro-5-[2'-tetrazol-5-yl)[1,1'-biphenyl]-4-yl]imidazo[1,5-a]pyridin-8-yl]-cis-2,5-pyrrolidinedione;

1-[3-Butyl-1-chloro-5,6,7,8-tetrahydro-5-[2'-(1H-tetrazol-5-yl)[1,1'-biphenyl]-4-yl]imidazo[1,5-a]pyridin-8-yl]-trans-2,5-pyrrolidinedione;

3-Butyl-8-phenylmethoxy-5,6,7,8-tetrahydro-5-[2'-(1H-tetrazol-5-yl)[1,1'-biphenyl]-4-yl]imidazo[1,5-a]pyridine; and 3-Butyl-5,6,7,8-tetrahydro-8-amino-5-[2'-(1H-tetrazol-5-yl) [1,1'-biphenyl]-4-yl]imidazo[1,5-a]pyridine.

20. A therapeutic method for treating a circulatory disorder, said method comprising administering to a subject having such disorder a therapeutically-effective amount of a compound of Formula II:

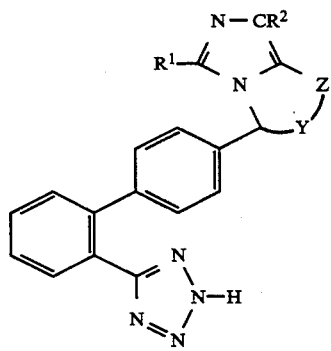

wherein Y is $(CH_2)_n$ and n is 1 to 3;
wherein Z is $C=R^3$ or $CR^4R^5$, or
wherein Y and Z together forms $-CR^7=CR^6-$, $-CH_2-CR^7=CR^6-$ or $-CH_2-CH_2-CR^7=CR^6-$;
wherein $R^1$ is alkyl;
wherein $R^2$ is selected from hydrido, halo, alkyl and aryl;
wherein $R^3$ is selected from oxygen, sulfur, hydroxyamino, alkylidene, alkylcarboxyalkylidene and carboxyalkylidene;
wherein $R^4$ is selected from hydrido, alkyl, hydroxyalkyl, carboxyl, carboxyalkyl, alkylcarboxyalkyl, aryl, aralkyl, hydroxyl, amino, carboxaralkyl, phthalimidyl, aralkoxy,

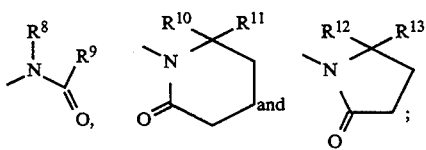

wherein $R^5$ is hydrido or hydroxyl;
wherein $R^6$ is selected from hydrido, alkyl, hydroxyalkyl, carboxy, carboxyalkyl, alkylcarboxyalkyl, aryl, and aralkyl;
wherein $R^7$ is hydrido or halo;
wherein $R^8$ is selected from hydrido, alkyl and aralkyl;
wherein $R^9$ is selected from alkyl, aryl, aralkyl, carboxyl, carboxyalkyl and hydrazidylcarboalkyl;
wherein $R^{10}$ is hydrido or alkyl;
wherein $R^{11}$ is selected from hydrido, alkyl, hydroxyalkyl, carboxyl and carboxyalkyl, or
wherein $R^{11}$ and $R^{10}$ taken together is $=O$;
wherein $R^{12}$ is hydrido or alkyl;
wherein $R^{13}$ is selected from hydrido, alkyl, hydroxyalkyl, carboxyl and carboxyalkyl, or
wherein $R^{13}$ and $R^{12}$ taken together is $=O$; or a pharmaceutically suitable salt thereof.

21. The method of claim 20 wherein $R^1$ is n-propyl or n-butyl;
wherein $R^2$ is selected from hydrido, chloro, methyl, ethyl, n-propyl, n-butyl, 2-ethylphenyl and 2,6-dimethylphenyl;
wherein $R^3$ is selected from oxygen, sulfur, hydroxyamino, $CHCO_2H$, $C(CH_2C_6H_5)CO_2H$, $C(C_2H_5)CO_2H$ and $CHCO_2C(CH_3)_3$;
wherein $R^4$ is selected from hydrido, ethyl, n-propyl, hydroxymethyl, hydroxyl, t-butoxycarbonylmethyl, phenyl, t-butoxycarbonylpropyl, $-(CH_2)_3CO_2H$, $-CH_2CO_2H$, $-(CH_2)_2CO_2H$, $-CH(CH_2C_6H_5)CO_2H$, $-CH(C_2H_5)CH_2CO_2H$, $-CH(CH_2C_6H_5)CH_2CO_2H$, phenylmethoxy, 2-ethylphenyl, 2,6-dimethylphenyl, phenethyl, benzyl, amino,

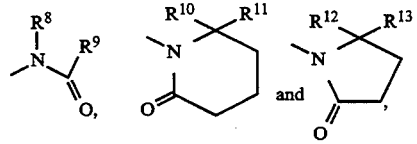

provided $R^4$ is selected from phenyl, benzyl and phenethyl only when $R^2$ is hydrido or chloro;
wherein $R^5$ is hydrido or hydroxyl, provided that when $R^5$ is hydroxyl, $R^4$ is ethyl or n-propyl;
wherein $R^6$ is selected from hydrido, ethyl, n-propyl, hydroxymethyl, $-(CH_2)_3CO_2H$, $-CH_2CO_2H$, $-(CH_2)_2CO_2H$, t-butoxycarbonylmethyl, t-butoxycarbonylpropyl, $-CH(CH_2C_6H_5)CO_2H$, $-CH(C_2H_5)$ $CH_2CO_2H$, $-CH(CH_2C_6H_5)CH_2CO_2H$, phenyl, 2-ethylphenyl, 2,6-dimethylphenyl, phenethyl and benzyl;
wherein $R^7$ is selected from hydrido, fluoro, chloro, bromo and iodo;
wherein $R^8$ is selected from hydrido, methyl, ethyl, propyl and benzyl, provided that $R^8$ is benzyl where $R^2$, if present, is hydrido or chloro;

wherein $R^9$ is selected from methyl, ethyl, phenyl, benzyl, —$CH_2CO_2H$ and —$(CH_2)_2CO_2H$, provided that $R^9$ and $R^8$ are not both benzyl;

wherein $R^{10}$ is hydrido or methyl;

wherein $R^{11}$ is selected from hydrido, methyl, ethyl, hydroxymethyl and carboxy, or wherein $R^{11}$ and $R^{10}$ taken together is =O;

wherein $R^{12}$ is hydrido or methyl; and wherein $R^{13}$ is selected from hydrido, methyl, ethyl, hydroxymethyl and carboxy, or wherein $R^{13}$ and $R^{12}$ taken together is =O; or a pharmaceutically suitable salt thereof.

22. The method of claim 21 wherein the compound is selected from compounds, and their pharmaceutically-acceptable salts, of the group of compounds consisting of 1,3-Dibutyl-5,6-dihydro-5-[2'-(1H-tetrazol-5-yl)[1,1'-biphenyl]-4-yl]imidazo[1,5-a]pyridine;

7-Bromo-1,3-dibutyl-5,6-dihydro-5-[2'-(1H-tetrazol-5-yl)[1,1'-biphenyl]-4-yl]imidazo[1,5-a]pyridine;

1,3-Dibutyl-5,6,7,8-tetrahydro-5-[2'-(1H-tetrazol-5-yl)[1,1'-biphenyl]-4-yl]imidazo[1,5-a]pyridine;

1,3-Dibutyl-5,6,7,8-tetrahydro-5-[2'-(1H-tetrazol-5-yl)[1,1'-biphenyl]-4-yl]imidazo[1,5-a]pyridin-8-ol;

1,3-Dibutyl-5,6-dihydro-5-[2'-(1H-tetrazol-5-yl)[1,1'-biphenyl]-4-yl]imidazo[1,5-a]pyridin-8(5H)-one;

1,3-Dibutyl-5,6-dihydro-8-phenyl-5-[2'-(1H-tetrazol-5-yl)[1,1'-biphenyl]-4-yl]imidazo[1,5-a]pyridine;

[1,3-Dibutyl-6,7-dihydro-5-[2'-(1H-tetrazol-5-yl)[1,1'-biphenyl]-4-yl]imidazo[1,5-a]pyridin-8(5H)-ylidene]acetic acid;

1-[1,3-Dibutyl-5,6,7,8-tetrahydro-5-[2'-(1H-tetrazol-5-yl) [1,1'-biphenyl]-4-yl]imidazo[1,5-a]pyridin-8-yl]-2,5-pyrrolidinedione;

4-[1,3-Dibutyl-5,6,7,8-tetrahydro-5-[2'-(1H-tetrazol-5-yl) [1,1'-biphenyl]-4-yl]imidazo[1,5-a]pyridin-8-yl]amino]-4-oxobutanoic acid, hydrazide;

1,3-Dibutyl-6,7-dihydro-5-[2'-(1H-tetrazol-5-yl)[1,1'-biphenyl]-4-yl]-5H-imidazo[1,5-a]azepine;

3-Butyl-5,6-dihydro-5-[2'-(1H-tetrazol-5-yl)[1,1'-biphenyl]-4-yl]imidazo[1,5-a]pyridine;

3-Butyl-5,6-dihydro-5-[2'-(1H-tetrazol-5-yl)[1,1'-biphenyl]-4-yl]imidazo[1,5-a]pyridin-8 (5H)-one;

3-Butyl-5,6,7,8-tetrahydro-5-[2'-(1H-tetrazol-5-yl) [1,1'-biphenyl]-4-yl]imidazo[1,5-a]pyridin-cis-8-ol;

3-Butyl-5,6,7,8-tetrahydro-5-[2'-(1H-tetrazol-5-yl) [1,1'-biphenyl]-4-yl]imidazo[1,5-a]pyridin-trans-8-ol;

1,1-Dimethylethyl [3-butyl-6,7-dihydro-5-[2'-(1H-tetrazol-5-yl)[1,1'-biphenyl]-4-yl]imidazo[1,5-a]pyridin-8(5H)-ylidene]acetate;

[3-Butyl-6,7-dihydro-5-[2'-(1H-tetrazol-5-yl)[1,1'-biphenyl]-4-yl]imidazo[1,5-a]pyridin-8(5H)-ylidene]acetic acid;

1,1-Dimethylethyl 3-butyl-5,6-dihydro-5-[2'-(1H-tetrazol-5-yl)[1,1'-biphenyl]-4-yl]imidazo[1,5-a]pyridin-8-acetate;

3-Butyl-5,6-dihydro-5-[2'-(1H-tetrazol-5-yl)[1,1'-biphenyl]-4-yl]imidazo[1,5-a]pyridin-8-acetic acid;

1,1-Dimethylethyl 3-butyl-5,6,7,8-tetrahydro-5-[2'-(1H-tetrazol-5-yl)[1,1'-biphenyl]-4-yl]imidazo[1,5-a]pyridin-cis-8-acetate;

3-Butyl-5,6,7,8-tetrahydro-5-[2'-(1H-tetrazol-5-yl) [1,1'-biphenyl]-4-yl]imidazo[1,5-a]pyridin-cis-8-acetic acid;

1,3-Dibutyl-5,6-dihydro-N-hydroxy-5-[2'-(1H-tetrazol-5-yl) [1.1'-biphenyl]-4-yl]imidazol[1,5-a]pyridin-8(7H)-imine;

1-[3-Butyl-5,6,7,8-tetrahydro-5-[2'-(1H-tetrazol-5-yl) [1,1'-biphenyl]-4-yl]imidazo[1,5-a]pyridin-8-yl]phthalimide;

1,3-Dibutyl-8-phenyl-5,6-dihydro-5-{2'-(1H-tetrazol-5-yl){1,1'-biphenyl]-4-yl]imidazo[1,5-a]pyridine;

1-[3-Butyl-5,6,7,8-tetrahydro-5-[2'-(1H-tetrazol-5-yl) [1,1 '-biphenyl]-4-yl]imidazo[1,5-a]pyridin-8-yl]-cis-2,5-pyrrolidinedione;

1-[3-Butyl-5,6,7,8-tetrahydro-5-[2'-(1H-tetrazol-5-yl) [1,1'-biphenyl]-4-yl]imidazo[1,5-a]pyridin-8-yl]-trans-2,5-pyrrolidinedione;

1-[3-Butyl-1-chloro-5,6,7,8-tetrahydro-5-[2'-(1H-tetrazol-5-yl)[1,1'-biphenyl]-4-yl]imidazo[1,5-a]pyridin-8-yl]-cis-2,5-pyrrolidinedione;

1-[3-Butyl-1-chloro-5,6,7,8-tetrahydro-5-[2'-(1H-tetrazol-5-yl)[1,1'-biphenyl]-4-yl]imidazo[1,5-a]pyridin-8-yl]-trans-2,5-pyrrolidinedione;

3-Butyl-8-phenylmethoxy-5,6,7,8-tetrahydro-5-[2'-(1H-tetrazol-5-yl)[1,1'-biphenyl]-4-yl]imidazo[1,5-a]pyridine; and 3-Butyl-5,6,7,8-tetrahydro-8-amino-5-[2'-(1H-tetrazol-5-yl) [1,1'-biphenyl]-4-yl]imidazo[1,5-a]pyridine.

23. The method of claim 20 wherein said circulatory disorder is a cardiovascular disorder.

24. The method of claim 20 wherein said circulatory disorder is hypertension.

25. The method of claim 20 wherein said circulatory disorder is congestive heart failure.

* * * * *